(12) United States Patent
Schaus et al.

(10) Patent No.: US 11,420,977 B2
(45) Date of Patent: Aug. 23, 2022

(54) LATE SV40 (LSF) INHIBITORS

(71) Applicant: Trustees of Boston University, Boston, MA (US)

(72) Inventors: Scott Edward Schaus, Boston, MA (US); Ulla Hansen, Bedford, MA (US); Hang Gyeong Chin, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/530,080

(22) Filed: Aug. 2, 2019

(65) Prior Publication Data

US 2020/0039996 A1 Feb. 6, 2020

Related U.S. Application Data

(60) Provisional application No. 62/713,741, filed on Aug. 2, 2018.

(51) Int. Cl.
*C07D 491/052* (2006.01)
*A61P 35/00* (2006.01)
*C07D 491/147* (2006.01)

(52) U.S. Cl.
CPC .......... *C07D 491/052* (2013.01); *A61P 35/00* (2018.01); *C07D 491/147* (2013.01)

(58) Field of Classification Search
CPC ................................................ C07D 491/052
See application file for complete search history.

(56) References Cited

U.S. PATENT DOCUMENTS

| | | | |
|---|---|---|---|
| 6,713,462 B2 | 3/2004 | Metcalf et al. | |
| 7,081,256 B2 | 7/2006 | Kubota et al. | |
| 8,440,705 B2 | 5/2013 | Lindquist et al. | |
| 9,802,948 B2 * | 10/2017 | Hansen | C07D 491/056 |
| 9,815,845 B2 * | 11/2017 | Hansen | C07D 491/056 |
| 2003/0130505 A1 | 7/2003 | Zhi et al. | |
| 2007/0287706 A1 | 12/2007 | Dickinson, Jr. et al. | |
| 2009/0081183 A1 | 3/2009 | Margolis et al. | |
| 2010/0004277 A1 | 1/2010 | Bulawa et al. | |
| 2010/0105906 A1 | 4/2010 | Bissantz et al. | |
| 2013/0158035 A1 * | 6/2013 | Hansen | A61K 31/4709 514/237.5 |
| 2013/0324570 A1 | 12/2013 | Hansen et al. | |
| 2017/0044175 A1 | 2/2017 | Hansen | |
| 2017/0107227 A1 * | 4/2017 | Hansen | C07D 491/056 |
| 2018/0051033 A1 | 2/2018 | Hansen et al. | |
| 2019/0152949 A1 | 5/2019 | Cyr et al. | |

FOREIGN PATENT DOCUMENTS

| | | |
|---|---|---|
| CN | 101410384 A | 4/2009 |
| EP | 2433634 A2 | 3/2012 |
| WO | 1998/36641 A1 | 8/1998 |
| WO | 2003/066630 A2 | 8/2003 |
| WO | 2007/136592 A2 | 11/2007 |
| WO | 2011/123427 A2 | 10/2011 |
| WO | 2012027392 A2 | 3/2012 |
| WO | 2012050985 A1 | 4/2012 |
| WO | 2013052465 A1 | 4/2013 |

OTHER PUBLICATIONS

STN-Chemical database registry # 725686-76-0 for 9-(2-ethoxyphenyl)-2,3,8,9-tetrahydro-1,4-Dioxino[2,3-g]quinolin-7(6H)-one Entered STN: Aug. 12, 2004.*
Online: "http://web.archive.org/web/20090414214134/http://www.htscompounds.com/index.html" dated Apr. 14, 2009, accessed Aug. 21, 2015.*
Wisclicenus, J. "Adolph Strecker's Short Textbook of Organic Chemistry" 1881, Spottiswoode: London, pp. 38-39.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Rautio et al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Santhekadur "The transcription factor LSF: a novel oncogene for hepatocellular carcinoma" Am J Cancer Res 2012;2(3):269-285.*
Cacciotti "SV40 replication in human mesothelial cells induces HGF/Met receptor activation: A model for viral-related carcinogenesis of human malignant mesothelioma" PNAS Oct. 9, 2001, vol. 98, No. 21, 12032-12037.*
Henry R. Henze and Charles M. Blair "The Number of Structurally Isomeric Alcohols of the Methanol Series " Journal of the American Chemical Society 1931, 3042.*
Traylor-Knowles et al., BMC Evolutionary Biology, 10:101 (2010). The evolutionary diversification of LSF and Grainyhead transcription factors preceded the radiation of basal animal lineages.
Veljkovic et al., Gene, 343:23-40 (2004). "Lineage-specific and ubiquitous biological roles of the mammalian transcription factor LSF."
Verhey, K.J. and J. Gaertig, The tubulin code. Cell Cycle, 2007. 6(17): p. 2152-60.
Weinstein et al., Cancer Res, 68:3077-3080 (2008). "Oncogene Addiction."
Wu, S. and J.C. Rice, A new regulator of the cell cycle: the PR-Set7 histone methyltransferase. Cell Cycle, 2011. 10(1): p. 68-72.
Yoo et al., J Clin Invest, 119:465-477 (2009). "Astrocyte elevated gene-1 regulates hepatocellular carcinoma development and progression."
Yoo et al., PNAS, 106:12938-12943 (2009). "Identification of genes conferring resistance to 5-fluorouracil."

(Continued)

*Primary Examiner* — David K O'Dell
(74) *Attorney, Agent, or Firm* — Nixon Peabody LLP; Ronald I. Eisenstein; Ravinderjit Braich

(57) ABSTRACT

The present invention is directed to compositions, methods and kits for treatment of cancer, e.g. heptacellular carcinoma (HCC). In some embodiments, the present invention discloses the use of a small-molecule compounds of Formula (I)-(V) to inhibit tubulin methylation or to modulate chromatin or cytoskeleton modification in a cell.

5 Claims, 31 Drawing Sheets

(56) References Cited

OTHER PUBLICATIONS

Yoo, B.K., et al., Transcription factor Late SV40 Factor (LSF) functions as an oncogene in hepatocellular carcinoma. Proc Natl Acad Sci USA, 2010. 107(18): p. 8357-62.
Zhang, T., S. Cooper, and N. Brockdorff, The interplay of histone modifications—writers that read. EMBO Rep, 2015. 16(11): p. 1467-81.
Zhong et al., J Biol Chem, 269:21269-21276 (1994). "Evidence that levels of the dimeric cellular transcription factor CP2 play little role in the activation of the HIV-1 long terminal repeat in vivo or following superinfection with herpes simplex virus type 1."
PUBCHEM-CID: 2943604, Structure, 1-8, (2005).
Hoj et al. "Small molecules revealed In a screen targeting epithelial scattering are inhibitors of microtubule polymerization." Journal of Biomolecular Screening 21.7 (2016): 671-679.
Andrews, N.C. and D.V. Faller, A rapid micropreparation technique for extraction of DNA-binding proteins from limiting numbers of mammalian cells. Nucleic Acids Res, 1991. 19(9): p. 2499.
Arand, J., et al., In vivo control of CpG and non-CpG DNA methylation by DNA methyltransferases. PLoS Genet, 2012.8(6): p. e1002750.
Bing et al., J Biol Chem., 275:31616-31623 (2000). "Nfkappa B interacts with serum amyloid A3 enhancer factor to synergistically activate mouse serum amyloid A3 gene transcription."
Bovolenta et al., J. Immunol., 163:6892-6897 (1999). "In vivo administration of recombinant IL-2 to individuals infected by HIV down-modulates the binding and expression of the transcriptioni factors Ying-Yang-1 and leader binding protein-1/late simian virus 40 factor.".
Bruni et al., J Biol Chem, 277:35481-35488 (2002). "Fe65, a ligand of the Alzheimer's beta-amyloid precursor protein, blocks cell cycle progression by down-regulating thymidylate synthase expression."
Chang et al., J. Med. Chem., 52:4883-4891 (2009). "Design and Synthesis of 2-(3-Benzo[b]thienyl)-6,7-methylenedioxyquinolin-4-one Analogues as Potent Antitumor Agents that Inhibit Tubulin Assembly."
Chin, H.G., et al., Transcription factor LSF-DNMT1 complex dissociation by FQI1 leads to aberrant DNA methylation and gene expression. Oncotarget, 2016. 7(50): p. 83627-83640.
Delcuve G.P., S. He, and J.R. Davie, Mitotic partitioning of transcription factors. J Cell Biochem, 2008. 105(1): p. 1-8.
Dillon, S.C., et al., The SET-domain protein superfamily: protein lysine methyltransferases. Genome Biol, 2005. 6(8): p. 227.
Drouin et al., J Immunol, 168:2847-2856 (2002). "The ubiquitously expressed DNA-binding protein Late SV40 Factor binds Ig switch regions and represses class switching to IgA."
Esteve, P.O., et al., Direct interaction between DNMT1 and G9a coordinates DNA and histone methylation during replication. Genes Dev, 2006. 20(22): p. 3089-103.
Fang, J., et al., Purification and functional characterization of SET8, a nucleosomal histone H4-lysine 20-specific methyltransferase. Curr Biol, 2002. 12(13): p. 1086-99.
Gottesfeld, J.M., "Mitotic repression of the transcriptional machinery" Trends Biochemistry Science, 1997. 22(6): p. 197-202.
Grant, T.J., et al., Antiproliferative small-molecule inhibitors of transcription factor LSF reveal oncogene addiction to LSF in hepatocellular carcinoma. Proc Natl Acad Sci USA, 2012. 109(12): p. 4503-8.
Guo, et al., "A polymorphism at the miR-502 binding site in the 3'-untranslated region of the histone methyltransferase SET8 is associated with hepatocellular carcinoma outcome." International Journal of Cancer, 2012. 131(6): p. 1318-1322.
Haigh et al., J. Chem. Inf. Model, 45:673-684 (2005). "Small molecule shape-fingerprints."
Hansen et al., Cell Cycle, 8:2146-2151 (2009). "Transcriptions factors LSF and E2Fs: Tandem cyclists driving G0 to S?".
Hou, L., et al., SET8 induces epithelialmesenchymal transition and enhances prostate cancer cell metastasis by cooperating with ZEB1. Mol Med Rep, 2016. 13(2): p. 1681-8.

Huang et al., Interferon Cytokine Res, 19:1403-1411 (1999). "Synergistic induction of mouse serum amyloid A3 promoter by the inflammatory mediators IL-1 and IL-6."
Janke, C. and J.C. Bulinski, Post-translational regulation of the microtubule cytoskeleton: mechanisms and functions. Nat Rev Mol Cell Biol, 2011. 12(12): p. 773-86.
Janke C., The tubulin code: molecular components, readout mechanisms, and functions. J Cell Biol, 2014. 206(4): p. 461-72.
Koehler et al., Curr. Opin. Chem. Biol., 14:331-340 (2010). "A complex task? Direct modulation of transcription factors with small molecules."
Komlodi-Pasztor E., D.L. Sackett, and A.T. Fojo, Inhibitors targeting mitosis: tales of how great drugs against a promising target were brought down by a flawed rationale. Clin Cancer Res, 2012. 18(1): p. 51 -63.
Laursen, L., "A preventable cancer." Nature, 2014. 516(7529): p. S2-3.
Li et al., J. Org. Chem., 70:2881-2883 (2005). "Trifluoroacetic acid-mediated hydroarylation: synthesis of dihydrocoumarins and dihydroquinolones."
Long, J.J., et al., Repression of TFIIH transcriptional activity and TFIIH-associated cdk7 kinase activity at mitosis. Mol Cell Biol, 1998. 18(3): p. 1467-76.
Lu, C., et al., Increased alpha-tubulinIb expression indicates poor prognosis and resistance to chemotherapy in hepatocellular carcinoma. Dig Dis Sci, 2013. 58(9): p. 2713-20.
Milite C., et al., The emerging role of lysine methyltransferase SETD8 in human diseases. Clin Epigenetics, 2016. 8:102. pp. 1-15.
Murata et al., Genes to Cells, 3:443-457 (1998). "Transcription factor CP2 is essential for lens-specific expression ofthe chicken alphaA-crystallin gene."
Nishioka, K., et al., PR-Set7 is a nucleosome-specific methyltransferase that modifies lysine 20 of histone H4 and is associated with silent chromatin. Mol Cell, 2002. 9(6): p. 1201-13.
Palozola, K.C., et al., Mitotic transcription and waves of gene reactivation during mitotic exit. Science, 2017. 358 (6359): p. 119-122.
Park, I.Y., et al., Dual Chromatin and Cytoskeletal Remodeling by SETD2. Cell, 2016. 166(4): p. 950-962.
Porta-De-La-Riva et al., J. Biochem., 435:563-568 (2011).
Powell et al., EMBO J, 19:4665-4675 (2000). "Inhibition of the mammalian transcription factor LSF induces s-phase-dependent apoptosis by downregulating thymidylate synthase expression."
Rajasekaran et al., "Small molecule inhibitors of Late SV40 Factor (LSF) abrogate hepatocellular carcinoma (HCC): Evaluation using an endogenous HCC model." Oncotarget 6(28): 26266-26277 (2015).
Rice, J.C., et al., Mitotic-specific methylation of histone H4 Lys 20 follows increased PR-Set7 expression and its Tocalization to mitotic chromosomes. Genes Dev, 2002. 16(17): p. 2225-30.
Saxena et al., Mol Cell Biol., 29:2335-2345 (2009). "Phosphorylation by cyclin C/cyclin-dependent kinase 2 following mitogenic stimulation of murine fibroblasts inhibits transcriptional activity of LSF during G1 progression."
Sharma et al., Biochem. Pharmacol, 80:666-673 (2010). "Exploiting the balance between life and death: targeted cancer therapy and 'oncogenic shock.'"
Shi, X., et al., Modulation of p53 function by SET8-mediated methylation at lysine 382. Mol Cell, 2007. 27(4): p. 636-46.
Shirra et al., J Biol Chem., 273:19260-19268 (1998). "LSF and NTF-1 share a conserved DNA-recognition motif yet required different oligomerization states to form a stable protein-DNA complex."
Singh et al., Chemical & Pharmaceutical Bulletin, 58(2):242-246 (2010). "Design and Synthesis of C-Ring Lactone- and Lactam-Based Podophyllotoxin Analogues as Anticancer Agents."
Song, Y. and S.T. Brady, Post-translational modifications of tubulin: pathways to functional diversity of microtubules. Trends Cell Biol, 2015. 25(3): p. 125-36.
Stanton, R.A., et al., Drugs that target dynamic microtubules: a new molecular perspective. Med Res Rev, 2011.31(3):p. 443-81.

(56) References Cited

OTHER PUBLICATIONS

Swendeman et al., J Biol Chem, 269:11663-11671 (1994). "Characterization of the genomic structure chromosomal Tocation, promoter and developmental expression fo the alpha-globin transcription factor CP2."

* cited by examiner

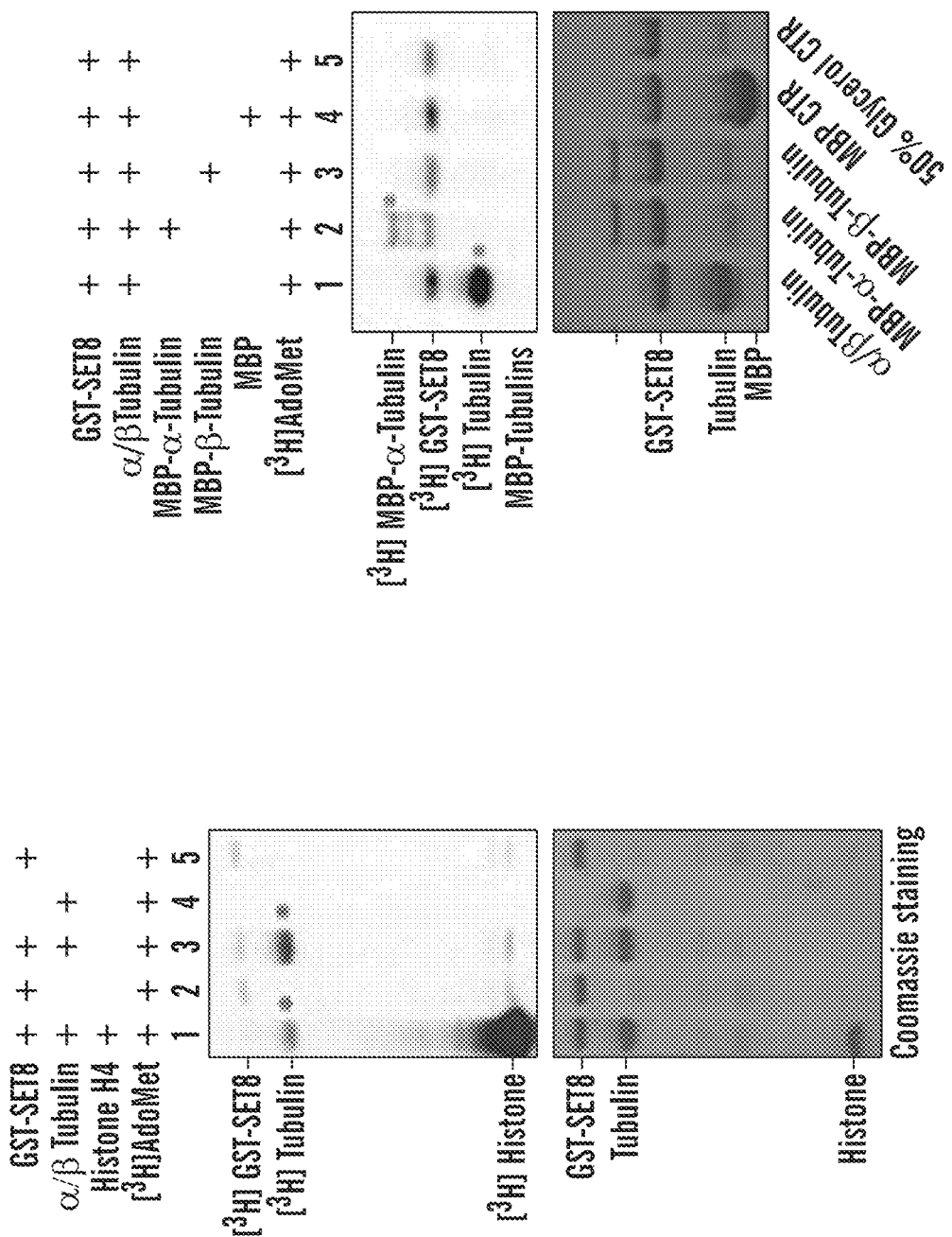

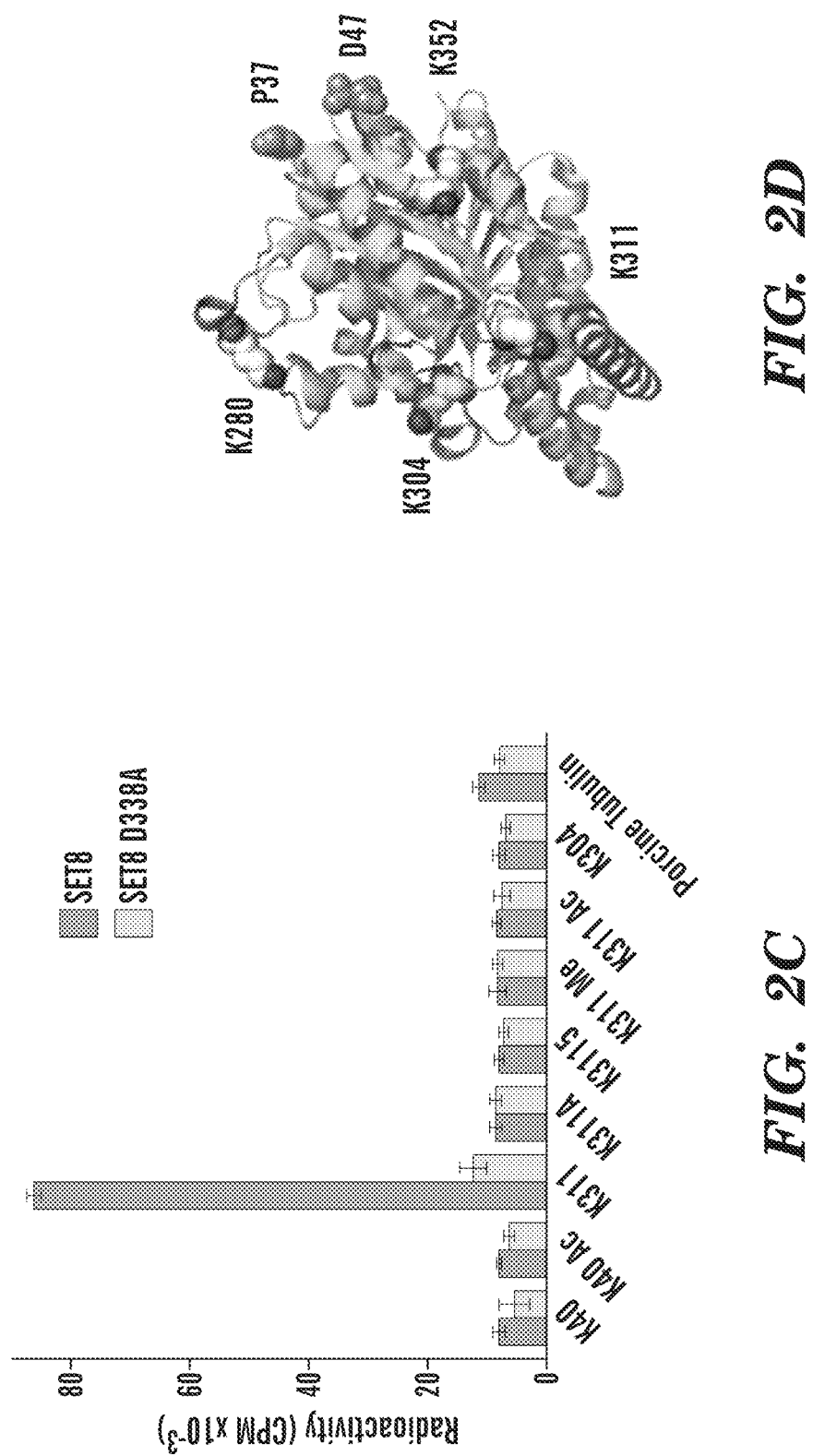

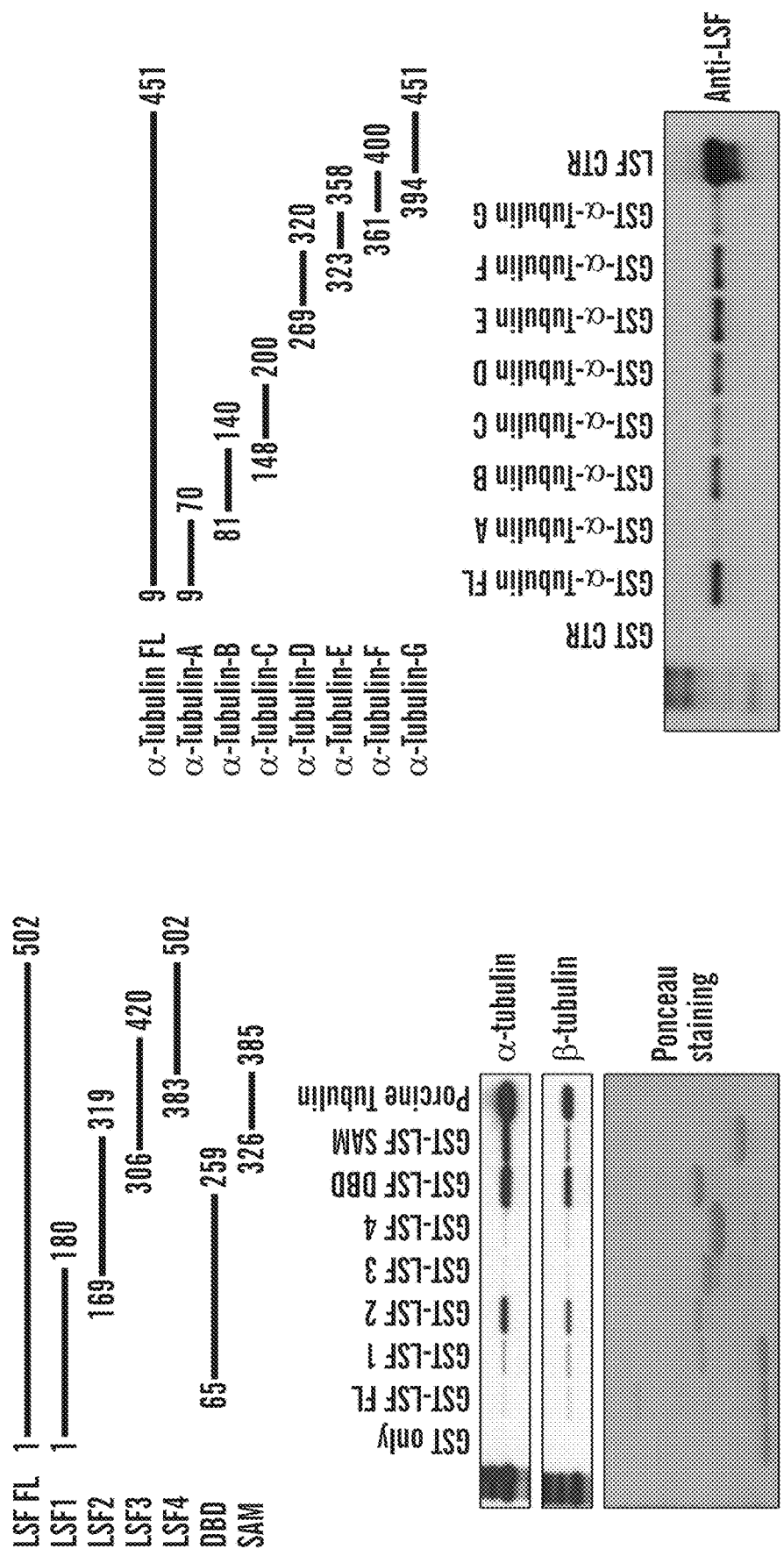

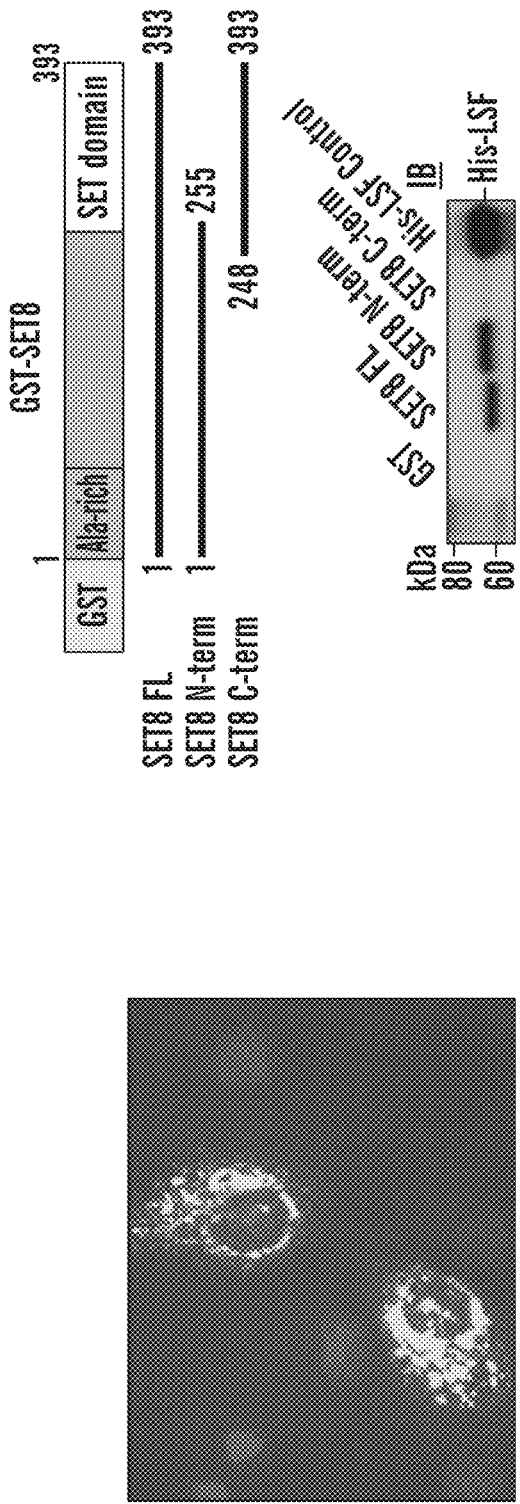
*FIG. 6A*
*FIG. 6B*
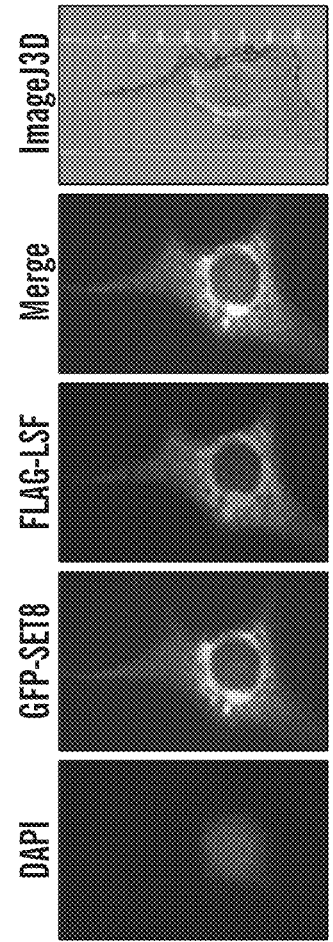
*FIG. 6C*

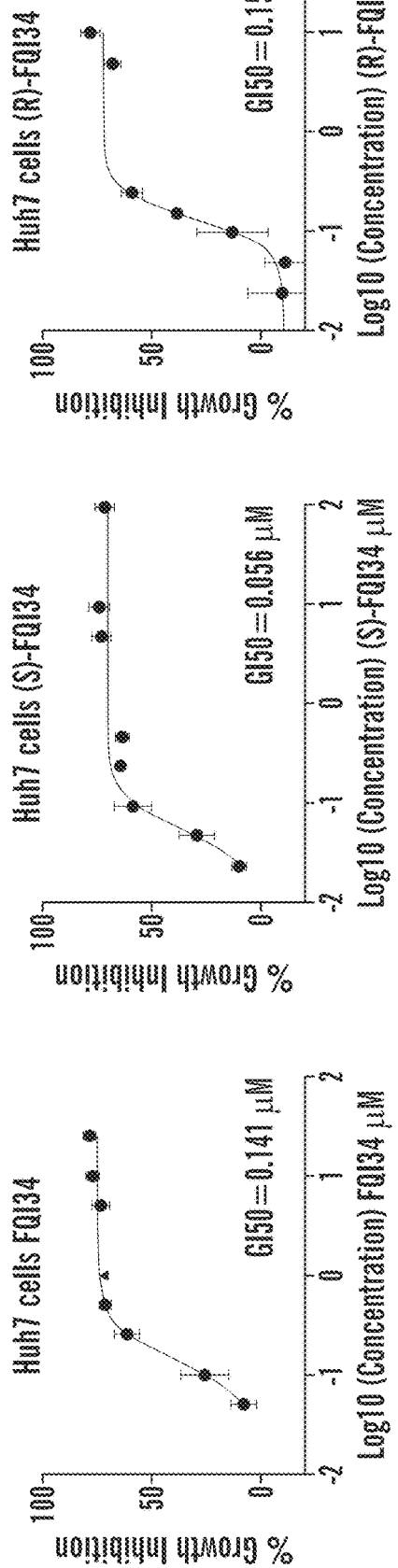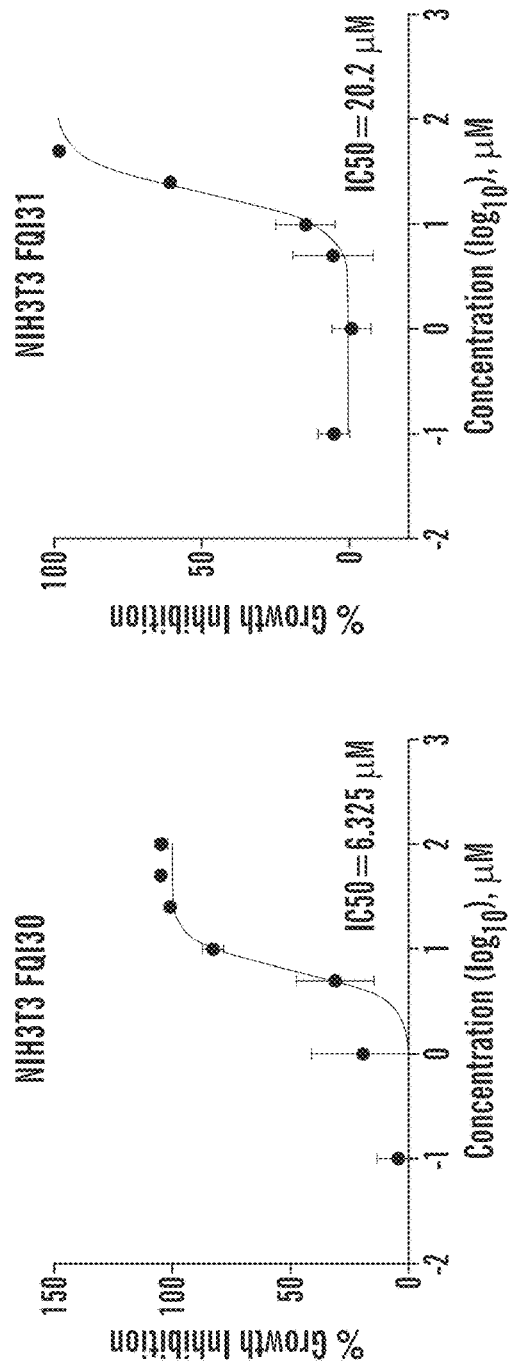
FIG. 10A  FIG. 10B  FIG. 10C  FIG. 11A  FIG. 11B

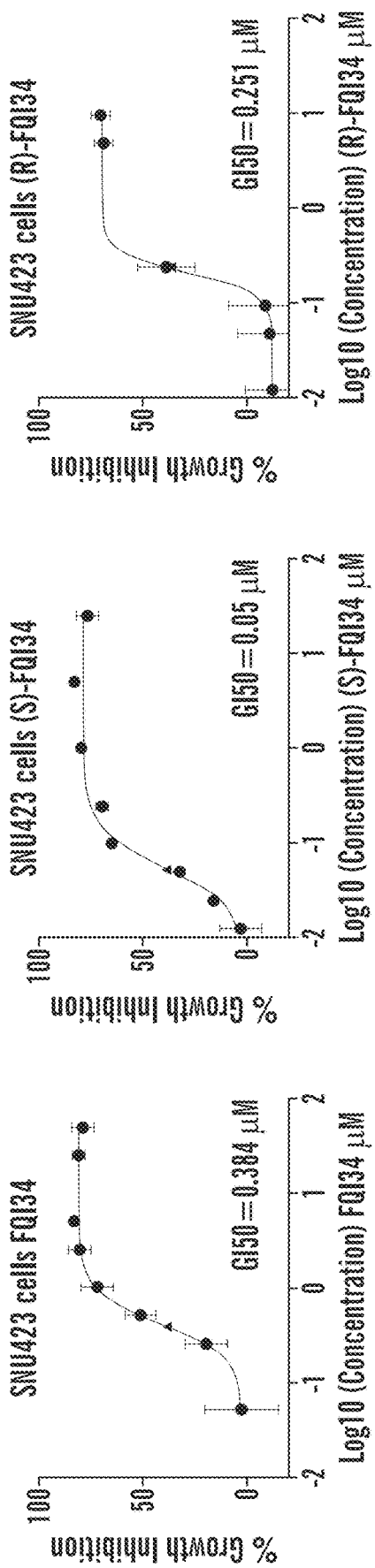
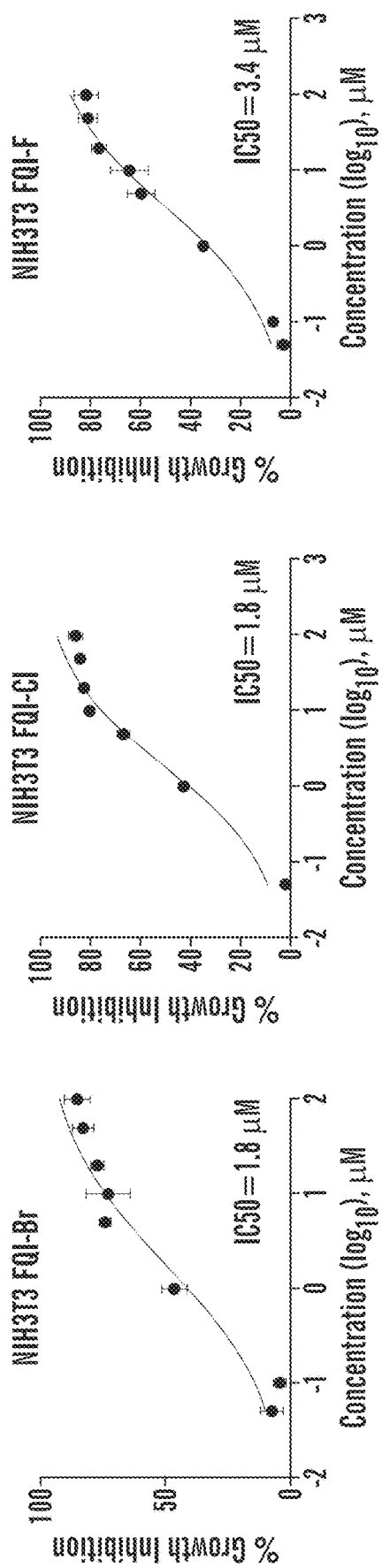
FIG. 12A  FIG. 12B  FIG. 12C
FIG. 13  FIG. 14  FIG. 15

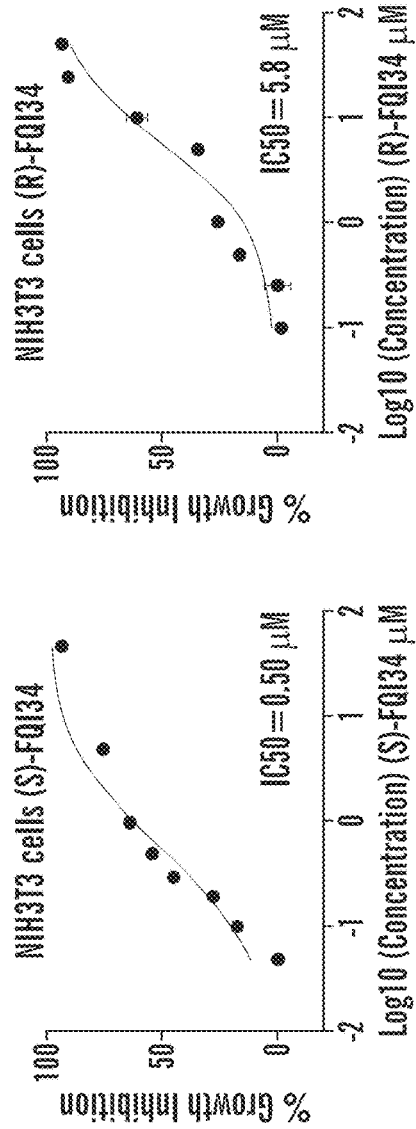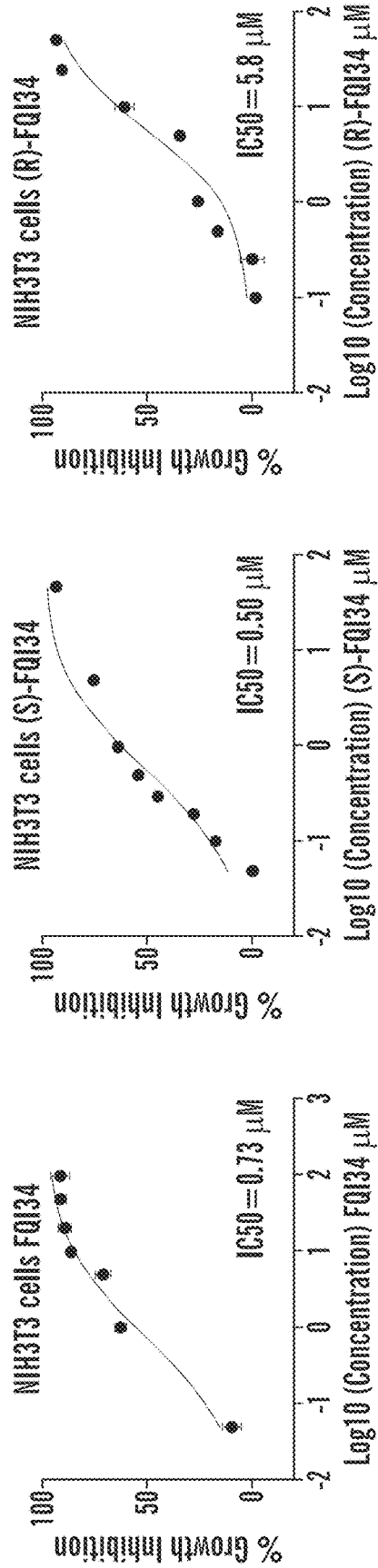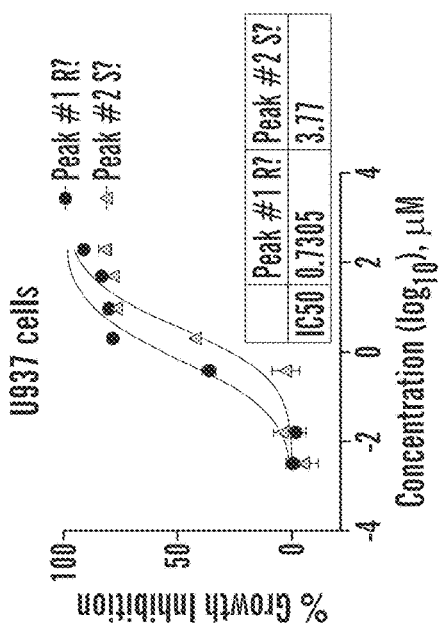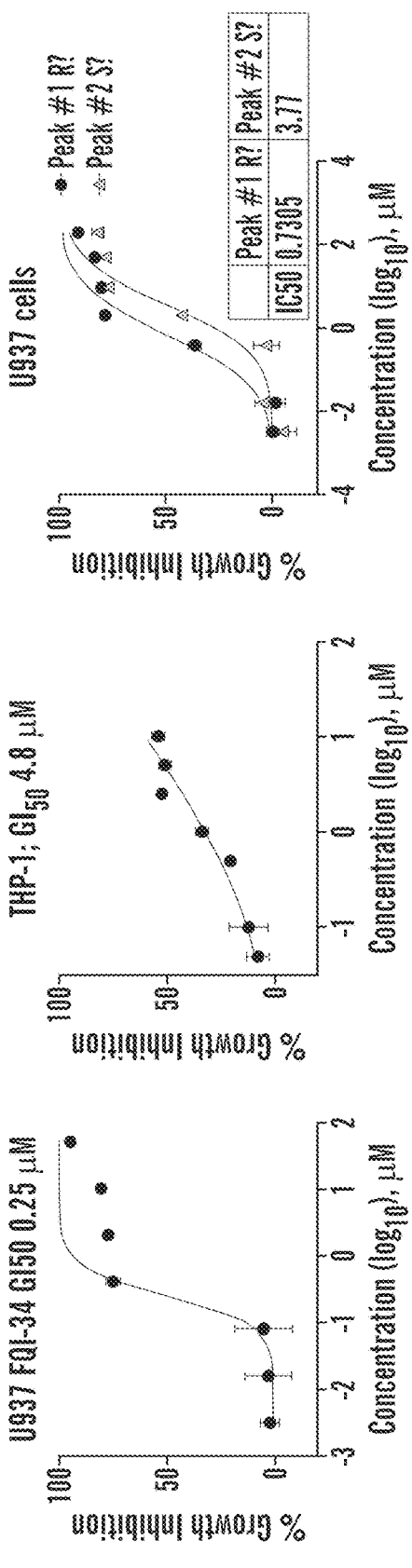
FIG. 16A  FIG. 16B  FIG. 16C
FIG. 17A  FIG. 17B  FIG. 17C

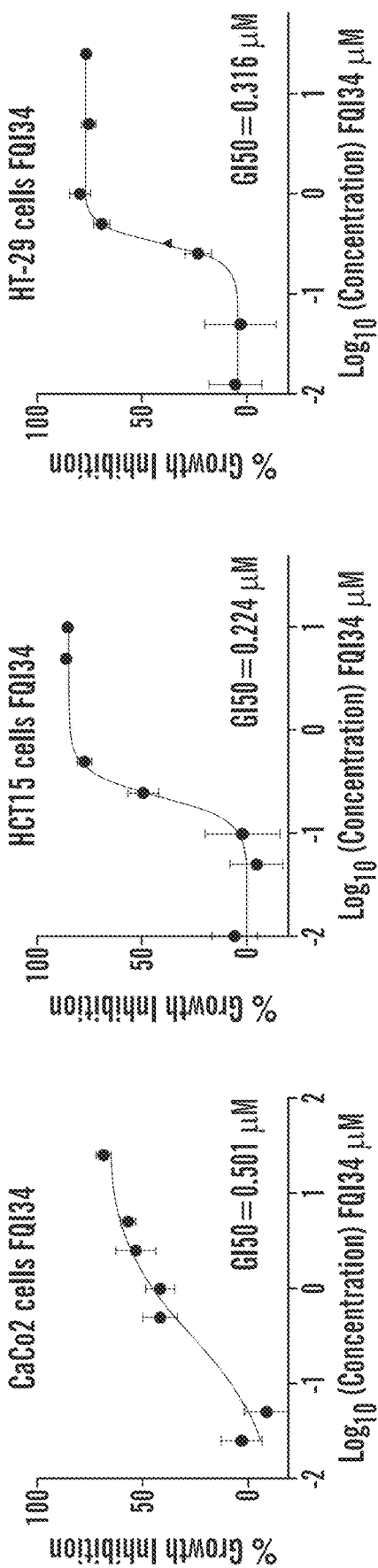
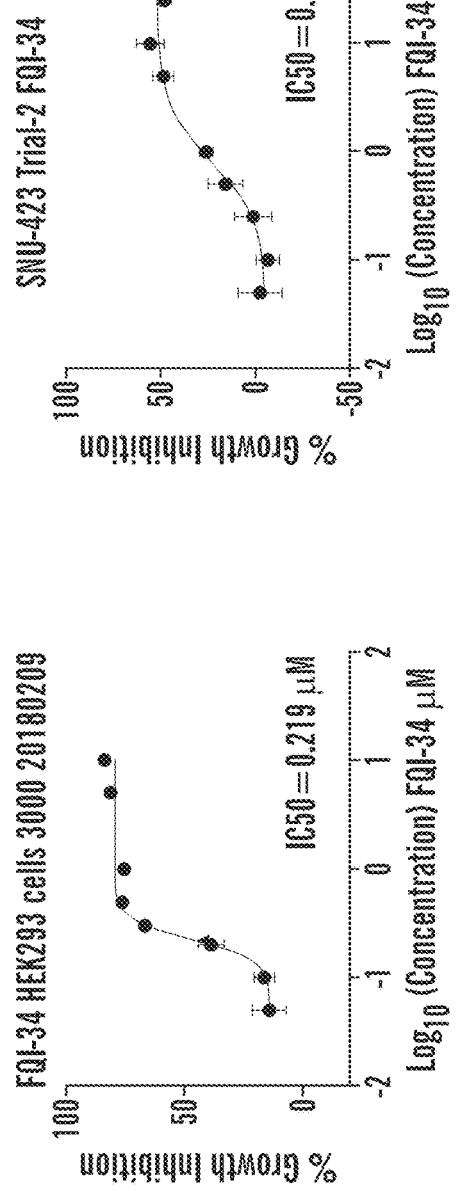
FIG. 20
FIG. 21
FIG. 22
FIG. 23
FIG. 24

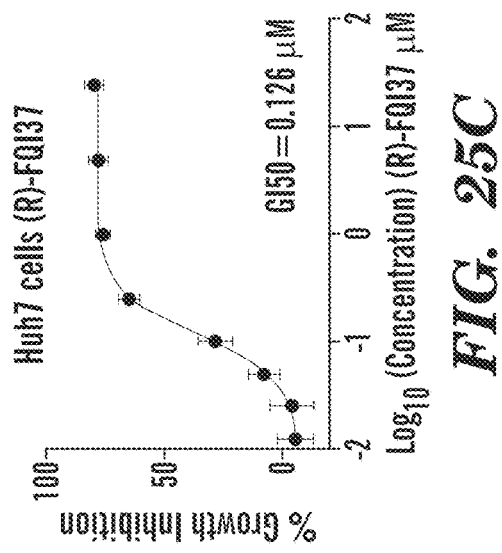
FIG. 25A     FIG. 25B     FIG. 25C
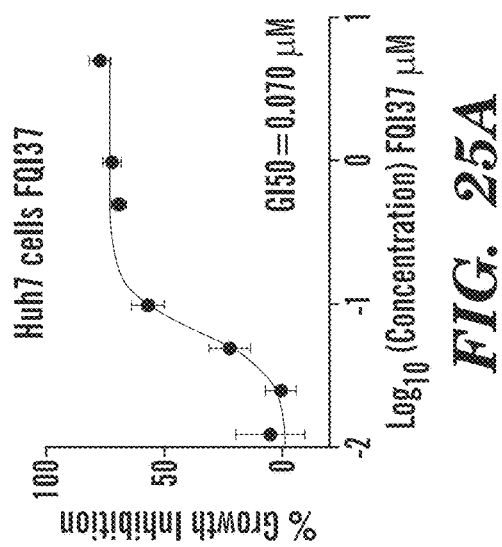
FIG. 26A     FIG. 26B     FIG. 26C

LATE SV40 (LSF) INHIBITORS

RELATED APPLICATIONS

This application claims benefit under 35 U.S.C. § 119(e) of U.S. Provisional Application No. 62/713,741, filed Aug. 2, 2018, content of which is incorporated herein by reference in its entirety.

GOVERNMENT SUPPORT

This invention was made with Government Support under Contract No. GM078240 awarded by the National Institutes of Health. The Government has certain rights in the invention.

FIELD OF THE INVENTION

The present invention generally relates to Late SV40 Factor (LSF) inhibitors and their uses, for example in a method for treating cancer, e.g., hepatocellular carcinoma (HCC).

BACKGROUND OF THE INVENTION

Microtubules are important in many cellular processes such as cell motility, protein and organelle transport, and mitosis and are a validated target for anticancer drugs. However, how tubulin is regulated or recruited for use in these cellular processes is less understood. Tubulin post-translational modifications are proposed to regulate microtubule functions and dynamics. Although many such modifications have been investigated, tubulin methylations and enzymes responsible for methylation have only recently begun to be described. Therefore, there is need to understand the process of tubulin methylation.

SET8/PR-Set7 is a protein-lysine N-methyltransferase responsible for the monomethylation of both histone and non-histone proteins in higher eukaryotes. It is functionally characterized as a histone H4 lysine 20-specific monomethyltransferase; this modification is a specific mark for transcriptional repression and is also enriched during mitosis. SET8 is required for cell proliferation, chromosome condensation, and cytokinesis, since deletion or RNAi mediated depletion of the enzyme impairs all these functions. Previous findings, in particular, suggest that SET8 and H4K20me1 are required for mitotic entry. SET8 also mediates monomethylation of other substrates, including p53, which results in repression of p53 target genes. However, how H4K20me1 is regulated and how it functions to promote cell cycle progression remains an open question, including the possibility that other non-histone substrates may be involved.

Transcription factor LSF is an oncogene in Hepatocellular Carcinoma (HCC), being dramatically overexpressed in HCC cell lines and patient samples. LSF is also generally required for cell cycle progression and cell survival. Initially, LSF was described as a regulator of G1/S progression, and essential for inducing expression of the gene encoding thymidylate synthase (TYMS) in late G1. However, the inventors have discovered, inter alia, additional involvement of LSF in mitosis. Particularly, inhibiting LSF with an exemplary small molecule inhibitor of LSF abrogated the DNA-binding and corresponding transcriptional activities of LSF, as well as specific LSF-protein interactions and inhibited growth of HCC tumors in multiple mouse models. In HCC cell lines, inhibition of LSF caused cell death via mitotic defect.

Hepatocellular carcinoma is a primary malignant tumor, which develops in the liver. HCC is one of the five most common cancers and the third leading cause of cancer deaths worldwide. The incidence of HCC is increasing despite a decrease in overall incidence of all cancers. In the United States, the estimated new cases of HCC for 2008 were 21,370, of which 18,410 were expected to die. There are multiple etiologies, with subcategories displaying distinct gene expression profiles. The prognosis of HCC remains poor. The mean 5-year survival rate is less than 10%. The mortality rate of HCC parallels that of its incidence because HCC is a tumor with rapid growth and early vascular invasion that is resistant to conventional chemotherapy.

Hepatocellular carcinoma (HCC) is characterized by late stage diagnosis and a poor prognosis for treatment, usually consisting of surgical resection of the tumor and chemotherapy. Currently, the only approved systemic treatments for late stage primary malignancies are sorafenib and regorafenib. The current treatment options for HCC are not optimal, especially following metastasis. Irradiation and chemotherapies have not so far proved to be satisfactory; surgery is the most effective treatment of HCC. However, surgery is only appropriate for patients with small resectable tumors. Only two, molecularly based drugs (Sorafenib and Regorafenib), which target tyrosine kinase receptors and the MEK/ERK pathway, have generated responses in patients as a single therapy. However, increased survival times with Sorafenib are only a few months. Regorafenib, a closely related compound, has recently been approved for treatment of sorafenib-resistant patients, although again with limited survival benefit. As such, it is imperative to discover novel, effective, and targeted therapies for this highly aggressive cancer. In particular, there is a strong need in the art for improved methods for treatment of HCC with small-molecule drugs.

SUMMARY OF THE INVENTION

The present invention is generally directed to methods, compositions and kits to treat cancer e.g. hepatocellular carcinoma (HCC), for example, by using inhibitors of late SV40 factor (LSF), such as a compound represented by Formula (I)-(V) as disclosed herein. In some embodiments, the LSF inhibitor, e.g., a compound of Formula (I)-(V) as disclosed herein, can be used to treat other cancers, for example, cervical cancer, colon cancers, pancreatic adenocarcinoma, ductal adenocarcinoma, colorectal adenocarcinoma, rectosigmoid carcinoma, monocytic lymphoma, kidney cancer, oral squamous cell carcinoma and the like.

The inventors have discovered that expression of LSF is up-regulated in subjects, e.g. human subjects, with HCC. The inventors have also discovered that inhibiting LSF using small-molecule compounds can decrease tumorigenesis and metastasis of HCC. Accordingly, the inventors have discovered that a family of small molecules that inhibit LSF as disclosed herein can be used as chemotherapeutics agents for treatment of HCC in subjects, such as human subjects. Further, expression of LSF can be used to identify a subject with HCC.

Accordingly, one aspect of the present invention relates to a compound of Formula (I)-(V) or enantiomers, prodrugs, derivatives, or pharmaceutically acceptable salts thereof.

Compounds of Formula (I) have the structure:

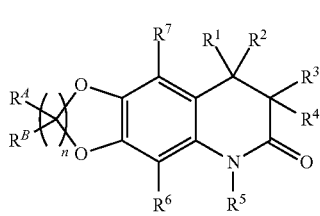

FORMULA (I)

wherein:
R$^1$ is an aryl substituted with at least one OR$^{3A}$ and optionally further substituted with halogen, C$_1$-C$_6$ alkyl, C$_3$-C$_8$ cycloalkyl, C$_1$-C$_6$ haloalkyl, C$_1$-C$_6$ heteroalkyl, C$_1$-C$_6$ alkoxy, C$_2$-C$_8$ alkenyl, amino (NH$_2$), mono(C$_1$-C$_6$ alkyl)amino or di(C$_1$-C$_6$ alkyl)amino;

R$^2$, R$^3$ and R$^4$ are each independently selected from the group consisting of hydrogen, halogen, C$_1$-C$_6$ alkyl, C$_1$-C$_6$ haloalkyl, C$_1$-C$_6$ heteroalkyl, OR$^{3A}$, SR$^{3A}$, SO$_2$R$^{3A}$, NR$^{3A}$R$^{4A}$, halogen, heteroaryl, and aryl, wherein the alkyl, haloalkyl, heteroalkyl, heteroaryl, and aryl can be optionally substituted with halogen, C$_1$-C$_6$ alkyl, C$_1$-C$_6$ haloalkyl, C$_1$-C$_6$ heteroalkyl, C$_1$-C$_6$ alkoxy, C$_2$-C$_8$ alkenyl, amino (NH$_2$), mono(C$_1$-C$_6$ alkyl)amino or di(C$_1$-C$_6$ alkyl)amino; or R$^2$ and R$^3$ together form a second bond between the carbons to which they are attached;

R$^5$ is hydrogen, C$_1$-C$_6$ alkyl, C$_1$-C$_6$ haloalkyl, C$_1$-C$_6$ heteroalkyl, aryl, heteroaryl, or halogen;

R$^6$ and R$^7$ are each independently selected from the group consisting of hydrogen, halogen, OR$^{3A}$, NR$^{3A}$R$^{4A}$, SR$^{3A}$, SO$_2$R$^{3A}$, C$_1$-C$_6$ alkyl, C$_1$-C$_6$ haloalkyl, C$_1$-C$_6$ heteroalkyl, aryl and heteroaryl;

R$^{3A}$ and R$^{4A}$ are each independently selected from the group consisting of hydrogen, C$_1$-C$_8$ alkyl, C$_2$-C$_8$ alkenyl, C$_2$-C$_8$ alkynyl, cycloalkyl, heterocyclyl, C$_1$-C$_8$ haloalkyl, C$_1$-C$_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, C$_1$-C$_4$ alkyl, C$_1$-C$_4$ haloalkyl, C$_1$-C$_4$ heteroalkyl or C$_1$-C$_6$ alkoxy;

each R$^A$ and R$^B$ is selected independently from the group consisting of hydrogen, halogen, OR$^{3A}$, NR$^{3A}$R$^{4A}$, SR$^{3A}$, SO$_2$R$^{3A}$, C$_1$-C$_6$ alkyl, C$_1$-C$_6$ haloalkyl, C$_1$-C$_6$ heteroalkyl, aryl and heteroaryl; and n is 2, 3 or 4, or enantiomers, prodrugs, derivatives, and pharmaceutically acceptable salts thereof.

It is noted that this invention contemplates using all combinations of the various substituents of Formula (I) and (II). For example, R$^1$ can be an aryl substituted with at least one OR$^{3A}$ and optionally further substituted with halogen, C$_1$-C$_6$ alkyl, C$_1$-C$_6$ haloalkyl, C$_1$-C$_6$ heteroalkyl, C$_1$-C$_6$ alkoxy, amino (NH$_2$), mono(C$_1$-C$_6$ alkyl)amino or di(C$_1$-C$_6$ alkyl)amino; R$^2$, R$^3$ and R$^4$ can be independently selected from the group consisting of H, halogen, C$_1$-C$_6$ alkyl, C$_1$-C$_6$ haloalkyl, and C$_1$-C$_6$ alkoxy; R$^5$ can be hydrogen or alkoxy; R$^6$ and R$^7$ can be independently selected from the group consisting of halogen, C$_1$-C$_6$ alkyl or C$_1$-C$_6$ haloalkyl; R$^{3A}$ can be hydrogen, C$_1$-C$_6$ alkyl, cycloalkyl or heterocyclyl, each of which can be optionally substituted; and n can be 1 or 2.

Compounds of Formula (II) have the structure:

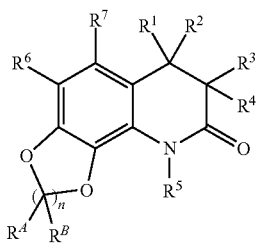

FORMULA (II)

wherein:
R$^1$, R$^2$, R$^3$ and R$^4$ are each independently selected from the group consisting of hydrogen, halogen, C$_1$-C$_6$ alkyl, C$_3$-C$_8$ cycloalkyl, C$_1$-C$_6$ haloalkyl, C$_1$-C$_6$ heteroalkyl, OR$^{3A}$, SR$^{3A}$, SO$_2$R$^{3A}$, NR$^{3A}$R$^{4A}$, halogen, heteroaryl, and aryl, wherein the alkyl, haloalkyl, heteroalkyl, heteroaryl, and aryl can be optionally substituted with halogen, C$_1$-C$_6$ alkyl, C$_1$-C$_6$ haloalkyl, C$_1$-C$_6$ heteroalkyl, C$_1$-C$_6$ alkoxy, C$_2$-C$_8$ alkenyl, amino (NH$_2$), mono (C$_1$-C$_6$ alkyl)amino or di(C$_1$-C$_6$ alkyl)amino; or R$^2$ and R$^3$ together form a second bond between the carbons to which they are attached;

R$^5$ is hydrogen, C$_1$-C$_6$ alkyl, C$_1$-C$_6$ haloalkyl, C$_1$-C$_6$ heteroalkyl, aryl, heteroaryl, or halogen;

R$^6$ and R$^7$ are each independently selected from the group consisting of hydrogen, halogen, OR$^{3A}$, NR$^{3A}$R$^{4A}$, SR$^{3A}$, SO$_2$R$^{3A}$, C$_1$-C$_6$ alkyl, C$_1$-C$_6$ haloalkyl, C$_1$-C$_6$ heteroalkyl, aryl and heteroaryl;

R$^{3A}$ and R$^{4A}$ are each independently selected from the group consisting of hydrogen, C$_1$-C$_8$ alkyl, C$_2$-C$_8$ alkenyl, C$_2$-C$_8$ alkynyl, cycloalkyl, heterocyclyl, C$_1$-C$_8$ haloalkyl, C$_1$-C$_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, C$_1$-C$_4$ alkyl, C$_1$-C$_4$ haloalkyl, C$_1$-C$_4$ heteroalkyl or C$_1$-C$_6$ alkoxy; and n is 1, 2, 3, or 4, or enantiomers, prodrugs, derivatives, and pharmaceutically acceptable salts thereof.

Compounds of Formula (III) have the structure:

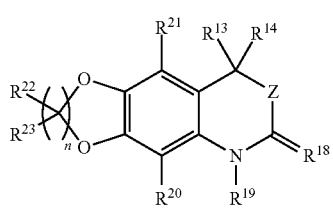

FORMULA (III)

wherein:
Z is NR$^{15}$ or CR$^{16}$R$^{17}$;

R$^3$, R$^{14}$, R$^5$, R$^{16}$ and R$^{17}$ are each independently selected from the group consisting of hydrogen, halogen, C$_1$-C$_6$ alkyl, C$_3$-C$_8$ cycloalkyl, C$_1$-C$_6$ haloalkyl, C$_1$-C$_6$ heteroalkyl, OR$^{3A}$, SR$^{3A}$, SO$_2$R$^{3A}$, NR$^{3A}$R$^{4A}$, halogen, heteroaryl, and aryl, wherein the alkyl, haloalkyl, heteroalkyl, heteroaryl, and aryl can be optionally substituted with halogen, C$_1$-C$_6$ alkyl, C$_1$-C$_6$ haloalkyl, C$_1$-C$_6$ heteroalkyl, C$_1$-C$_6$ alkoxy, C$_2$-C$_8$ alkenyl, amino (NH$_2$), mono(C$_1$-C$_6$ alkyl)amino or di(C$_1$-C$_6$ alkyl)

amino; or $R^{14}$ and $R^{16}$ together form a second bond between the carbons to which they are attached;

$R^{18}$ is O, S or $NR^{19A}$;

$R^{19}$ is hydrogen, $C_1$-$C_6$ alkyl, $C_1$-$C_6$ haloalkyl, $C_1$-$C_6$ heteroalkyl, aryl, heteroaryl, or halogen; or $R^{19}$ and $R^{19A}$ together with the nitrogens they are attached to form an optionally substituted heterocyclyl or optionally substituted heteroaryl;

$R^{20}$ and $R^{21}$ are each independently selected from the group consisting of hydrogen, halogen, $OR^{3A}$, $NR^{3A}R^{4A}$, $SR^{3A}$, $SO_2R^{3A}$, $C_1$-$C_6$alkyl, $C_1$-$C_6$haloalkyl, $C_1$-$C_6$ heteroalkyl, aryl and heteroaryl;

$R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$haloalkyl, $C_1$-$C_4$ heteroalkyl or $C_1$-$C_6$ alkoxy;

each $R^{22}$ and $R^{23}$ is selected independently from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl; and n is 1, 2, 3 or 4, or enantiomers, prodrugs, derivatives, and pharmaceutically acceptable salts thereof.

In some embodiments of compounds of Formula (III), when $R^{18}$ is O then n is not 1 or Z is $NR^{15}$. In some other embodiments of compounds of Formula (III), when Z is $CR^{16}R^{17}$ and $R^{18}$ is O then $R^{19}$ and $R^{19A}$ together with the nitrogens they are attached to form an optionally substituted heterocyclyl or optionally substituted heteroaryl, or $R^{13}$ is an aryl substituted with $OR^{3A}$, where $R^{3A}$ is a cyclyl.

Compounds of Formula (IV) have the structure:

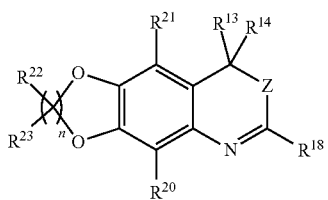

FORMULA (IV)

wherein:

Z is $NR^{15}$ or $CR^{16}R^{17}$;

$R^{13}$, $R^{14}$, $R^{15}$, $R^{16}$ and $R^{17}$ are each independently selected from the group consisting of hydrogen, halogen, $C_1$-$C_6$ alkyl, $C_3$-$C_8$ cycloalkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl) amino; or $R^{14}$ and $R^{16}$ together form a second bond between the carbons to which they are attached;

$R^{18}$ is $NQ_1Q_2$, wherein $Q_1$ and $Q_2$ are independently selected from the group consisting of hydrogen, alkyl, alkenyl, alkynyl, cycloalkyl or aryl optionally substituted with halogen, $C_1$-$C_4$ alkyl, $C_1$-$C_4$ haloalkyl, $C_1$-$C_4$ heteroalkyl or $C_1$-$C_6$ alkoxy or $Q_1$ and $Q_2$ together with the nitrogen they are attached to can form a heterocycly or heteroaryl, which can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl) amino;

$R^{20}$ and $R^{21}$ are each independently selected from the group consisting of hydrogen, halogen, $OR^{3A}$, $NR^{3A}R^{4A}$, $SR^{3A}$, $SO_2R^{3A}$, $C_1$-$C_6$alkyl, $C_1$-$C_6$haloalkyl, $C_1$-$C_6$ heteroalkyl, aryl and heteroaryl;

$R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$haloalkyl, $C_1$-$C_4$ heteroalkyl or $C_1$-$C_6$ alkoxy;

each $R^{22}$ and $R^{23}$ is selected independently from the group consisting of hydrogen, halogen, $OR^{3A}$, $NR^{3A}R^{4A}$, $SR^{3A}$, $SO_2R^{3A}$, $C_1$-$C_6$alkyl, $C_1$-$C_6$haloalkyl, $C_1$-$C_6$ heteroalkyl, aryl and heteroaryl; and n is 1, 2, 3 or 4, or enantiomers, prodrugs, derivatives, and pharmaceutically acceptable salts thereof.

It is noted that this invention contemplates using all combinations of the various substituents of Formula (III) and (IV). For example, $R^{13}$ can be an aryl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino; $R^{14}$, $R^{15}$, $R^{16}$ and $R^{17}$ can be independently selected from the group consisting of H, halogen, $C_1$-$C_6$ alkyl, $C_1$-$C_6$ haloalkyl, and $C_1$-$C_6$ alkoxy; $R^{19}$ can be hydrogen or $C_1$-$C_6$alkyl; $R^{20}$ and $R^{21}$ can be independently selected from the group consisting of hydrogen, halogen, $C_1$-$C_6$ alkyl and $C_1$-$C_6$ haloalkyl, or $R^{19}$ and $R^{19A}$ together with the nitrogens they are attached can form an optionally substituted heterocyclyl or heteroaryl; $R^{3A}$ can be hydrogen, $C_1$-$C_6$ alkyl, cycloalkyl or heterocyclyl, each of which can be optionally substituted; $R^{20}$ and $R^{21}$ can be independently H or halogen; $Q_1$ and $Q_2$ can be independently selected from the group consisting of hydrogen, alkyl, and alkenyl, or $Q_1$ and $Q_2$ together with the nitrogen they are attached to can form an optionally substituted heterocycly or heteroaryl; and n can be 1 or 2.

Compounds of Formula (V) have the structure:

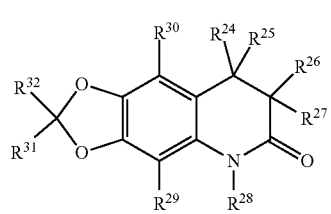

FORMULA (V)

wherein:

$R^{24}$ is an aryl substituted with at least one $C_1$-$C_6$ alkoxyl and one di($C_1$-$C_{24}$ alkyl)amino, halogen or $C_2$-$C_8$ alkenyl, wherein the substituted aryl can be optionally further substituted with halogen, $C_1$-$C_4$ alkyl, $C_1$-$C_4$ haloalkyl, $C_1$-$C_4$ heteroalkyl, di($C_1$-$C_{24}$ alkyl)amino or combinations thereof;

$R^{25}$ and $R^{26}$ are hydrogen or $R^{25}$ and $R^{26}$ together form a second bond between the carbons to which they are attached;

$R^{27}$ is hydrogen;

$R^{28}$ is selected from the group consisting of hydrogen and $C_1$-$C_6$ alkyl;

$R^{29}$ and $R^{30}$ are each independently selected from the group consisting of hydrogen, F, Br, Cl and I;

$R^{31}$ and $R^{32}$ are each independently selected from the group consisting of hydrogen, F, Br, Cl, and I;

or enantiomers, prodrugs, derivatives, and pharmaceutically acceptable salts thereof.

It is noted that this invention contemplates using all combinations of the various substituents of Formula (V). For example, $R^{24}$ can be a phenyl substituted with at least one $C_1$-$C_6$ alkoxyl and one di($C_1$-$C_6$ alkyl)amino, halogen or $C_2$-$C_8$ alkenyl; $R^{25}$, $R^{26}$ and $R^{26}$ can be hydrogen; $R^{28}$ can be hydrogen or lower alkyl; $R^{29}$, $R^{30}$, $R^{31}$ and $R^{32}$ can be independently H, F, or Br.

In some embodiments, the compounds of Formula (I)-(V) can be inhibitors of late SV40 factor (LSF). Without limitations, inhibition of LSF can be determined using any method available, including, but not limited to in vitro assays.

Another aspect of the present invention relates to a method to inhibit LSF in a subject, for example, using a compound of Formula (I)-(V) or enantiomers, prodrugs, derivatives, or pharmaceutically acceptable salts thereof.

Yest another aspect of the present invention relates to a method for treating cancer in a subject, the method comprising administering an effective amount of a compound of Formula (I)-(V) to a subject in need thereof.

In some embodiments of various aspects of the invention, the cancer is hepatocellular carcinoma (HCC).

Another aspect of the present invention relates to a method of inhibiting tubulin methylation in a cell, the method comprising administering to the cell an effective amount of compound of an inhibitor of LSF. In some embodiments, the inhibitor of LSF is a compound of Formula (I)-(V).

Yet another aspect of the present invention relates to a method of modulating chromatin or cytoskeleton modification in a cell, the method comprising administering to the cell an effective amount of an inhibitor of LSF. In some embodiments, the inhibitor of LSF is a compound of Formula (I)-(V).

In some embodiments of the various aspects disclosed herein a compound of any one of Formula (I)-(V) is orally bioavailable.

BRIEF DESCRIPTION OF THE DRAWINGS

FIG. 1A is an image showing colocalization of SET8 and α-tubulin in COS7 cells. GFP-SET8 was expressed in asynchronous cells and tubulin was detected with anti-α-tubulin antibody. Merged image shows colocalization of SET8 and α-tubulin. FIG. 1B shows co-immunoprecipitation from HEK293T cells of endogenous tubulins with SET8 (left) and of SET8 with transiently expressed Flag-tagged tubulins (right). Left panel: The positive control is 99% pure tubulin; * represents a nonspecific band. FIG. 1C shows GST-pull down analysis of purified porcine brain tubulin using full-length or overlapping segments of SET8 fused to GST (bottom left) and MBP-pull down analysis of purified GST-SET8 using overlapping segments of MBP-α-tubulin (bottom right).

FIG. 2A-2D show that histone methyltransferase SET8 methylates α-tubulin at K280, K311, and K352. FIG. 2A shows that purified porcine tubulin is methylated by SET8. Autoradiogram (top) of methyltransferase assays, shows methylation of tubulin (*) and automethylation of SET8. Coomassie-staining (bottom) indicates purity of components. FIG. 2B shows that recombinant human α-tubulin, but not β-tubulin, is methylated by SET8. Autoradiogram (top) and Coomassie-staining (bottom) are as in FIG. 2A. FIG. 2C is a bar graph showing specific methylation of K311-containing α-tubulin peptide by SET8 in vitro. FIG. 2D is a 3-dimensional structure of α-tubulin, indicating positions of lysines targeted by SET8.

FIG. 3A-3E show that LSF interacts with SET8 and tubulin. FIG. 3A shows co-immunoprecipitation of endogenous LSF and SET8 from cellular extracts. Antibodies for immunoblotting are indicated on the right. FIG. 3B are bands showing immunoblotting of purified porcine brain tubulin which shows the presence of LSF, using LSF monoclonal antibody. The lower band indicates non-specific binding to the vast quantity of tubulin. FIG. 3C shows co-immunoprecipitation of α-tubulin with endogenous LSF and SET8 in cellular extracts. FIG. 3D shows GST-pull down analysis of purified porcine tubulin using overlapping segments of LSF. FIG. 3E shows GST-pull down analysis of recombinant purified His-tagged LSF using overlapping segments of α-tubulin.

FIG. 4A is a graph showing tubulin polymerization assay in the presence of low concentrations of LSF (Millipore kit). FIG. 4B are bands showing co-immunoprecipitation of LSF with endogenous α-tubulin from HEK293T cells which was disrupted upon treatment with 2.5 µM FQI1 for 24 hr. FIG. 4C is a graph showing tubulin polymerization assay in the presence of FQI1 and FQI2 (Cytoskeleton kit). Nocodazole was used as a control to inhibit polymerization. FIG. 4D is an image showing treatment of synchronized HCC cells with FQI1 results in abnormal mitotic phenotypes including mitotic arrest with condensed chromosomes (bottom left) and multi-aster formation (bottom right). Cells were synchronized at the G1/S border and released in presence of 5 µM FQI1. Fixed cells were stained with α-tubulin antibody and DAPI.

FIG. 5A shows that LSF enhances tubulin methylation by SET8. Autoradiograms of methyltransferase assays with tubulin indicated (*). Coomassie staining demonstrates equivalent protein levels throughout. FIG. 5B shows that FQI1 decreases tubulin methylation by SET8. Autoradiograms of methyltransferase assays with tubulin indicated (*). At 100 µM (lane 4), methylation is decreased ~3-fold. FIG. 5C shows that FQI1 does not affect SET8 methylation of Histone H4. FIG. 5D shows co-immunoprecipitation of endogenous α-tubulin with endogenous SET8 is diminished upon the treatment with 2.5 µM FQI1 for 24 h. FIG. 5E is a schematic model showing recruitment of SET8 to tubulin by LSF, and the subsequent methylation of α-tubulin by SET8.

FIG. 6A-6C show co-localization of SET8 and LSF in COS-7 cells. FIG. 6A is an image showing GFP-SET8-expressing plasmid was transfected into COS-7 cells; GFP-SET8 expression was visualized by confocal microscopy; one plane of the image is shown. FIG. 6B shows GST-pull down analysis of purified His-LSF using full-length or partial, overlapping segments of SET8 fused to GST. Purified His-LSF was loaded in the last lane, as a positive control. FIG. 6C is an image showing plasmids expressing FLAG-LSF and GFP-SET8 were transfected into the cells;

anti-FLAG antibody was visualized with a fluorescing secondary antibody. The merged image indicates colocalization, concentrated largely near the nuclear membrane (Manders correlation coefficient of LSF and SET8 is 0.9). Although LSF is a transcription factor functioning in the nucleus, the inventors observed that the majority was expressed in the cytoplasm when overexpressed as GFP-LSF or 3×FlagLSF. Only a minority was detected in the nucleus.

Figure 7A:
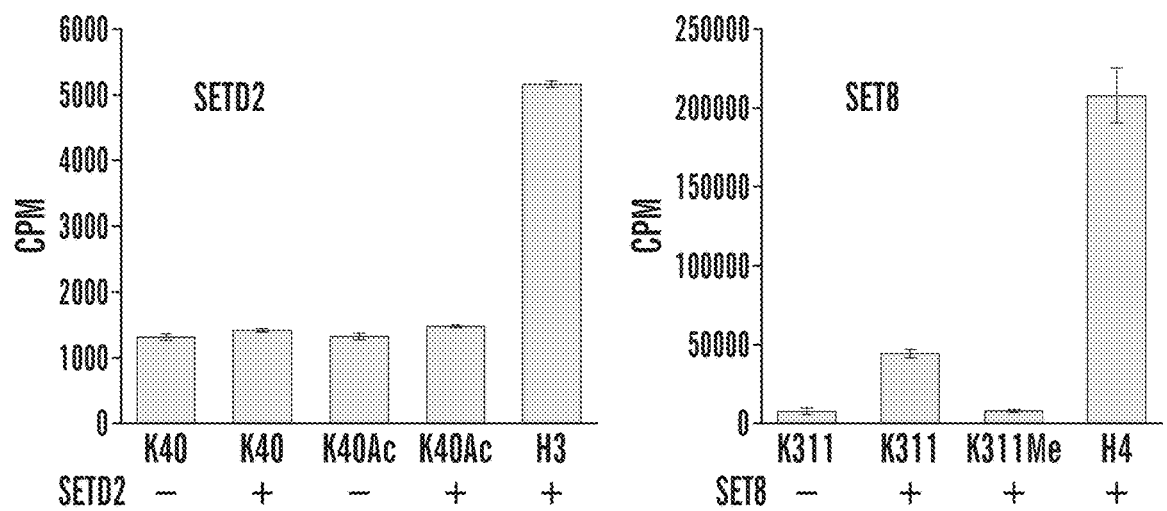
Figure 7B:
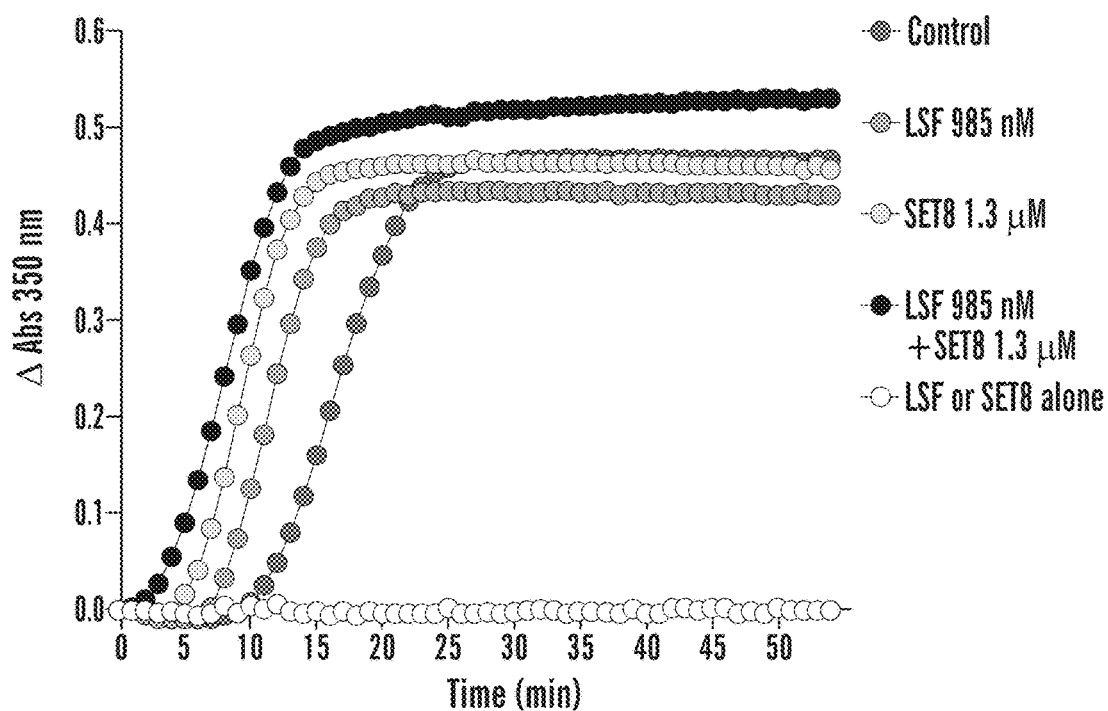

FIG. 7A are bar graphs showing in vitro peptide assay for methylation. Activity on K311 by SET8 (FL) enzyme is much more robust (right) than activity on K40 by SETD2 (FL) (left) under the same reaction conditions. FIG. 7B is a graph showing in vitro tubulin polymerization assay in the presence of SET8, LSF or both together. Concentrations of proteins are indicated.

Figure 8A:
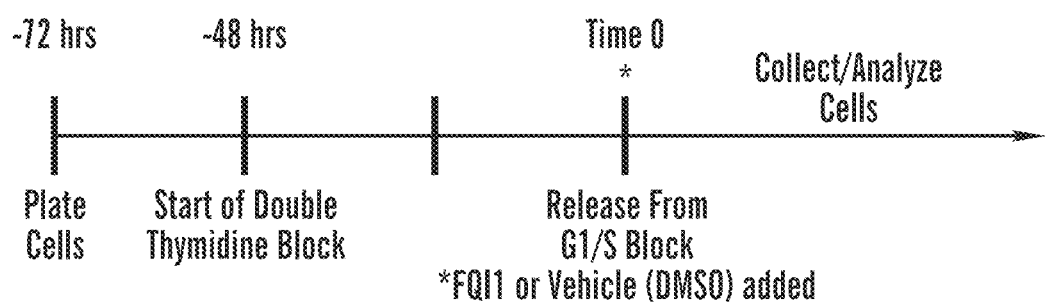
Figure 8B:
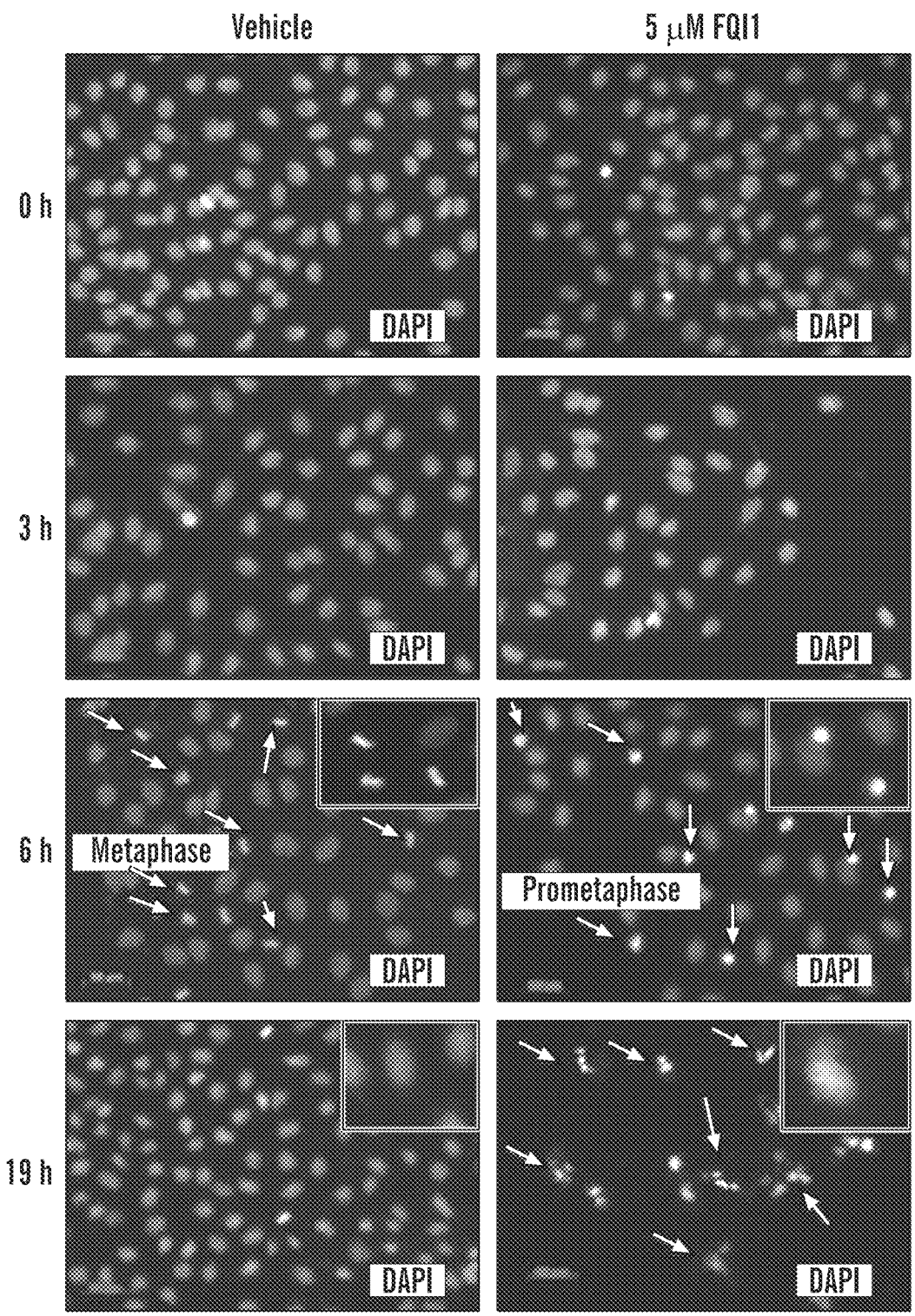
Figure 8C:
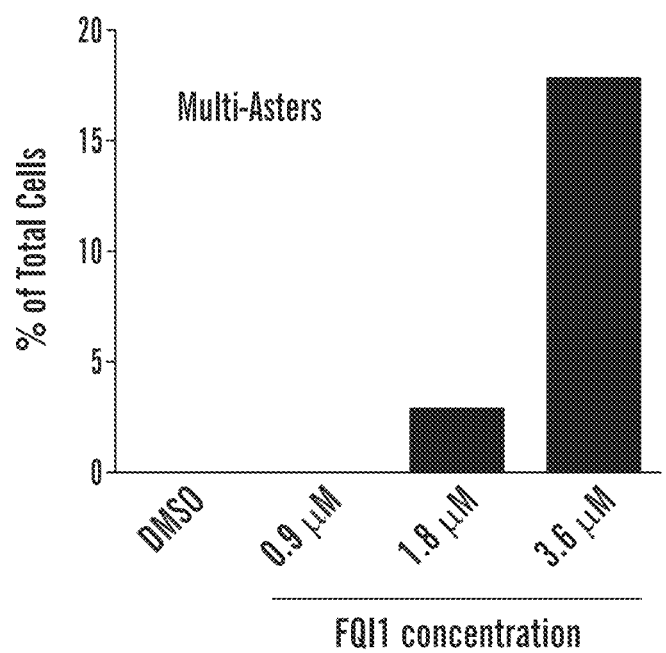
Figure 8D:
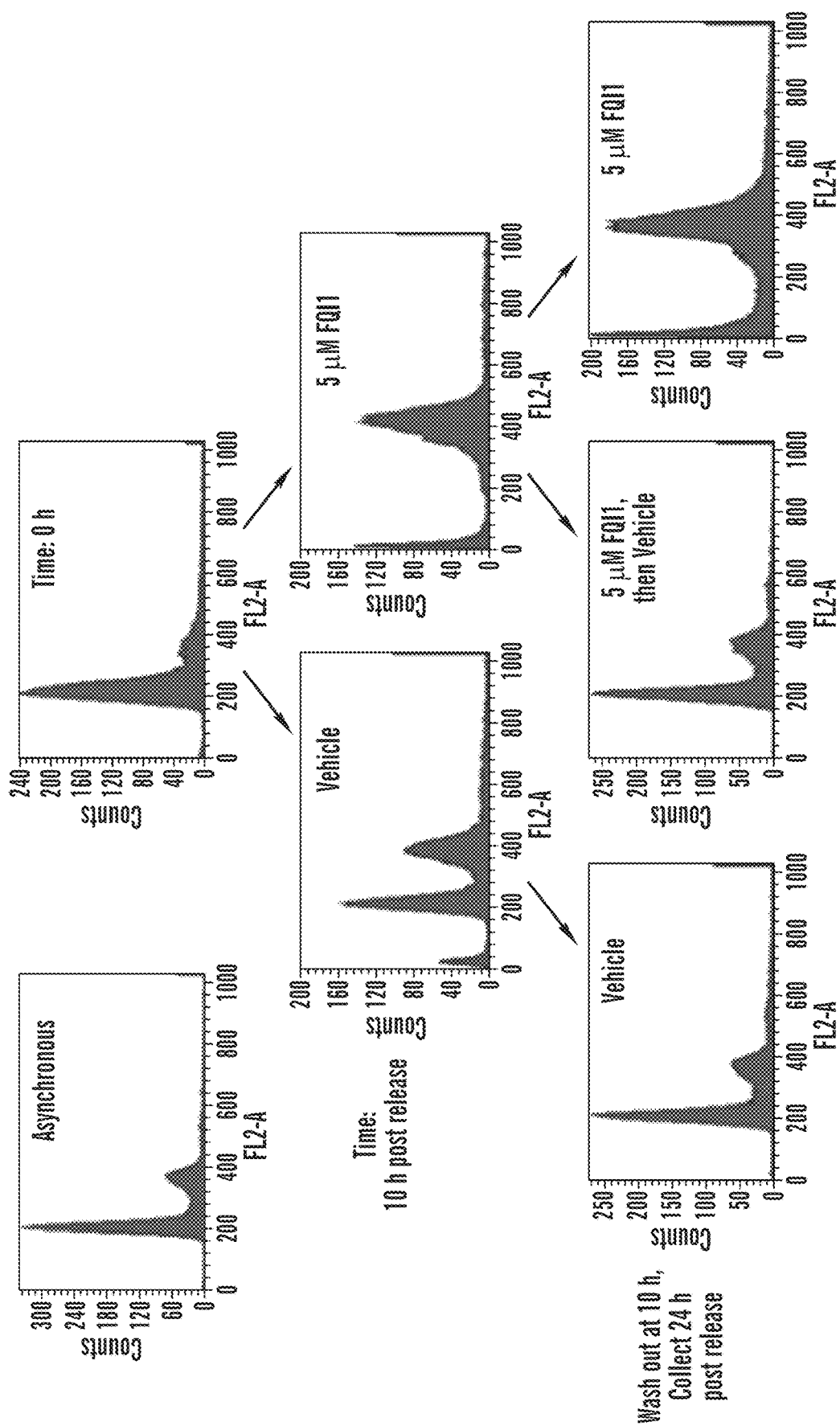

FIG. 8A-8D show that FQI1 causes mitotic defects. FIG. 8A shows illustration of the protocol for FQI1 incubation in synchronized HeLa cells. FIG. 8B is an image showing DAPI staining of synchronized cells, treated as indicated in panel FIG. 8A and analyzed at 20× magnification. Samples were collected at 0, 3, 6, and 19 hours post release from a G1/S block in presence of DMSO or FQI1. Insets represent individual cells in more detail. Arrows represent cells in metaphase or prometaphase, respectively, at the 6 hour time point. FIG. 8C is a bar graph showing quantification from 75-100 total cells analyzed by DNA and α-tubulin morphologies, indicating cells containing multi-asters, at 9 hours post release from a G1/S block. Data are representative of 2 experiments. FIG. 8D is a graph showing that the mitotic arrest mediated by limited FQI1 treatment of synchronized cells is reversible. Synchronized cells were released in the presence of 5 μM of FQI1 from a G1/S block. Ten hours after the release, the cells were washed and then either incubated with media alone or re-incubated with media in the presence of 5 μM FQI1. Samples were collected 24 hours post release. Fixed cells were stained with propidium iodide to analyze DNA content. Shown are cellular DNA profiles of synchronized cells harvested immediately prior to release from the G1/S block (0 h), at 10 hours post release for cells released with vehicle or 5 μM FQI1, or at 24 hours post release for cells treated throughout only with vehicle, initially with 5 μM FQI1 for 10 hours, but then incubated in the absence of FQI1 for the final 14 h, or with 5 μM FQI1 throughout.

Figures 9A, 9B:
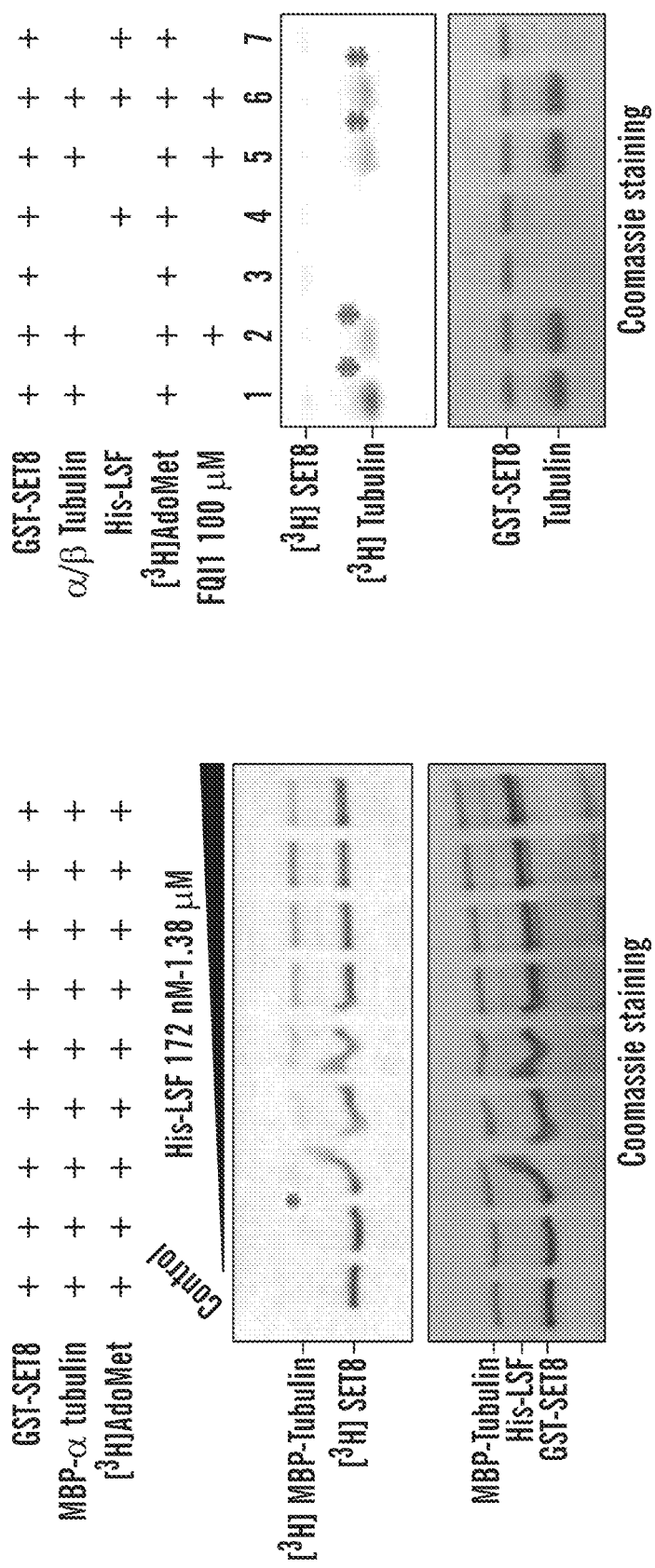
Figure 18A:
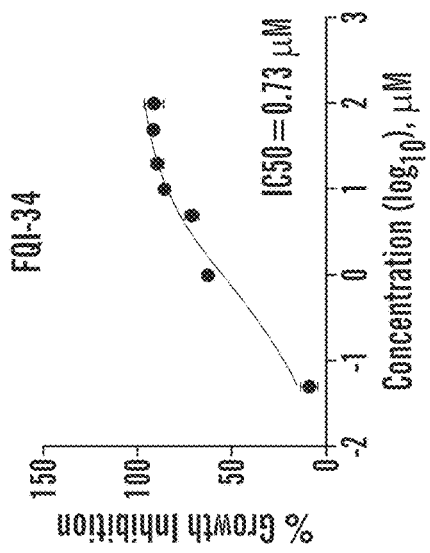
Figure 18B:
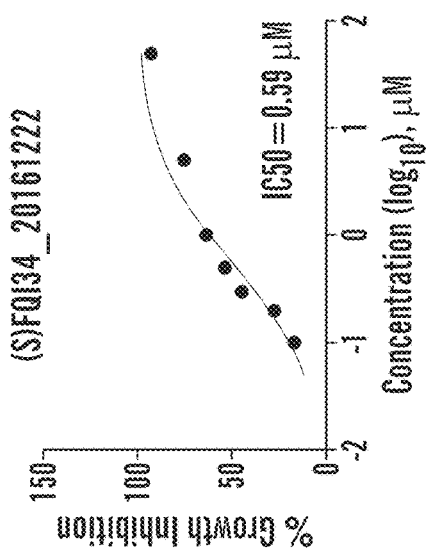
Figure 18C:
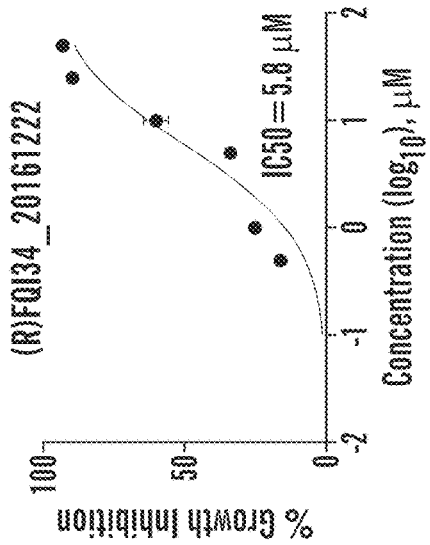
Figure 19A:
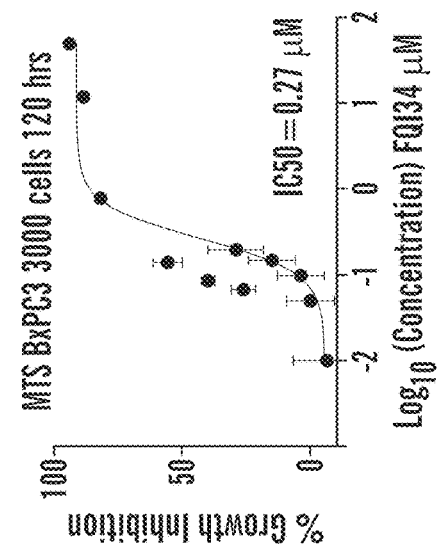
Figure 19B:
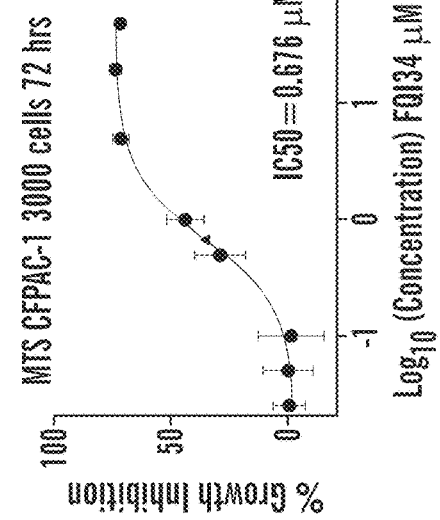
Figure 19C:
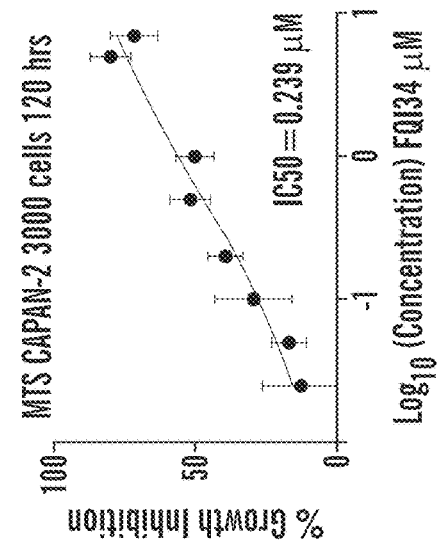
Figure 27C:
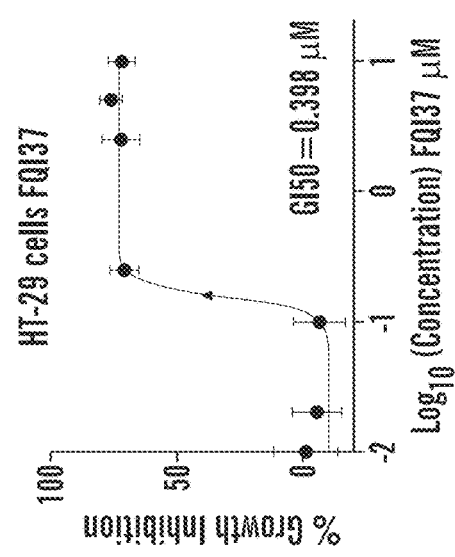
Figure 26D:
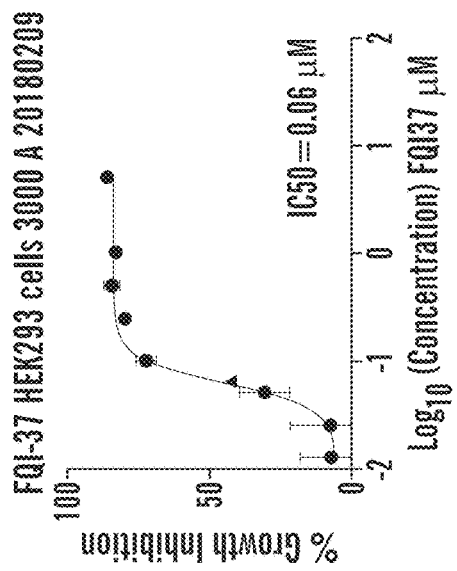
Figure 27B:
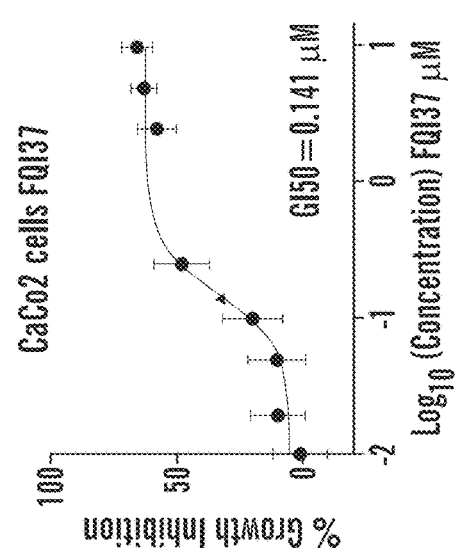
Figure 27A:
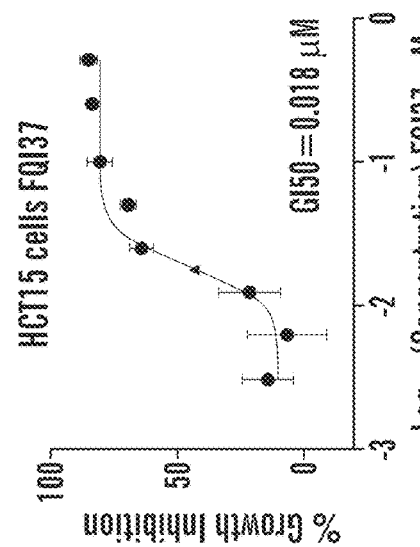
Figures 28A, 28B:
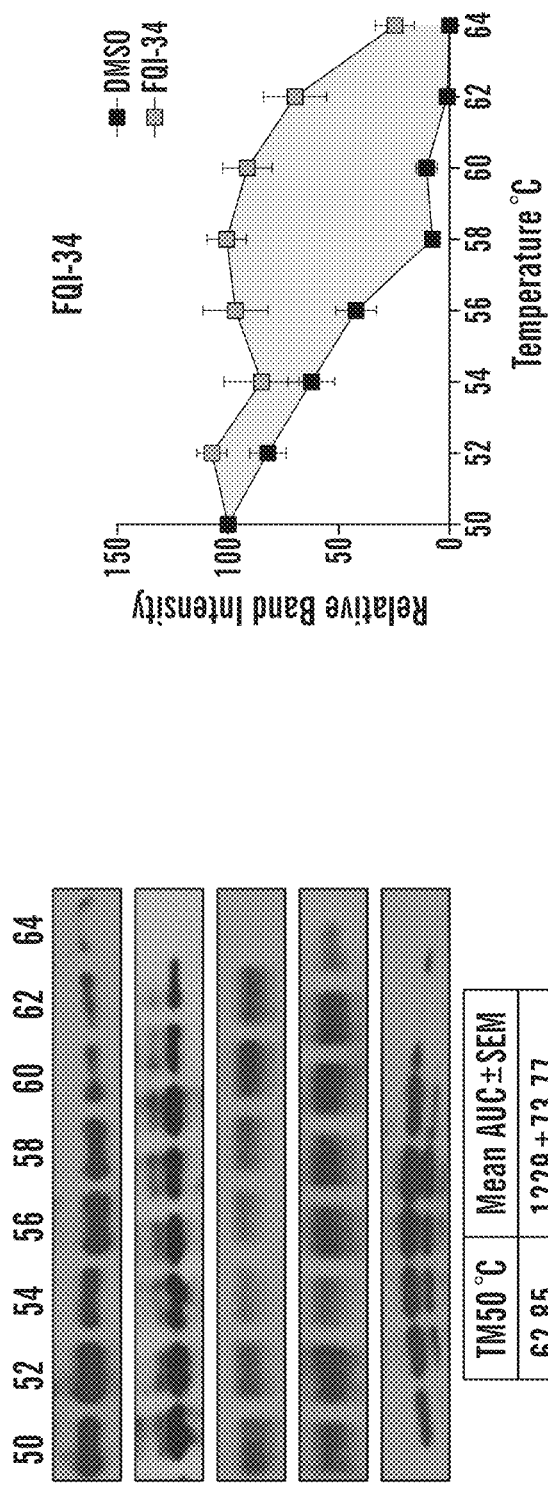
Figure 29B:
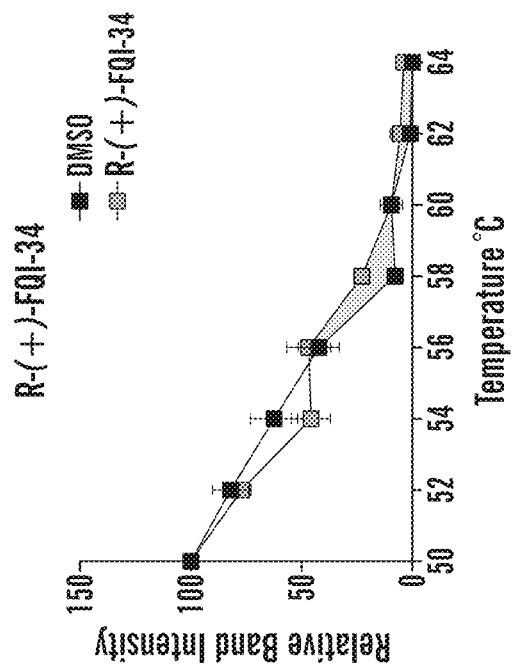
Figure 29A:
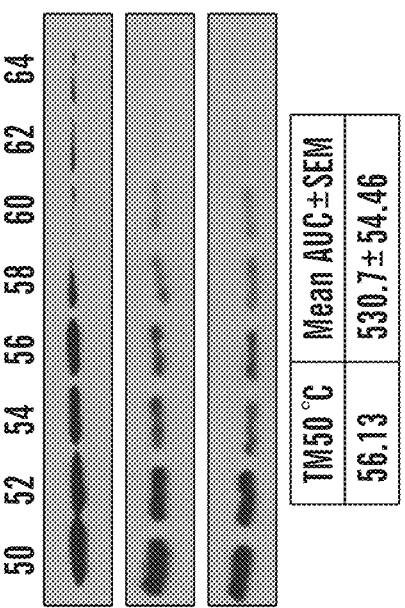

FIG. 9A-9B show that LSF and FQI1 modulate tubulin methylation by SET8. FIG. 9A shows that LSF enhances methylation of recombinant MBP-α-tubulin by SET8. Autoradiograms of methyltransferase assays with methylated tubulin indicated (*), plus automethylation of SET8. FIG. 9B shows autoradiogram of methyltransferase assays with purified tubulin in the presence of FQI1, with or without 862 nM LSF.

FIGS. 10A-27C are line graphs showing growth inhibition (as % control) of various cancer cell lines with exemplary compounds.

Figure 30B:
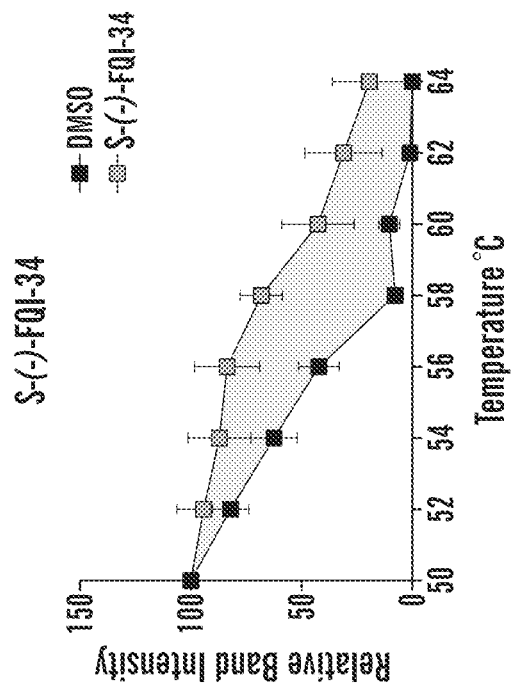
Figure 30A:
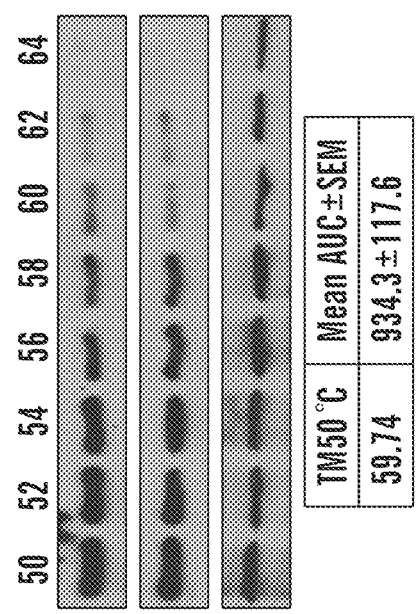
Figure 31B:
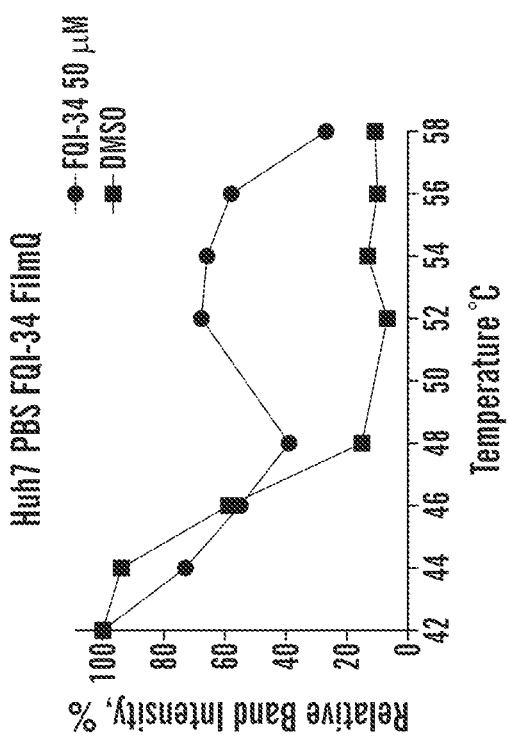
Figure 31A:
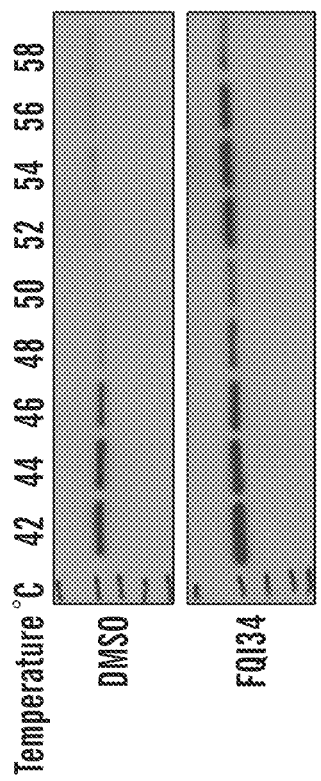
Figure 32B:
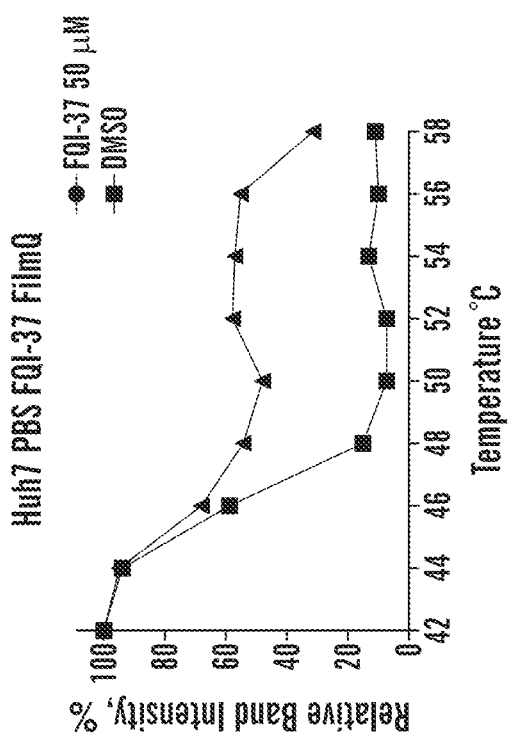
Figure 32A:
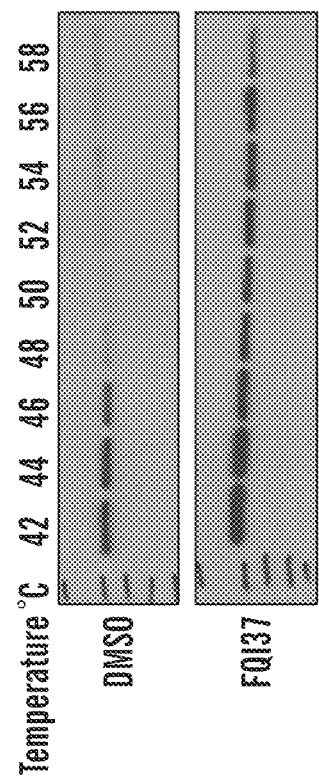

FIGS. 28A-30B show target binding assessment by Cellular Thermal Shift Assay for racemic FQI-34 (FIGS. 28A and 28B), (R)-(+)-FQI-34 or (R)-FQI-34 (FIGS. 29A and 29B) and (S)-(−)-FQI-34 or (S)-FQI-34 (FIGS. 30A and 30B).

FIGS. 31A-32B show target binding assessment by Cellular Thermal Shift Assay for FQI-34 (FIGS. 31A and 31B) and FQI-37 (FIGS. 32A and 32B) in HuH7 cells.

Figure 33:
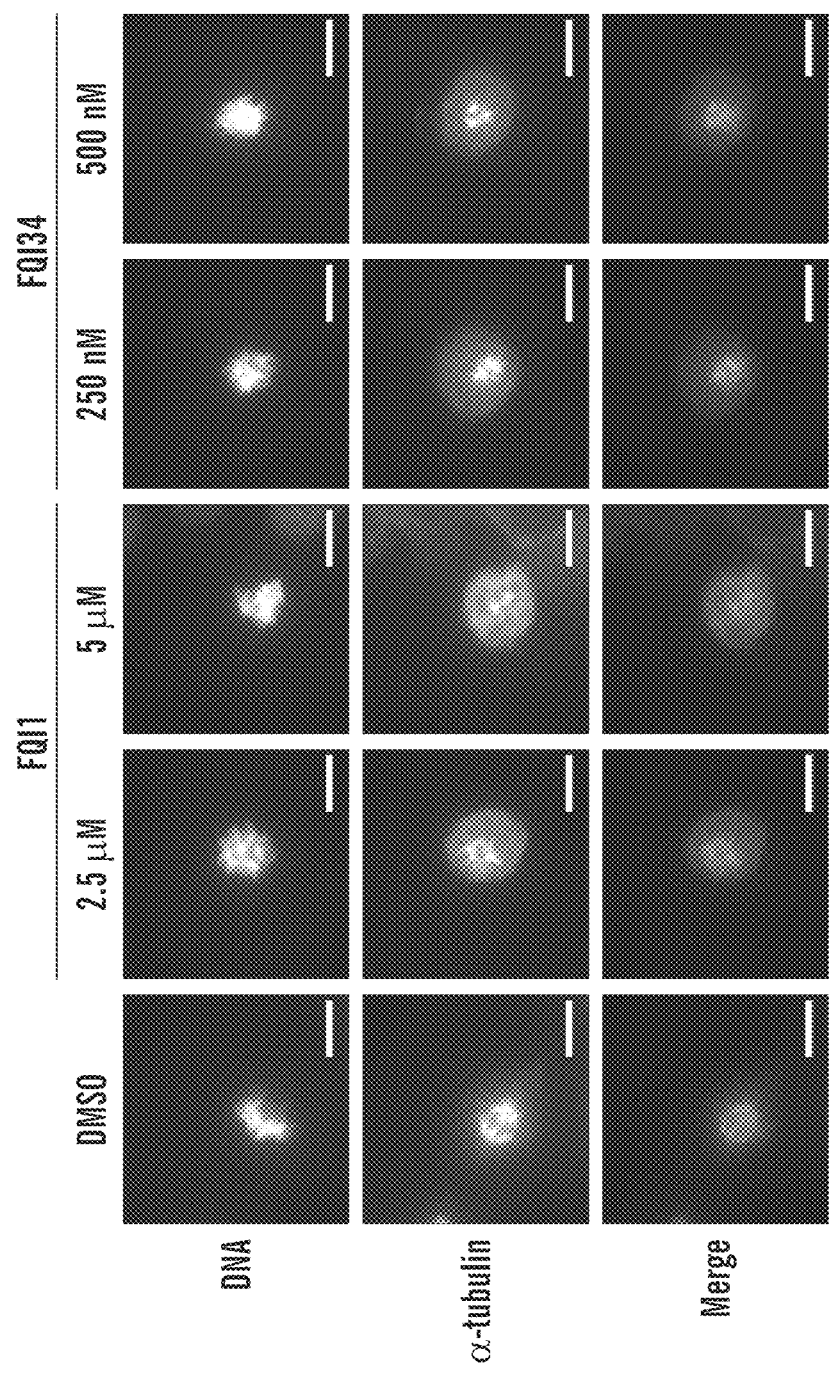

FIG. 33 shows FQI34 treatment causes mitotic defects with at least 10-fold greater potency than does FQI1. Scale bars are 10 μm.

DETAILED DESCRIPTION OF THE INVENTION

The inventors have discovered inter alia, small-molecule compounds of Formula (I) to (IV). These small molecule compounds as disclosed herein can cause cell death of cancer cell lines and primary cancer cells in an in vitro assay, e.g., HCC cancer cell lines, pancreatic cancer lines, ductal cell lines, colorectal cell lines, breast cancer cell lines, colon cancer cell lines, ovarian cancer cell lines etc. Therefore, in one aspect, the disclosure provides small-molecule compounds of Formula (I) to (IV). In another aspect of the present invention, the compounds disclosed herein can be used in a method for inhibiting LSF and/or for treatment of cancers in subjects, e.g. HCC and other cancers.

Accordingly, in some embodiments, the present invention provides compositions and methods comprising compounds of Formula (I)-(IV) for treatment of hepatocellular carcinoma in a subject. In some embodiments, the present invention relates in part to the use of small-molecule compounds of Formula (I)-(IV) for treatment of cancer, e.g. hepatocellular carcinoma (HCC), brain cancer, breast cancer, colon cancer, head and neck squamous cell carcinoma, lung cancer, pancreatic cancer, ductal adenocarcinoma, colorectal adenocarcinoma, rectosigmoid carcinoma, kidney cancer, monocytic lymphoma, ovarian cancer, thyroid cancer, etc.

In various embodiments, the disclosure provides a compound of Formula (I) or Formula (II):

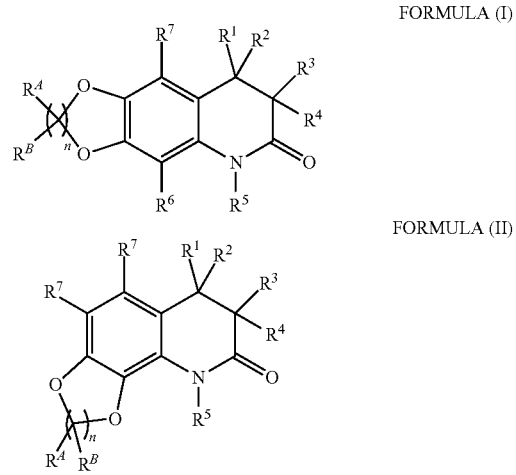

In compounds of Formula (I) and (II), $R^1$ can be an aryl substituted with at least one $OR^{3A}$ and optionally further substituted with halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino groups.

Exemplary aryl groups for $R^1$ of Formula (I) and (II) include, but are not limited to phenyl, 1-naphthyl, 2-naphthyl, biphenyl, pyridine, quinoline, furan, thiophene, pyrrole, imidazole, pyrazole, diphenylether, diphenylamine, benzophenone, and the like. Exemplary halogen substituents for aryl of $R^1$ include but are not limited to, fluorine, chlorine, bromine and iodine. Exemplary alkyl substituents for aryl of $R^1$ include but are not limited to, methyl, ethyl, n-propyl, isopropyl, n-butyl, isobutyl, sec-butyl, tert-butyl, pentyl, hexyl, and the like. Exemplary cycloalkyl for aryl of $R^1$ include but are not limited to, optionally substituted cyclopropyl, cyclobutyl, cyclopentyl, cyclohexyl and the like. Exemplary alkoxy substituents for aryl of $R^1$, include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like. Exemplary monoalkylamino substituents for aryl of $R^1$ include but are not limited to, methylamino, ethylamino, n-propylamino, isopropylamino, n-butylamino, isobutylamino, sec-butylamino, tert-butylamino, pentylamino, hexylamino, and the like.

Exemplary dialkylamino substituents for aryl of $R^1$ of Formula (I) and (II) include, but are not limited to, dimethylamino, diethylamino, dipropylamino, dibutylamino, dipentylamino, dihexylamino, and the like. Additional exemplary dialkylamino substituents for aryl of $R^1$ include, but are not limited to, amino substituted with two different alkyl groups, for example, a first alkyl group selected from methyl, ethyl, n-propyl, isopropyl, n-butyl, isobutyl, sec-butyl, tert-butyl, pentyl and hexyl, and a second alkyl group selected from methyl, ethyl, n-propyl, isopropyl, n-butyl, isobutyl, sec-butyl, tert-butyl, pentyl and hexyl, where the first and the second alkyl groups are different. Exemplary haloalkyl substituents for aryl of $R^1$ include, but are not limited to, alkyl groups, such as methyl, ethyl, n-propyl, isopropyl, n-butyl, isobutyl, sec-butyl, tert-butyl, pentyl and hexyl, where 1, 2, 3, 4, 5, 6, or all H are replaced by independently selected halogen, for example, $CH_2F$, $CHF_2$, and $CF_3$. Exemplary alkenyl substituents for the aryl of $R^1$ include, but are not limited to, ethenyl, n-propenyl, isopropenyl, n-butenyl, isobutenyl, pentenyl, isopentenyl, hexenyl and the like.

In some compounds of Formula (I) or (II), $R^1$ is an aryl substituted with one $OR^{3A}$ group and optionally substituted with one or more additional substituents. In some embodiments, $R^1$ is an aryl substituted with at least one $OR^{3A}$ and optionally further substituted with one or more substituents selected independently from halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono ($C_1$-$C_6$ alkyl) amino or di($C_1$-$C_6$ alkyl) amino groups. In some further embodiments, $R^1$ is an aryl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$alkyl) amino or di($C_1$-$C_6$ alkyl) amino groups.

In some compounds of Formula (I) and (II), $R^1$ is an aryl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$alkyl) amino or di($C_1$-$C_6$alkyl) amino groups. For example, $R^1$ is an aryl substituted with at least one $C_1$-$C_6$ alkoxy and at least one halogen, amino ($NH_2$), mono ($C_1$-$C_6$alkyl) amino or di($C_1$-$C_6$alkyl) amino groups. In some preferred embodiments, $R^1$ is an aryl substituted with at least one $C_1$-$C_6$ alkoxy and at least one halogen or di($C_1$-$C_6$ alkyl) amino group.

In the compounds of Formula (I) and (II), $R^1$ can be an aryl substituted with one $OR^{3A}$ and one halogen, or with one $OR^{3A}$ and two halogens, or with one $OR^{3A}$ and three halogens. $R^1$ can also be aryl substituted with two $OR^{3A}$ and one halogen, or with two $OR^{3A}$ and two halogens, or with three $OR^{3A}$ and one halogen, and the like. Similarly, $R^1$ can be aryl substituted with one $OR^{3A}$ and one di($C_1$-$C_6$ alkyl)amino or with one $OR^{3A}$ and two di($C_1$-$C_6$ alkyl)amino groups and so on.

In some compounds of Formula (I) and (II), $R^1$ is a phenyl substituted with at least one $OR^{3A}$ and optionally further substituted with one or more substituents selected independently from halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino group. In yet some other embodiments, $R^1$ is a phenyl substituted with at least one $C_1$-$C_6$ alkoxy and at least one halogen, $C_1$-$C_6$alkyl, $C_1$-$C_6$haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino groups.

In some compounds of Formula (I) and (II), $R^1$ is a phenyl substituted with at least one $C_1$-$C_6$ alkoxy and at least one substituent selected independently from halogen, amino ($NH_2$), mono ($C_1$-$C_6$ alkyl) amino or di($C_1$-$C_6$ alkyl) amino group. In some preferred embodiments, $R^1$ is a phenyl substituted with at least one $C_1$-$C_6$ alkoxy and at least one halogen or di($C_1$-$C_6$ alkyl) amino.

Without limitations, the aryl of the $R^1$ of Formula (I) and (II) can be substituted at any position. Thus, when the aryl is substituted with a single substituent, the substituent can be present at any of ortho, meta or para positions. For example, when the aryl of the $R^1$ group is substituted with a $C_1$-$C_6$alkoxyl, the alkoxyl group can be at the ortho position.

When the aryl is substituted with two substituents, they can present at ortho and ortho; ortho and meta; ortho and para, meta and meta, or meta and para positions. For example, when the aryl of $R^1$ group is substituted with a $C_1$-$C_6$alkoxyl and a second substituent, the alkoxyl can be present at one of the ortho positions and the second substituent can be present at the meta, ortho or para position. In some embodiments, the $C_1$-$C_6$alkoxyl is at the ortho position and the second substituent is at the para position.

In some embodiments, $R^1$ of Formula (I) and (II) is a phenyl substituted with at least one $C_1$-$C_6$ alkoxyl and at least one di($C_1$-$C_{24}$alkyl)amino. In some embodiments, $R^1$ is

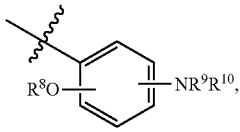

wherein $R^1$ is $C_1$-$C_6$alkyl and $R^9$ and $R^{10}$ are independently selected $C_1$-$C_{24}$alkyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl.

Without limitations, $R^9$ and $R^{10}$ can be same or different. Moreover, they can comprise the same number of carbons or different number of carbons. In some embodiments, $R^9$ and $R^{10}$ are selected independently from $C_1$-$C_6$ alkyl groups. Exemplary alkyls for the $R^9$ and $R^{10}$ group include, but are not limited to, methyl, ethyl, propyl, isopropyl, 1-butyl, 2-butyl, 2-methylpropyl, pentyl, t-butyl, and hexyl. In some embodiments, $R^9$ and $R^{10}$ are methyl.

In some embodiments, $R^1$ is a phenyl substituted with at least one $C_1$-$C_6$ alkoxyl and at least one halogen. In some embodiments, $R^1$ is

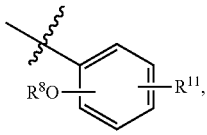

wherein $R^8$ is $C_1$-$C_6$alkyl and $R^{11}$ is halogen, $C_1$-$C_6$ haloalkyl or $C_2$-$C_6$alkenyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl. In some embodiments, $R^{11}$ is selected from the group consisting of Br, F, and Cl.

In some compounds of Formula (I) and (II), $R^1$ can be selected from the group consisting of

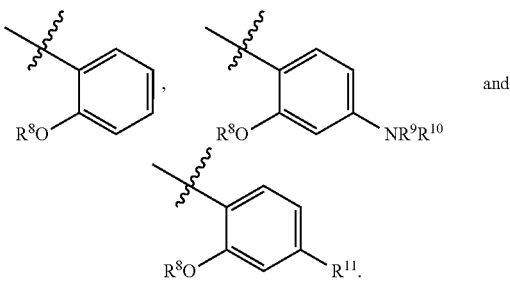

In some preferred embodiments of compounds of Formula (I) and (II), $R^1$ is

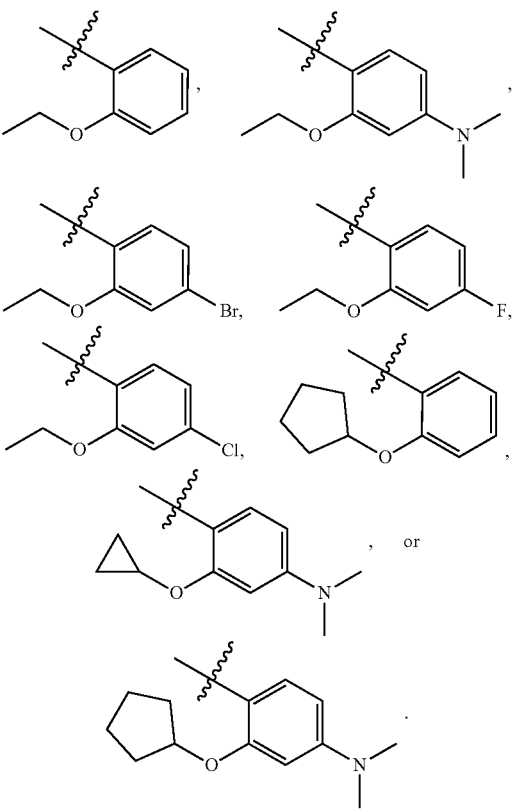

In compounds of Formula (I) and (II), each of $R^2$, $R^3$ and $R^4$ can be independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino (NH$_2$), mono($C_1$-$C_6$ alkyl) amino or di($C_1$-$C_6$ alkyl)amino. In some embodiments, $R^2$ and $R^3$ together form a second bond between the carbons to which they are attached. Without limitations, $R^2$, $R^3$ and $R^4$ can be same, all different or two same and one different. For example, $R^2$ and $R^3$ can be same and $R^4$ can be different, or $R^2$ and $R^4$ can be same and $R^3$ can be different, or $R^3$ and $R^4$ can be same and $R^2$ can be different. In some embodiments, $R^2$, $R^3$ and $R^4$ are the same.

In some embodiments of compounds of formula (I) and (II), $R^2$, $R^3$ and $R^4$ are independently selected from the group consisting of H, halogen, $C_1$-$C_6$ alkyl, $C_1$-$C_6$ haloalkyl, and $C_1$-$C_6$ alkoxy. For example, $R^2$, $R^3$ and $R^4$ can be selected independently from the group consisting of hydrogen or halogen, wherein the halogen can be fluorine, chlorine, bromine or iodine. In some preferred embodiments, each of $R^2$, $R^3$ and $R^4$ is H.

It is noted that the carbon to which $R^1$ and $R^2$ are attached in compounds of Formula (I) or Formula (II) can be chiral. Accordingly, in some compounds of Formula (I) or Formula (II), the carbon to which $R^1$ and $R^2$ are attached has the S configuration. In some other compounds of Formula (I) or Formula (II), the carbon to which $R^1$ and $R^2$ are attached has the R configuration.

In compound of Formula (I) and (II), $R^3$ can be hydrogen, $C_1$-$C_6$ alkyl, $C_1$-$C_6$ haloalkyl, $C_1$-$C_6$ heteroalkyl, aryl, heteroaryl, or halogen. In some embodiments, $R^5$ is hydrogen or $C_1$-$C_6$ alkyl. For example, $R^5$ can by hydrogen, methyl, ethyl, n-propyl, isopropyl, n-butyl, isobutyl, sec-butyl, tert-butyl, pentyl, hexyl, and the like. In some preferred embodiments, $R^5$ is H.

In various compounds of Formula (I) and (II), $R^6$ and $R^7$ can be independently selected from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl. Without limitation, $R^6$ and $R^7$ can be same or different. In some embodiments, $R^6$ and $R^7$ are selected independently from the group consisting of hydrogen, halogen, $C_1$-$C_6$ alkyl and $C_1$-$C_6$ haloalkyl. Without limitations, alkyl can be optionally substituted methyl, ethyl, n-propyl, isopropyl, n-butyl, isobutyl, sec-butyl, tert-butyl, pentyl, hexyl, and the like and halogen can be fluorine, chlorine, bromine or iodine. In some embodiments, $R^6$ and $R^7$ are hydrogen.

In compounds of Formula (I) and (II), $R^{3A}$ and $R^{4A}$ can be same or different. For example, each $R^{3A}$ and $R^{4A}$ can be selected independently from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

In some embodiments, each $R^{3A}$ and $R^{4A}$ is selected independently from the group consisting of hydrogen, $C_1$-$C_6$ alkyl, cycloalkyl and heterocyclyl, wherein the alkyl, cycloalkyl and heterocyclyl can be optionally substituted with halogen, $C_1$-$C_4$alkyl, $C_1$-$C_4$haloalkyl, $C_1$-$C_4$ heteroalkyl or $C_1$-$C_6$ alkoxy. In some preferred embodiments, each $R^{3A}$ and $R^{4A}$ is independently a $C_1$-$C_6$ alkyl or $C_3$-$C_8$ cycloalkyl.

In compounds of Formula (I) and (II), $R^A$ and $R^B$ can be same or different. For example, each $R^A$ and $R^B$ can be selected independently from the groups consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl. In some embodiments, each $R^A$ and $R^B$ is selected independently from the group consisting of H, Br, Cl, F and I.

This invention contemplates using all combinations of the various substituents. Thus, any combination of the above-mentioned substituents falling with the Formula (I) and (II) can be used.

In various compound of Formula (I) and (II), n can be 1, 2, 3, or 4. For example, n can be 1 or 2. In some preferred embodiments, n is 2.

Exemplary compounds of Formula (I) include, but are not limited to, the following:

(FQI-35)

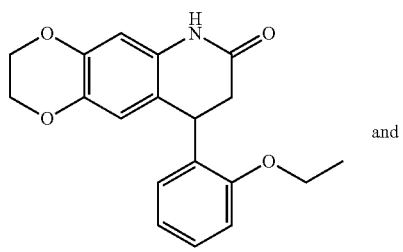

and (FQI-37)

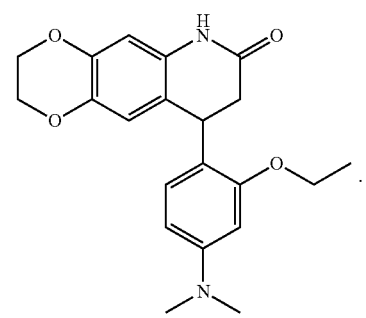

A preferred compound of Formula (I) is FQI-37. In some embodiments of the various aspects described herein, the compound FQI-37 is the S-isomer, also referred to as (S)-FQI-37 herein, having the structure:

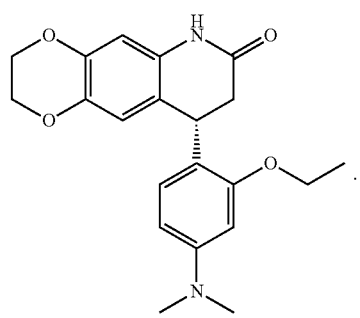 [SMILES: CCOc1cc(N(C)C)ccc1[C@H]1CC(=O)Nc2cc3c(cc21)OCCO3]

In some embodiments of the various aspects described herein, the compound FQI-37 is the R-isomer isomer, also referred to as (R)-FQI-37 herein, having the structure:

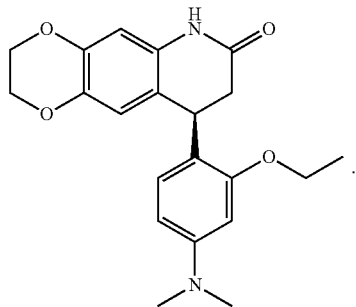 [SMILES: CCOc1cc(N(C)C)ccc1[C@@H]1CC(=O)Nc2cc3c(cc21)OCCO3]

Exemplary compounds of Formula (II) include, but are not limited to, the following:

(FQI-36)

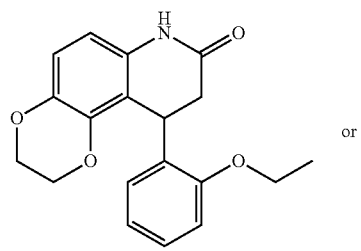

or (FQI-38)

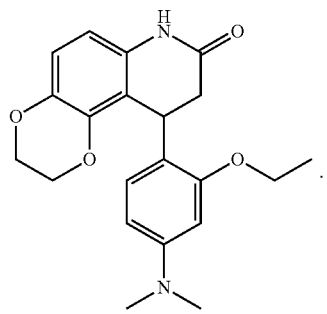

In various embodiments, the disclosure provides a compound of Formula (III) or Formula (IV):

FORMULA (III)

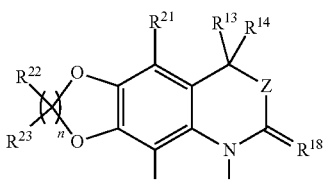

FORMULA (IV)

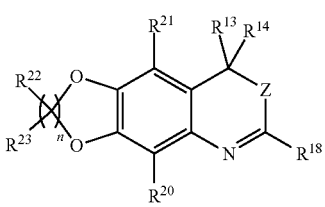

In various compounds of Formula (III), $R^{18}$ can be O, S or $NR^{19A}$. For example, $R^{18}$ can be O or S. In some embodiments, $R^{18}$ is O. In some other embodiments, $R^{18}$ is S.

In compounds of Formula (III), $R^{19}$ can be hydrogen, $C_1$-$C_6$ alkyl, $C_1$-$C_6$ haloalkyl, $C_1$-$C_6$ heteroalkyl, aryl, heteroaryl, or halogen. In some embodiments, $R^{19}$ is hydrogen or $C_1$-$C_6$alkyl. In some preferred embodiments, $R^{19}$ is H. In some compounds of Formula (III), $R^{18}$ is $NR^{19A}$, and $R^{19}$ and $R^{19A}$, together with the nitrogens they are attached to, form an optionally substituted 5-8 membered heterocyclyl or heteroaryl.

In various compounds of Formula (IV), $R^{18}$ can be $NQ_1Q_2$, wherein $Q_1$ and $Q_2$ are independently selected from the group consisting of hydrogen, alkyl, alkenyl, alkynyl, cycloalkyl or aryl optionally substituted with halogen, $C_1$-$C_4$ alkyl, $C_1$-$C_4$ haloalkyl, $C_1$-$C_4$ heteroalkyl or $C_1$-$C_6$ alkoxy. Without limitations, $Q_1$ and $Q_2$ can be the same or different.

In some embodiments, $R^{18}$ of Formula (IV) is $NQ_1Q_2$, where $Q_1$ and $Q_2$ are selected independently from hydrogen, $C_1$-$C_6$ alkyl, $C_1$-$C_6$ haloalkyl, $C_1$-$C_6$ heteroalkyl, $C_3$-$C_8$ cycloalkyl, and $C_2$-$C_8$ alkenyl. In some embodiments, at least one of $Q_1$ and $Q_2$ is H and the other is a $C_1$-$C_6$alkyl. For example, one of $Q_1$ and $Q_2$ is H and the other is methyl, ethyl, n-propyl, isopropyl, n-butyl, isobutyl, sec-butyl, tert-butyl, pentyl, or hexyl. In some embodiments, $Q_1$ and $Q_2$ are the same. For example, both of $Q_1$ and $Q_2$ are H, methyl, ethyl, n-propyl, isopropyl, n-butyl, isobutyl, sec-butyl, tert-butyl, pentyl, or hexyl. In some embodiments, $Q_1$ and $Q_2$ together with the nitrogen they are attached to can form a heterocycly or heteroaryl, which can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino group.

In compounds of Formula (III) and (IV), Z can be $NR^{15}$ or $CR^{16}R^{17}$. In some compounds of Formula (III) and (IV), Z is $CH_2$ or NH. In some embodiments of compounds of Formula (III), when $R^{18}$ is O then either n is not 1 or Z is $NR^{15}$. some embodiments of compounds of Formula (III), when Z is $CR^{16}R^{17}$ and $R^{18}$ is O then (i) $R^{19}$ and $R^{19A}$ together with the nitrogens they are attached to form an optionally substituted heterocyclyl or optionally substituted heteroaryl; or (ii) $R^{13}$ is an aryl substituted with $OR^{3A}$, where $R^{3A}$ is a cyclyl.

In compounds of Formula (III) and (IV) $R^{13}$, $R^{14}$, $R^{15}$, $R^{16}$ and $R^{17}$ can each be selected independently from the group consisting of hydrogen, halogen, $C_1$-$C_6$ alkyl, $C_3$-$C_8$ cycloalkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$alkyl)amino or di($C_1$-$C_6$alkyl) amino. In some embodiments, $R^{14}$ and $R^{16}$ together can form a second bond between the carbons to which they are attached.

In some compounds of Formula (III) and (IV), $R^{13}$ can be an aryl substituted with at least one $OR^{3A}$ and optionally further substituted with halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino groups.

Exemplary aryl groups for $R^{13}$ of Formula (III) and (IV) include, but are not limited to phenyl, 1-naphthyl, 2-naphthyl, biphenyl, pyridine, quinoline, furan, thiophene, pyrrole, imidazole, pyrazole, diphenylether, diphenylamine, benzophenone, and the like. Exemplary halogen substituents for aryl of $R^{13}$ include but are not limited to, fluorine, chlorine, bromine and iodine. Exemplary alkyl substituents for aryl of $R^{13}$ include but are not limited to, methyl, ethyl, n-propyl, isopropyl, n-butyl, isobutyl, sec-butyl, tert-butyl, pentyl, hexyl, and the like. Exemplary cycloalkyl for aryl of $R^{13}$ include but are not limited to, optionally substituted cyclopropyl, cyclobutyl, cyclopentyl, cyclohexyl and the like. Exemplary alkoxy substituents for aryl of $R^{13}$, include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like. Exemplary monoalkylamino substituents for aryl of $R^{13}$ include but are not limited to, methylamino, ethylamino, n-propylamino, isopropylamino, n-butylamino, isobutylamino, sec-butylamino, tert-butylamino, pentylamino, hexylamino, and the like.

Exemplary dialkylamino substituents for aryl of $R^{13}$ of Formula (III) and (IV) include, but are not limited to, dimethylamino, diethylamino, dipropylamino, dibutylamino, dipentylamino, dihexylamino, and the like. Additional exemplary dialkylamino substituents for aryl of $R^{13}$ include, but are not limited to, amino substituted with two different alkyl groups, for example, a first alkyl group selected from methyl, ethyl, n-propyl, isopropyl, n-butyl, isobutyl, sec-butyl, tert-butyl, pentyl and hexyl, and a second alkyl group selected from methyl, ethyl, n-propyl, isopropyl, n-butyl, isobutyl, sec-butyl, tert-butyl, pentyl and hexyl, where the first and the second alkyl groups are different. Exemplary haloalkyl substituents for aryl of $R^{13}$ include, but are not limited to, alkyl groups, such as methyl, ethyl, n-propyl, isopropyl, n-butyl, isobutyl, sec-butyl, tert-butyl, pentyl and hexyl, where 1, 2, 3, 4, 5, 6, or all H are replaced by independently selected halogen, for example, $CH_2F$, $CHF_2$, and $CF_3$. Exemplary alkenyl substituents for the aryl of $R^{13}$ include, but are not limited to, ethenyl, n-propenyl, isopropenyl, n-butenyl, isobutenyl, pentenyl, isopentenyl, hexenyl and the like.

In some compounds of Formula (III) or (IV), $R^{13}$ is an aryl substituted with one OR A group and optionally substituted with one or more additional substituents. In some embodiments, $R^1$ is an aryl substituted with at least one OR A and optionally further substituted with one or more substituents selected independently from halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono ($C_1$-$C_6$ alkyl) amino or di($C_1$-$C_6$ alkyl) amino groups. In some further embodiments, $R^{13}$ is an aryl substituted with at least one $OR^{3A}$ and optionally further substituted with one or more of halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$alkyl) amino or di($C_1$-$C_6$ alkyl) amino groups.

In some compounds of Formula (III) and (IV), $R^{13}$ is an aryl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino groups. For example, $R^{13}$ is an aryl substituted with at least one $C_1$-$C_6$ alkoxy and at least one halogen, amino ($NH_2$), mono ($C_1$-$C_6$alkyl) amino or di($C_1$-$C_6$alkyl) amino groups. In some preferred embodiments, $R^{13}$ is an aryl substituted with at least one $C_1$-$C_6$ alkoxy and at least one halogen or di($C_1$-$C_6$ alkyl) amino group.

In the compounds of Formula (III) and (IV), $R^{13}$ can be an aryl substituted with one $OR^{3A}$ and one halogen, or with one $OR^{3A}$ and two halogens, or with one $OR^{3A}$ and three halogens. $R^1$ can also be aryl substituted with two $OR^{3A}$ and one halogen, or with two $OR^{3A}$ and two halogens, or with three $OR^{3A}$ and one halogen, and the like. Similarly, $R^{13}$ can be aryl substituted with one $OR^{3A}$ and one di($C_1$-$C_6$ alkyl) amino or with one $OR^{3A}$ and two di($C_1$-$C_6$ alkyl)amino groups and so on.

In some compounds of Formula (III) and (IV), $R^{13}$ is a phenyl substituted with at least one $OR^{34}$ and optionally further substituted with one or more substituents selected independently from halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino group. In yet some other embodiments, $R^{13}$ is a phenyl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino groups.

In some compounds of Formula (III) and (IV), $R^{13}$ is a phenyl substituted with at least one $C_1$-$C_6$ alkoxy and at least one substituent selected independently from halogen, amino ($NH_2$), mono ($C_1$-$C_6$ alkyl) amino or di($C_1$-$C_6$ alkyl) amino group. In some preferred embodiments, $R^{13}$ is a phenyl substituted with at least one $C_1$-$C_6$ alkoxy and at least one halogen or di($C_1$-$C_6$ alkyl) amino.

Without limitations, the aryl of the $R^{13}$ of Formula (III) and (IV) can be substituted at any position. Thus, when the aryl is substituted with a single substituent, the substituent can be present at any of ortho, meta or para positions. For example, when the aryl of the $R^{13}$ group is substituted with a $C_1$-$C_6$alkoxyl, the alkoxyl group can be at the ortho position.

When the aryl is substituted with two substituents, they can present at ortho and ortho; ortho and meta; ortho and para, meta and meta, or meta and para positions. For example, when the aryl of $R^{13}$ group is substituted with a $C_1$-$C_6$alkoxyl and a second substituent, the alkoxyl can be present at one of the ortho positions and the second substituent can be present at the meta, ortho or para position. In some embodiments, the $C_1$-$C_6$alkoxyl is at the ortho position and the second substituent is at the para position.

In some embodiments, $R^{13}$ of Formula (III) and (IV) is a phenyl substituted with at least one $C_1$-$C_6$ alkoxyl and at least one di($C_1$-$C_{24}$alkyl)amino. In some embodiments, $R^{13}$ is

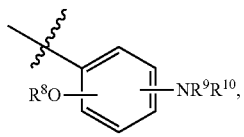

wherein $R^8$ is $C_1$-$C_6$alkyl and $R^9$ and $R^{10}$ are independently selected $C_1$-$C_{24}$alkyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl.

Without limitations, $R^9$ and $R^{10}$ can be same or different. Moreover, they can comprise the same number of carbons or different number of carbons. In some embodiments, $R^9$ and $R^{10}$ are selected independently from $C_1$-$C_6$ alkyl groups. Exemplary alkyls for the $R^9$ and $R^{10}$ group include, but are not limited to, methyl, ethyl, propyl, isopropyl, 1-butyl, 2-butyl, 2-methylpropyl, pentyl, t-butyl, and hexyl. In some embodiments, $R^9$ and $R^{10}$ are methyl.

In some embodiments, $R^{13}$ is a phenyl substituted with at least one $C_1$-$C_6$ alkoxyl and at least one halogen. In some embodiments, $R^{13}$ is

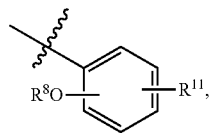

wherein $R^8$ is $C_1$-$C_6$alkyl and $R^{11}$ is halogen, $C_1$-$C_6$ haloalkyl or $C_2$-$C_6$alkenyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl. In some embodiments, $R^{11}$ is selected from the group consisting of Br, F, and Cl.

In some compounds of Formula (III) and (IV), $R^{13}$ can be selected from the group consisting of

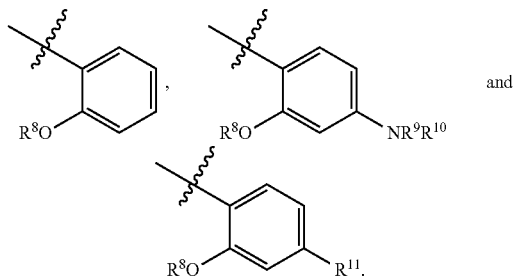

In some preferred embodiments of compounds of Formula (III) and (IV), $R^{13}$ is

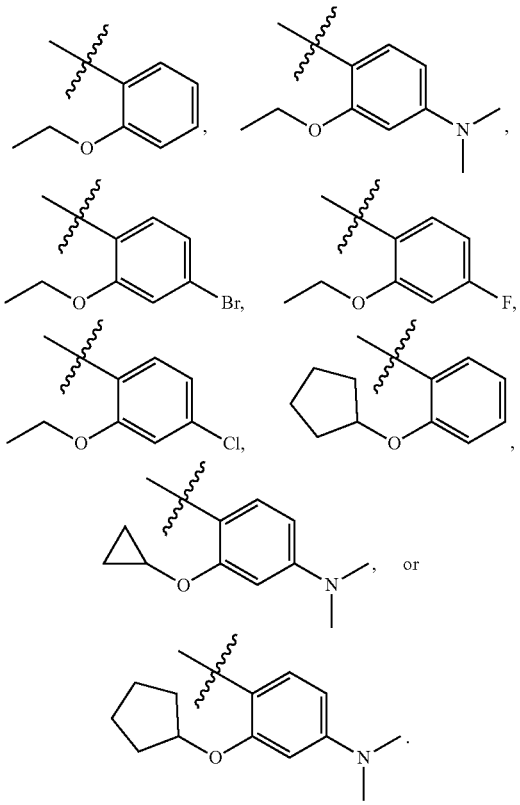

In compounds of Formula (III) and (IV), each of $R^{14}$, $R^{15}$, $R^{16}$ and $R^{17}$ can be independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino. In some embodiments, $R^{14}$ and $R^{16}$ together form a second bond between the carbons to which they are attached. Without limitations, $R^{14}$, $R^{15}$, $R^{16}$ and $R^{17}$ can be same, all different or some same and some different. For example, $R^{14}$ and $R^{15}$ can be same or they can be different. In some embodiments, $R^{14}$ and $R^{15}$ are the same. When present $R^{16}$ and $R^{17}$ can be different from $R^{14'}$ same as $R^{14}$, or one same and one different from $R^{14}$. For example, $R^{14}$, $R^{16}$ and $R^{17}$ can be different, or $R^{14}$ and $R^{16}$ can be same and $R^{17}$ can be different, or $R^{14}$ and $R^{17}$ can be same and $R^{16}$ can be different, or $R^{16}$ and $R^{17}$ can be same and $R^{14}$ can be different. In some embodiments, $R^{14}$, $R^{16}$ and $R^{17}$ are the same.

In some embodiments of compounds of formula (III) and (IV), $R^{14}$, $R^{15}$, $R^{16}$ and $R^{17}$ are independently selected from the group consisting of H, halogen, $C_1$-$C_6$ alkyl, $C_1$-$C_6$ haloalkyl, and $C_1$-$C_6$ alkoxy. For example, $R^{14}$, $R^{15}$, $R^{16}$ and $R^{17}$ can be selected independently from the group consisting of hydrogen or halogen, wherein the halogen can be fluorine, chlorine, bromine or iodine. In some preferred embodiments, each of $R^{14}$, $R^{15}$, $R^{16}$ and $R^{17}$ is H.

In some embodiments of compounds of formula (III) and (IV), $R^{14}$ is H, halogen, $C_1$-$C_6$alkyl, $C_1$-$C_6$haloalkyl or $C_1$-$C_6$ alkoxy; and $R^5$ is $C_1$-$C_6$alkyl or $C_3$-$C_8$cycloalkyl. Exemplary alkyls for $R^{14}$ and $R^{15}$ include, but are not limited to, methyl, ethyl, n-propyl, isopropyl, n-butyl, isobutyl, sec-butyl, tert-butyl, pentyl, hexyl, and the like. Exemplary cycloalkyl for $R^{14}$ include, but are not limited to, optionally substituted cyclopropyl, cyclobutyl, cyclopentyl, cyclohexyl and the like. Exemplary alkoxy for $R^{14}$, include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like. In some embodiments, $R^{14}$ is H and $R^{15}$ is selected from the group consisting of methyl, ethyl, n-propyl, isopropyl, n-butyl, isobutyl, sec-butyl, tert-butyl, pentyl, and hexyl.

It is noted that the carbon in compounds of Formula (III) or Formula (IV) to which $R^{13}$ and $R^{14}$ are attached can be chiral. Accordingly, in some compounds of Formula (III) or Formula (IV), the carbon to which $R^{13}$ and $R^{14}$ are attached has the S configuration. In some other compounds of Formula (III) or Formula (IV), the carbon to which $R^1$ and $R^2$ are attached has the R configuration.

In various compounds of Formula (III) and (IV), $R^{20}$ and $R^{21}$ can be independently selected from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl. Without limitation, $R^6$ and $R^7$ can be same or different. In some embodiments, $R^{20}$ and $R^{21}$ are selected independently from the group consisting of hydrogen, halogen, $C_1$-$C_6$ alkyl and $C_1$-$C_6$ haloalkyl. Without limitations, alkyl can be optionally substituted methyl, ethyl, n-propyl, isopropyl, n-butyl, isobutyl, sec-butyl, tert-butyl, pentyl, hexyl, and the like and halogen can be fluorine, chlorine, bromine or iodine. In some embodiments, $R^{20}$ and $R^{21}$ are hydrogen.

In compounds of Formula (III) and (IV), $R^{3A}$ and $R^{4A}$ can be same or different. For example, each $R^{3A}$ and $R^{4A}$ can be selected independently from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy.

In some embodiments, each $R^{3A}$ and $R^{4A}$ is selected independently from the group consisting of hydrogen, $C_1$-$C_6$ alkyl, cycloalkyl and heterocyclyl, wherein the alkyl, cycloalkyl and heterocyclyl can be optionally substituted with halogen, $C_1$-$C_4$alkyl, $C_1$-$C_4$haloalkyl, $C_1$-$C_4$ heteroalkyl or $C_1$-$C_6$ alkoxy. In some preferred embodiments, each $R^{3A}$ and $R^{4A}$ is independently a $C_1$-$C_6$alkyl or $C_3$-$C_8$ cycloalkyl.

In compounds of Formula (III) and (IV), $R^{22}$ and $R^{23}$ can be same or different. For example, each $R^{22}$ and $R^{23}$ can be selected independently from the groups consisting of hydrogen, halogen, OR A, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl. In some embodiments, each $R^{22}$ and $R^{23}$ is selected independently from the group consisting of H, Br, Cl, F and I.

This invention contemplates using all combinations of the various substituents. Thus, any combination of the above-mentioned substituents falling with the Formula (III) and (IV) can be used.

In various compounds of Formula (III) and (IV), n can be 1, 2, 3, or 4. For example, n can be 1 or 2. In some preferred embodiments, n is 1.

Exemplary compounds of Formula (III) include, but are not limited to, the following:

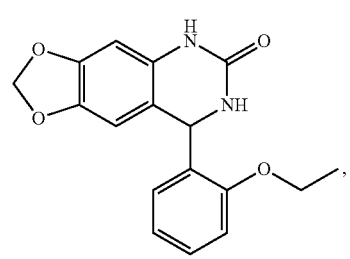

(FQI-Urea)

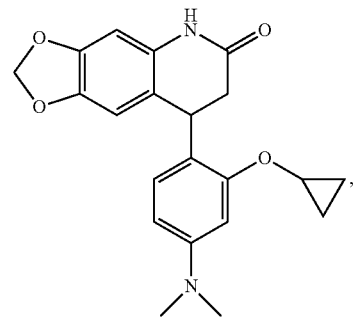

(FQI-39)

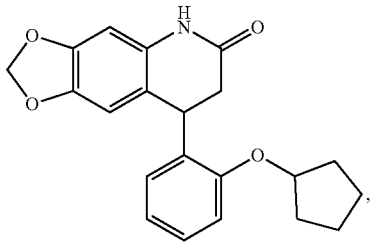

(FQI-41)

(FQI-42)

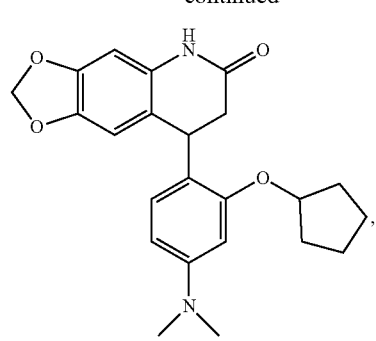

(Thio-FQI-1)

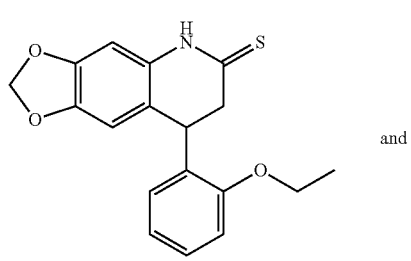
and (Tri-FQI-1)

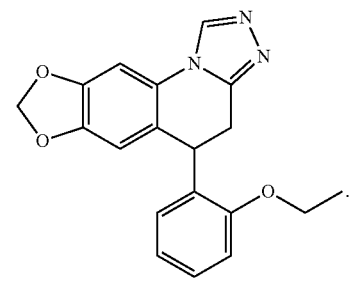

Exemplary compounds of Formula (IV) include, but are not limited to, the following:

(FQI-30)

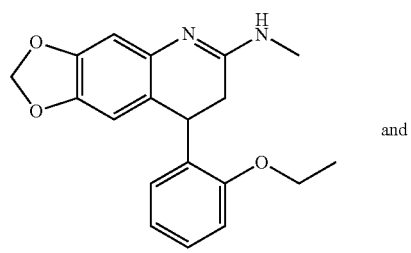
and (FQI-31)

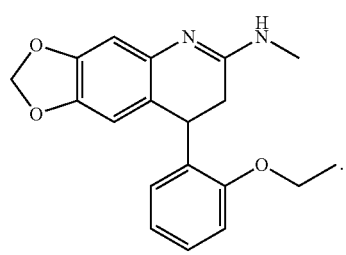

For clarification, compounds disclosed in U.S. Pat. Nos. 9,597,325, 9,802,948, and 9,815,845, and US Patent Application Publication US2017/0107227 are excluded from the compounds of Formulas (I)-(IV).

In some embodiments, a compound of any of formulas (I) to (IV) as disclosed herein can be used to treat various cancers, such as liver cancer (hepatocellular carcinoma), brain cancer, breast cancer, colon cancer, head and neck squamous cell carcinoma, lung cancer, pancreatic cancer, ductal adenocarcinoma, colorectal adenocarcinoma, rectosigmoid carcinoma, kidney cancer, monocytic lymphoma, ovarian cancer, and thyroid cancer; HIV; inflammation-related diseases such as hepatitis B virus (HBV), hepatitis C (HCV), cirrhosis and Alzheimer's disease. In some embodiments, the liver diseases can be any selected from, but not limited to, HBV, HCV, cirrhosis, hepatic adenoma, hepatic angiosarcoma and hepatic angiosarcomas; emphysema; and hereditary hemochromatosis.

In some embodiments, a compound of any of formulas (I) to (IV) as disclosed herein can be used to treat other cancers, for example, cervical cancer, colon cancers, melanomas and the like. Other cancers which can be treated include any cancer with overexpression of LSF in the tumor, for example, but not limited to, oligodendroglioma, meningioma, GBM, breast cancer, colon cancer, Non-Hodgkin's small cell carcinoma (HNSCC), lung cancer (adrenocarcinomas), lung cancer (small cell carcinoma), pancreatic cancer, ovarian cancer, thyroid cancer and undifferentiated cancer.

In some embodiments, a compound of any of formulas (I) to (IV) as disclosed herein can be used to treat any cancer cell type. Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In one preferred embodiment, a compound of any of formulas (I) to (IV) as disclosed herein is used to treat a subject with hepatocellular carcinoma (HCC).

In another embodiment, a subject at high risk of developing HCC is suitable for treatment with the compositions of the invention comprising at least a LSF inhibitor as disclosed herein.

Hepatocellular carcinoma (HCC) is one of the five most common cancers worldwide. The incidence of HCC is increasing despite a decrease in overall incidence of all cancers. In the United States, the estimated new cases of HCC for 2008 were 21,370, of which 18,410 were expected to die. The mean 5-year survival rate is less than 10%. The mortality rate of HCC parallels that of its incidence because HCC is a tumor with rapid growth and early vascular invasion that is resistant to conventional chemotherapy, and only suboptimal systemic therapy is available for the advanced disease.

To date, other than curative resection, treatments for HCC have had minimal impact on survival. Unfortunately, approximately 90% of HCC patients have unresectable HCC. Moreover, even after potentially curative hepatectomy in patients with resectable HCC, new HCC arises in the cirrhotic remnants in 70% of these patients, and frequently arises in the grafted liver following orthotopic liver transplantation. Other approaches to treating HCC, such as intralesional ethanol injection, chemoembolization, radiofrequency ablation, cryosurgery and radiation therapy have demonstrated some success in selected patient populations; however, the efficacies of these approaches have not been definitively established. Both percutaneous intralesional ethanol injection and transarterial chemoembolization have shown limited success, but not without risks of serious side effects. Radiotherapy is not usually an option because liver is very radiosensitive.

All systemic therapies for HCC to date are associated with uniformly poor outcomes, and only two chemotherapeutic agents (sorafenib and regorafenib), alone or in combination with other treatments, have been associated with any improvement in survival rates (Fuchs et al., 94 Cancer 3186 (2002) and Bruix et al., Lancet (2017), 389(10064), 56-66). In addition, most patients with HCC have underlying liver disease so their ability to tolerate to undergo surgery is compromised. Therefore, there is a strong need in the art to provide improved methods for treatment of HCC.

Accordingly, one aspect of the invention provides methods for therapeutic and prophylactic treatment of cancers, e.g., HCC by administering to a subject a pharmaceutical composition comprising an effective amount of a compound of Formula (I)-(IV) and enantiomers, prodrugs, derivatives, and pharmaceutically acceptable salts thereof.

As described herein, compounds of Formula (I)-(IV) can inhibit late SV40 factor or late Simian Virus 40 factor (LSF). LSF is also known as aliases LBP-1c (leader binding protein-1c), LBP-1d, SEF (SAA3 enhancer factor), TFCP2 (transcription factor CP2) and CP2.

LSF is a DNA-binding transcription factor that is required in multiple cell types for cell cycle progression and regulates diverse cellular and viral promoters. It binds to the alpha-globin promoter and activates transcription of the alpha-globin gene. It has been reported that LSF facilitates entry into G1/S phase of the cell cycle, promotes DNA synthesis, and functions as an antiapoptotic factor. LSF also regulates erythroid gene expression, plays a role in the transcriptional switch of globin gene promoters, and it activates many other cellular and viral gene promoters. The gene product interacts with certain inflammatory response factors, and polymorphisms of this gene can be involved in the pathogenesis of Alzheimer's disease.

A major cellular target of LSF is the thymidylate synthase (TS) gene (TYMS), which encodes the rate-limiting enzyme in the production of dTTP, required for DNA synthesis. TS has been a long-standing chemotherapeutic target for cancer treatments, and recently it was discussed that elevated levels of LSF in hepatocellular carcinoma cell lines can contribute to chemoresistance to one commonly utilized thymidylate synthetase inhibitor, 5-fluorouracil. Inhibition of LSF abrogates TS induction, induces either arrest at the GUS transition, or in apoptosis after entry into S phase. Thus, LSF plays an important role in DNA synthesis and cell survival. In the liver, LSF is activated by inflammatory cytokines and regulates the expression of acute phase proteins.

The present invention relates in part to methods and compositions to inhibit LSF, more specifically, with small-molecule LSF inhibitors. In some embodiments, inhibitors of LSF as disclosed herein can be used to inhibit the cellular LSF activity. In some embodiments, LSF inhibitors as disclosed herein can decrease expression (level) of LSF. In some embodiments, the inhibitor of LSF is selected from the group consisting of compounds of Formula (I)-(IV).

Inventors have discovered inter alia that three regulators of mitosis, SET8, LSF, and tubulin, all interact with each other both in vitro and within cells. Further, SET8 is a microtubule-associated methyltransferase that methylates lysines on α-tubulin. SET8 does not methylate LSF, but in parallel to how proteins recruit chromatin writers to target histones, LSF stimulates methylation of tubulin by SET8. LSF enhances tubulin polymerization in vitro, showing that this protein may also influence microtubule dynamics. The inventors also discovered that inhibiting LSF with an exemplary small molecule LSF abrogated LSF-tubulin interactions in cells, and disrupted mitotic spindle formation via a non-transcriptional mechanism.

Accordingly, another aspect of the present invention relates to a method of inhibiting tubulin methylation or modulating chromatin/cytoskeleton modification in a cell, the method comprising administering to the cell an effective amount of compound of an inhibitor of LSF.

In some embodiments of the various aspects disclosed herein, the inhibitor of LSF is a compound of Formula (I)-(IV).

In some embodiments of the various aspects disclosed herein, the inhibitor of LSF is an LSF inhibitor described in U.S. Pat. Nos. 9,597,325, 9,802,948, and 9,815,845, and US Patent Application Publication US2017/0107227, content of each of which is incorporated herein by reference in its entirety. For example, the LSF inhibitor can be a compound of Formula (V):

FORMULA (V)

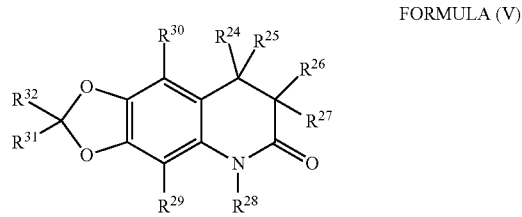

In compounds of Formula (V), $R^1$ can be an unsubstituted aryl or an aryl substituted with at least one $OR^{3,4}$ and optionally further substituted with halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino groups.

Exemplary aryl groups for $R^{24}$ of Formula (V) include, but are not limited to phenyl, 1-naphthyl, 2-naphthyl, biphenyl, pyridine, quinoline, furan, thiophene, pyrrole, imidazole, pyrazole, diphenylether, diphenylamine, benzophenone, and the like. Exemplary halogen substituents for aryl of $R^{24}$ include but are not limited to, fluorine, chlorine, bromine and iodine. Exemplary alkyl substituents for aryl of $R^{24}$ include but are not limited to, methyl, ethyl, n-propyl, isopropyl, n-butyl, isobutyl, sec-butyl, tert-butyl, pentyl, hexyl, and the like. Exemplary cycloalkyl for aryl of $R^{24}$ include but are not limited to, optionally substituted cyclopropyl, cyclobutyl, cyclopentyl, cyclohexyl and the like. Exemplary alkoxy substituents for aryl of $R^{24}$, include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like. Exemplary monoalkylamino substituents for aryl of $R^{24}$ include but are not limited to, methylamino, ethylamino, n-propylamino, isopropylamino, n-butylamino, isobutylamino, sec-butylamino, tert-butylamino, pentylamino, hexylamino, and the like.

Exemplary dialkylamino substituents for aryl of $R^{24}$ of Formula (V) include, but are not limited to, dimethylamino, diethylamino, dipropylamino, dibutylamino, dipentylamino, dihexylamino, and the like. Additional exemplary dialkylamino substituents for aryl of $R^{24}$ include, but are not limited to, amino substituted with two different alkyl groups, for example, a first alkyl group selected from methyl, ethyl, n-propyl, isopropyl, n-butyl, isobutyl, sec-butyl, tert-butyl, pentyl and hexyl, and a second alkyl group selected from methyl, ethyl, n-propyl, isopropyl, n-butyl, isobutyl, sec-butyl, tert-butyl, pentyl and hexyl, where the first and the second alkyl groups are different. Exemplary haloalkyl substituents for aryl of $R^{24}$ include, but are not limited to, alkyl groups, such as methyl, ethyl, n-propyl, isopropyl, n-butyl, isobutyl, sec-butyl, tert-butyl, pentyl and hexyl, where 1, 2, 3, 4, 5, 6, or all H are replaced by independently selected halogen, for example, $CH_2F$, $CHF_2$, and $CF_3$. Exemplary alkenyl substituents for the aryl of $R^{24}$ include, but are not limited to, ethenyl, n-propenyl, isopropenyl, n-butenyl, isobutenyl, pentenyl, isopentenyl, hexenyl and the like.

In some compounds of Formula (V), $R^{24}$ is an aryl substituted with one $OR^{34}$ group and optionally substituted with one or more additional substituents. In some embodiments, $R^{24}$ is an aryl substituted with at least one $OR^{34}$ and optionally further substituted with one or more substituents selected independently from halogen, $C_1$-$C_6$ alkyl, $C_3$-$C_8$ cycloalkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono ($C_1$-$C_6$ alkyl) amino or di($C_1$-$C_6$ alkyl) amino groups. In some further embodiments, $R^{24}$ is an aryl substituted with at least one $OR^{34}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$alkyl) amino or di($C_1$-$C_6$ alkyl) amino groups.

In some compounds of Formula (V), $R^{24}$ is an aryl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino groups. For example, $R^{24}$ is an aryl substituted with at least one $C_1$-$C_6$ alkoxy and at least one halogen, amino ($NH_2$), mono ($C_1$-$C_6$alkyl) amino or di($C_1$-$C_6$alkyl) amino groups. In some preferred embodiments, $R^{24}$ is an aryl substituted with at least one $C_1$-$C_6$ alkoxy and at least one halogen or di($C_1$-$C_6$ alkyl) amino group.

In the compounds of Formula (V), $R^{24}$ can be an aryl substituted with one $OR^{34}$ and one halogen, or with one $OR^{34}$ and two halogens, or with one $OR^{34}$ and three halogens. $R^1$ can also be aryl substituted with two $OR^{34}$ and one halogen, or with two $OR^{34}$ and two halogens, or with three $OR^{34}$ and one halogen, and the like. Similarly, $R^{24}$ can be aryl substituted with one $OR^{34}$ and one di($C_1$-$C_6$ alkyl) amino or with one $OR^{34}$ and two di($C_1$-$C_6$alkyl)amino groups and so on.

In some compounds of Formula (V), $R^{24}$ is a phenyl substituted with at least one $OR^{34}$ and optionally further substituted with one or more substituents selected independently from halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino group. In yet some other embodiments, $R^{24}$ is a phenyl substituted with at least one $C_1$-$C_6$ alkoxy and at least one halogen, $C_1$-$C_6$alkyl, $C_1$-$C_6$haloalkyl, $C_1$-$C_6$ heteroalkyl, $C_1$-$C_6$ alkoxy, amino ($NH_2$), mono ($C_1$-$C_6$ alkyl) amino or di($C_1$-$C_6$ alkyl) amino groups.

In some compounds of Formula (V), $R^{24}$ is a phenyl substituted with at least one $C_1$-$C_6$ alkoxy and at least one substituent selected independently from halogen, amino ($NH_2$), mono ($C_1$-$C_6$ alkyl) amino or di($C_1$-$C_6$ alkyl) amino group. In some preferred embodiments, $R^1$ is a phenyl substituted with at least one $C_1$-$C_6$ alkoxy and at least one halogen or di($C_1$-$C_6$ alkyl) amino.

Without limitations, the aryl of the $R^1$ of Formula (V) can be substituted at any position. Thus, when the aryl is substituted with a single substituent, the substituent can be present at any of ortho, meta or para positions. For example, when the aryl of the $R^{24}$ group is substituted with a $C_1$-$C_6$alkoxyl, the alkoxyl group can be at the ortho position. When the aryl is substituted with two substituents, they can present at ortho and ortho; ortho and meta; ortho and para, meta and meta, or meta and para positions. For example, when the aryl of $R^{24}$ group is substituted with a $C_1$-$C_6$alkoxyl and a second substituent, the alkoxyl can be present at one of the ortho positions and the second substituent can be present at the meta, ortho or para position. In some embodiments, the $C_1$-$C_6$alkoxyl is at the ortho position and the second substituent is at the para position.

In some embodiments, $R^{24}$ of Formula (V) is a phenyl substituted with at least one $C_1$-$C_6$ alkoxyl and at least one di($C_1$-$C_{24}$alkyl)amino. In some embodiments, $R^1$ is

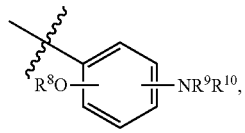

wherein $R^8$ is $C_1$-$C_6$alkyl and $R^9$ and $R^{10}$ are independently selected $C_1$-$C_{24}$alkyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl.

Without limitations, $R^9$ and $R^{10}$ can be same or different. Moreover, they can comprise the same number of carbons or different number of carbons. In some embodiments, $R^9$ and $R^{10}$ are selected independently from $C_1$-$C_6$ alkyl groups. Exemplary alkyls for the $R^9$ and $R^{10}$ group include, but are not limited to, methyl, ethyl, propyl, isopropyl, 1-butyl, 2-butyl, 2-methylpropyl, pentyl, t-butyl, and hexyl. In some embodiments, $R^9$ and $R^{10}$ are methyl.

In some embodiments, $R^{24}$ is a phenyl substituted with at least one $C_1$-$C_6$ alkoxyl and at least one halogen. In some embodiments, $R^1$ is

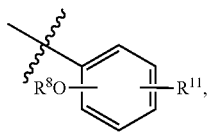

wherein $R^8$ is $C_1$-$C_6$alkyl and $R^{11}$ is halogen, $C_1$-$C_6$ haloalkyl or $C_2$-$C_6$alkenyl. Exemplary alkyls for the $R^8$ group include, but are not limited to, methyl, ethyl, propyl, isopropyl, 1-butyl, 2-butyl, 2-methylpropyl, pentyl, t-butyl, and hexyl. In some embodiments, $R^8$ is methyl or ethyl. In some embodiments, $R^{11}$ is selected from the group consisting of Br, F, and Cl.

In some compounds of Formula (V), $R^{24}$ can be selected from the group consisting of

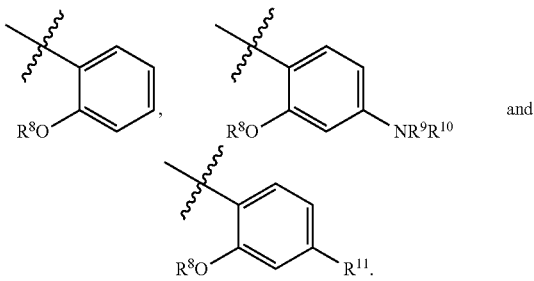

In some preferred embodiments of compounds of Formula (V), $R^1$ is

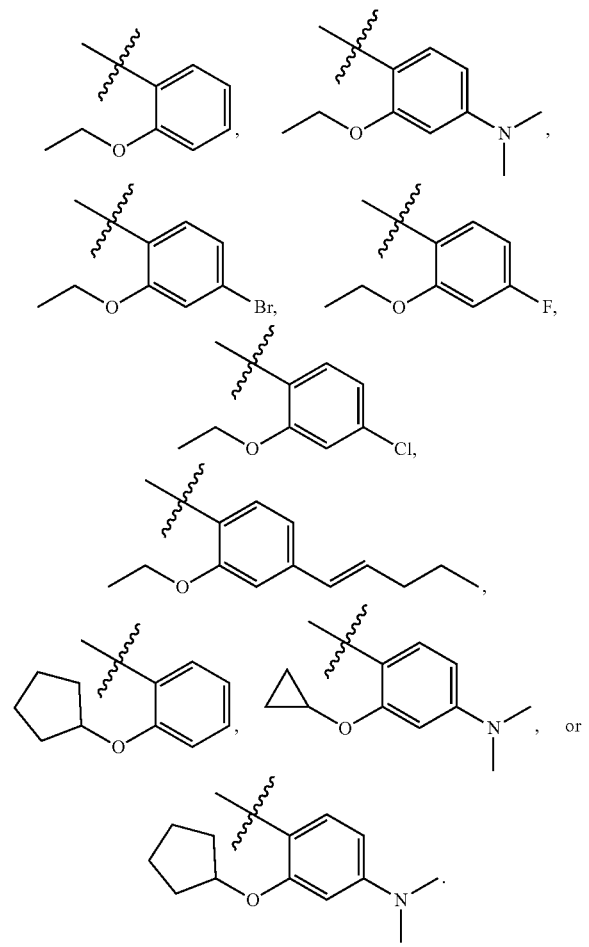

In compounds of Formula (V), each of $R^{25}$, $R^{26}$ and $R^{27}$ can be independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl) amino or di($C_1$-$C_6$ alkyl)amino. In some embodiments, $R^{25}$ and $R^{26}$ together form a second bond between the carbons to which they are attached. Without limitations, $R^{25}$, $R^{26}$ and $R^{27}$ can be same, all different or two same and one different. For example, $R^{25}$ and $R^{26}$ can be same and $R^{27}$ can be different, or $R^{25}$ and $R^{27}$ can be same and $R^{26}$ can be different, or $R^{26}$ and $R^{27}$ can be same and $R^{25}$ can be different. In some embodiments, $R^{25}$, $R^{26}$ and $R^{27}$ are the same.

In some embodiments of compounds of formula (V), $R^{25}$, $R^{26}$ and $R^{27}$ are independently selected from the group consisting of H, halogen, $C_1$-$C_6$ alkyl, $C_1$-$C_6$haloalkyl, and $C_1$-$C_6$ alkoxy. For example, $R^{25}$, $R^{26}$ and $R^{27}$ can be selected independently from the group consisting of hydrogen or halogen, wherein the halogen can be fluorine, chlorine, bromine or iodine. In some preferred embodiments, each of $R^{25}$, $R^{26}$ and $R^{27}$ is H.

It is noted that the carbon in compounds of Formula (V) to which $R^{24}$ and $R^{25}$ are attached can be chiral. Accordingly, in some compounds of Formula (V), the carbon to which $R^{24}$ and $R^{25}$ are attached has the S configuration. In some other compounds of Formula (V), the carbon to which $R^{24}$ and $R^{25}$ are attached has the R configuration In compound of Formula (V), $R^{28}$ can be hydrogen, $C_1$-$C_6$ alkyl, $C_1$-$C_6$ haloalkyl, $C_1$-$C_6$ heteroalkyl, aryl, heteroaryl, or halogen. In some embodiments, $R^{28}$ is hydrogen or $C_1$-$C_6$ alkyl. For example, $R^{28}$ can by hydrogen, methyl, ethyl, n-propyl, isopropyl, n-butyl, isobutyl, sec-butyl, tert-butyl, pentyl, hexyl, and the like. In some preferred embodiments, $R^{28}$ is H.

In various compounds of Formula (V), $R^{29}$ and $R^{30}$ can be independently selected from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl. Without limitation, $R^{29}$ and $R^{30}$ can be same or different. In some embodiments, $R^{29}$ and $R^{30}$ are selected independently from the group consisting of hydrogen, halogen, $C_1$-$C_6$ alkyl and $C_1$-$C_6$ haloalkyl. Without limitations, alkyl can be optionally substituted methyl, ethyl, n-propyl, isopropyl, n-butyl, isobutyl, sec-butyl, tert-butyl, pentyl, hexyl, and the like and halogen can be fluorine, chlorine, bromine or iodine. In some embodiments, $R^{29}$ and $R^{30}$ are hydrogen.

In compounds of Formula (V), $R^{3A}$ and $R^{4A}$ can be same or different. For example, each $R^{3A}$ and $R^{4A}$ can be selected independently from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy. In some embodiments, each $R^{3A}$ and $R^{4A}$ is selected independently from the group consisting of hydrogen, $C_1$-$C_6$ alkyl, cycloalkyl and heterocyclyl, wherein the alkyl, cycloalkyl and heterocyclyl can be optionally substituted with halogen, $C_1$-$C_4$ alkyl, $C_1$-$C_4$ haloalkyl, $C_1$-$C_4$ heteroalkyl or $C_1$-$C_6$ alkoxy. In some preferred embodiments, each $R^{3A}$ and $R^{4A}$ is independently a $C_1$-$C_6$ alkyl or $C_3$-$C_8$ cycloalkyl.

In compounds of Formula (V), $R^{31}$ and $R^{32}$ can be same or different. For example, each $R^{31}$ and $R^{32}$ can be selected independently from the groups consisting of hydrogen, halogen, $OR^{3A}$, $NR^{3A}R^{4A}$, $SR^{3A}$, $SO_2R^{3A}$, $C_1$-$C_6$alkyl, $C_1$-$C_6$ haloalkyl, $C_1$-$C_6$ heteroalkyl, aryl and heteroaryl. In some embodiments, each $R^{31}$ and $R^{32}$ is selected independently from the group consisting of H, Br, Cl, F and I. In some preferred embodiments, $R^{31}$ and $R^{32}$ are H.

As noted, this invention contemplates using all combinations of the various substituents. Thus, any combination of the above-mentioned substituents falling with the Formula (V) can be used.

Exemplary compounds of Formula (V) include, but are not limited to, the following:

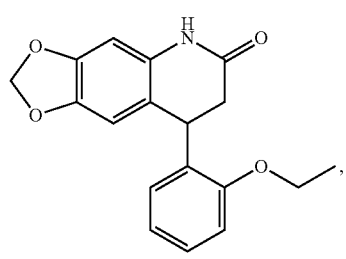
(FQI-1)

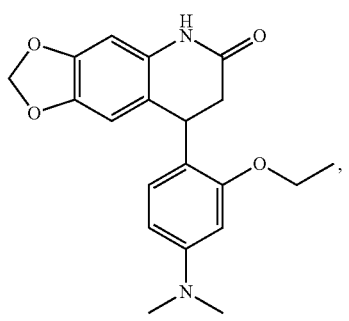
(FQI-34)

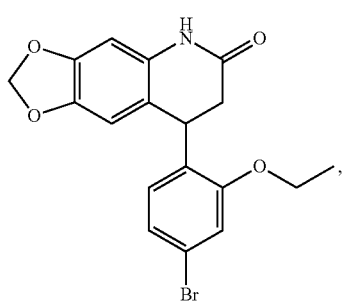
(FQI-Br)

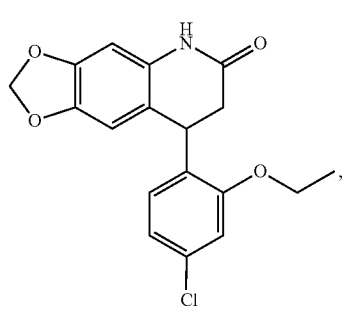
(FQI-Cl)

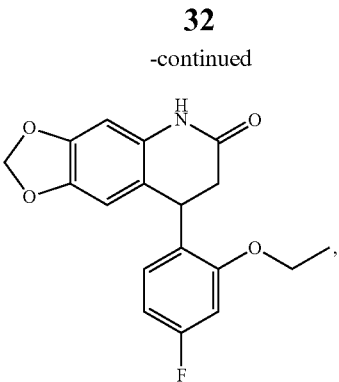
(FQI-F)

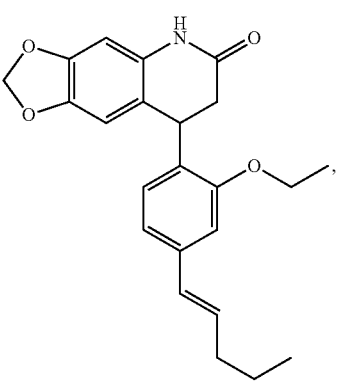
(FQI32)

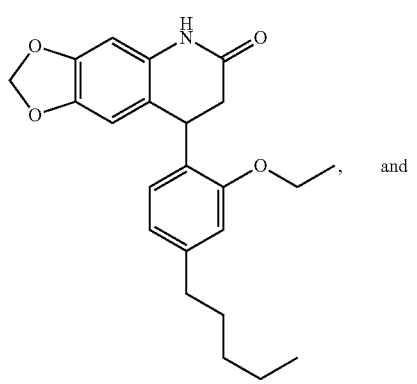
(FQI33)

and

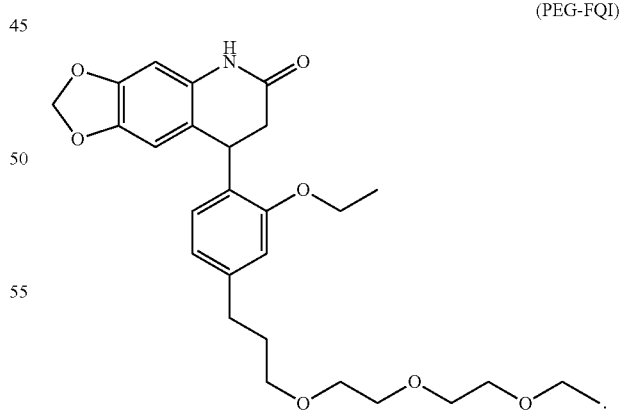
(PEG-FQI)

In some embodiments of the various aspects described herein, the compound FQI-34 is the S-isomer, also referred to as (S)-FQI-34 herein, having the structure:

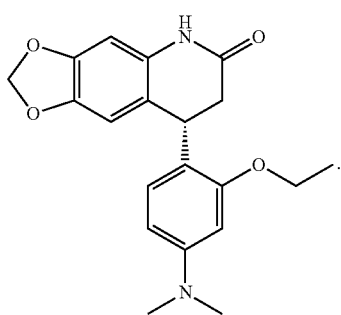 [SMILES: CCOc1cc(N(C)C)ccc1[C@H]1CC(=O)Nc2cc3c(cc21)OCO3]

In some embodiments of the various aspects described herein, the compound FQI-34 is the R-isomer isomer, also referred to as (R)-FQI-34 herein, having the structure:

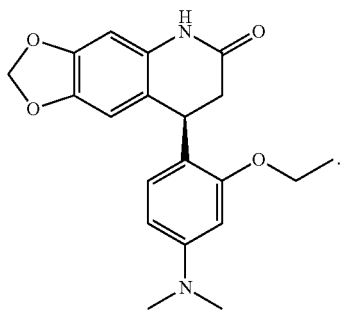 [SMILES: CCOc1cc(N(C)C)ccc1[C@@H]1CC(=O)Nc2cc3c(cc21)OCO3]

In one embodiment, a LSF inhibitor is a compound of Formula (I)-(V) or enantiomers, prodrugs, derivatives or pharmaceutically acceptable salts thereof. In some embodiments, a LSF inhibitor is the compound FQI-37 or enantiomers, prodrugs, derivatives or pharmaceutically acceptable salts thereof. In some embodiments, a LSF inhibitor is the compound selected from the group consisting of FQI-36, FQI-38, FQI-35, FQI-30, FQI-31, FQI-Urea, FQI-39, FQI-41, FQI-42, Thio-FQI-1, Tri-FQI-1 or enantiomers, prodrugs, derivatives or pharmaceutically acceptable salts thereof. In some embodiments, a LSF inhibitor is the compound selected from the group consisting of FQI-1, FQI-34, FQI-Br, FQI-Cl, FQI-F, FQI-32 or enantiomers, prodrugs, derivatives or pharmaceutically acceptable salts thereof.

Compounds of Formula (I)-(V) can be formulated in a pharmaceutical composition described herein. Further, compounds of Formula (I)-(V) can be used in the methods, e.g., a method for inhibiting LSF or treating cancer disclosed herein.

One of the major targets of LSF is thymidylate synthase (TS) gene (TYMS), which encodes the rate-limiting enzyme in the production of dTTP, required for DNA synthesis. Additional examples of LSF-downstream genes are disclosed in Yoo et al, PNAS, 2010, 107; 8357-8362, and include without limitation SPP1 (encoding osteopontin), complement factor H (CFH), TSPAN8, S100A10, CDH17, EFNB2, ZEB1, REG1A, REG3A, SAA4, TAGLN, FGFR2, EGFR, CYP2B7P1, CYP2B6, GPX2, DPYD, PKLR, LEF1, ICAM2 and IGFBP7.

In some embodiments, the genes downstream of LSF are tumor-associated genes, such as relating to invasion and metastasis, angiogenesis, epithelial-mesenchymal transition (EMT), cell growth, drug metabolism, senescence, cell adhesion, glycolysis, Wnt signaling, Hippo signaling, growth and regeneration, inflammatory response, e.g. acute phase proteins, and modulators of matrix-degrading enzymes e.g. MMP9. LSF is a transcription factor encoded by TFCP2. Thus, inhibiting LSF can disrupt or inhibit LSF binding to DNA and/or interaction of LSF with other proteins to form a complex.

Accordingly, in some embodiments, inhibition of cellular LSF activity can be determined by measuring the level of downstream genes regulated by the transcription factor LSF. The effect of LSF on expression (level) of LSF-targeted or LSF-downstream genes can be stimulatory or inhibitory. For example, one gene induced by LSF is SPP1 encoding OPN. Thus, an inhibition of biological activity of LSF results in a decrease in level of SPP1 mRNA and/or a decrease in the amount of the respective encoded protein, OPN. In another embodiment, one gene inhibited by LSF is TAGLN. Thus, an inhibition of biological activity of LSF leads to an increase in level of TAGLN mRNA. In some embodiments, the cellular activity of LSF can be measured by a reduction in the level of TS.

In further embodiments, inhibition of LSF can decrease expression of LSF, for example, a reduction in protein level, and/or a decrease in gene transcript level (e.g. mRNA) of LSF.

As disclosed herein, inhibitors of LSF can decrease functional transcriptional activity or the expression of LSF (e.g., such as protein level of LSF, and/or gene transcript level of LSF), by at least about 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. The expression of LSF can be measured by standard methods known to a skilled artisan such as western blot, ELISA, and quantitative PCR as well as the methods provided in Examples section.

In some embodiments, inhibitors of LSF as disclosed herein can inhibit or decrease cellular LSF activity by at least about 10%, relative to the activity level in the absence of inhibitors of LSF, e.g., at least about 15%, at least about 20%, at least about 30%, at least about 40%, at least about 50%, at least about 60%, at least about 70%, at least about 80%, at least about 90%, 95%, 99% or even 100%. In certain embodiments, inhibitors of LSF as disclosed herein can decrease expression of downstream genes up-regulated by LSF, e.g. SPP1 encoding OPN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF. In alternative embodiments, inhibitors of LSF can increase expression of downstream genes down-regulated by LSF, e.g. TAGLN, by about at least 10%, at least about 15%, at least about 20%, at least about 30%, at least about 40%, at least about 50%, at least about 60%, at least about 70%, at least about 80%, at least about 90%, 95%, 99% or even 100%, as compared to the expression in the absence of inhibitors of LSF.

Inhibition of LSF has been previously discussed as a potential treatment of latent HIV infection or cancer in general, or as a therapeutic regulator of immune function, specifically when there is a need thereof to decrease inflammatory response (U.S. Patent Application No.: US 2009/0081183 and International Patent Application No.: WO1998/36641, which are incorporated herein in their entirety by reference). However, these patent applications do not teach or describe any small-molecule LSF inhibitors of the invention as disclosed herein, or the use thereof for treatment of hepatocellular carcinoma (HCC).

The ability of a compound to inhibit LSF can be assessed in some instances by measuring a decrease in expression of LSF as compared to the level of LSF in the absence of inhibitors of LSF. In some embodiments, the ability of a compound to inhibit LSF can be assessed by measuring a decrease in the biological activity, e.g., transcriptional activity of LSF as compared to the level of transcriptional activity of LSF in the absence of inhibitors of LSF. The expression of LSF includes the amount of RNA transcribed from a gene, e.g. TFCP2 that encodes LSF, and/or the amount of LSF proteins that is obtained by translation of RNA transcribed from a gene, e.g. TFCP2. For example, a LSF inhibitor as disclosed herein can inhibit expression of LSF by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor.

Additionally, ability of a compound to inhibit LSF can be also assessed by measuring a decrease in or an inhibition of biological activity of LSF as compared to a negative control, e.g. the experimental condition in the absence of LSF inhibitors. The biological activity of LSF can refer to the ability of LSF to modulate expression of LSF-targeted genes such as thymidylate synthase (TYMS) and/or LSF-downstream genes, such as secreted phosphoprotein 1 (SPP1), complement factor H (CFH) and other tumor-associated genes (see Yoo et al., PNAS, 2010, 107; 8357-8362, which is incorporated herein in its entirety by reference). Accordingly, a LSF inhibitor as disclosed herein can inhibit biological activity of LSF, such as a decrease in expression of SPP1 that encodes OPN (also known as secreted phosphoprotein 1, SPP1), by at least about 10%, at least about 15%, at least about 20%, at least about 30%, at least about 40%, at least about 50%, at least about 60%, at least about 70%, at least about 80%, at least about 90%, 95%, 99% or even 100%, as compared to a reference level in the absence of a LSF inhibitor. In some embodiments, ability of a compound to inhibit LSF is assessed by inhibition of LSF-induced tumorigenesis and metastasis of cancer cells, e.g. hepatocellular carcinoma cells in vitro or in an in vivo animal model as demonstrated in WO2012/050985, U.S. Pat. Nos. 9,802,948, 9,815,845 and 9,597,325, contents of all which are incorporated herein by reference in their entirety, as compared to a reference condition without treatment with such a LSF inhibitor. In such embodiments, a LSF inhibitor can decrease a tumor weight and volume by at least about 15%, at least about 20%, at least about 30%, at least about 40%, at least about 50%, at least about 60%, at least about 70%, at least about 80%, at least about 90%, 95%, 99% or even 100%, as compared to no treatment with a LSF inhibitor.

It was previously reported in Yoo et al., (PNAS, 2010; 107; 8357-8362) that the level of LSF expression is useful to identify a subject with HCC. Accordingly, a subject amenable to treatment using the methods and compositions as disclosed herein can be identified by measuring the level of LSF in a biological sample obtained from the subject and if the level of LSF in the biological sample from the subject is higher by a statistically significant amount relative to a reference level of LSF, the subject likely is at risk of having HCC, and accordingly, can be administered a composition comprising at least one small molecule inhibitor of LSF selected from any of formula (I) to (IV) as disclosed herein.

A subject is identified as suffering from HCC or having a disordered characterized by increased LSF expression, when the expression level of LSF in a biological sample obtained from the subject is higher relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. The extent of increase in LSF expression can indicate the grades and stages of HCC (See Yoo et al., PNAS, 2010; 107; 8357-8362). Accordingly, subjects identified with HCC or having a disorder characterized by increased LSF expression can be treated with an effective dose of a pharmaceutical composition as disclosed herein comprising a LSF inhibitor selected from any of formula (I) to (IV) as disclosed herein to inhibit or delay progression of HCC.

In some embodiments, a biological sample is a tissue sample, e.g. a liver sample.

In some embodiments, the level of LSF in a biological sample is compared to a reference level, or a reference biological sample, such as a biological sample from adjacent liver tissue (not pathologically abnormal, or such as biological sample obtained from an age-matched normal control (e.g. an age-matched subject not having HCC or an age-matched normal healthy subject).

In other embodiments, in order to determine the therapeutic efficacy of the treatment (e.g. treatment of HCC), a reference level can be the level of LSF expression or the level of expression of LSF target genes measured at a previous time point from the same subject on a treatment regimen.

The methods of the present invention also are useful for monitoring a course of treatment being administered to a subject. The methods can be used to monitor both therapeutic treatment on symptomatic subject and prophylactic treatment on asymptomatic subject.

A treatment administered to a subject is considered to be effective if the level of expression of LSF or of LSF target genes in a biological sample obtained from the subject is decreased relative to a reference level of LSF by at least about 20%, at least about 30%, at least about 40%, at least about 50%, at least about 60%, at least about 70%, at least about 80%, at least about 90%, at least about 95%, at least about 98%, about 99% or about 100%. In such embodiments, the reference level is the measurement of LSF or of LSF target genes at a previous time point from the same subject who has been administered to the treatment regimen. Based on the outcome of treatment, the dosage and frequency of administration using the methods and compositions as disclosed herein can be adjusted accordingly by one of skill in the art.

In one embodiment, the biological sample for analysis is a liver sample, wherein the sample comprises at least one cell. One can use any immunoassay to determine the level of LSF or of LSF target genes in a biological sample, such as ELISA or immunohistochemical methods of detecting LSF or LSF target genes which are commonly known in the art and are encompassed for use in the present invention.

In some embodiments, a method of determining the presence and/or level of LSF in a biological sample from a subject comprises performing a binding assay. Any reasonably specific binding partner can be used. For example, the binding partner is labeled. For example, the assay is an immunoassay, especially between LSF and an antibody that recognizes LSF, especially a labeled antibody. It can be an antibody raised against part or all of it, such as a monoclonal antibody or a polyclonal antiserum of high specificity for LSF. In some embodiments, the antibodies is specific to mammalian LSF, such as human LSF.

Thus, any anti-LSF antibody can be used in the method to determine the presence and/or level of LSF in a biological sample, which can be used to detect the increased or decreased level of LSF present in a diagnostic sample. Such antibodies can be raised by any of the methods well known in the immunodiagnostics field.

In some embodiments, an immunoassay is carried out by measuring the extent of the protein/antibody interaction of the LSF/antibody interaction. Any known method of immunoassay may be used. A sandwich assay or ELISA is preferred. In this method, a first antibody to the marker protein is bound to the solid phase such as a well of a plastics microtitre plate, and incubated with the sample and with a labeled second antibody specific to the protein to be assayed. Alternatively, an antibody capture assay could be used. In some embodiments, a biological test sample is allowed to bind to a solid phase, and the anti-LSF protein antibody is then added and allowed to bind. After washing away unbound material, the amount of antibody bound to the solid phase is determined using a labeled second antibody against the first.

In some embodiments, a label is preferably an enzyme. The substrate for the enzyme may be, for example, color-forming, fluorescent or chemiluminescent.

In some embodiments, a binding partner, e.g. an antibody or a ligand binding to LSF in the binding assay is preferably a labeled specific binding partner, but not necessarily an antibody. The binding partner will usually be labeled itself, but alternatively it may be detected by a secondary reaction in which a signal is generated, e.g. from another labeled substance.

In some embodiments, one can use an amplified form of assay, whereby an enhanced "signal" is produced from a relatively low level of protein to be detected. One particular form of amplified immunoassay is enhanced chemiluminescent assay. Conveniently, the antibody is labeled with horseradish peroxidase, which participates in a chemiluminescent reaction with luminol, a peroxide substrate and a compound which enhances the intensity and duration of the emitted light, typically 4-iodophenol or 4-hydroxycinnamic acid.

In another embodiment, an amplified immunoassay can be used which is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, in some embodiments, one method to determine the level of LSF in a biological sample is to use a two dimensional gel electrophoresis to yield a stained gel and the increased or decreased level of the protein detected by an increased an increased or decreased intensity of a protein-containing spot on the stained gel, compared with a corresponding control or comparative gel.

In some embodiments, methods to determine the amount of LSF in a biological sample does not necessarily require a step of comparison of the level of LSF with a control sample (e.g. from a normal healthy subject), but it can be carried out with reference either to a control or a comparative sample. Thus, in relation to HCC, measuring the amount of LSF in a biological sample can be used to determine the stage of progression, if desired with reference to results obtained earlier from the same subject or by reference to standard values that are considered typical of the stage of the disease.

In this way, the invention can be used to determine whether, for example after treatment of the subject with a LSF inhibitor, the disease has progressed or not. The result can lead to a prognosis of the outcome of the disease.

In some embodiments, one method to detect the presence and/or the level of LSF in a biological sample is to perform immunohistochemical assay on a biopsy sample, such as a liver sample. The methods for detecting the presence and/or a level of protein on a biopsy sample are well within the level of skill in the art. In alternative embodiments, the mRNA level of LSF in a biological sample is determined by quantitative PCR with primers designed according to the nucleotide sequence of LSF. The design for primers of LSF can be performed easily by one of the skill in the art.

In various embodiments, the level of LSF can be measured and used in combination with other biomarkers for HCC such as AFP to diagnose HCC in a subject. Other biomarkers for HCC include, but not limited to, those described, for example, in US 2013/0107227, content of which is incorporated herein by reference in its entirety.

All structures of any of formula (I) to (V) are provided herein for illustrative purpose and disclose a particular isomer. However, one of ordinary skill in the art will recognize all possible isomers of the structures of any of formula (I) to (V). Therefore, other isomers such as enantiomers of any of formula (I) to (V) are considered to fall within the scope of the invention. As used herein, the term "isomer" refers to a compound having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. The designations "R" and "S" are used to denote the absolute configuration of the molecule about its chiral center. The designations may appear as a prefix or as a suffix; they may or may not be separated from the isomer by a hyphen; they may or may not be hyphenated; and they may or may not be surrounded by parentheses. The designations "(+)" and "(−)" are employed to designate the sign of rotation of plane-polarized light by the compound, with (−) meaning that the compound is levorotatory (rotates to the left). A compound prefixed with (+) is dextrorotatory (rotates to the right). Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

In various embodiments, compounds of formula (I) to (V) include enantiomers, derivatives, prodrugs, and pharmaceutically acceptable salts thereof.

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

In some embodiments, prodrugs of compounds selected from any of formula (I) to (V) also fall within the scope of the invention. As used herein, a "prodrug" refers to a compound that can be converted via some chemical or physiological process (e.g., enzymatic processes and metabolic hydrolysis) to a compound selected from the group consisting of compounds of formula (I) to (V).

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech. ll:*345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "*Prodrugs*", *Br. J. Clin. Pharmac.* 28: 497-507 (1989), content of all of which is herein incorporated by reference in its entirety.

Compounds of formula (I) to (V) also include pharmaceutically acceptable salts thereof. As used herein, the term "pharmaceutically-acceptable salts" refers to the conventional nontoxic salts or quaternary ammonium salts of LSF inhibitors as disclosed herein, e.g., from non-toxic organic or inorganic acids. These salts can be prepared in situ in the administration vehicle or the dosage form manufacturing process, or by separately reacting a LSF inhibitor in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

In some embodiments, compounds of Formula (I)-(IV) or a pharmaceutical composition thereof as disclosed herein can be used in conjunction with other therapeutic treatment of HCC such as hepatointralesional ethanol injection, chemoembolization, radiofrequency ablation, cryosurgery, radiation therapy, percutaneous intralesional ethanol injection, transarterial chemoembolization, and radiotherapy.

In some embodiments of the various aspects disclosed herein, the composition or method can further comprise administering an additional anti-cancer therapy to the subject. For example, administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some embodiments of the various aspects disclosed herein, the treatment is administered to a subject currently receiving standard of care chemotherapeutics or other alternative anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of cancer by administering one or more compounds represented by Formula (I)-(IV) in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the anti-tumor activity of a chemotherapeutic agent or radiation therapy or increase the selective cytotoxicity of a chemotherapeutic agent.

The phrase "combination therapy" as described herein means administration of one or more compounds represented by Formula (I)-(IV) and a therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of one or more compounds represented by Formula (I)-(IV) in further combination with other compounds and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

In some embodiments, compounds represented by formula (I)-(IV) as disclosed herein or a pharmaceutical composition thereof can be used to treat HCC subjects who are not responsive to any prior treatment of HCC, or show little/no improvement from any prior treatment of HCC, e.g. continued progression or worsening of HCC. In such embodiments, the HCC subjects can be treated again with the previous therapeutic method in combination with an inhibitor of LSF. In alternative embodiments, they can be administered with a LSF inhibitor or a pharmaceutical composition thereof alone, or concurrently with alternative therapeutic methods.

It has been previously reported that LSF is a downstream gene of astrocyte elevated gene-1 (AEG-1), which is overexpressed in >90% of human HCC patients and induces chemoresistance of HCC to a chemotherapeutic agent, such as 5-fluorouracil (5-FU). Accordingly, in some embodiments, an inhibitor of LSF described herein can be administered prior to, or concurrently with at least one chemotherapeutic agent such as 5-FU. Other exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In one embodiment, a LSF inhibitor or a pharmaceutical composition thereof as disclosed herein can be combined with Sorafenib for treatment of HCC.

As a prophylactic measure against HCC recurrence or metastasis, compounds represented by formula (I)-(IV) as disclosed herein or a pharmaceutical composition thereof can be administered after surgery or after aforementioned treatments for HCC where solid tumors have been removed or eliminated. In some embodiments, subjects with resectable HCC can be treated with any of compounds represented by formula (I)-(IV) or a pharmaceutical composition thereof after hepatectomy or liver transplantation to prevent the recurrence of HCC.

Most cases of HCC are developed from either chronic infection with hepatitis B or hepatitis C virus (HBV or HCV, respectively), or hepatic cirrhosis due to alcoholism. Chronic hepatitis can progress into cirrhosis (a noncancerous liver disease associated with fibrosis and abnormal nodules), which increases the risk of developing HCC. Subjects with chronic hepatitis and/or cirrhosis, therefore form a high risk population. Accordingly, in some embodiments, any of compounds represented by formula (I)-(IV) can be used in conjunction with other therapeutic treatment for liver diseases such as infection with HBV, HCV or cirrhosis, as a preventive measure against the onset of HCC.

In some embodiments, any of compounds of formula (I) to (IV) as disclosed herein can be administered to a subject with a high risk of developing hepatocellular carcinoma. For example, subjects amenable to treatment by methods and compositions as disclosed herein, e.g. using an inhibitor of LSF, are subjects having a risk factor for HCC. Examples of risk factors for HCC include, but not limited to, HBV, HCV, chronic alcohol consumption, exposure to aflatoxin B1 in food (which is a liver carcinogenic chemical produced by a mold called *Aspergillus flavus* after exposure of food to a hot and humid environment), hepatic adenoma resulted from the use of female hormones (estrogens) and protein-building (anabolic) steroids, exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia. In some embodiments, a LSF inhibitor can be used alone or combined with other therapeutic treatment of the aforementioned diseases or disorders. In further embodiments, subjects who have been previously subjected to high risk of developing HCC can be continually treated with an inhibitor of LSF or a pharmaceutical composition thereof, even after they have discontinued treatment of liver diseases such as HBV, HCV or cirrhosis.

Other indications that can be contemplated for the use of LSF inhibitors of the invention as disclosed herein include diseases or disorders, in which expression and/or biological activity of LSF is up-regulated, e.g. by inflammatory cytokines, or in which it is desirable to decrease or inhibit LSF. Non-limiting examples of such diseases or disorders include HIV and inflammation-associated diseases including Alzheimer's disease.

It has been previously reported that LSF activates cell survival-regulating pathways, such as MEK/ERK and NF-κB pathways, and is up-regulated in various cancers (see Yoo et al., PNAS, 2010, 107; 8357-8362 and Kotarba et al., Cancer Lett. (2018), 28 (420), 72-79). Accordingly, in some embodiments, a LSF inhibitor disclosed herein can be used alone or in combination with chemotherapeutic agents for treatment of other various cancers such as brain cancer, breast cancer, colon cancer, cervical cancer, head and neck squamous cell carcinoma, lung cancer, pancreatic cancer, ovarian cancer, and thyroid cancer. Exemplary chemotherapeutic agents include Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In some embodiments, diseases or disorders associated with LSF-induced MEK/ERK activation can be contemplated for treatment with a LSF inhibitor as disclosed herein alone or in combination with inhibitors of MEK/ERK pathway such as PD98059 and U0126.

In some embodiments, a subject amenable or suitable for treatment with a composition comprising any of compounds of formula (I) to (V) as disclosed herein can be selected based on an increased level of LSF expression in a biological sample, or tumor or cancer sample as compared to a control reference LSF expression level, e.g., in a normal non-cancerous sample. In some embodiments, a subject is at risk of having a cancer if the level of LSF expression in the biological sample from the subject is above a pre-determined reference LSF expression threshold level. In some embodiments, the reference LSF expression threshold level is based on the level of LSF expression in a non-cancer cell or non-tumor tissue, or a control cell line, or cells from a normal tissue sample, where the tissue sample is from adjacent, non-pathological tissue of the subject, or a biological tissue sample from a tissue matched, and species matched and age matched biological sample. In some embodiments, the reference level is based on a reference sample is from a non-cancer matched tissue sample.

In some embodiments, the level of LSF expression is measured in a biological sample comprising a tumor sample. In some embodiments, a biological sample obtained from the subject comprises cancer cells, and can be a biological sample which is serum plasma, blood or tissue sample. In some embodiments, a biological sample is selected from the group consisting of; a tissue sample; a tumor sample; a tumor cell; a biopsy sample; ex vivo cultivated sample; ex vivo cultivated tumor sample; surgically dissected tissue sample, blood sample, plasma sample, cancer sample, lymph fluid sample or primary ascite sample. In alternative embodiments, the biological sample includes, for example blood, plasma, serum, urine, spinal fluid, plural fluid, nipple aspirates, lymph fluid, external secretions of the skin, respiratory, internal and genitourinary tracts, bile, tears, sweat, saliva, organs, milk cells and primary ascite cells, biopsy tissue sample, a cancer biopsy tissue sample, an in vitro or ex vivo cultivated biopsy tissue sample.

Screening for HCC: In some embodiments, a subject amenable to treatment according to the methods as disclosed herein is screened for HCC. A convention biomarker for HCC is alpha-fetoproteins (AFP). Yang et al., 123 J. Cancer Res Clin Oncol. 357 (1997). Individuals with elevated serum levels of AFP can be an indication of hepatocellular carcinoma. Other biomarkers for HCC include, but not limited to, the ones disclosed in the U.S. Patent Application Nos.: US2009/0317844, US2010/0015605, US 2010/0120631, and International Patent Application Nos.: WO 2010/048304, WO 2005/0233392, and WO2008/056854, which are incorporated herein in their entirety by reference. One of the skill in the art can easily perform the measurement of mRNA or protein level of these biomarkers in a biological sample e.g. blood from a subject such as human, using the standard methods in the art. In some embodiments, a subject identified with HCC is administered a LSF inhibitor according to the methods as disclosed herein.

As disclosed herein, a subject with HCC can also be selected by detecting a high level of LSF expression in a biological sample such as a liver sample from the subject as compared to a reference level. In one embodiment, the reference level is the level of LSF in a normal healthy subject.

In addition, a biopsy can be used to diagnose HCC. (Walter et al., 24 Curr Opin Gastroenterol. 312 (2008)). Other diagnostic methods for HCC known to one of the skill in the art include imaging methods such as ultrasound, computed tomography (CT) scan and MRI (Scholmerich et al., 52 Gut. 1224 (2004)). In various embodiments, a pharmaceutical composition comprising compounds of Formula (I)-(IV) as disclosed herein can be administered to a subject diagnosed with HCC or HCC susceptibility.

In some embodiments, a subject undergoing treatment of HCC, e.g. chemotherapy, can be treated alone or in combination with the methods and compositions of the invention as disclosed herein. For example, the inventors have previously reported in collaboration with other scientists that inhibition of LSF can increase sensitivity of HCC cells to chemotherapeutic agents, such as, but not limited to 5-fluorouracil (5-FU) (see Yoo et al., PNAS, 2010; 107; 8357-8362). Accordingly, in some embodiments, subjects with no response to current HCC therapeutic treatment, e.g. HCC subjects who have shown chemoresistance to chemotherapeutic agents such as 5-FU, can be administered with a LSF small molecule inhibitor as disclosed herein using the methods and compositions of the invention, prior to or concurrently with chemotherapy.

Detection of hepatocellular carcinoma can be difficult as most of the patients who develop this tumor have no symptoms other than those inflicted with their longstanding liver disease. The onset of abdominal pain, weight loss, early satiety, jaundice and a palpable mass in the upper abdomen usually indicate an advanced cancer. Accordingly, in some embodiments, subjects at high risk for HCC can be administered an inhibitor of LSF as disclosed herein in the methods and compositions for prevention of the development of HCC (e.g. prophylactic treatment). For example, subjects highly susceptible to HCC are subjects with HBV, HCV, chronic alcohol consumption, an exposure to aflatoxin B1 in food (which is a liver carcinogenic chemical produced by a mold called *Aspergillus flavus* after food has been stored in a hot and humid environment), hepatic adenoma resulted from the use of female hormones (estrogens) and protein-building (anabolic) steroids, an exposure to thorotrast (a previously used contrast agent for imaging, which caused a cancer of the blood vessels in the liver called hepatic angiosarcoma), hepatic angiosarcomas (resulted from a prolonged exposure to vinyl chloride, a compound used in the plastics industry), hereditary hemochromatosis (a disorder that causes the body to accumulate excessive amounts of iron), emphysema and cirrhosis (resulted from alpha 1 anti-trypsin deficiency) and hereditary tyrosinemia.

In additional embodiments, for prophylactic treatment (e.g. to prevent reoccurrence of HCC), subjects who was diagnosed with HCC before and HCC is in remission can be selected for treatment with a LSF inhibitor as disclosed herein using the methods and compositions of the invention. For example, subjects who had their HCC tumor removed by hepatectomy and/or liver transplantation, or who had their HCC tumor reduced or stabilized by other therapeutic methods are amenable to administration of a LSF inhibitor or a pharmaceutical composition thereof as disclosed herein.

In yet other embodiments, subjects amenable to therapeutic treatment with methods and compositions of the invention, e.g. using a LSF inhibitor as disclosed herein, include subjects in need of inhibition of LSF. For example, it has been reported that HIV patients, or individuals in need for a decrease in inflammatory response or immune function can be treated by inhibiting LSF (Bovolenta et al, 163 J. Immuno. 6892, (1999), U.S. Patent Application No.:

US2009/0081183 and International Application No.: WO1998/36641, which are incorporated herein in their entirety by reference). Accordingly, a LSF inhibitor of the invention as disclosed herein can be administered alone, or concurrently with other LSF inhibitors such as IL2, or peptides, antibodies or antisense RNA against LSF, to subjects in which inhibition of LSF is desirable, such as HIV.

In still another embodiment, a subject who has other cancers such as breast cancer but has an up-regulated expression of LSF as compared to a reference level can be selected for therapeutic treatment with methods and compositions of the invention using a LSF inhibitor as disclosed herein. In some embodiments, a reference level is the expression of LSF in a normal healthy subject. In other embodiments, a reference level is the expression of LSF in the same subject measured at the previous time point of the treatment regime. Other cancer indications that can be used for the purposes of the invention include brain cancer, colon cancer, head and neck squamous cell carcinoma, lung cancer, pancreatic cancer, cervical cancer, ovarian cancer, and thyroid cancer.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Amount of compounds of Formula (I)-(V) in the pharmaceutical composition can be based on weight, moles, or volume. In some embodiments, the pharmaceutical composition comprises at least 0.0001% of compounds of Formula (I)-(V). In some embodiments, the pharmaceutical composition comprises at least 0.1% of compounds of Formula (I)-(V). In some embodiments, the pharmaceutical composition comprises at least 0.5% of compounds of Formula (I)-(V). In some embodiments, the pharmaceutical composition comprises at least 1% of compounds of Formula (I)-(V). In some embodiments, the pharmaceutical composition comprises at least 2% of compounds of Formula (I)-(V). In some embodiments, the pharmaceutical composition comprises at least 3% of compounds of Formula (I)-(V). In some embodiments, the pharmaceutical composition comprises at least 4% of compounds of Formula (I)-(V). In some embodiments, the pharmaceutical composition comprises at least 5% of compounds of Formula (I)-(V). In some embodiments, the pharmaceutical composition comprises at least 10% of compounds of Formula (I)-(V). In some embodiments, the pharmaceutical composition comprises 0.01%-99% of the compounds of Formula (I)-(V). In some embodiments, the pharmaceutical composition comprises 0.05%-90% of the compounds of Formula (I)-(V). In some embodiments, the pharmaceutical composition comprises 0.1%-85% of the compounds of Formula (I)-(V). In some embodiments, the pharmaceutical composition comprises 0.5%-80% of the compounds of Formula (I)-(V). In some embodiments, the pharmaceutical composition comprises 1%-75% of the compounds of Formula (I)-(V). In some embodiments, the pharmaceutical composition comprises 2%-70% of the compounds of Formula (I)-(V). In some embodiments, the pharmaceutical composition comprises 3%-65% of the compounds of Formula (I)-(V). In some embodiments, the pharmaceutical composition comprises 4%-60% of the compounds of Formula (I)-(V). In some embodiments, the pharmaceutical composition comprises 5%-50% of the compounds of Formula (I)-(V).

It will also be appreciated that certain of the compounds of Formula (I)-(V) can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compounds of Formula (I)-(V) which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the compounds of Formula (I)-(V) together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the compounds of Formula (I)-(V), the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compounds of Formula (I)-(V) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosterate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

The compounds of Formula (I)-(V) can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compounds of Formula (I)-(V) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of Formula (I)-(V) with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or nonaqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

Another aspect of the present invention relates to pharmaceutical compositions for treatment of diseases or disorders where it is therapeutically beneficial to inhibit LSF, e.g hepatocellular carcinoma. In some embodiments, a pharmaceutical composition of the invention comprises a therapeutically effective amount of at least one LSF inhibitor selected from any of the compounds represented by formula (I) to (V) disclosed herein. In one embodiment, a LSF inhibitor is a compound of formula (I). In some embodiments, a LSF inhibitor is a compound selected from the group consisting of compounds of formula (II) to (IV). In some embodiments, a LSF inhibitor is the compound FQI-37. In some embodiments, a LSF inhibitor is FQI-36, FQI-38, FQI-35, FQI-30, FQI-31, FQI-Urea, FQI-39, FQI-41, FQI-42, Thio-FQI-1, Tri-FQI-1. In various embodiments, a LSF inhibitor is an enantiomer, a prodrug, a derivative, or a pharmaceutically acceptable salt of a compound of any of formula (I) to (V).

A LSF inhibitor as disclosed herein selected from any of formula (I) to (V) can be used in an amount of about 0.001 to 10 mg/kg of body weight or about 0.005 to 8 mg/kg of body weight or about 0.01 to 6 mg/kg of body weight or about 0.1 to 0.2 mg/kg of body weight or about 1 to 2 mg/kg of body weight. In some embodiments, an inhibitor of LSF can be used in an amount of about 0.1 to 1000 µg/kg of body weight or about 1 to 100 µg/kg of body weight or about 10 to 50 µg/kg of body weight. In some embodiments, a LSF inhibitor as disclosed herein selected from any of formula (I) to (V) can be used at a concentration of about 0.001 mg/ml or 0.1 mg/ml or a higher concentration of 0.1 mg/ml. In some embodiments, a pharmaceutical composition comprises at least one LSF inhibitor at a concentration of about 0.01 µM to 300 µM, or about 0.1 µM to 150 µM, or about 1 µM to 50 µM, or about 1 µM to 25 µM. The dosage may vary within this range depending upon the dosage form employed and the route of administration utilized. In some embodiments, a pharmaceutical composition does not comprise LSF inhibitors of Formula (V). In some embodiments, a pharmaceutical composition does not comprise LSF inhibitors described in U.S. application Ser. No. 15/713,956, U.S. Pat. Nos. 9,802,948, 9,815,845, 9,597,325 and WO 2012/050985 which are incorporated herein in their entirety by reference.

Depending on routes of administration, one of skill in the art can determine and adjust an effective dosage of a LSF inhibitor disclosed herein to a subject such as a human subject accordingly, by determining pharmacokinetics and bioavailability of a LSF inhibitor and analyzing dose-response relationship specific to a LSF inhibitor in animal models such as a mouse.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

The data obtained from the cell culture assays and animal studies can be used in formulating a range of dosage for use in humans. The therapeutically effective dose can be determined by one of ordinary skill in the art, e.g. using cell culture assays. An effective dose of a LSF inhibitor can be determined in an animal model by measuring the tumor weight and tumor volume over the course of treatment with a LSF inhibitor as compared to no treatment. In some embodiments, a dosage comprising a LSF inhibitor is considered to be effective if the dosage inhibits or decreases the growth of tumor weight and/or tumor volume by at least about 15%, at least about 20%, at least about 30%, at least about 40%, at least about 50%, at least about 60%, at least about 70%, at least about 80%, at least about 90%, 95%, 99% or even 100%, as compared to a control (e.g. in the absence of a LSF inhibitor). In some embodiments, a therapeutically effective amount of a LSF inhibitor administered to a subject is dependent upon factors known to a person of ordinary skill, including bioactivity and bioavailability of a LSF inhibitor (e.g. half-life and stability of a LSF inhibitor in the body), chemical properties of a LSF inhibitor (e.g molecular weight, hydrophobicity and solubility); route and frequency of administration, time of administration (e.g. before or after a meal), and the like. Further, it will be understood that the specific dose of the pharmaceutical composition comprising a LSF inhibitor as disclosed herein to provide the therapeutic or prophylactic benefits can depend on a variety of factors including physical condition of the subject (e.g. age, gender, weight), medical history of the subject (e.g. medications being taken, other diseases or disorders) and clinical condition of the subject (e.g. health condition, stage of the disease). The precise dose of a pharmaceutical composition comprising a LSF inhibitor can be determined by methods known to a skilled artisan such as pharmacologists and physicians.

According to the invention, a LSF inhibitor as disclosed herein selected from any of formula (I) to (V) can be administered prophylactically or therapeutically to a subject prior to, simultaneously or sequentially with other therapeutic regimens or agents (e. g. multiple drug regimens), in a therapeutically effective amount. In some embodiments, a LSF inhibitor administered concurrently with other therapeutic agents can be administered in the same or different compositions.

The phrase "racemic mixture" refers to a mixture of the two enantiomers of one compound. An ideal racemic mixture is one wherein there is a 50:50 mixture of both enantiomers of a compound such that the optical rotation of the (+) enantiomers cancels out the optical rotation of the (−) enantiomers. In some embodiments, a pharmaceutical composition for treatment of cancer, e.g., HCC as disclosed herein comprises a compound of FQI-37. In some embodiments, a pharmaceutical composition for treatment of cancer, e.g., HCC as disclosed herein comprises the compound FQI-36, FQI-38, FQI-35, FQI-30, FQI-31, FQI-Urea, FQI-39, FQI-41, FQI-42, Thio-FQI-1, Tri-FQI-1 or enantiomers, prodrugs, derivatives or pharmaceutically acceptable salts thereof.

In some embodiments, a pharmaceutical composition comprising at least one LSF inhibitor further comprises a second therapeutic agent. In one embodiment, the second therapeutic agent is a chemotherapeutic agent such as Sorafenib or 5-FU. In some embodiments, the second therapeutic agent is a second LSF inhibitor, e.g. a compound selected from any of formula (I) to (V). In some embodiments, a second LSF inhibitor is an enantiomer of a first LSF inhibitor as disclosed herein. In other embodiments, the second therapeutic agent is a therapeutic for liver diseases such as HBV, HCV and cirrhosis.

In prophylactic applications, pharmaceutical compositions (or medicaments) comprising a LSF inhibitor can be administered to a subject susceptible to, or otherwise at risk of, a disease or disorder mediated by elevated levels of LSF in an amount sufficient to eliminate or reduce the risk or delay the onset of the disease. In one embodiment, the disease or disorder to be prevented is hepatocellular carcinoma (HCC). As most HCCs are generated from the background of hepatitis B virus (HBV) or hepatitis C virus (HCV), a subject with HBV or HCV can be subjected to an effective amount or dose of a pharmaceutical composition comprising a LSF inhibitor described herein. In one embodiment, a pharmaceutical composition of the invention disclosed herein comprises a compound of formula (I)-(IV), or enantiomers, prodrugs, derivatives or pharmaceutically acceptable salts thereof. In some embodiments, an effective amount or dose of a pharmaceutical composition comprising a LSF inhibitor disclosed herein can be administered to a subject at high risk of HCC. In additional embodiments, a pharmaceutical composition further comprises a second therapeutic agent, e.g. therapeutics to treat high-risk factors such as liver diseases (e.g HBV). Representative high-risk factors of HCC include hepatic cirrhosis, chronic alcohol consumption, (prolonged) exposure to liver carcinogenic chemicals such as aflatoxin B1 in food, thorotrast in diagnostic contrast agent and vinyl chloride, hepatic adenoma, hepatic angiosarcoma, hepatic angiosarcomas, hereditary hemochromatosis, emphysema and cirrhosis resulted from alpha 1 anti-trypsin deficiency, and hereditary tyrosinemia. In various embodiments, individuals that have discontinued treatment for high-risk factors of HCC can still be subjected to a pharmaceutical composition comprising an effective dose of compound selected from any of formula (I) to (IV) as disclosed herein for prevention of development of HCC. For such embodiments, an effective dose of a LSF inhibitor can be higher or lower than the previous dosage.

In therapeutic applications, according to the invention provided herein, when an effective amount or effective dose of a pharmaceutical composition comprising a LSF inhibitor selected from any of formula (I) to (IV) of the present invention is administered to the subject with cancer, e.g. hepatocellular carcinoma, progression of cancer, e.g. HCC, can be delayed or inhibited. In some embodiments, administration of an effective amount or effective dose of a pharmaceutical composition comprising a LSF inhibitor selected from any of formula (I) to (V) to a subject with hepatocellular carcinoma can inhibit or delay progression of HCC. In further embodiments, treating subjects with an effective dose of a pharmaceutical composition comprising a LSF inhibitor can prevent or delay metastasis of HCC in the subject. In some embodiments, a LSF inhibitor used for therapeutic treatment of various diseases, e.g. HCC, using the methods and compositions disclosed herein is the compound FQI-37. In some embodiments, a LSF inhibitor used for therapeutic treatment of various diseases, e.g. HCC, using the methods and compositions disclosed herein is the compound FQI-36, FQI-38, FQI-35, FQI-30, FQI-31, FQI-Urea, FQI-39, FQI-41, FQI-42, Thio-FQI-1, Tri-FQI-1 or enantiomers, prodrugs, derivatives or pharmaceutically acceptable salts thereof.

In therapeutic applications, a relatively high dosage in relatively short intervals is sometimes required until progression of the disease is reduced or terminated, or until the subject shows partial or complete amelioration of symptoms of disease. Thereafter, the subject can be administered a prophylactic regime. For example, subjects with HCC can be treated with a LSF inhibitor as disclosed herein at an effective dose in a therapeutic regimen accordingly to prevent or delay the progression of HCC or metastasis. In other embodiments, a LSF inhibitor can be administered using the methods and compositions as disclosed herein to chemotherapy subjects in order to increase sensitivity to chemotherapy. In some embodiments, an inhibitor of LSF as disclosed herein can be administered to subjects prior to, concurrently with, or sequentially to treatment with chemotherapeutic drugs, e.g. Sorafenib. In further embodiments, HCC subjects selected for other therapeutic procedures or surgeries, such as hepatectomy, intralesional ethanol injection, or chemoembolization, can be subjected to a treatment with a LSF inhibitor as disclosed herein. For example, a pharmaceutical composition of the invention can be administered prior to, during or after therapeutic procedures. Route of administration can vary with therapeutic procedures or surgeries and can be determined by a skilled artisan. In yet another embodiment, compositions and methods of the invention can be used as an adjuvant therapy.

In some embodiments, the subject is a human, and in alternative embodiments the subject is a non-human mammal. Treatment dosages need to be titrated to optimize safety and efficacy. The amount of a LSF inhibitor depends on the stage of the disease, e.g. HCC as well as whether a second therapeutic agent is also administered. The second therapeutic agent can be an agent to treat a different disease or disorder. In some embodiments, the second therapeutic agent can be a chemotherapeutic agent such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). In alternative embodiments, the second therapeutic agent can be a second LSF inhibitor. In some embodiments, a second LSF inhibitor can be selected from the group consisting of compounds of Formula (I) to (IV), and enantiomers, prodrugs and pharmaceutically acceptable salts thereof. In one embodiment, a second LSF inhibitor can be an enantiomer of a first LSF inhibitor. In further embodiments, a second therapeutic agent is another therapeutics to target another disease, or another disorder, or a different symptom. In combination with other therapeutics, the dosage of a LSF inhibitor can be reduced, compared to the standard dosage of a LSF inhibitor when administered alone.

In some embodiments, the frequency of administration can vary significantly from once a day, once every other day, once every 3 days, once weekly, once monthly to once a year, depending on the disease of cancer (e.g., stage of cancer) such as HCC stage, and/or mode of administration.

Generally, effective dosages and dosing schedules can be adjusted based on, for example, the outcome of the treatment such as whether the progression rate of HCC is slower or terminated, or whether at least one of the symptoms associated with HCC is reduced. In accordance with the teachings provided herein, the effectiveness of the treatment can be monitored by obtaining a biological sample from a subject, e.g. a blood serum sample, and determining the level of biomarkers for HCC, such as AFP in the serum sample, using methods well known in the art and the diagnostic methods. The efficacy of the treatment can also be monitored by imaging modalities such as CT scan, MRI, ultrasound, and the like that are known to a skilled artisan.

In some embodiments, the daily dose administered to a subject in a form of a bolus composition comprising a LSF inhibitor can be given in a single dose, in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease. It is also within the skill of the art to start doses at levels lower than required to achieve the desired therapeutic effect and to gradually increase the dosage until the desired effect is achieved.

In various embodiments, a LSF inhibitor selected from any of formula (I) to (IV) can be a pro-drug, where it is activated by a second agent. Accordingly, in such embodiments, administration of such the second agent which activates the pro-drug into its active form can be administered the same time, concurrent with, or prior to, or after the administration of the pharmaceutical composition comprising a LSF inhibitor as disclosed herein.

In some embodiments, a LSF inhibitor selected from any of formula (I) to (IV) as disclosed herein is often administered as pharmaceutical compositions comprising an active therapeutic agent, i.e. a LSF inhibitor, and a variety of other pharmaceutically acceptable components. See Remington's Pharmaceutical Science (15th ed., Mack Publishing Company, Easton, Pa., 1980). The formulation of the compositions depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, non-therapeutic, non-immunogenic stabilizers and the like. However, some reagents suitable for administration to animals may not necessarily be used in compositions for human use.

Exemplary embodiments of the various aspects disclosed herein are as follows:

Embodiment 1: A compound of Formula (I):

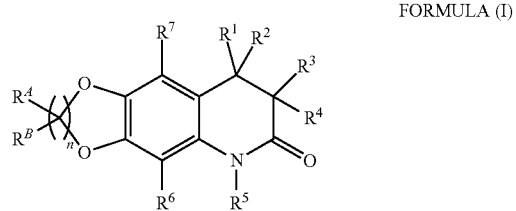

FORMULA (I)

wherein: $R^1$ is an aryl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$alkyl)amino or di($C_1$-$C_6$alkyl)amino; $R^2$, $R^3$ and $R^4$ are each independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino; or $R^2$ and $R^3$ together form a second bond between the carbons to which they are attached; $R^5$ is hydrogen, $C_1$-$C_6$ alkyl, $C_1$-$C_6$ haloalkyl, $C_1$-$C_6$ heteroalkyl, aryl, heteroaryl, or halogen; $R^6$ and $R^7$ are each independently selected from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl; $R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy; each $R^A$ and $R^B$ is selected independently from the group consisting of hydrogen, halogen, $OR^{3A}$, $NR^{3A}R^{4A}$, $SR^{3A}$, $SO_2R^{3A}$, $C_1$-$C_6$alkyl, $C_1$-$C_6$haloalkyl, $C_1$-$C_6$ heteroalkyl, aryl and heteroaryl; and n is 2, 3 or 4, or enantiomers, prodrugs, derivatives, and pharmaceutically acceptable salts thereof.

Embodiment 2: A compound of Formula (II):

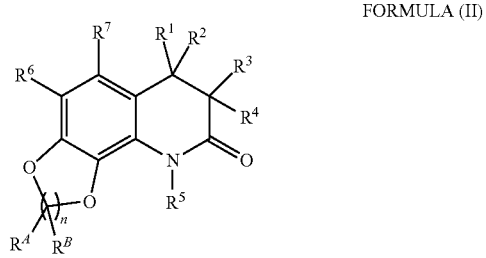

FORMULA (II)

wherein: $R^1$, $R^2$, $R^3$ and $R^4$ are each independently selected from the group consisting of hydrogen, halogen, $C_1$-$C_6$ alkyl, $C_1$-$C_6$ haloalkyl, $C_1$-$C_6$ heteroalkyl, $OR^{3A}$, $SR^{3A}$, $SO_2R^{3A}$, $NR^{3A}R^{4A}$, halogen, heteroaryl, and aryl, wherein the alkyl, haloalkyl, heteroalkyl, heteroaryl, and aryl can be optionally substituted with halogen, $C_1$-$C_6$alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino; or $R^2$ and $R^3$ together form a second bond between the carbons to which they are attached; $R^5$ is hydrogen, $C_1$-$C_6$ alkyl, $C_1$-$C_6$ haloalkyl, $C_1$-$C_6$ heteroalkyl, aryl, heteroaryl, or halogen; $R^6$ and $R^7$ are each independently selected from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl; $R^{3A}$ and $R^{4A}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy; each $R^A$ and $R^B$ is selected independently from the group consisting of hydrogen, halogen, $OR^{3A}$, $NR^{3A}R^{4A}$, $SR^{3A}$, $SO_2R^{3A}$, $C_1$-$C_6$ alkyl, $C_1$-$C_6$ haloalkyl, $C_1$-$C_6$ heteroalkyl, aryl and heteroaryl; and n is 1, 2, 3, or 4, or enantiomers, prodrugs, derivatives, and pharmaceutically acceptable salts thereof.

Embodiment 3: The compound of embodiment 2, wherein $R^1$ is an aryl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl) amino.

Embodiment 4: The compound of any one of embodiments 1-3, wherein $R^1$ is an aryl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino.

Embodiment 5: The compound of any one of embodiments 1-4, wherein $R_1$ is an aryl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino.

Embodiment 6: The compound of any one of embodiments 1-5, wherein $R^1$ is an aryl substituted with at least one $C_1$-$C_6$ alkoxy and at least one halogen, amino ($NH_2$), mono ($C_1$-$C_6$ alkyl)amino or di($C_1$-$C_6$ alkyl)amino.

Embodiment 7: The compound of any one of embodiments 1-6, wherein $R^1$ is an aryl substituted with at least one $C_1$-$C_6$ alkoxy and at least one halogen or di($C_1$-$C_6$ alkyl)amino.

Embodiment 8: The compound of any one of embodiments 1-3, wherein $R^1$ is a phenyl substituted with at least one $OR^{3A}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino.

Embodiment 9: The compound of any one of embodiments 1-4, wherein $R_1$ is a phenyl substituted with at least one $C_1$-$C_6$ alkoxy and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino.

Embodiment 10: The compound of any one of embodiments 1-5, wherein $R^1$ is a phenyl substituted with at least one $C_1$-$C_6$ alkoxy and at least one halogen, amino ($NH_2$), mono($C_1$-$C_6$ alkyl)amino or di($C_1$-$C_6$ alkyl)amino.

Embodiment 11: The compound of any one of embodiments 1-6, wherein $R^1$ is a phenyl substituted with at least one $C_1$-$C_6$ alkoxy and at least one halogen or di($C_1$-$C_6$ alkyl)amino.

Embodiment 12: The compound of any one of embodiments 1-3, wherein $R^1$ is an aryl substituted with an $OR^{3A}$.

Embodiment 13: The compound of embodiment 11, wherein $R^1$ is a phenyl substituted with an $OR^{3A}$.

Embodiment 14: The compound of embodiment 12, wherein $R^1$ is a phenyl substituted with a $C_1$-$C_6$ alkoxy.

Embodiment 15: The compound of embodiment 1, wherein $R^1$ is selected from the group consisting of

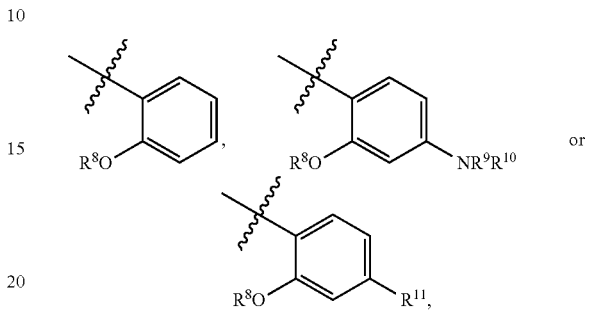

wherein $R^8$ is $C_1$-$C_6$ alkyl or $C_1$-$C_8$ cycloalkyl; $R^9$ and $R^{10}$ are independently H or $C_1$-$C_6$ alkyl; and $R^{11}$ is halogen or $C_1$-$C_6$ haloalkyl.

Embodiment 16: The compound of embodiment 14, wherein $R^1$ is

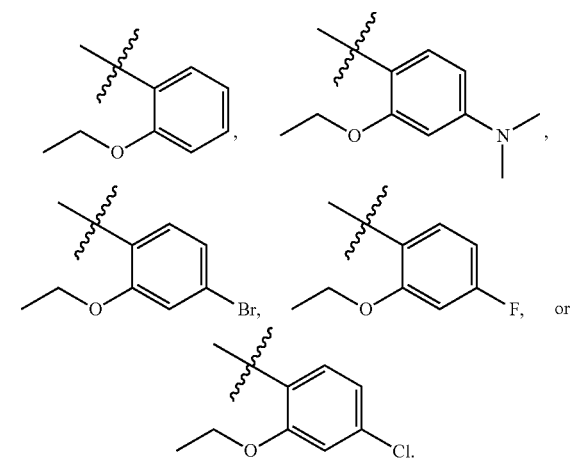

Embodiment 17: The compound of embodiment 16, wherein $R^1$ is

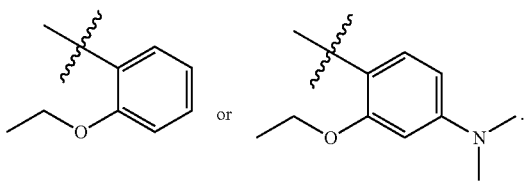

Embodiment 18: The compound of any one of embodiments 1-17, wherein $R^2$, $R^3$ and $R^4$ are independently selected from the group consisting of H, halogen, $C_1$-$C_6$ alkyl, $C_1$-$C_6$ haloalkyl, and $C_1$-$C_6$ alkoxy.

Embodiment 19: The compound of any one of embodiments 1-18, wherein $R^2$, $R^3$ and $R^4$ are independently selected from the group consisting of H or halogen.

Embodiment 20: The compound of any one of embodiments 1-19, wherein $R^2$, $R^3$ and $R^4$ are H.

Embodiment 21: The compound of any one of embodiments 1-20, wherein $R^5$ is hydrogen or $C_1$-$C_6$ alkyl.

Embodiment 22: The compound of any one of embodiments 1-21, wherein $R^5$ is H.

Embodiment 23: The compound of any one of embodiments 1-22, wherein $R^6$ and $R^7$ are independently selected from the group consisting of hydrogen, halogen, $C_1$-$C_6$ alkyl or $C_1$-$C_6$ haloalkyl.

Embodiment 24: The compound of any one of embodiments 1-23, wherein $R^6$ and $R^7$ are H.

Embodiment 25: The compound of any one of embodiments 1-24, wherein $R^{34}$ is hydrogen, $C_1$-$C_6$ alkyl, cycloalkyl or heterocyclyl, wherein the alkyl, cycloalkyl and heterocyclyl can be optionally substituted with halogen, $C_1$-$C_4$ alkyl, $C_1$-$C_4$haloalkyl, $C_1$-$C_4$ heteroalkyl or $C_1$-$C_6$ alkoxy.

Embodiment 26: The compound of any one of embodiments 1-25, wherein $R^{34}$ is a $C_1$-$C_6$ alkyl or $C_3$-$C_8$ cycloalkyl.

Embodiment 27: The compound of any one of embodiments 1-26, wherein each $R^A$ and $R^B$ is independently H, Br, Cl, F or I.

Embodiment 28: The compound of any one of embodiments 1-27, wherein n is 2.

Embodiment 29: The compound of embodiment 2, wherein the compound is (FQI-36) or (FQI-38).

Embodiment 30: The compound of embodiment 1, wherein the compound is (FQI-35) or (FQI-37).

Embodiment 31: A compound of Formula (III):

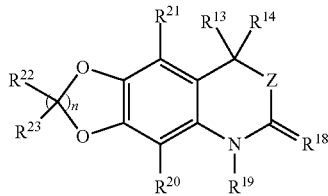

FORMULA (III)

wherein: Z is $NR^{15}$ or $CR^{16}R^{17}$; $R^{13}$, $R^{14}$, $R^{15}$, $R^{16}$ and $R^{17}$ are each independently selected from the group consisting of hydrogen, halogen, $C_1$-$C_6$ alkyl, $C_1$-$C_6$ haloalkyl, $C_1$-$C_6$ heteroalkyl, $OR^{34}$, $SR^{34}$, $SO_2R^{34}$, $NR^{34}R^{44}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_5$ alkenyl, amino ($NH_2$), mono($C_1$-$C_6$ alkyl)amino or di($C_1$-$C_6$ alkyl)amino; or $R^{14}$ and $R^{16}$ together form a second bond between the carbons to which they are attached; $R^{18}$ is O, S or $NR^{19A}$; $R^{19}$ is hydrogen, $C_1$-$C_6$ alkyl, $C_1$-$C_6$ haloalkyl, $C_1$-$C_6$ heteroalkyl, aryl, heteroaryl, or halogen; or $R^{19}$ and $R^{19A}$ together with the nitrogens they are attached to form an optionally substituted heterocyclyl or optionally substituted heteroaryl; $R^{20}$ and $R^{21}$ are each independently selected from the group consisting of hydrogen, halogen, $OR^{34}$, $NR^{34}R^{44}$, $SR^{34}$, $SO_2R^{34}$, $C_1$-$C_6$ alkyl, $C_1$-$C_6$ haloalkyl, $C_1$-$C_6$ heteroalkyl, aryl and heteroaryl; $R^{34}$ and $R^{44}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy; each $R^{22}$ and $R^{23}$ is selected independently from the group consisting of hydrogen, halogen, $OR^{34}$, $NR^{34}R^{44}$, $SR^{34}$, $SO_2R^{34}$, $C_1$-$C_6$ alkyl, $C_1$-$C_6$ haloalkyl, $C_1$-$C_6$ heteroalkyl, aryl and heteroaryl; and n is 1, 2, 3 or 4, or enantiomers, prodrugs, derivatives, and pharmaceutically acceptable salts thereof, provided: (i) when $R^{18}$ is O then n is not 1 or Z is $NR^{15}$; or (ii) when Z is $CR^{16}R^{17}$ and $R^{18}$ is O then $R^{19}$ and $R^{19A}$ together with the nitrogens they are attached to form an optionally substituted heterocyclyl or optionally substituted heteroaryl, or $R^{13}$ is an aryl substituted with $OR^{34}$, where $R^{34}$ is a cyclyl.

Embodiment 32: A compound of Formula (IV):

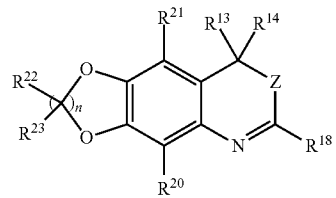

FORMULA (IV)

wherein: Z is $NR^{15}$ or $CR^{16}R^{17}$; $R^{13}$, $R^{14}$, $R^{15}$, $R^{16}$ and $R^{17}$ are each independently selected from the group consisting of hydrogen, halogen, $C_1$-$C_6$ alkyl, $C_1$-$C_6$ haloalkyl, $C_1$-$C_6$ heteroalkyl, $OR^{34}$, $SR^{34}$, $SO_2R^{34}$, $NR^{34}R^{44}$, halogen, heteroaryl, and aryl, wherein the alkyl, haloalkyl, heteroalkyl, heteroaryl, and aryl can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino; or $R^4$ and $R^{16}$ together form a second bond between the carbons to which they are attached; $R^{18}$ is $NQ_1Q_2$, wherein $Q_1$ and $Q_2$ are independently selected from the group consisting of hydrogen, alkyl, alkenyl, alkynyl, cycloalkyl or aryl optionally substituted with halogen, $C_1$-$C_4$ alkyl, $C_1$-$C_4$ haloalkyl, $C_1$-$C_4$ heteroalkyl or $C_1$-$C_6$ alkoxy or $Q_1$ and $Q_2$ together with the nitrogen they are attached to can form a heterocycly or heteroaryl, which can be optionally substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino; $R^{20}$ and $R^{21}$ are each independently selected from the group consisting of hydrogen, halogen, $OR^{34}$, $NR^{34}R^{44}$, $SR^{34}$, $SO_2R^{34}$, $C_1$-$C_6$ alkyl, $C_1$-$C_6$ haloalkyl, $C_1$-$C_6$ heteroalkyl, aryl and heteroaryl; $R^{34}$ and $R^{44}$ are each independently selected from the group consisting of hydrogen, $C_1$-$C_8$ alkyl, $C_2$-$C_8$ alkenyl, $C_2$-$C_8$ alkynyl, cycloalkyl, heterocyclyl, $C_1$-$C_8$ haloalkyl, $C_1$-$C_8$ heteroalkyl, heteroaryl, and aryl, wherein the alkyl, alkenyl, alkynyl, cycloalkyl, heterocyclyl, haloalkyl, heteroalkyl, heteroaryl, and aryl can be optionally substituted with halogen, $C_1$-$C_4$ alkyl, $C_1$-$C_4$ haloalkyl, $C_1$-$C_4$ heteroalkyl or $C_1$-$C_6$ alkoxy; each $R^{22}$ and $R^{23}$ is selected independently from the group consisting of hydrogen, halogen, $OR^{34}$, $NR^{34}R^{44}$, $SR^{34}$, $SO_2R^{34}$, $C_1$-$C_6$ alkyl, $C_1$-$C_6$ haloalkyl, $C_1$-$C_6$ heteroalkyl, aryl and heteroaryl; and n is 1, 2, 3 or 4, or enantiomers, prodrugs, derivatives, and pharmaceutically acceptable salts thereof.

Embodiment 33: The compound of embodiment 31 or 32, wherein $R^{13}$ is an aryl substituted with at least one $OR^{34}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, amino ($NH_2$), mono($C_1$-$C_6$ alkyl)amino or di($C_1$-$C_6$ alkyl)amino.

Embodiment 34: The compound of any one of embodiments 31-33, wherein $R^{13}$ is an aryl substituted with at least one $OR^{34}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino.

Embodiment 35: The compound of any one of embodiments 31-34 wherein $R^{13}$ is an aryl substituted with at least one $OR^{34}$ and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino, wherein $R^{34}$ is $C_1$-$C_6$ alkyl or $C_1$-$C_9$ cycloalkyl.

Embodiment 36: The compound of any one of embodiments 31-35, wherein $R^{13}$ is an aryl substituted with at least one $OR^{34}$ and at least one halogen, amino ($NH_2$), mono($C_1$-$C_6$ alkyl)amino or di($C_1$-$C_6$ alkyl)amino, wherein $R^{34}$ is $C_1$-$C_6$ alkyl or $C_1$-$C_9$ cycloalkyl.

Embodiment 37: The compound of any one of embodiments 31-36, wherein $R^{13}$ is an aryl substituted with at least one $OR^{34}$ and at least one halogen or di($C_1$-$C_6$ alkyl)amino wherein $R^{34}$ is $C_1$-$C_6$ alkyl or $C_1$-$C_9$ cycloalkyl.

Embodiment 38: The compound of embodiment any one of embodiments 31-34, wherein $R^3$ is a phenyl substituted with at least one $OR^{34}$ and optionally further substituted with halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino, wherein $R^{34}$ is $C_1$-$C_6$ alkyl or $C_1$-$C_9$ cycloalkyl.

Embodiment 39: The compound of any one of embodiments 31-35, wherein $R^{13}$ is a phenyl substituted with at least one $OR^{34}$ and at least one halogen, $C_1$-$C_6$ alkyl, $C_1$-$C_6$ haloalkyl, $C_1$-$C_6$ heteroalkyl, $C_1$-$C_6$ alkoxy, amino ($NH_2$), mono($C_1$-$C_6$ alkyl)amino or di($C_1$-$C_6$ alkyl)amino, wherein $R^{34}$ is $C_1$-$C_6$alkyl or $C_1$-$C_9$ cycloalkyl.

Embodiment 40: The compound of any one of 31-36, wherein $R^{13}$ is a phenyl substituted with at least one $OR^{34}$ and at least one halogen, amino ($NH_2$), mono($C_1$-$C_6$ alkyl) amino or di($C_1$-$C_6$ alkyl)amino, wherein $R^{34}$ is $C_1$-$C_6$ alkyl or $C_1$-$C_9$ cycloalkyl.

Embodiment 41: The compound of any one of embodiments 31-37, wherein $R^{13}$ is a phenyl substituted with at least one OR A and at least one halogen or di($C_1$-$C_6$ alkyl)amino, wherein $R^{34}$ is $C_1$-$C_6$alkyl or $C_1$-$C_9$ cycloalkyl.

Embodiment 42: The compound of any one of embodiments 31-34, wherein $R^{13}$ is an aryl substituted with $OR^{34}$.

Embodiment 43: The compound of embodiment 41, wherein $R^{13}$ is a phenyl substituted with $OR^{34}$.

Embodiment 44: The compound of embodiment 42, wherein $R^{13}$ is a phenyl substituted with a $C_1$-$C_6$ alkoxy or $C_1$-$C_9$ cycloalkyl.

Embodiment 45: The compound of embodiment 31, wherein $R^{13}$ is selected from the group consisting of

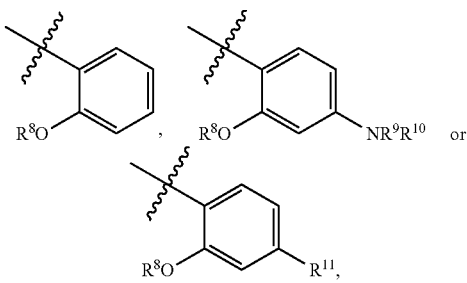

wherein $R^8$ is $C_1$-$C_6$ alkyl or $C_1$-$C_9$ cycloalkyl; $R^9$ and $R^{10}$ are independently H or $C_1$-$C_6$ alkyl; and $R^{11}$ is halogen or $C_1$-$C_6$ haloalkyl.

Embodiment 46: The compound of embodiment 44, wherein $R^{13}$ is

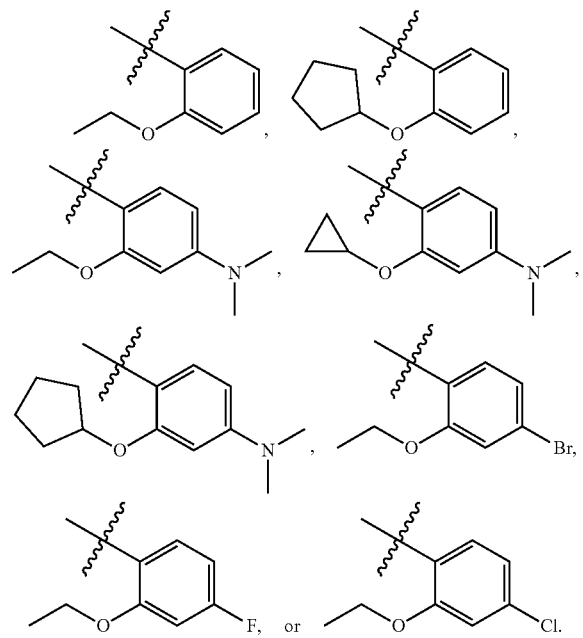

Embodiment 47: The compound of any one of embodiments 31-46, wherein $R^{14}$, $R^{15}$, $R^{16}$ and $R^{17}$ are independently selected from the group consisting of H, halogen, $C_1$-$C_6$ alkyl, $C_1$-$C_6$ haloalkyl, and $C_1$-$C_6$ alkoxy.

Embodiment 48: The compound of any one of embodiments 31-47, wherein $R^{14}$, $R^{15}$, $R^{16}$ and $R^{17}$ are independently selected from the group consisting of H or halogen.

Embodiment 49: The compound of any one of embodiments 31-46, wherein $R^{14}$ is H, halogen, $C_1$-$C_6$ alkyl, $C_1$-$C_6$ haloalkyl or $C_1$-$C_6$ alkoxy; and $R^{15}$ is $C_1$-$C_6$ alkyl.

Embodiment 50: The compound of any one of embodiments 31-49, wherein $R^{19}$ is hydrogen or $C_1$-$C_6$ alkyl.

Embodiment 51: The compound of any one of embodiments 31-50, wherein $R^{19}$ is H.

Embodiment 52: The compound of any one of embodiments 31-51, wherein $R^{20}$ and $R^{21}$ are independently selected from the group consisting of hydrogen, halogen, $C_1$-$C_6$ alkyl or $C_1$-$C_6$ haloalkyl.

Embodiment 53: The compound of any one of embodiments 31-52, wherein $R^{20}$ and $R^{21}$ are independently H or halogen.

Embodiment 54: The compound of any one of embodiments 31-53, wherein $R^{20}$ and $R^{21}$ are H.

Embodiment 55: The compound of any one of embodiments 31-54, wherein $R^{34}$ is hydrogen, $C_1$-$C_6$ alkyl, cycloalkyl or heterocyclyl, wherein the alkyl, cycloalkyl and heterocyclyl can be optionally substituted with halogen, $C_1$-$C_4$ alkyl, $C_1$-$C_4$ haloalkyl, $C_1$-$C_4$ heteroalkyl or $C_1$-$C_6$ alkoxy.

Embodiment 56: The compound of any one of embodiments 31-55, wherein $R^{34}$ is a $C_1$-$C_6$ alkyl or $C_3$-$C_8$ cycloalkyl.

Embodiment 57: The compound of any one of embodiments 31-56, wherein each $R^{22}$ and $R^{23}$ is independently H, Br, Cl, F or I.

Embodiment 58: The compound of any one of embodiments 31-57, wherein n is 1 or 2.

Embodiment 59: The compound of embodiment 32, wherein the compound is (FQI-30) or (FQI-31).

Embodiment 60: The compound of embodiment 31, wherein the compound is (FQI-Urea), (FQI-39), (FQI-41), (FQI-42), (Thio-FQI-1) or (Tri-FQI-1).

Embodiment 61: A method for treating cancer in a subject, the method comprising administering an effective amount of a compound of any one of embodiments 1-60 to a subject in need thereof.

Embodiment 62: The method of embodiment 61, wherein the cancer is selected from the group consisting of breast cancer, colon cancer, ovarian cancer, pancreatic cancer, lung cancer, kidney cancer, cancers of the hematopoietic system, cancers of the endometrium, cervical cancer, cancers of the upper digestive tract, stomach cancer, liver cancers and cancers of the small intestine.

Embodiment 63: The method of embodiment 62, wherein cancer is hepatocellular carcinoma (HCC).

Embodiment 64: A method of inhibiting tubulin methylation in a cell, the method comprising administering to the cell an effective amount of inhibitor of late SV40 factor (LSF).

Embodiment 65: A method of modulating chromatin or cytoskeleton modification in a cell, the method comprising administering to the cell an effective amount of inhibitor of late SV40 factor.

Embodiment 66: The method of any one of embodiments 61-65, wherein the inhibitor of late SV40 factor is a compound of any one of embodiments 1-60.

Embodiment 67: The method of embodiment 64 or 65, wherein the inhibitor of LSF is a compound of Formula (V):

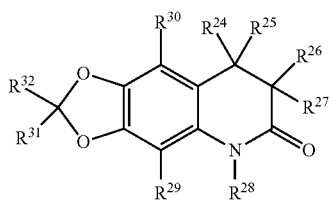

FORMULA (V)

wherein: $R^{24}$ is an aryl substituted with at least one $C_1$-$C_6$ alkoxyl and optionally di($C_1$-$C_{24}$ alkyl)amino, halogen or $C_2$-$C_8$ alkenyl, wherein the substituted aryl can be optionally further substituted with halogen, $C_1$-$C_4$ alkyl, $C_1$-$C_4$ haloalkyl, $C_1$-$C_4$ heteroalkyl, di($C_1$-$C_{24}$ alkyl)amino or combinations thereof; $R^{25}$ and $R^{26}$ are hydrogen or $R^{25}$ and $R^{26}$ together form a second bond between the carbons to which they are attached; $R^{27}$ is hydrogen; $R^{28}$ is selected from the group consisting of hydrogen and $C_1$-$C_6$ alkyl; $R^{29}$ and $R^{30}$ are each independently selected from the group consisting of hydrogen, F, Br, Cl and I; $R^{31}$ and $R^{32}$ are each independently selected from the group consisting of hydrogen, F, Br, Cl, and I; or enantiomers, prodrugs, derivatives, and pharmaceutically acceptable salts thereof.

Embodiment 68: The method of Embodiment 67, wherein the compound of Formula (V) is selected from the groups consisting of (FQI-1), (FQI-34), (FQI-Br), (FQI-Cl), and (FQI-F).

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Definitions

The structure definitions such as "alkyl" are provided below for nomenclature purposes. They do not exclude the meaning as those acquired in the art to which this invention pertains. The term "alkyl" as used herein refers to a linear, branched, or cyclic saturated hydrocarbon group typically although not necessarily containing 1 to about 24 carbon atoms, preferably 1 to about 12 carbon atoms, more preferably 1 to about 6 carbon atoms or a lower alkyl, such as methyl, ethyl, n-propyl, isopropyl, n-butyl, isobutyl, sec-butyl, tert-butyl, pentyl, hexyl, and the like, as well as cycloalkyl groups such as cyclopropyl, cyclobutryl, cyclopentyl, cyclohexyl, cycloheptyl, cyclooctyl and the like. The term "cycloalkyl" intends a cyclic alkyl group, typically having 3 to 10, preferably 3 to 8, carbon atoms. The term "substituted alkyl" refers to alkyl substituted with one or more substituent groups, and the terms "heteroalkyl" and "heteroatom-containing alkyl" refer to alkyl in which at least one carbon atom is replaced with a heteroatom. The term "haloalkyl" as used herein refers to an alkyl structure with at least one substituent of fluorine, chorine, bromine or iodine, or with combinations thereof. If not otherwise indicated, the term "alkyl" includes linear, branched, cyclic, unsubstituted, substituted, and/or heteroatom-containing alkyl, respectively.

The term "alkenyl" as used herein refers to a linear, branched, or cyclic hydrocarbon group of 2 to about 16 carbon atoms containing at least one double bond, such as ethenyl, n-propenyl, isopropenyl, n-butenyl, isobutenyl, n-pentenyl, iso-pentenyl, hexenyl, heptenyl, octenyl, decenyl, tetradecenyl, hexadecenyl, eicosenyl, tetracosenyl, and the like. Preferred alkenyl groups herein contain 2 to about 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the term "alkenyl" includes linear, branched, cyclic, unsubstituted, substituted, and/or heteroatom-containing alkenyl, respectively.

The term "alkynyl" as used herein refers to a linear or branched-chain hydrocarbon group having one or more carbon-carbon triple-bonds and having from 2 to about 8 carbon atoms. Examples of alkynyl groups include ethynyl, propynyl, butynyl, pentynyl and the like.

The term "alkoxy" as used herein intends an alkyl group bound through a single, terminal ether linkage; that is, an "alkoxy" group may be represented as —O-alkyl where alkyl is as defined herein. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, 1-naphthyl, 2-naphthyl, biphenyl, pyridine, quinoline, furan, thiophene, pyrrole, imidazole, pyrazole, diphenylether, diphenylamine, benzophenone, and the like. "Substituted aryl" refers to an aryl moiety substituted with one or more, (e.g., one, two, three, four or more) substituent groups, and the terms "heteroatom-containing aryl" and "heteroaryl" refer to aryl substituents in which at least one carbon atom is replaced with a heteroatom such as oxygen, nitrogen and sulfur. The term "heteroaryl" includes ring systems such as pyridine, quinoline, furan, thiophene, pyrrole, imidazole and pyrazole and the like.

The term "heterocycyl" as used herein refers to a single ring or multiple rings that are fused together, directly linked, or indirectly inked (such that the different rings are bound to a common group such as a methylene or ethylene moiety), in which at least one carbon atom is replaced with a heteroatom such as oxygen, nitrogen and sulfur. Preferred heterocycyl groups contain 3 to 24 carbon atoms, and particularly preferred heterocycyl groups contain 3 to 14 carbon atoms. For example, a heterocycyl group can be a five-membered ring with at least one carbon replaced by oxygen or nitrogen.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. In one embodiment, the bicyclic or polycyclic ring may be fused ring. The fusion of the ring may be across a bond between two atoms, i.e. two cyclic rings share one bond or two atoms, for example, a decalin; the fusion of the ring may be across a sequence of atoms, i.e. two cyclic rings share three or more atoms, for example a norbornane.

By "substituted" as in "substituted alkyl," "substituted aryl," and the like, as alluded to in some of the definitions as described herein, is meant that in the alkyl, aryl, or other moiety, at least one hydrogen atom bound to a carbon (or other) atom is replaced with one or more non-hydrogen substituents. Examples of such substituents include, without limitation: halogen, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aryl alkoxy, $C_6$-$C_{24}$ alkyl aryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), and $C_5$-$C_{24}$ aryl (preferably $C_5$-$C_{14}$ aryl). In preferred embodiments, the substituents as used herein are halogen, $C_1$-$C_4$ alkyl, $C_1$-$C_4$ haloalkyl, $C_1$-$C_4$ heteroalkyl, $C_1$-$C_6$ alkoxy, mono($C_1$-$C_6$alkyl)amino or di($C_1$-$C_6$alkyl)amino.

In addition, the functional groups as described herein may, if a particular group permits, be further substituted with one or more additional functional groups or with one or more hydrocarbyl moieties such as those specifically enumerated herein. Analogously, the hydrocarbyl moieties described herein may be further substituted with one or more functional groups or additional hydrocarbyl moieties such as those specifically enumerated.

The term 'disorder' or 'disease' used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In one embodiment, the disorder or disease is cancer. In one embodiment, the disease or disorder is liver cancer, e.g., hepatocellular carcinoma. In one embodiment, the disease or disorder is a cancer selected from the group selected from: colon cancer, breast cancer, ovarian cancer, melanomia, endometrium cancer, pancreatic cancer, prostate cancer, bone cancer, kidney cancer, leukemia, large intestine cancer, lung cancer, small cell lung carcinoma (SSLC), stomach cancer and other cancers.

The term 'cancer' and 'malignancy' are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations. A small molecule LSF inhibitor as disclosed herein which "inhibits" cancer metastasis may result in the delayed appearance of secondary tumors, slowed development of primary or secondary tumors, decreased occurrence of secondary tumors, slowed or decreased severity of secondary effects of disease, arrested tumor growth and regression of tumors, among others. In the extreme, complete inhibition is referred to herein as prevention (e.g., virtually complete inhibition, no metastasis if it had not occurred, no further metastasis if there had already been metastasis of a cancer, or virtually complete inhibition of the growth of a primary tumor caused by re-seeding of the tumor by a metastasized cell).

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, lack of contact inhibition and density limitation of growth, lack of growth factor or serum dependence, tumor specific markers levels, invasiveness, tumor growth in suitable animal hosts such as nude mice, and the like, in vitro, in vivo, and ex vivo (see also Freshney, Culture of Animal Cells: A Manual of Basic Technique (3rd ed. 1994)).

A "tumorigenic cell," as used herein, is a cell that, when introduced into a suitable site in a subject, can form a tumor. The cell may be non-metastatic or metastatic. A variety of types of tumorigenic and/or metastatic cells can be used in a method of the invention, including cells from metastatic epithelial cancers, carcinomas, melanoma, leukemia, etc. The tumor cells may be, e.g., from cancers of breast, lung, colon, bladder, prostate, liver, gastrointestinal tract, endometrium, tracheal-bronchial tract, pancreas, uterus, ovary, nasopharynges, prostate, bone or bone marrow, brain, skin or other suitable tissues or organs. In a preferred embodiment, the cancer cells are of human origin.

The term "tumor" or "tumor cell" are used interchangeably herein, refers to the tissue mass or tissue type of cell that is undergoing abnormal proliferation.

A "metastatic" cell, as used herein, refers to a cell that has a potential for metastasis and, when used in a method of the invention, is able to seed a tumor or a cell colony of interest. A "highly metastatic" cell, as used herein, refers to a cell that has a high potential for metastasis; e.g., cells from a cell line such as, but not limited to LM2, MDA-MB-231, PC-3, DU-145, Lewis Lung carcinoma, can be considered to be highly metastatic cells. Metastatic cells can be generated in a variety of ways, which are discussed further below.

A "sarcoma" refers to a type of cancer cell that is derived from connective tissue, e.g., bone (osteosarcoma) cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

The term "tissue" is intended to include intact cells, blood, blood preparations such as plasma and serum, bones, joints, muscles, smooth muscles, and organs.

The term "subject" includes human and other mammalian subjects that receive either prophylactic or therapeutic treatment. Accordingly, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The terms "a reference sample" or "a reference level" as used interchangeably herein refer to a negative control of the condition. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level or sample used herein refers to the level measured at a previous time point from a subject being treated.

The term "tissue" is intended to include intact cells, blood, blood preparations such as plasma and serum, bones, joints, muscles, smooth muscles, and organs. In one embodiment, the tissue is liver tissue.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer. As used herein with respect to cancer, the term treating is used to refer to the reduction of a symptom and/or a biochemical marker of inappropriate proliferation, for example a reduction in at least one biochemical marker of cancer by at least 10%. For example but are not limited to, a reduction in a biochemical marker of cancer, for example a reduction in, as an illustrative example only, at least one of the following biomarkers; CD44, telomerase, TGF-, TGF-, erbB-2, erbB-3, MUC1, MUC2, CK20, PSA, CA125, FOBT, osteopontin (OPN), alpha-fetoprotein (AFP) by 10%, or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered as effective treatments by the methods as disclosed herein. In other embodiments, treatment can be therapeutic in terms of eliminating or reducing at least one symptom of the condition or disease. For example, in the case of HCC, therapeutic treatment refers to inhibiting or delaying the progression of HCC in a subject that is already inflicted with HCC. Measurable lessening includes any statistically significant decline in a measurable marker or symptom, such as measuring a tumor size or level of a biomarker.

As used herein, the term "treating" includes preventing the progression and/or reducing or reversing at least one adverse effect or symptom of a condition, disease or disorder associated with inappropriate proliferation, for example cancer. Accordingly, in some embodiments, treatment can be prophylactic in terms of completely or partially preventing a disease or sign or symptom of cancer. For example, subjects at high risk of cancer, e.g., HCC, such as HBV or HCV, can be subjected to prophylactic treatment to prevent the onset of HCC. In some embodiments, prophylactic treatment can be administered to subjects who had prior treatment of a disease and the disease is in remission. For example, for subjects who have their HCC tumors removed or stabilized by previous therapeutic methods can be prophylactically treated (e.g. with a LSF inhibitor as disclosed herein) to prevent the recurrence and metastasis of HCC.

As used herein, the terms "prevent," "preventing," and "prevention" refer to the avoidance or delay in manifestation of one or more symptoms or measurable markers of a disease or disorder. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the complete avoidance or prevention of symptoms or markers, but also a reduced severity or degree of any one of those symptoms or markers, relative to those symptoms or markers arising in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. LSF or LSF target genes, it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, the small-molecule LSF inhibitors as disclosed herein decrease the activity or expression of LSF. Preferably, this decrease is at least about 5%, at least about 10%, at least about 25%, at least about 50%, at least about 75%, at least about 80%, or even at least about 90% of the level of expression or activity under control conditions. The term "level" as used herein in reference to LSF refers to expression or activity of LSF.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" as used herein refers to the amount of at least one agent of pharmaceutical composition to reduce or stop at least one symptom of the abnormal proliferation, for example a symptom of a cancer or malignancy. For example, an effective amount using the methods as disclosed herein would be considered as the amount sufficient to reduce a symptom of the abnormal proliferation, for example at least one symptom of a cancer or malignancy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease. Accordingly, the term "effective amount" or "therapeutically effective amount" as used herein refers to the amount of therapeutic agent (e.g. at least one small molecule inhibitor of LSF of Formula (I) to (V) as disclosed herein) of pharmaceutical composition to alleviate at least some of the symptoms of cancer e.g. HCC. In some embodiments, small molecule inhibitors of Formula (I) to (IV) can be used. Stated another way, "therapeutically effective amount" of a small molecule LSF inhibitor as disclosed herein is the amount of a LSF inhibitor which exerts a beneficial effect on, for example, cancer, e.g., HCC. Beneficial effects include inhibition or delay of cancer, e.g., HCC progression. The dosage administered, as single or multiple doses, to an individual will vary depending upon a variety of factors, including pharmacokinetic properties of a LSF inhibitor, the route of administration, conditions and characteristics (sex, age, body weight, health, size) of subjects, extent of symptoms, concurrent treatments, frequency of treatment and the effect desired.

An "agent" is a chemical molecule of synthetic or biological origin. In the context of the present invention, an agent is generally a molecule that can be used in a pharmaceutical composition. In some embodiments, the agent is chemotherapeutic agents. In some embodiments, the agent is small-molecule LSF inhibitors as disclosed herein. In some embodiments, the agent can provide a therapeutic value. In some embodiments, the small molecule LSF inhibitors as disclosed herein can be used as a preventative or prophylactic treatment for prevention of cancer, e.g., where a subject is at risk or is likely to develop cancer. In other embodiments, the agent is used solely to implement the invention, e.g. pharmaceutically acceptable carriers as disclosed herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The terms "administered" and "subjected" are used interchangeably in the context of treatment of a disease or disorder. Both terms refer to a subject being treated with an effective dose of pharmaceutical composition comprising a LSF inhibitor of the invention by methods of administration such as parenteral or systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least an inhibitor of LSF as disclosed herein such that it enters the animal's system and, thus, is subject to metabolism and other like processes, for example, subcutaneous administration. In some embodiments, the administration is oral administration. Without limitations, oral administration can be in the form of solutions, suspensions, tablets, pills, capsules, sustained-release formulations, oral rinses, powders and the like.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following, including the Examples, but the scope of the invention should not be limited thereto.

The term "inhibit LSF" as used herein refers to inhibiting expression (level) of LSF and/or biological activity of LSF. In some embodiments, the term "inhibit LSF" refers to a decrease in the protein level of LSF and/or gene transcript level of LSF. For example, inhibition of LSF can result in a reduction in the gene expression of TFCP2 encoding LSF. The term "inhibit LSF" also refers to a down-regulation or an inhibition of biological activity of LSF, e.g. the function of LSF to modulate expression of LSF-regulated downstream genes such as; thymidylate synthetase (TYMS), secreted phosphoprotein 1 (SPP1), complement factor H (CFH) and fibronectin 1 (FN1) (see Porta-de-la-Riva M, et al (2011) J. Biochem. 435:563-8, which is incorporated herein in its entirety by reference).

The terms "cellular LSF activity" and "biological activity of LSF" are used herein interchangeably. Both terms refer to the ability of LSF to regulate cellular processes downstream of LSF, for example, to modulate the expression of genes that are downstream of LSF. In some embodiments, the biological activity of LSF can elicit a stimulatory effect on expression of LSF-downstream genes. In other embodiments, the biological activity of LSF can induce an inhibitory effect on expression of LSF-downstream genes. In yet other embodiments, the biological activity of LSF may be due to interactions with other cellular proteins.

The phrase "level of LSF" as used herein encompasses the expression and/or biological activity of LSF. As described herein, the term "expression" refers to the amount of the protein obtained by translation of RNA transcribed from a gene, and/or the amount of RNA transcribed from a gene.

The term "regulate" used herein in reference to expression of a gene, refers to producing an effect on, for example, gene expression. In some embodiments, the effect can be stimulatory, such as increasing expression of a gene. In some embodiments, the effect can be inhibitory, such as decreasing expression of a gene. The terms "regulate" and "modulate" are interchangeably used herein.

The terms "inhibitors of LSF" and "LSF inhibitors" used interchangeably herein, generally refers to agents that inhibit LSF. They can be of synthetic or biological origins. They can be organic, or inorganic molecules, or peptides, antibodies or antisense RNA that inhibit LSF. Inhibitors of LSF of the invention are chemical entities or molecules that can inhibit expression of LSF and/or biological activity of LSF, as disclosed herein, for example, compounds of any of formula (I) to (V), and enantiomers, prodrugs, derivatives and pharmaceutically acceptable salts thereof.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1: Synthesis of Exemplary Compounds

Exemplary compounds were synthesized as follows:

(E)-N-(2,3-dihydrobenzo[b][1,4]dioxin-6-yl)-3-(2-ethoxyphenyl)acrylamide

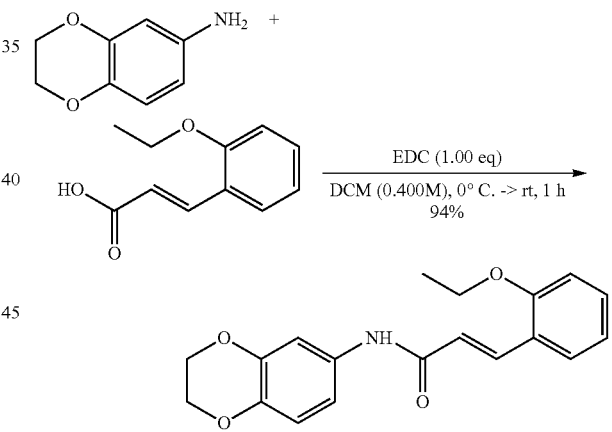

(E)-3-(2-ethoxyphenyl)prop-2-enoic acid (577 mg, 3.00 mmol) was weighed into a flame-dried 250 mL round bottom flask and placed under an atmosphere of nitrogen. Anhydrous DCM (7.50 mL) was added, and the flask was cooled to 0° C. 3,4-(ethylenedioxy)aniline (453 mg, 3.00 mmol, 369 uL) was added in one portion, followed by EDC.HCl (575 mg, 3.00 mmol). The reaction was warmed to ambient temperature and stirred for 1 h. Upon completion, the reaction mixture was diluted with 300 mL ethyl acetate and 100 mL of 1M HCl. The biphasic solution was filtered to remove insoluble material, and the layers were separated. The organic layer washed with an additional portion of 1M HCl (100 mL), saturated aqueous sodium bicarbonate (1×100 mL), and brine (1×100 mL). The organic layer was then dried over sodium sulfate, filtered, and condensed in vacuo to give (E)-N-(2,3-dihydro-1,4-benzodioxin-6-yl)-3-

(2-ethoxyphenyl)prop-2-enamide (0.918 g, 2.82 mmol, 94.0% yield) as a yellow solid, and used without further purification.

¹H NMR: (400 MHz, Chloroform-d) δ 8.01 (d, J=15.5 Hz, 1H), 7.49 (d, J=7.0 Hz, 1H), 7.37-7.27 (overlap, 3H), 7.02 (d, J=7.2 Hz, 1H), 6.93 (d, J=7.5 Hz, 1H), 6.89 (d, J=8.5 Hz, 1H), 6.81 (d, J=8.5 Hz, 1H), 6.63 (d, J=15.5 Hz, 1H), 4.29-4.20 (overlap, 4H), 4.10 (q, J=6.5 Hz, 2H), 1.47 (t, J=6.5 Hz, 3H). ESI-MS: [M+H]⁺ calculated for $C_{19}H_{19}NO_4$ 326.131; found 326.459. UV: λ (max) 254.2 nm 9-(2-ethoxyphenyl)-2,3,8,9-tetrahydro-[1,4]dioxino[2,3-g]quinolin-7(6H)-one (FQI-35) and 10-(2-ethoxyphenyl)-2,3,9,10-tetrahydro-[1,4]dioxino[2,3-f]quinolin-8(7H)-one (FQI-36)

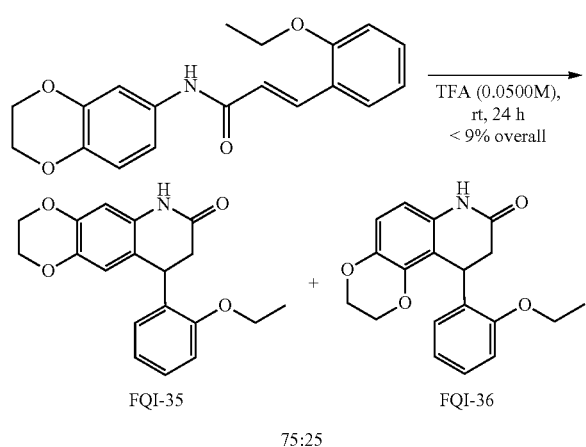

N-(2,3-dihydrobenzo[b][1,4]dioxin-6-yl)-3-(2-ethoxyphenyl)acrylamide (325 mg, 1.00 mmol) was dissolved in TFA (20.0 mL) in flame dried 50 mL flask equipped with a stir bar. The mixture was stirred at RT for 24 h, then concentrated in vacuo. The residue was neutralized with ~20 mL saturated aq. sodium bicarbonate, then extracted 3× with 50 mL DCM. The combined organics were rinsed with water, then brine, and dried over anhydrous sodium sulfate to give a crude mixture with ~75:25 FQI-35:FQI-36 that is inseparable via silica or alumina chromatography. Purification was accomplished with preparative reverse-phase HPLC, giving 9-(2-ethoxyphenyl)-3,6,8,9-tetrahydro-2H-[1,4]dioxino[2,3-g]quinolin-7-one (20.6 mg, 0.0635 mmol, 6.35% yield), and 10-(2-ethoxyphenyl)-3,7,9,10-tetrahydro-2H-[1,4]dioxino[2,3-f]quinolin-8-one (7.53 mg, 0.0231 mmol, 2.31% yield).

FQI-35: ¹H NMR: (400 MHz, Chloroform-d) δ 7.33 (s, 1H), 7.19 (ddd, J=7.5, 7.5, 2.1 Hz, 1H), 6.87 (d, J=7.5 Hz, 1H), 6.84 (d, J=7.5 Hz, 1H), 6.50 (s, 1H), 6.33 (s, 1H), 4.61 (dd, J=7.2, 6.7 Hz, 1H), 4.27-4.21 (m, 2H), 4.21-4.15 (m, 2H), 4.11-4.02 (m, 2H), 2.92 (dd, J=16.2, 7.2 Hz, 1H), 2.81 (dd, J=16.2, 6.7 Hz, 1H), 1.40 (t, J=6.9 Hz, 3H). ESI-MS: [M+H]⁺ calculated for $C_{19}H_{19}NO_4$ 326.131; found 326.283. UV: λ (max) 321.2 nm FQI-36: ¹H NMR: (400 MHz, Chloroform-d) δ 7.14 (t, J=7.6 Hz, 1H), 6.85 (d, J=8.0 Hz, 1H), 6.80 (d, J=8.7 Hz, 1H), 6.71 (t, J=7.9 Hz, 1H), 6.55 (d, J=7.9 Hz, 1H), 6.34 (d, J=8.6 Hz, 1H), 4.90 (d, J=7.9 Hz, 1H), 4.21-4.14 (overlap, 4H), 4.10 (d, J=6.9 Hz, 2H), 2.93 (d, J=15.9 Hz, 1H), 2.84 (m, 1H), 1.48 (t, J=7.0 Hz, 3H). ESI-MS: [M+H]⁺ calculated for $C_{19}H_{19}NO_4$ 326.131; found 326.283. UV: λ (max) 227.2

2-bromo-N-(2,3-dihydrobenzo[b][1,4]dioxin-6-yl)acetamide

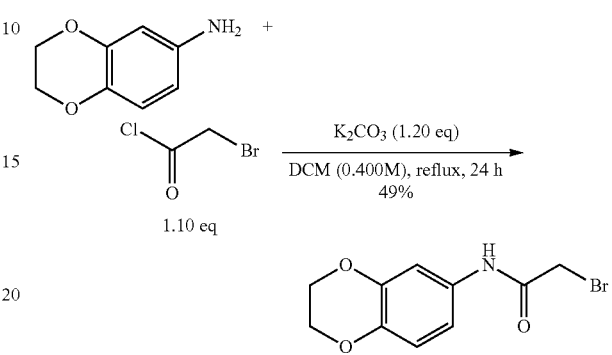

In a flame dried 100 mL flask equipped with a stir bar, 2,3-dihydro-1,4-benzodioxin-6-amine (2.27 g, 15.0 mmol, 1.84 mL) and potassium carbonate (2.49 g, 18.0 mmol) were suspended in DCM (50.0 mL). Bromoacetyl chloride (2.60 g, 16.5 mmol, 1.37 mL) was added slowly, and the flask was flushed with Ar, and fitted with a reflux condenser and Ar balloon. The reaction mixture was heated and stirred at reflux for 24 h. After cooling to RT, the mixture was slowly poured into 100 mL of ice water. The aqueous solution was extracted with DCM (2×100 mL), the organic phase was dried over anhydrous sodium sulfate, filtered, and the solvent was evaporated to furnish 2-bromo-N-(2,3-dihydro-1,4-benzodioxin-6-yl)acetamide (2.00 g, 7.33 mmol, 48.9% yield) as a solid. Crude solid was sufficiently pure by NMR and used in subsequent step without further purification.

¹H NMR: (500 MHz, DMSO-d6) δ 10.21 (s, 1H), 7.21 (d, J=2.5 Hz, 1H), 6.95 (dd, J=8.7, 2.5 Hz, 1H), 6.80 (d, J=8.7 Hz, 1H), 4.27-4.13 (overlap, 4H), 3.98 (s, 2H). ¹³C NMR: (125 MHz, DMSO-d6) δ 164.28, 142.96, 139.72, 132.24, 116.91, 112.43, 108.31, 64.18, 63.93, 30.43. ESI-MS: [M+H]⁺ calculated for $C_{10}H_{10}BrNO_3$ 273.982; found 274.058. UV: λ (max) 262.2 nm N-(2,3-dihydro-1,4-benzodioxin-6-yl)-2-dimethoxyphosphoryl-acetamide

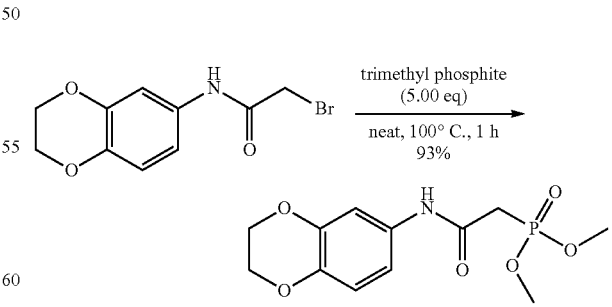

2-bromo-N-(2,3-dihydro-1,4-benzodioxin-6-yl)acetamide (1.84 g, 6.76 mmol) was transferred into a flame dried pear shaped 50 mL flask equipped with a stir bar, followed by trimethyl phosphite (4.20 g, 33.8 mmol, 4.00 mL). The mixture was purged with Ar, and fitted with a reflux condenser and Ar balloon. The reaction was then heated to 100° C. for 1 h. After cooling to RT, the reaction was rinsed into a 500 mL separatory funnel with ~100 mL DCM, and washed 3× with 150 mL H₂O. The organic layer was rinsed with brine (~20 mL), dried over anhydrous Na₂SO₄, and concentrated under high vacuum (~0.1 mm Hg), giving N-(2,3-dihydro-1,4-benzodioxin-6-yl)-2-dimethoxyphosphoryl-acetamide (1.90 g, 6.32 mmol, 93.4% yield), and used after concentration without further purification.

¹H NMR: (400 MHz, Chloroform-d) δ 8.72 (s, 1H), 7.15 (d, J=2.4 Hz, 1H), 6.88 (dd, J=8.7, 2.5 Hz, 1H), 6.74 (d, J=8.7 Hz, 1H), 4.27-4.18 (overlap, 4H), 3.82 (d, J=11.2 Hz, 6H), 3.01 (d, J=20.9 Hz, 2H). ¹³C NMR: (100 MHz, Chloroform-d) δ 161.74, 161.70, 143.35, 140.46, 131.71, 117.08, 113.50, 109.68, 64.48, 64.36, 53.51, 53.44, 35.96, 34.67. ESI-MS: [M+H]⁺ calculated for $C_{12}H_{16}NO_6P$ 302.072; found 302.155. UV: λ (max) 254.2 nm 4-(dimethylamino)-2-ethoxybenzaldehyde

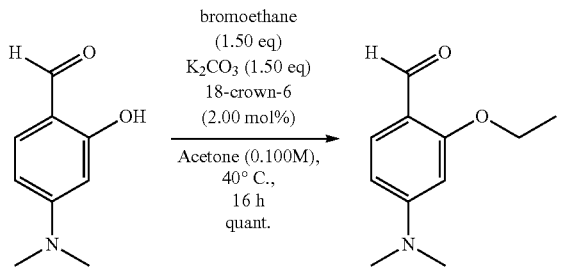

In a flame dried 500 mL round bottom flask was prepared a solution of 4-(dimethylamino)-2-hydroxy-benzaldehyde (3.00 g, 18.2 mmol) in Acetone (181.6 mL) followed by addition of bromoethane (9.89 g, 90.8 mmol, 6.78 mL), anhydrous potassium carbonate (3.76 g, 27.2 mmol) and 18-crown-6 (96.0 mg, 0.363 mmol). The reaction mixture was fitted with a reflux condenser and heated at 40° C. for 16 h, and then cooled to room temperature. The reaction was filtered and the filtered solid washed with acetone. The filtrate was evaporated to dryness to give 4-(dimethylamino)-2-ethoxy-benzaldehyde (3.51 g, 18.2 mmol) in quantitative yield.

¹H NMR: (400 MHz, Chloroform-d) δ 10.20 (s, 1H), 7.73 (d, J=9.0 Hz, 1H), 6.29 (d, J=9.0 Hz, 1H), 6.02 (s, 2H), 4.12 (q, J=7.0 Hz, 2H), 3.07 (s, 3H), 1.47 (t, J=7.0 Hz, 3H). ¹³C NMR: (125 MHz, Chloroform-d) δ 187.60, 163.45, 155.99, 129.92, 114.65, 104.53, 93.76, 70.10, 63.79, 40.21, 14.72. IR (KBr): υ (max) 2979, 2905, 2763, 1659, 1587, 1553, 1526, 1440, 1372, 1360, 1287, 1241, 1108, 806 cm⁻¹. Melting point: 59° C. UV: λ (max) 351.8 nm. ESI-MS: [M+H]⁺ calculated for $C_{11}H_{15}NO_2$ 194.11; found 193.80.

N-(2,3-dihydro-1,4-benzodioxin-6-yl)-3-[4-(dimethylamino)-2-ethoxy-phenyl]prop-2-enamide

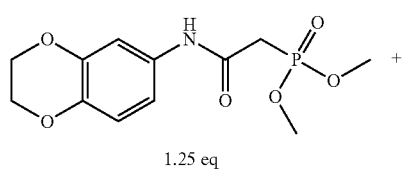

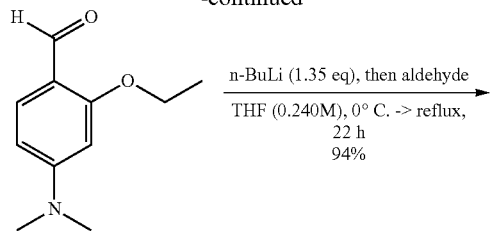

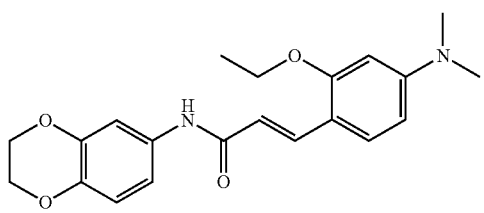

N-(2,3-dihydro-1,4-benzodioxin-6-yl)-2-dimethoxyphosphoryl-acetamide (640 mg, 2.12 mmol) was dissolved in THF (5.66 mL) in a flame dried 25 mL flask equipped with a stir bar. The flask was flushed with Ar and fitted with an Ar balloon, then cooled to 0° C. n-Butyl lithium (1.6 M in hexanes, 2.29 mmol, 1.35 eq, 1.43 mL) was added dropwise via syringe. The mixture was allowed to warm to RT and stir for 30 min. After equilibrating, solid 4-(dimethylamino)-2-ethoxy-benzaldehyde (328 mg, 1.70 mmol, 1.00 eq) was quickly added as a single portion. The flask was fitted with a reflux condenser and Ar balloon, and the mixture was heated to reflux for 22 h. After cooling to RT, the reaction mixture was quenched by the addition of ~5 mL saturated aq. ammonium chloride, and transferred to a 500 mL separatory funnel, rinsing with DCM and water. The organics were diluted with an additional ~150 mL DCM, and 50 mL water. The DCM layer was removed and washed with an additional 3×50 mL water, then dried over sodium sulfate and concentrated in vacuo. The crude residue was purified by flash chromatography (SiO₂; gradient from 0 to 50% EtOAc in hexanes) to afford N-(2,3-dihydro-1,4-benzodioxin-6-yl)-3-[4-(dimethylamino)-2-ethoxy-phenyl]prop-2-enamide (591 mg, 1.60 mmol, 94.4% yield) as a ~3:1 mixture of E:Z isomers.

¹H NMR (E-isomer): (400 MHz, Chloroform-d) δ 7.91 (d, J=15.5 Hz, 1H), 7.37 (d, J=8.7 Hz, 1H), 7.09 (s, 1H), 7.00 (s, 1H), 6.80 (d, J=8.7 Hz, 1H), 6.46 (d, J=18.1 Hz, 1H), 6.29 (d, J=8.7 Hz, 1H), 6.15 (s, 1H), 4.30-4.20 (overlap, 4H) 4.10 (q, J=6.8 Hz, 2H), 3.32 (s, 1H), 3.01 (s, 7H), 1.48 (t, J=6.6 Hz, 3H).

¹H NMR (Z-isomer): (400 MHz, Chloroform-d) 7.75 (d, J=15.5 Hz, 1H), 7.17 (d, J=8.8 Hz, 1H), 6.86 (d, J=8.5 Hz, 1H), 6.77 (d, J=2.2 Hz, 1H), 6.71 (dd, J=8.4, 2.3 Hz, 1H), 6.22 (d, J=8.1 Hz, 1H), 6.07 (s, 1H), 4.30-4.20 (overlap, 4H) 3.95 (q, J=6.8 Hz, 2H), 2.96 (s, 6H), 1.20 (t, J=6.9 Hz, 3H).

ESI-MS: [M+H]⁺ calculated for $C_{21}H_{24}N_2O_4$ 369.174; found 369.200. UV: λ (max) 338.2 nm

9-[4-(dimethylamino)-2-ethoxy-phenyl]-3,6,8,9-tetrahydro-2H-[1,4]dioxino[2,3-g]quinolin-7-one (FQI-37)

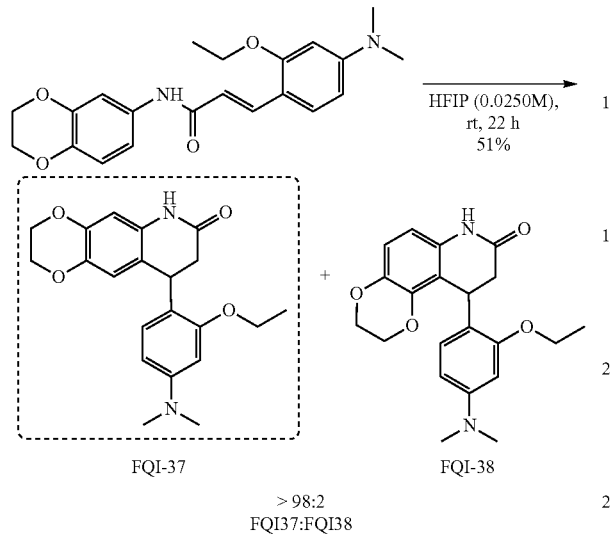

FQI-37          FQI-38

\>98:2
FQI37:FQI38

HFIP (91.2 mL) was added to an oven dried 250 mL flask equipped with a large football shaped stir bar, and quickly flushed with Ar. To the stirred solvent was added powdered N-(2,3-dihydro-1,4-benzodioxin-6-yl)-3-[4-(dimethyl-amino)-2-ethoxy-phenyl]prop-2-enamide (840 mg, 2.28 mmol). The mixture was again quickly flushed with Ar and stoppered with an Ar balloon, and stirred at RT for 22 h. The mixture was condensed in vacuo, and the residue was purified by flash chromatography (SiO$_2$; gradient from 20 to 60% EtOAc in hexanes) to give 9-[4-(dimethylamino)-2-ethoxy-phenyl]-3,6,8,9-tetrahydro-2H-[1,4]dioxino[2,3-g]quinolin-7-one (434 mg, 1.15 mmol, 50.6% yield, 98% purity), with <2% of the undesired FQI-38 isomer present based on NMR integration.

$^1$H NMR: (500 MHz, Chloroform-d) δ 7.42 (s, 1H), 6.75 (d, J=8.4 Hz, 1H), 6.50 (s, 1H), 6.30 (s, 1H), 6.26 (d, J=2.4 Hz, 1H), 6.23 (dd, J=8.4, 2.5 Hz, 1H), 4.51 (m, 1H), 4.25-4.20 (m, 2H), 4.19-4.14 (m, 2H), 4.10-3.99 (m, 2H), 2.92 (s, 6H), 2.90 (dd, J=16.0, 8.1 Hz, 1H), 2.75 (dd, J=16.2, 6.3 Hz, 1H), 1.38 (t, J=7.0 Hz, 3H). $^{13}$C NMR: (125 MHz, Chloroform-d) δ 171.07, 157.28, 151.20, 142.61, 139.39, 131.23, 128.75, 120.97, 118.00, 117.16, 104.97, 103.98, 97.30, 64.72, 64.37, 63.59, 40.90, 37.40, 34.78, 15.09. ESI-MS: [M+H]$^+$ calculated for C$_{21}$H$_{24}$N$_2$O$_4$ 369.174; found 370.302. UV: λ (max) 266.2 nm

10-[4-(dimethylamino)-2-ethoxy-phenyl]-3,7,9,10-tetrahydro-2H-[1,4]dioxino[2,3-f]quinolin-8-one (FQI-38)

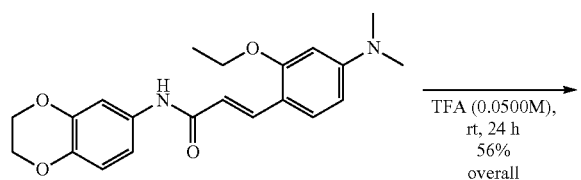

TFA (0.0500M), rt, 24 h
56% overall

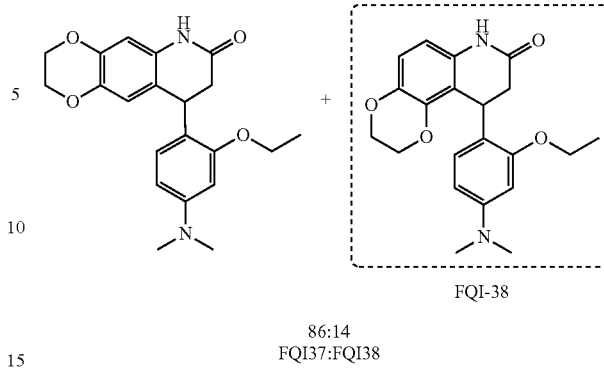

86:14
FQI37:FQI38

N-(2,3-dihydro-1,4-benzodioxin-6-yl)-3-[4-(dimethyl-amino)-2-ethoxy-phenyl]prop-2-enamide (100. mg, 0.271 mmol) was dissolved in TFA (5.43 mL) in a 20 mL scintillation vial equipped with a stir bar. The mixture was stirred at RT for 24 h, then concentrated in vacuo. The residue was neutralized with ~10 mL saturated aq. sodium bicarbonate, then extracted 3× with 20 mL DCM. The combined organics were rinsed with water, then brine, and dried over anhydrous sodium sulfate to give a crude mixture with ~86:14 FQI-37:FQI-38 that is inseparable via silica or alumina chromatography. Purification was accomplished with preparative reverse-phase HPLC, giving 10-[4-(dimethylamino)-2-ethoxy-phenyl]-3,7,9,10-tetrahydro-2H-[1,4]dioxino[2,3-f]quinolin-8-one (6.20 mg, 0.0168 mmol, 6.20% yield).

$^1$H NMR: H NMR (400 MHz, Chloroform-d) δ 7.54 (s, 1H), 6.76 (d, J=8.6 Hz, 1H), 6.38 (d, J=8.4 Hz, 1H), 6.33 (d, J=8.5 Hz, 1H), 6.25 (d, J=2.0 Hz, 1H), 6.06 (dd, J=8.5, 2.3 Hz, 1H), 4.80 (d, J=6.1 Hz, 1H), 4.16 (s, 4H), 4.11 (t, 7.0 Hz, 2H), 2.95-2.84 (overlap, 7H), 2.77 (dd, J=16.3, 7.2 Hz, 1H), 1.47 (t, J=7.0 Hz, 3H). ESI-MS: [M+H]$^+$ calculated for C$_{21}$H$_{24}$N$_2$O$_4$ 369.174; 369.288. UV: λ (max) 229.2 nm.

(2-(benzo[d][1,3]dioxol-5-ylamino)-2-oxoethyl)triphenylphosphonium bromide

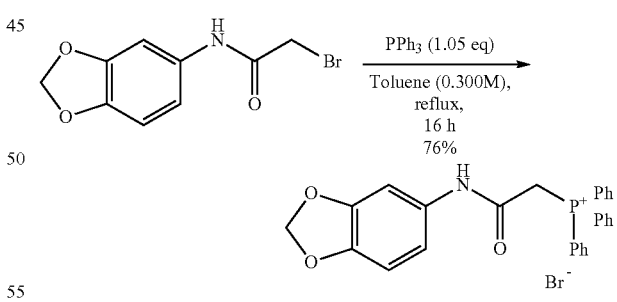

A solution of triphenylphosphine (20.7 g, 78.9 mmol, 1.05 eq) dissolved in toluene (251 mL) was prepared in a 500 mL RBF. To the solution was added N-(1,3-benzodioxol-5-yl)-2-bromo-acetamide (19.4 g, 75.2 mmol, 1.00 eq) in one portion. The resulting slurry was heated to reflux and stirred for 16 h. The resulting grey precipitate was filtered, rinsed with toluene, and dried in vacuo to afford (2-(benzo[d][1,3]dioxol-5-ylamino)-2-oxoethyl)triphenylphosphonium bromide (29.8 g, 57.3 mmol, 76.2% yield) as a grey powder. Crude product was used in subsequent steps without further purification.

$^1$H NMR (500 MHz, DMSO-d6) δ 11.01 (s, 1H), 7.89-7.78 (overlap, 9H), 7.77-7.70 (overlap, 6H), 7.06 (d, J=2.0 Hz, 1H), 6.84 (dd, J=8.4, 2.0 Hz, 1H), 6.79 (d, J=8.4 Hz, 1H), 5.95 (s, 2H), 5.30 (d, J=14.9 Hz, 2H). $^{13}$C NMR (125 MHz, DMSO-d6) δ 161.16, 147.03, 143.68, 134.93, 133.88, 133.79, 132.16, 130.08, 129.98, 119.01, 118.31, 112.52, 108.08, 101.45, 101.18. IR (KBr): υ (max) 3155, 2907, 1665, 1486, 1502, 1436, 1245, 1114, 1035, 929, 737, 690 cm$^{-1}$. Melting Point: 225° C. UV: λ (max) 219.9. ESI-MS (UPLC): [M-Br]$^+$ calculated for C$_{27}$H$_{23}$NO$_3$P 440.141; found 440.12.

2-cyclopropoxy-4-(dimethylamino)benzaldehyde

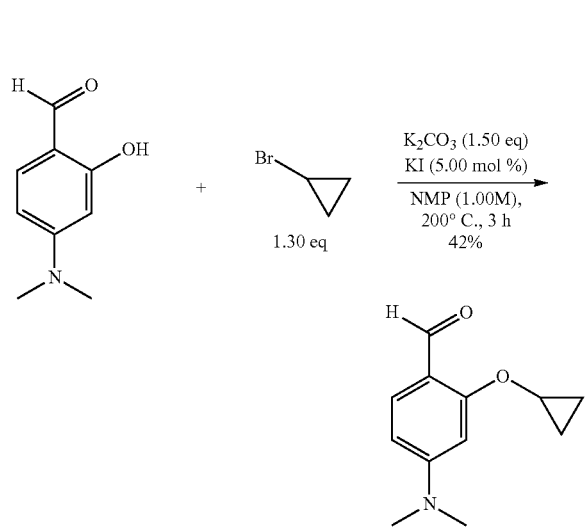

In a flame dried reaction tube equipped with a stir bar was added 4-(dimethylamino)-2-hydroxy-benzaldehyde (165 mg, 1.00 mmol), cyclopropyl bromide (157 mg, 1.30 mmol, 104 uL), potassium carbonate (207 mg, 1.50 mmol), potassium iodide (8.30 mg, 0.0500 mmol) and NMP (1.00 mL). The vial was flushed with Ar, sealed with a teflon septa crimp cap, and stirred at 200° C. for 3 h. The reaction was cooled to RT, and vacuum filtered to remove undissolved solids, rinsing with DCM. The organics were concentrated in vacuo, and the residue was purified by flash chromatography on a 12 g SiO$_2$ cartridge (gradient from 0 to 20% EtOAc in hexanes) to afford 2-(cyclopropoxy)-4-(dimethylamino)benzaldehyde (87.0 mg, 0.420 mmol, 42% yield).

$^1$H NMR: (400 MHz, Chloroform-d) δ 10.09 (s, 1H), 7.72 (d, J=8.8 Hz, 1H), 6.46 (d, J=2.3 Hz, 1H), 6.32 (dd, J=8.8, 2.3 Hz, 1H), 3.81 (tt, J=6.0, 3.3 Hz, 1H), 3.09 (s, 6H), 0.90-0.79 (overlap, 4H). ESI-MS: [M+H]$^+$ calculated for C$_{12}$H$_{15}$NO$_2$ 206.110; found 207.187. UV: λ (max) 353.2 nm.

N-(1,3-benzodioxol-5-yl)-3-[2-(cyclopropoxy)-4-(dimethylamino)phenyl]prop-2-enamide

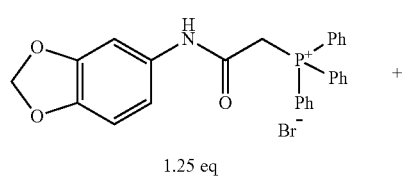

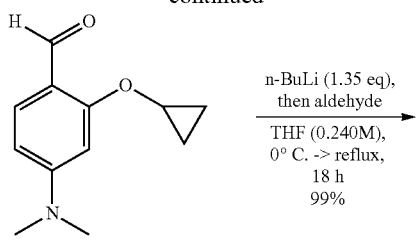

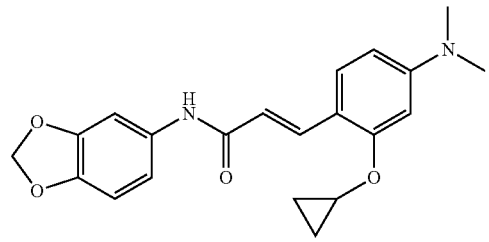

A solution of 2-(1,3-benzodioxol-5-ylamino)-2-oxo-ethyl]-triphenyl-phosphonium bromide (276 mg, 0.530 mmol, 1.25 eq) in THF (1.61 mL) was prepared in a flame dried 5 mL flask and flushed with Ar. The mixture was cooled to 0° C., followed by dropwise addition of n-butyl-lithium (1.6 M in hexanes, 357 uL, 0.571 mmol, 1.35 eq). The flask was allowed to warm to rt and stirred for 30 minutes. After equilibration, a solution of 2-(cyclopropoxy)-4-(dimethylamino)benzaldehyde (87.0 mg, 0.424 mmol, 1.00 eq) dissolved in minimal THF was added to the reaction vial. The flask was fitted with a reflux condenser and Ar balloon and was heated to reflux for 16 h. The reaction was quenched by the addition of 3 mL saturated aq. ammonium chloride, and extracted 3× with 20 mL DCM. The organics were dried over anhydrous sodium sulfate and concentrated in vacuo. The residue was purified by flash chromatography (SiO$_2$; 50% EtOAc in hexanes) to afford N-(1,3-benzodioxol-5-yl)-3-[2-(cyclopropoxy)-4-(dimethylamino)phenyl] prop-2-enamide (154 mg, 0.419 mmol, 98.9% yield) as a ~5:1 mixture of E:Z isomers.

$^1$H NMR: (400 MHz, Chloroform-d) (E isomer) δ 7.83 (d, J=15.5 Hz, 1H), 7.36 (d, J=8.8 Hz, 1H), 7.07 (s, 1H), 6.85 (d, J=8.2 Hz, 1H), 6.75 (d, J=8.2 Hz, 1H), 6.58 (d, J=2.1 Hz, 1H), 6.39 (d, J=15.5 Hz, 1H), 6.31 (dd, J=8.8, 2.1 Hz, 1H), 5.95 (s, 2H), 3.78 (m, 1H), 3.04 (s, 6H), 0.92-0.73 (overlap, 4H). ESI-MS: [M+H]$^+$ calculated for C$_{21}$H$_{22}$N$_2$O$_4$ 367.158; found 367.259. UV: λ (max) 340.2 nm.

8-[2-(cyclopropoxy)-4-(dimethylamino)phenyl]-7,8-dihydro-5H-[1,3]dioxolo[4,5-g]quinolin-6-one (FQI-39)

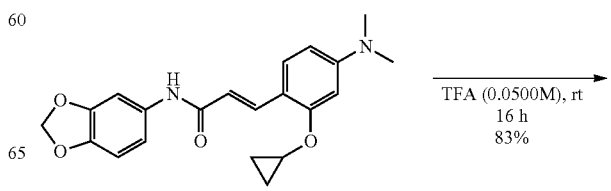

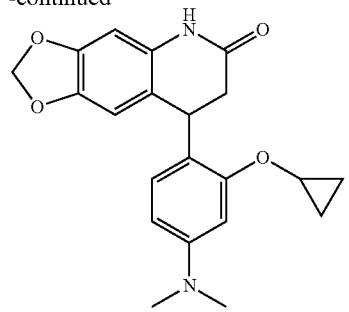

In a flame dried 10 mL flask equipped with a stir bar, N-(1,3-benzodioxol-5-yl)-3-[2-(cyclopropoxy)-4-(dimethylamino)phenyl]prop-2-enamide (100 mg, 0.273 mmol) was dissolved in TFA (5.46 mL) and the flask purged with Ar. The mixture was stirred at RT for 22 h until starting material consumption was observed by TLC. The reaction was concentrated by rotary evaporation and the residue neutralized with ~10 mL saturated aq. sodium bicarbonate. The mixture was extracted 3× with 20 mL DCM, and combined organics were rinsed with water, then brine, and dried over anhydrous sodium sulfate. The crude material was purified by flash chromatography (SiO$_2$; gradient from 25 to 50% gradient EtOAc in hexanes) to afford 8-[2-(cyclopropoxy)-4-(dimethylamino)phenyl]-7,8-dihydro-5H-[1,3]dioxolo[4,5-g]quinolin-6-one (83.3 mg, 0.227 mmol, 83.3% yield) as a light orange solid.

$^1$H NMR: (500 MHz, Chloroform-d) δ 8.51 (s, 1H), 6.73 (d, J=8.5 Hz, 1H), 6.68 (d, J=2.4 Hz, 1H), 6.41 (s, 1H), 6.39 (s, 1H), 6.25 (dd, J=8.5, 2.4 Hz, 1H), 5.87 (s, 2H), 4.40 (dd, J=7.5, 6.5 Hz, 1H), 3.75 (tt, J=5.9, 3.2 Hz, 1H), 2.94 (s, 6H), 2.83 (dd, J=16.2, 7.5 Hz, 1H), 2.74 (dd, J=16.2, 6.5 Hz, 1H), 0.80-0.69 (overlap, 4H). $^{13}$C NMR: (125 MHz, Chloroform-d) δ 171.65, 157.22, 151.08, 146.84, 143.59, 131.56, 128.77, 119.94, 117.53, 108.51, 105.23, 101.22, 98.22, 97.60, 50.57, 40.81, 37.18, 35.15, 6.46, 6.45. ESI-MS: [M+H]$^+$ calculated for C$_{21}$H$_{22}$N$_2$O$_4$ 367.158; found 368.317. UV: λ (max) 264.2 nm.

2-cyclopropoxybenzaldehyde

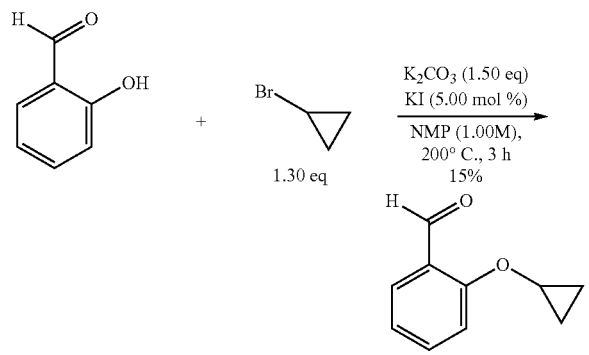

In a flame dried reaction tube equipped with a stir bar was added Salicylaldehyde (24 mg, 2.00 mmol, 212 uL), cyclopropyl bromide (157 mg, 1.30 mmol, 104 uL), potassium carbonate (207 mg, 1.50 mmol), potassium iodide (8.30 mg, 50.00 μmol) and NMP (1.00 mL). The vial was flushed with Ar, sealed with a teflon septa crimp cap, and stirred at 200° C. for 3 h. The reaction was cooled to rt, and vacuum filtered to remove undissolved solids, rinsing with DCM. The organics were concentrated in vacuo, and the residue was purified by flash chromatography on a 12 g SiO$_2$ cartridge (gradient from 0 to 20% EtOAc in hexanes) to afford 2-(cyclopropoxy)benzaldehyde (48.0 mg, 0.296 mmol, 14.8% yield).

$^1$H NMR: NMR (400 MHz, Chloroform-d) δ 10.39 (s, 1H), 7.81 (dd, J=7.7, 1.7 Hz, 1H), 7.56 (ddd, J=7.7, 7.6, 1.7 Hz, 1H), 7.36 (d, J=8.4 Hz, 1H), 7.04 (dd, J=7.6, 7.5 Hz, 1H), 3.84 (m, 1H), 0.93-0.74 (overlap, 4H). ESI-MS: [M+H]$^+$ calculated for C$_{10}$H$_{10}$O$_2$ 163.068; found 163.120. UV: λ (max) 306.2 nm.

N-(benzo[d][1,3]dioxol-5-yl)-3-(2-cyclopropoxyphenyl)acrylamide

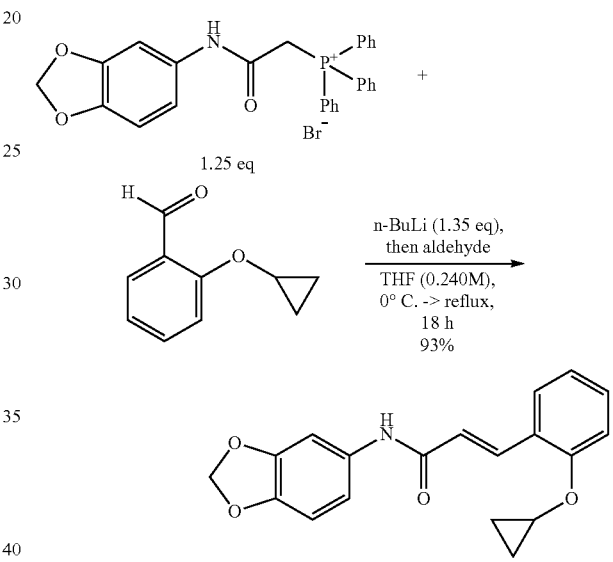

A solution of [2-(1,3-benzodioxol-5-ylamino)-2-oxoethyl]-triphenyl-phosphonium bromide (45.7 mg, 0.0878 mmol) in THF (0.350 mL) was prepared in a flame dried 5 mL flask and flushed with Ar. The mixture was cooled to 0° C., followed by dropwise addition of n-butyl lithium (1.6 M in hexanes, 60.0 uL, 0.950 mmol, 1.35 eq). The flask was allowed to warm to rt and stirred for 30 minutes. After equilibration, a solution of 2-(cyclopropoxy)benzaldehyde (11.0 mg, 0.0700 mmol) dissolved in minimal THF was added to the reaction vial. The flask was fitted with a reflux condenser and Ar balloon and was heated to reflux for 16 h. The reaction was quenched by the addition of 3 mL saturated aq. ammonium chloride, and extracted 3× with 10 mL DCM. The organics were dried over anhydrous sodium sulfate and concentrated in vacuo. The residue was purified by flash chromatography (SiO$_2$; 50% EtOAc in hexanes) to afford N-(1,3-benzodioxol-5-yl)-3-[2-(cyclopropoxy)phenyl]prop-2-enamide (21.1 mg, 0.0653 mmol, 92.8% yield) as a ~2:1 mixture of E:Z isomers.

ESI-MS: [M+H]+ calculated for C$_{19}$H$_{17}$NO$_4$ 324.116; found 324.209. UV: λ (max) 328.2 nm.

8-[2-(cyclopropoxy)phenyl]-7,8-dihydro-5H-[1,3]dioxolo[4,5-g]quinolin-6-one (FQI-40)

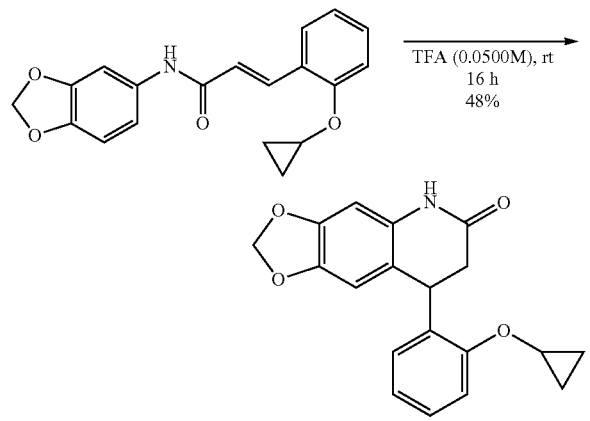

In a flame dried 5 mL flask equipped with a stir bar, N-(1,3-benzodioxol-5-yl)-3-[2-(cyclopropoxy)phenyl]prop-2-enamide (21.1 mg, 0.0653 mmol) was dissolved in TFA (1.31 mL) and the flask purged with Ar. The mixture was stirred at RT for 24 h, resulting in poor conversion by TLC, at which point an additional 1.31 mL HFIP was added to the reaction. The mixture was allowed to stir for an additional 24 h, resulting in improved conversion by TLC. The reaction was concentrated by rotary evaporation and the residue neutralized with ~5 mL saturated aq. sodium bicarbonate. The mixture was extracted 3× with 10 mL DCM, and combined organics were rinsed with water, then brine, and dried over anhydrous sodium sulfate. The crude material was purified by flash chromatography (SiO$_2$; gradient from 25 to 50% EtOAc in hexanes) to afford 8-[2-(cyclopropoxy)phenyl]-7,8-dihydro-5H-[1,3]dioxolo[4,5-g]quinolin-6-one (10.2 mg, 0.0315 μmol, 48.3% yield).

$^1$H NMR: (400 MHz, Chloroform-d) δ 8.28 (s, 1H), 7.32-7.19 (overlap, 2H), 6.86 (d, J=6.3 Hz, 2H), 6.41 (s, 2H), 6.39 (s, 2H), 5.90 (s, 2H), 4.51 (t, J=6.7 Hz, 1H), 3.76 (m, 1H), 2.90-2.73 (overlap, 2H), 0.86-0.66 (overlap, 4H). ESI-MS: [M+H]+ calculated for C$_{19}$H$_{17}$NO$_4$ 324.116; found 324.209. UV: λ (max) 254.2 nm.

2-(cyclopentyloxy)benzaldehyde

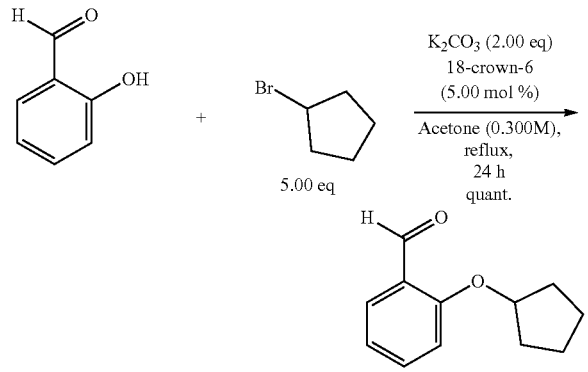

In a flame dried 25 mL pear shaped flask equipped with a stir bar was added salicylaldehyde (244.2 mg, 2.00 mmol, 212 uL) followed by anhydrous Acetone (6.67 mL). The flask was flushed with nitrogen, and to the mixture was added solid anhydrous potassium carbonate (553 mg, 4.00 mmol) and 18-crown-6 (26.4 mg, 0.100 mmol), followed by cyclopentyl bromide (1.49 g, 10.0 mmol, 1.07 mL) as one portion. The flask was fitted with a reflux condenser and nitrogen balloon, and stirred at reflux for 24 h. The mixture was filtered by vacuum filtration, the solution condensed in vacuo, and residue purified by flash chromatography (SiO$_2$, 10% EtOAc in Toluene) to afford 2-(cyclopentoxy)benzaldehyde (0.381 g, 2.00 mmol) in quantitative yield.

$^1$H NMR (400 MHz, CHCl$_3$): (1:1 mixture of hydrate rotamers) δ 8.00 (d, J=16.0 Hz, 1H) (rotamer A), 7.85 (d, J=16.5 Hz, 1H) (rotamer B), 7.56 (ddd, J=20.1, 7.7, 1.3 Hz, 1H), 7.33 (dd, J=8.0 Hz, 8.0 Hz, 1H), 7.18 (d, J=16.1 Hz, 1H) (rotamer A), 6.94 (overlap, 2H), 6.75 (d, J=16.5 Hz, 1H) (rotamer B), 4.86 (m, 1H), 2.38 (s, 2H) (OH), 1.94 (m, 4H), 1.83 (m, 2H), 1.67 (m, 2H). ESI-MS: [M–H]+ calculated for C$_{12}$H$_{14}$O$_2$ 191.099; found 191.175. UV: λ (max) 308.2 nm.

N-(benzo[d][1,3]dioxol-5-yl)-3-(2-(cyclopentyloxy)phenyl)acrylamide

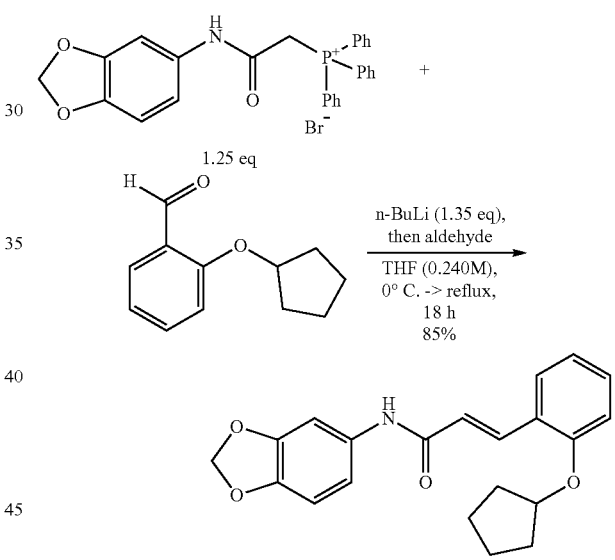

In a flame dried 10 mL flask equipped with a stir bar was dissolved [2-(1,3-benzodioxol-5-ylamino)-2-oxo-ethyl]-triphenyl-phosphonium bromide (650 mg, 1.25 mmol, 1.25 eq) in THF (4.17 mL) under Ar. The mixture was cooled to 0° C., and n-butyl lithium (1.6 M in hexanes) 1.35 mmol, 843 uL) was added dropwise via syringe. The mixture was allowed to warm to RT and stir for 30 min. After equilibrating, 2-(cyclopentoxy)benzaldehyde (190 mg, 1.00 mmol) was quickly added as a solid in a single portion. The flask was fitted with a reflux condenser and Ar balloon, and the mixture was heated to reflux overnight. The mixture was quenched by the addition of 20 mL saturated aq. ammonium chloride, and extracted 3× with 20 mL DCM. The combined organics were dried over anhydrous sodium sulfate, concentrated in vacuo, and the residue was purified by flash chromatography (SiO$_2$, 25% EtOAc in hexanes) to afford (E)-N-(1,3-benzodioxol-5-yl)-3-[2-(cyclopentoxy)phenyl]prop-2-enamide (0.299 g, 851 μmol, 85.1% yield) as a ~10:1 mixture of E:Z isomers.

ESI-MS: [M+H]+ calculated for $C_{21}H_{21}NO_4$ 352.147; found 352.306. UV: λ (max) 330.2 nm.

8-(2-(cyclopentyloxy)phenyl)-7,8-dihydro-[1,3]dioxolo[4,5-g]quinolin-6(5H)-one (FQI-41)

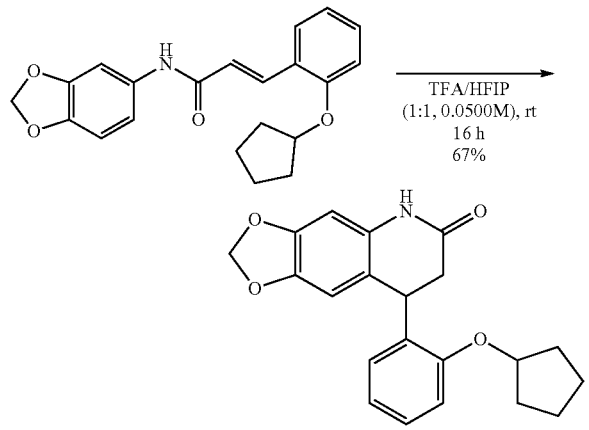

In a flame dried 25 mL flask equipped with a stir bar, N-(1,3-benzodioxol-5-yl)-3-[2-(cyclopentoxy)phenyl]prop-2-enamide (175.7 mg, 0.500 mmol) was dissolved in a mixture of TFA (5.00 mL) and HFIP (5.00 mL). The flask was fitted with an Ar balloon and stirred at RT for 16 h. The reaction was concentrated by rotary evaporation and the residue was neutralized with ~20 mL saturated aq. sodium bicarbonate. The mixture was extracted 3× with 20 mL DCM, and combined organics were rinsed with water, then brine, and dried over anhydrous sodium sulfate. The crude solid was purified by column chromatography (SiO₂, gradient from 25 to 50% EtOAc in hexanes) to afford 8-[2-(cyclopentoxy)phenyl]-7,8-dihydro-5H-[1,3]dioxolo[4,5-g]quinolin-6-one (0.118 g, 0.336 mmol, 67.1% yield).

¹H NMR: (400 MHz, Chloroform-d) δ 7.43 (s, 1H), 7.19 (t, J=6.6 Hz, 1H), 6.90-6.84 (overlap, 2H), 6.81 (t, J=7.0 Hz, 1H), 6.43 (s, 1H), 6.34 (s, 1H), 5.90 (d, J=1.9 Hz, 2H), 4.81 (m, 1H), 2.94 (dd, J=16.2, 7.3 Hz, 1H), 2.79 (dd, J=16.2, 6.7 Hz, 1H), 1.95-1.77 (overlap, 4H), 1.76-1.67 (m, 2H), 1.67-1.58 (m, 2H). ¹³C NMR: (125 MHz, Chloroform-d) δ 171.53, 155.31, 147.02, 143.68, 131.70, 130.03, 128.75, 128.20, 120.29, 119.04, 112.60, 108.46, 101.27, 97.75, 79.22, 36.74, 36.33, 33.22, 32.91, 24.20, 24.16. ESI-MS: [M+H]+ calculated for $C_{21}H_{21}NO_4$ 352.147; found 352.306. UV: λ (max) 229.2 nm.

2-(cyclopentoxy)-4-(dimethylamino)benzaldehyde

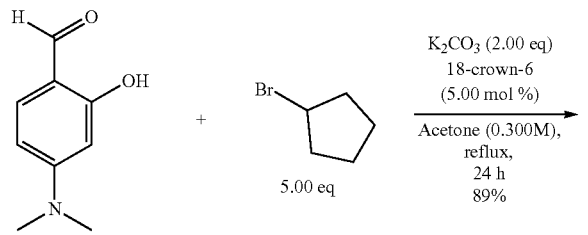

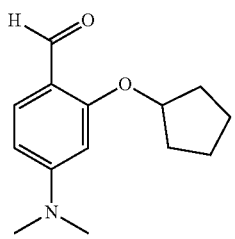

In a flame dried 25 mL heart shaped flask equipped with a stir bar was added 4-(dimethylamino)-2-hydroxy-benzaldehyde (330 mg, 2.00 mmol) followed by anhydrous Acetone (6.67 mL). The flask was flushed with nitrogen, and to the mixture was added solid anhydrous potassium carbonate (553 mg, 4.00 mmol) and 18-crown-6 (26.4 mg, 0.100 mmol), followed by cyclopentyl bromide (1.49 g, 10.0 mmol, 1.07 mL) as one portion. The flask was fitted with a reflux condenser and nitrogen balloon, and stirred at reflux for 24 h. The mixture was filtered by vacuum filtration, the solution condensed in vacuo, and residue purified by flash chromatography (SiO₂, 10% EtOAc in toluene) to afford 2-(cyclopentoxy)-4-(dimethylamino)benzaldehyde (0.416 g, 1.78 mmol, 89.2% yield).

¹H NMR: (400 MHz, Chloroform-d) δ 10.16 (s, 1H), 7.73 (d, J=8.9 Hz, 1H), 6.29 (dd, J=8.9, 2.0 Hz, 1H), 6.04 (d, J=2.1 Hz, 1H), 4.87 (ddd, J=8.5, 5.2, 3.5 Hz, 1H), 3.07 (s, 6H), 2.01-1.89 (overlap, 4H), 1.88-1.75 (m, 2H), 1.71-1.60 (m, 2H). ESI-MS: [M+H]+ calculated for $C_{14}H_{19}NO_2$ 234.142; found 235.241. UV: λ (max) 317.2 nm.

N-(benzo[d][1,3]dioxol-5-yl)-3-(2-(cyclopentyloxy)-4-(dimethylamino)phenyl)acrylamide

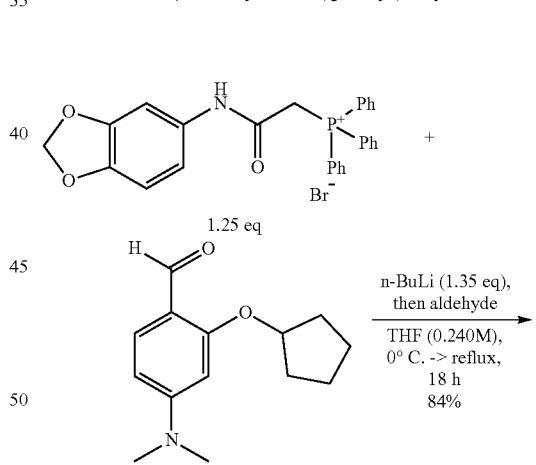

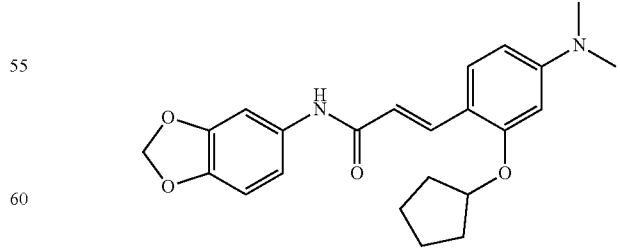

In a flame dried 10 mL flask equipped with a stir bar was dissolved [2-(1,3-benzodioxol-5-ylamino)-2-oxo-ethyl]-triphenyl-phosphonium bromide (650. mg, 1.25 mmol, 1.25 eq) in THF (4.17 mL) under Ar. The mixture was cooled to 0° C., and n-butyl lithium (1.6 M in hexanes) 1.35 mmol, 843 uL) was added dropwise via syringe. The mixture was allowed to warm to RT and stir for 30 min. After equilibrating, 2-(cyclopentoxy)-4-(dimethylamino)benzaldehyde (233 mg, 1.00 mmol, 1.00 eq.) was quickly added as a solid in a single portion. The flask was fitted with a reflux condenser and Ar balloon, and the mixture was heated to reflux overnight. The mixture was quenched by the addition of 20 mL saturated aq. ammonium chloride, and extracted 3× with 20 mL DCM. The combined organics were dried over anhydrous sodium sulfate, concentrated in vacuo, and the residue was purified by flash chromatography ($SiO_2$, 25% EtOAc in hexanes) to afford N-(1,3-benzodioxol-5-yl)-3-[2-(cyclopentoxy)-4-(dimethylamino)phenyl]prop-2-enamide (332 mg, 0.841 mmol, 84.1% yield) as a ~10:1 mixture of E:Z isomers.

$^1$H NMR: (400 MHz, Chloroform-d) (E isomer) δ 7.89 (d, J=15.6 Hz, 1H), 7.37 (d, J=8.6 Hz, 2H), 7.04 (s, 1H), 6.85 (d, J=7.4 Hz, 1H), 6.75 (d, J=8.3 Hz, 1H), 6.41 (d, J=15.6 Hz, 1H), 6.28 (dd, J=8.8, 2.3 Hz, 1H), 6.16 (s, 1H), 5.95 (s, 2H), 4.84 (m, 1H), 3.01 (s, 7H), 2.00-1.87 (overlap, 4H), 1.86-1.75 (m, 2H), 1.72-1.59 (m, 2H). ESI-MS: [M+H]$^+$ calculated for $C_{23}H_{26}N_2O_4$ 395.189; found 395.311. UV: λ (max) 374.2 nm.

8-[2-(cyclopentoxy)-4-(dimethylamino)phenyl]-7,8-dihydro-5H-[1,3]dioxolo[4,5-g]quinolin-6-one (FQI-42)

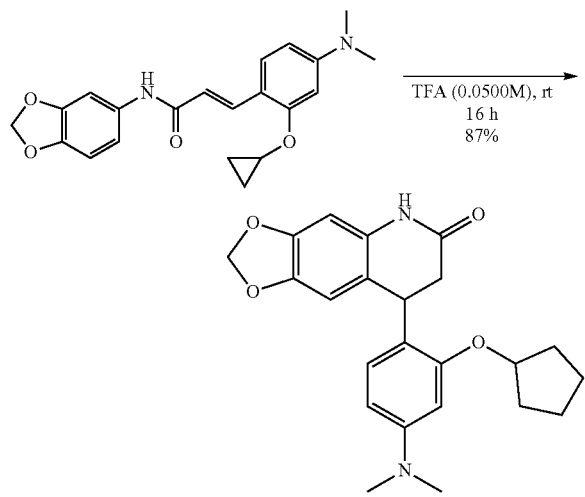

In a flame dried 25 mL flask equipped with a stir bar, N-(1,3-benzodioxol-5-yl)-3-[2-(cyclopentoxy)-4-(dimethylamino)phenyl]prop-2-enamide (197 mg, 0.500 mmol) was dissolved in a mixture of TFA (10.0 mL) The flask was fitted with an Ar balloon and stirred at RT for 16 h. The reaction was concentrated by rotary evaporation and the residue was neutralized with ~20 mL saturated aq. sodium bicarbonate. The mixture was extracted 3× with 20 mL DCM, and combined organics were rinsed with water, then brine, and dried over anhydrous sodium sulfate. The crude solid was purified by column chromatography ($SiO_2$, gradient from 25 to 50% EtOAc in hexanes) to afford 8-[2-(cyclopentoxy)-4-(dimethylamino)phenyl]-7,8-dihydro-5H-[1,3]dioxolo[4,5-g]quinolin-6-one (171 mg, 0.432 mmol, 86.5% yield).

$^1$H NMR: (400 MHz, Chloroform-d) δ 7.49 (s, 1H), 6.74 (d, J=8.5 Hz, 1H), 6.43 (s, 1H), 6.32 (s, 1H), 6.27 (d, J=2.2 Hz, 1H), 6.21 (dd, J=8.5, 2.2 Hz, 1H), 5.91-5.85 (m, 2H), 4.80 (s, 1H), 4.40 (m, 1H), 2.96-2.90 (overlap, 7H), 2.73 (dd, J=16.2, 6.3 Hz, 1H), 1.91-1.77 (overlap, 4H), 1.75-1.64 (m, 2H), 1.64-1.57 (m, 2H). $^{13}$C NMR: (125 MHz, Chloroform-d) δ 172.02, 156.17, 151.07, 146.73, 143.54, 131.52, 129.14, 120.17, 118.25, 108.45, 104.57, 101.15, 98.31, 97.64, 79.00, 40.86, 37.09, 35.80, 33.30, 32.99, 24.20, 24.17. ESI-MS: [M+H]$^+$ calculated for $C_{23}H_{26}N_2O_4$ 395.189; found 395.355. UV: λ (max) 224.2 nm.

8-(2-ethoxyphenyl)-7,8-dihydro-[1,3]dioxolo[4,5-g]quinoline-6(5H)-thione (Thio-FQI1)

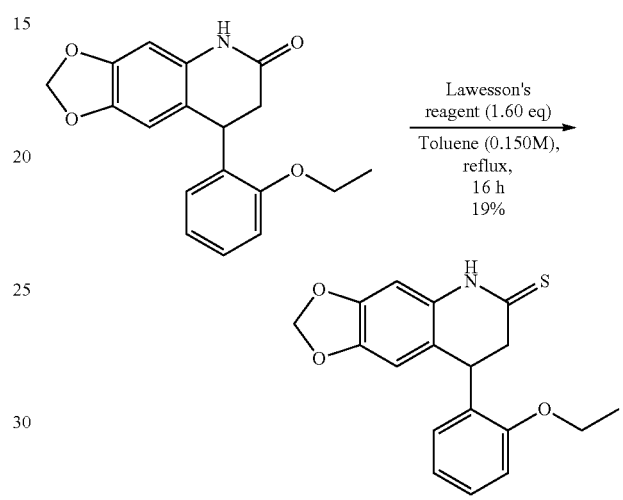

FQI1 (200 mg, 0.643 mmol, 1.0 equiv) was weighed into a dry reaction vial under an atmosphere of nitrogen. Dry toluene (4.3 mL) was added, followed by Lawesson's reagent (416 mg, 1.02 mmol, 1.6 equiv). The vial was tightly sealed and the reaction was heated to reflux overnight. After cooling, the solvent was removed in vacuo and the residue was purified by flash column chromatography (gradient of 20% to 70% ethyl acetate in hexanes). Fractions which contained product were pooled to give 120 mg of an impure red oil which was recrystallized from dichloromethane/hexanes to give Thio-FQI1 as white needles (40 mg, 19%). Mp: $^1$H NMR (400 MHz, CDCl$_3$) δ 9.69 (br. s., 1H), 7.20 (ddd, J=2.9, 6.0, 8.3 Hz, 1H), 6.89-6.82 (m, 3H), 6.46 (d, J=3.1 Hz, 2H), 5.93 (d, J=1.2 Hz, 2H), 4.54 (dd, J=6.4, 7.8 Hz, 1H), 4.10-4.02 (m, 2H), 3.42 (dd, J=7.8, 17.0 Hz, 1H), 3.23 (dd, J=6.4, 17.0 Hz, 1H), 1.40 (t, J=7.0 Hz, 3H).

8-(4-chloro-2-ethoxyphenyl)-7,8-dihydro-[1,3]dioxolo[4,5-g]quinoline-6(5H)-thione (Thio-FQI1-Cl)

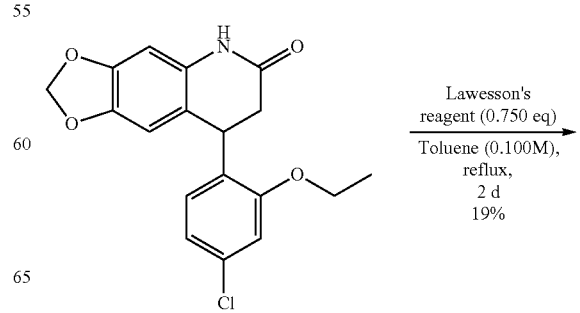

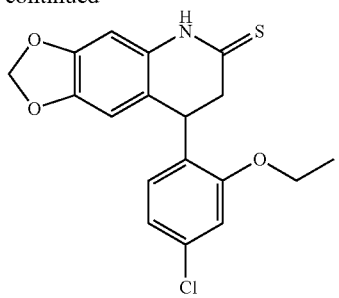

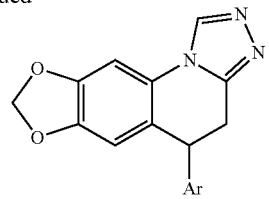

FQI1 triazoles

FQI1-Cl (300 mg, 0.870 mmol, 1.00 equiv) was weighed into a dry reaction vial under an atmosphere of nitrogen. Dry toluene (8.70 mL) was added, followed by Lawesson's reagent (176 mg, 0.435 mmol, 0.500 eq). The vial was tightly sealed and the reaction was heated to reflux overnight. After 24 h, the reaction was incomplete by TLC, at which time the vial was cooled, opened to add an additional portion of Lawesson's reagent (87.9 mg, 0.217 mmol, 0.250 equiv), re-purged with nitrogen, sealed and refluxed for an additional 24 h. No noticeable change in TLC was observed and the reaction was stopped at 48 h total time. After cooling, the solvent was removed in vacuo and the residue was purified by flash column chromatography (gradient of 20% to 70% ethyl acetate in hexanes) to afford 8-(4-chloro-2-ethoxy-phenyl)-7,8-dihydro-5H-[1,3]dioxolo[4,5-g]quinoline-6-thione (Thio-FQI1-Cl) (62.0 mg, 0.171 mmol, 19.7% yield) as an off-white powdery solid.

$^1$H NMR: (400 MHz, Chloroform-d) δ 9.62 (s, 1H), 6.86 (s, 1H), 6.81 (dd, J=8.3, 1.7 Hz, 1H), 6.72 (d, J=8.3 Hz, 1H), 6.46 (d, J=1.7 Hz, 2H), 5.95 (s, 2H), 4.47 (dd J=7.0, 6.7 Hz, 1H), 4.05 (q, J=6.8 Hz, 2H), 3.38 (dd, J=16.8, 7.0 Hz, 1H), 3.19 (dd, J=16.8, 6.7 Hz, 1H), 1.42 (t, J=6.8 Hz, 3H). ESI-MS: [M+H]$^+$ calculated for $C_{18}H_{16}ClNO_3S$ 362.054; found 362.197. UV: λ (max) 332.2 nm General Procedure C: Synthesis of Triazolo-Dihydroquinolines (FQI1 Triazoles, FQI1-Triazole and Tri-FQI-Cl) Via Methyl Imidate Intermediate (Second Generation Route)

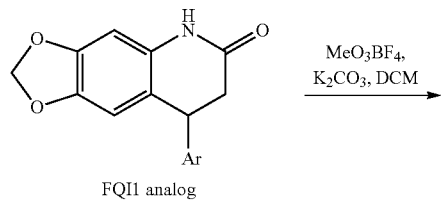

FQI1 analog

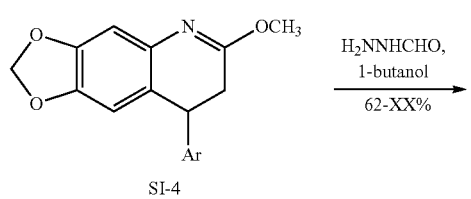

SI-4

The appropriate FQI1 analog (1.0 equiv) was suspended in anhydrous dichloromethane (0.2M concentration) in a vial under nitrogen. Trimethyloxonium tetrafluoroborate (1.5 equiv) was added in one portion, followed by potassium carbonate (4.0 equiv). The reaction was stirred at room temperature overnight, until UPLC-MS indicated >80% conversion to methyl imidate SI-3. The reaction mixture was diluted 50 mL DCM and washed with 25 mL water. The organic layer was dried over sodium sulfate, condensed, and carried on to the next step without further purification.

Crude SI-4 was dissolved in 1-butanol (0.15M) in a vial under nitrogen. Formic acid hydrazide (1.2 equiv) was added in one portion, and the vial was heated on a block to reflux overnight. The butanol was removed in vacuo and the residue was dry-loaded onto silica. Flash column chromatography (1% ethanol in ether to elute unreacted quinolinone starting material, followed by 10% ethanol in ether to elute the triazole) to afford the desired triazole.

5-(2-ethoxyphenyl)-4,5-dihydro-[1,3]dioxolo[4,5-g][1,2,4]triazolo[4,3-a]quinolone (FQI1-triazole)

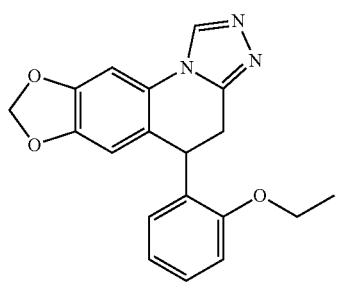 [SMILES: CCOc1ccccc1C1Cc2nncn2-c2cc3c(cc21)OCO3]

5-(2-ethoxyphenyl)-4,5-dihydro-[1,3]dioxolo[4,5-g][1,2,4]triazolo[4,3-a]quinoline (FQI1-triazole) was obtained as an off-white solid via reaction of FQI1 according to General Procedure A (62% over two steps). $^1$H NMR (400 MHz, CDCl$_3$) δ 8.56 (s, 1H), 7.15 (dt, J=1.6, 7.8 Hz, 1H), 6.97 (s, 1H), 6.85 (d, J=8.2 Hz, 1H), 6.77-6.69 (m, 1H), 6.62 (dd, J=1.6, 7.4 Hz, 1H), 6.54 (s, 1H), 5.95 (d, J=1.2 Hz, 2H), 4.67 (t, J=6.6 Hz, 1H), 4.11-3.96 (m, 2H), 3.50 (dd, J=7.0, 16.0 Hz, 1H), 3.30 (dd, J=6.3, 16.0 Hz, 1H); $^{13}$C NMR (100 MHz, CDCl$_3$) δ 155.9, 149.8, 147.3, 146.4, 137.2, 128.5, 128.4, 127.9, 125.9, 123.4, 120.4, 111.4, 109.2, 111.4, 109.2, 101.7, 97.8, 63.4, 36.2, 26.5, 14.6. ESI-MS: [M+H]$^+$ calculated for $C_{19}H_{17}N_3O_3$ 336.127; found 336.373. UV: λ (max) 223.89.

5-(4-chloro-2-ethoxyphenyl)-4,5-dihydro-[1,3]di-oxolo[4,5-g][1,2,4]triazolo[4,3-a]quinolone (Tri-FQI1-Cl)

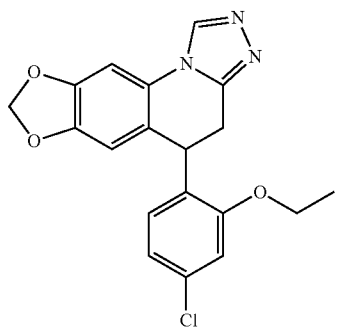 [SMILES: CCOc1cc(Cl)ccc1C1Cc2nncn2-c2cc3c(cc21)OCO3]

5-(4-chloro-2-ethoxyphenyl)-4,5-dihydro-[1,3]dioxolo[4,5-g][1,2,4]triazolo[4,3-a]quinoline (Tri-FQI1-Cl) was obtained as an off white solid via reaction of FQI1-Cl according to General Procedure C (33.9% over two steps). $^1$H NMR (400 MHz, Chloroform-d) δ 8.54 (s, 1H), 6.97 (s, 1H), 6.86 (d, J=1.8 Hz, 1H), 6.74 (dd, J=8.2, 1.8 Hz, 1H), 6.57 (s, 1H), 6.53 (d, J=8.2 Hz, 1H), 4.64 (dd, J=6.5, 6.5 Hz, 1H), 4.13-3.98 (m, 2H), 3.50 (dd, J=16.1, 6.5 Hz, 1H), 3.31 (dd, J=16.1, 6.5 Hz, 1H), 1.41 (t, J=7.0 Hz, 3H). ESI-MS: [M+H]$^+$ calculated for $C_{19}H_{16}Cl\ N_3O_3$ 370.088; found 370.318. UV: λ (max) 231.89.

Example 2: Cell Growth Inhibition Assay

Cell lines and culture conditions: Human colon cancer cells Caco-2, HT29 and HCT15, human pancreatic cancer cells BxPC3, CFPAC-1, and CAPAN-2, liver cancer cells SNU423 and kidney cells HEK293, were obtained from American Type Culture Collection (Rockville, USA). QGY-7703 cells and NIH-3T3 cells were cultured in DMEM (Dulbecco's modification of Eagle's Medium; Corning) supplemented with 10% Fetal Bovine Serum (FBS; Invitrogen) and 10% Fetal Calf Serum (FCS; Atlanta Biologicals) respectively. U937, BxPC3, HCT15 and THP-1 cells were grown in RPMI-1640 (Roswell Park Memorial Institute; Corning) supplemented with 10% Fetal Bovine Serum (FBS; Invitrogen). CFPAC-1 cells were cultured in Iscove's Modified Dulbecco's Medium (ATCC) supplemented with 10% FBS. CAPAN-2 and HT29 cells were cultured in McCoy's 5a medium supplemented with 10% FBS. Caco2 cells were grown in Eagle's Minimum Essential Medium (ATCC) with final 20% FBS concentration. All cells were maintained at 37° C. in 5% $CO_2$ at constant humidity.

MTS cell proliferation assay: Cells were counted using a hemacytometer and were plated at 3000-1500 cells per well, in a 96-well format. For SAR studies 1,500 QGY-7703 or NIH-3T3 cells were seeded in each well of 96-well plates for approximately 20 hours, and then treated with compound or DMSO (vehicle control) at appropriate concentrations (DMSO at final concentration of 1%). For other cell proliferation assay 3000 BxPC3, CFPAC-1, CAPAN-2, HEK293, HCT15, HT29, or SNU423 cells were seeded in in each well approximately 20 hrs prior to the treatment. For U937 and THP-1 suspension cells, 2,500 cells were added to the wells of a 96-well plate on the day of treatment. After a 72-hour (or 120 hrs for BxPC3, CAPAN-2, SNU423) incubation with compound or vehicle, cell growth was assessed via the Promega CellTiter 96® AQueous One Solution Cell Proliferation Assay, a colorimetric method to determine the number of viable cells. 20 μL of the CellTiter 96® AQueous One Solution Reagent was added directly into cultured wells and incubated for approximately one hour, after which the absorbance at 490 nm was read with a 96-well plate reader (Opys MR Microplate Reader). $GI_{50}$ values were determined from plots of the percentage of compound-treated cell growth to vehicle cell growth vs. compound concentration (GraphPad Prism; non-linear regression, log inhibitor verse normalized response with variable slope). Results are shown in FIGS. 10A-27C.

TABLE 1

Exemplary representative cancer cell lines used in this example.

| Cell Line | Age | Gender | Derivation | Proliferation (doubling time) |
|---|---|---|---|---|
| BxPC-3 | 61 | Female | Pancreatic adenocarcinoma | 60 hrs |
| Capan-2 | 56 | Male | Pancreatic adenocarcinoma | 96 hrs |
| CFPAC-1 | 26 | Male | Ductal adenocarcinoma, CF | 31 hrs |
| CaCo-2 | 72 | Female | Colorectal adinocarcinoma, Duke's C primary | 20-24 hr |
| HCT-15 | N/A | Male | Colorectal adenocarcinoma | 20-24 hr |
| HT-29 | 44 | Female | Rectosigmoid carcinoma | 24 hr |
| SNU-423 | 40 | Male | Hepatocellular carcinoma | 72 hr |
| HEK293 | fetus | N/A | Embryonic kidney | 24 hr |
| NIH3T3 | N/A | Mouse | Mouse embryonic fibroblast | 20 hr |
| U937 | 37 | Male | Monocytic lymphoma | 95-100 hr |
| THP-1 | 1 | Male | Monocytic lymphoma | 26 hr |
| HuH7 | 57 | Male | Hepatocellular carcinoma | |

Cellular thermal shift assay: QGY-7703 cells were cultured as in the MTS assay. Cells were seeded into 10 cm plates and allowed to reach 60-80% confluency. After trypsinization (0.05% Trypsin-EDTA, Invitrogen), the cell pellet was washed twice with ice-cold 1×PBS (137 mM NaCl, 2.7 mM KCl, 10 mM $Na_2HPO_4$, 2 mM $KH_2PO_4$, pH 7.2). The cell pellet was lysed by addition of 200 μL freshly prepared ice-cold modified RIPA buffer (50 mM Tris-Cl pH 7.4, 1% NP-40, 0.1% sodium deoxycholate, 0.1% SDS, 150 mM NaCl, 10 mM EDTA) supplemented with 1 mM Pefabloc (Sigma-Aldrich), and flash frozen in liquid nitrogen followed by thawing at room temperature for a total of three cycles. Cell lysate was centrifuged at 20,000×g for 20 minutes to clarify after third freeze/thaw. Supernatant was either treated immediately or saved at −80° C. for future use. 200 μL of the lysate was treated with dihydroquinolinone (addition of 2 μL 50 mM Stock; 500 μM final in 1% DMSO) or vehicle (2 μL DMSO), gently flicked to mix, and incubated for 30 minutes at room temperature. After treatment, the lysate was separated into 20 μL aliquots for thermal denaturation. Lysate was heated at the given temperature for 5 minutes, then placed on ice for 5 minutes and subsequently centrifuged at 20,000×g for 10 minutes to separate soluble protein from aggregates. 10 μL of the supernatant containing the soluble protein was saved at −20° C. for immunoblot analysis. Equal amounts of supernatant were loaded onto a 10% polyacrylamide gel. Separated proteins were transferred onto polyvinylidene difluoride (PVDF) membranes. Membranes were blocked in 5% milk/TBST (50 mM Tris-Cl, pH 7.5, 150 mM NaCl, 0.1% Tween-20), and then probed overnight at 4° C. with primary antibody (anti-LSF (Millipore; 1:500 dilution in 5% bovine serum albumin in TBST). Secondary goat anti-rabbit HRP-IgG antibody (1:3000 in blocking buffer) was incubated with membranes for 1 hour at room temperature. Protein bands were detected with Immobilon Western Chemiluminescent HRP-Substrate (Millipore) and developed on a Kodak RP X-OMAT Developer. Immunoblots were quantified using Image J and graphed using GraphPad PRISM. Area-under-curve (AUC) for the quantified Western blots were calculated with GraphPad PRISM. Non-parametric t-test was calculated to determine statistical significance between the curves. $Tm_{50}$ values were calculated using non-linear regression (inhibitor-vs-response, variable slope). Results are shown in FIGS. 28A-30B.

Example 3: Lysine Methylation of α-Tubulin by Microtubule-Associated SET8 is Facilitated by LSF Microtubules (MTs) are major cytoskeletal components that play important roles in key cellular processes such as structural support, localization of organelles, and chromosome segregation [1,2]. A number of post-translational modifications (PTMs) of microtubules have been reported, which contribute to the functional diversity of microtubules and affect MT dynamics and organization [3]. This led to the hypothesis of a tubulin code, where tubulin modifications specify biological outcomes through changes in higher-order microtubule structure by recruiting and interacting with effector proteins. Notably, tubulin methylation has been less studied than other types of tubulin modification, such as detyrosination, glutamylation, glycylation, acetylation, and phosphorylation, although in the parallel histone code hypothesis, methylation is the most common and well-understood modification.

SET8/PR-Set7 is a protein-lysine N-methyltransferase responsible for the monomethylation of both histone and non-histone proteins in higher eukaryotes [4]. It is functionally characterized as a histone H4 lysine 20-specific monomethyltransferase [5]; this modification is a specific mark for transcriptional repression and is also enriched during mitosis [6, 7]. SET8 is required for cell proliferation, chromosome condensation, and cytokinesis, since deletion or RNAi mediated depletion of the enzyme impairs all these functions. Previous findings, in particular, suggest that SET8 and H4K20me1 are required for mitotic entry [8]. SET8 also mediates monomethylation of other substrates, including p53, which results in repression of p53 target genes [9]. However, how H4K20me1 is regulated and how it functions to promote cell cycle progression remains an open question, including the possibility that other non-histone substrates may be involved.

Transcription factor LSF is an oncogene in Hepatocellular Carcinoma (HCC), being dramatically overexpressed in HCC cell lines and patient samples [10]. LSF is also generally required for cell cycle progression and cell survival [11]. Initially, LSF was described as a regulator of G1/S progression [12], and essential for inducing expression of the gene encoding thymidylate synthase (TYMS) in late G1. However, its additional involvement in mitosis was suggested during characterization of the effects of Factor Quinolinone Inhibitor 1 (FQI1), a specific small molecule inhibitor of LSF [13]. FQI1 abrogates the DNA-binding and corresponding transcriptional activities of LSF [15], as well as specific LSF-protein interactions [14] and inhibits growth of HCC tumors in multiple mouse models. In tumor cell lines FQI1 causes cell death via mitotic defect.

Results

SET8 Directly Interacts with Tubulin

Figure 1A:
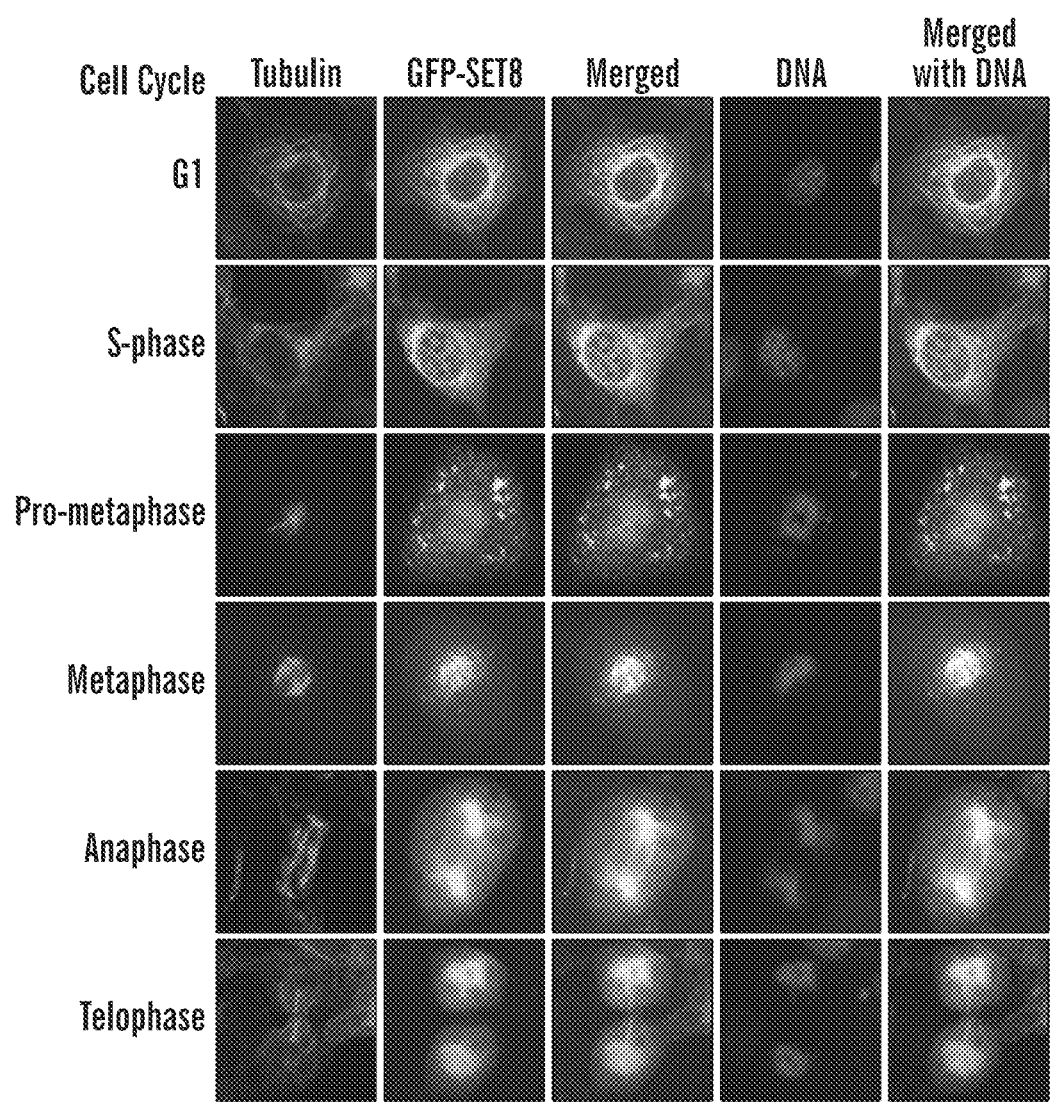
FIG. 1A-1C show that SET8 associates with tubulin in cells and directly interacts with α-tubulin in vitro.
Figure 1B:
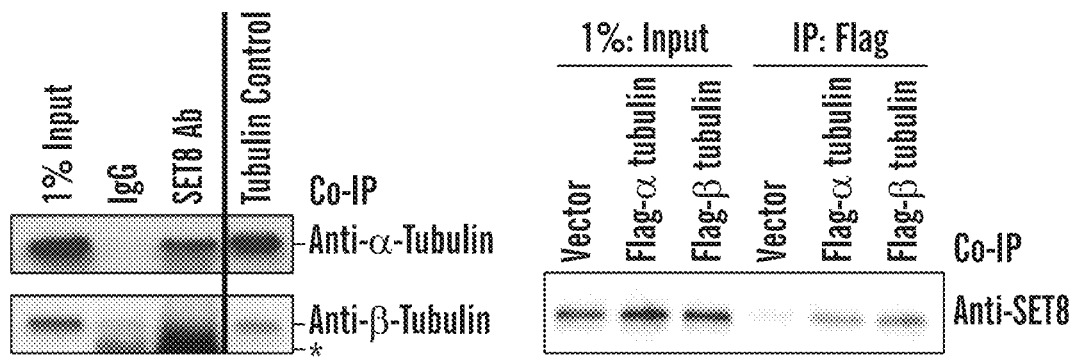
Figure 1C:
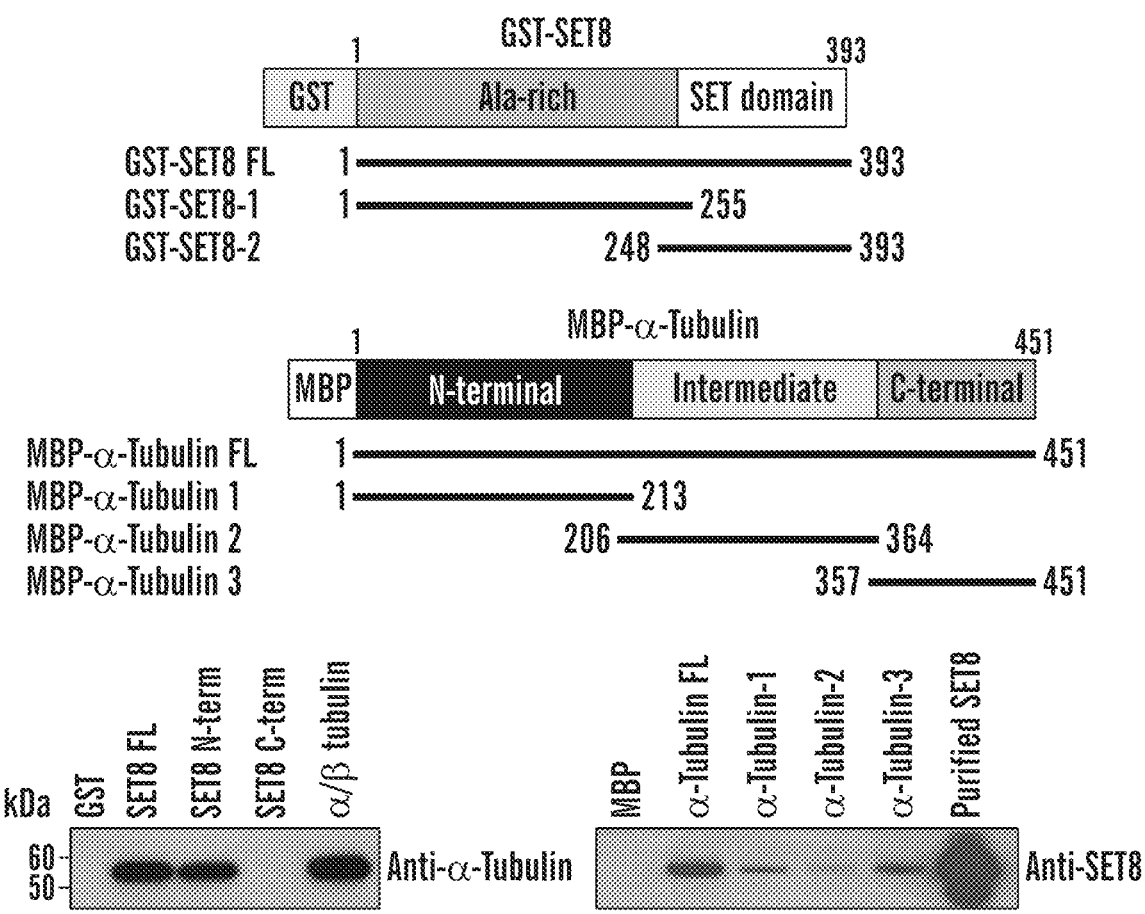

Analysis of commercial tubulin preparations (99% pure) by mass-spectroscopy identified anticipated associated proteins (e.g. MAP1, MAP2), but surprisingly also peptides covering SET8 as shown in Table 2. This raised the question of whether SET8 might target MT-related substrates. Indeed, upon overexpressing GFP-SET8 in COS7 cells, the majority of GFP-SET8 was localized in the cytoplasm (FIG. 6A), and appeared to be closely aligned with MTs. Therefore, the inventors screened cytoplasmic components by staining with relevant fluorescence dyes along with GFP-SET8 expression. In contrast to ER, Golgi, and actin, tubulin significantly co-localized with SET8 at stages throughout the cell cycle (FIG. 1A). Most obviously, in G1 phase when tubulin is filamentous and distributed throughout the cytoplasm, SET8 exhibited the same pattern. In S phase, as expected from previous studies, some SET8 was also nuclear (FIG. 1A). To determine whether endogenous cellular SET8 associates with tubulin, the inventors immunoprecipitated protein complexes from HEK293T cell extracts. Using antibody against SET8, α-tubulin was clearly detected, and conversely, upon expression of Flag-tagged α-tubulin in the cells, SET8 co-immunoprecipitated with Flag-α-tubulin (FIG. 1A). In addition, although endogenous β-tubulin was not robustly present upon immunoprecipitation with SET8 antibody, endogenous SET8 did also co-immunoprecipitate with Flag-tagged β-tubulin (FIG. 1B). To determine whether these interactions are direct and to map which protein regions interact, a series of proteins fusing glutathione S-transferase (GST) to human SET8 were tested for interactions in vitro with purified tubulin preparations and conversely, a series of proteins fusing maltose binding protein (MBP) to α-tubulin were tested for interactions with SET8 purified from *E. coli*. The GST and MBP pull down assays revealed that purified tubulin interacted with only the N-terminal portion of SET8, and that SET8 directly interacted predominantly with the C-terminal fragment of α-tubulin (FIG. 1C). The fusion protein of MBP to β-tubulin did not directly interact with SET8. Taken together, these data demonstrate that α-tubulin and SET8 directly interact with each other.

TABLE 2

Mass-spectrometry analysis of purified porcine tubulin*: top-scoring proteins.

| †Unique Peptides | ‡Total Peptides | UniProt Reference # | Gene Symbol | Name |
|---|---|---|---|---|
| 82 | 1704 | Q13885_TBB2A_Human | TUBB2A | Tubulin beta 2A class IIa |
| 77 | 1605 | Q71U36_TBA1A_Human | TUBA1A | Tubulin alpha 1a |

TABLE 2-continued

Mass-spectrometry analysis of purified porcine tubulin*: top-scoring proteins.

| †Unique Peptides | ‡Total Peptides | UniProt Reference # | Gene Symbol | Name |
| --- | --- | --- | --- | --- |
| 74 | 1226 | Q9NQR1_SETD8_Human | SETD8 | Lysine methyltransferase 5A |
| 40 | 611 | Q13509_TBB3_Human | TUBB3 | Tubulin beta 3 class III |
| 18 | 65 | P10636_TAU_Human | MAPT | Microtubule associated protein tau |
| 17 | 24 | P31150_GDIA_Human | GDI1 | GDP dissociation inhibitor 1 |
| 8 | 8 | P38646_GRP75_Human | HSPA9 | HSP family member 9 |
| 7 | 10 | P11137_MTAP2_Human | MAP2 | Microtubule associated protein 2 |
| 2 | 5 | Q92841_DDX17_Human | DDX17 | DEAD-box helicase 17 |
| 2 | 4 | K7ESM5_K7ESM5_Human | TUBB6 | Tubulin beta 6 class V |
| 2 | 2 | P09972_ALDOC_Human | ALDOC | Aldolase, fructose bisphosphate C |
| 2 | 2 | Q14651_PLSI_Human | PLS1 | Plastin 1 |
| 2 | 2 | P80404_GABT_Human | ABAT | 4-aminobutyrate aminotransferase |
| 2 | 2 | P14136_GFAP_Human | GFAP | Glial fibrillary acidic protein |

*Tubulin purified from brain; 99% pure.
†Unique peptides: total of 761.
‡Total peptides: 7519; Total proteins: 143; Protein FDR: 0.00%; One hit wonders: 79.

SET8 Methylates α-Tubulin

SET8 was characterized historically as a nucleosomal H4K20 specific methyltransferase, and subsequently as a regulator of the non-histone protein p53. However, since SET8 bound strongly to α-tubulin, it was tested whether tubulin is a novel substrate of the enzyme. Purified porcine tubulin was incubated with the cofactor S-adenosyl-L-[methyl-3H] methionine (AdoMet) and purified, recombinant GST-SET8. Tubulin was radioactively labeled in the presence of both SET8 and S-adenosyl-L-[methyl-3H] methionine (FIG. 2A, lane 3), but not upon addition of either tubulin or SET8 alone (FIG. 2A, lanes 2 and 4). Interestingly, when histone H4 was also included in the reaction, the amount of tubulin modification was reduced (FIG. 2A, lane 1), suggesting that histone H4 strongly competed with tubulin for the methylation activity of SET8. Automethylation of SET8 was also significantly reduced by addition of histone H4.

Since purified porcine tubulin is composed of α-and β-tubulin heterodimers, it was sought to determine which species is methylated by SET8. Recombinant fusion proteins of either α-tubulin or β-tubulin with MBP were purified and incubated with SET8 along with the radioactive methyl donor. Both SET8 and tubulin were labeled upon incubation with a/P tubulin (porcine) and MBP-α-tubulin (FIG. 2B, lanes 1 and 2), but only SET8 was modified with addition of MBP-β-tubulin (FIG. 2B, lane 3). These data indicate that α-tubulin is the target for SET8.

In order to dissect which lysine residue(s) of α-tubulin are methylated, both in purified tubulin samples and by SET8 in vitro, purified porcine tubulin was analyzed by mass spectrometry. As a negative control, tubulin was incubated solely with AdoMet. The spectral analysis of purified porcine tubulin alone detected only K304 monomethylation on α-tubulin. In the presence of SET8 and AdoMet, three additional lysine residues, K280, K311 and K352 of α-tubulin, were mono-methylated. Consistent with the experiments using recombinant MBP fusion proteins, these data suggest that the binding of SET8 to α-tubulin results in methylation of at least amino acids residues K280, K311 and K352. K311 is of particular interest, as its surrounding sequence, RHGK, is similar to SET8 targets in H4 (RHRK) and p53 (RHKK). As expected, acetylated lysine on α-tubulin from the same samples, particularly of K40 and K124 was also observed, as previously reported.

In order to test the inherent targeting of α-tubulin K311 by SET8, peptides spanning K311, as well as K40, reported to be methylated by SETD2 [15], and K304, modified in the purified porcine tubulin, were incubated with either purified wild type SET8 or catalytically inactive SET8 (D338A) in vitro. Only the K311-containing peptide was methylated, and this activity was abolished if the K311 residue was either mutated (K311A, K311S) or already modified (K31 line, K31 lac) (FIG. 2C). The in vitro targeting of the α-tubulin K311-containing peptide by SET8 is robust (FIG. 7A). Methylation by SETD2 of the α-tubulin K40-containing peptide was not detectable over background in these experiments, despite methylation of histone H3 in vitro (FIG. 7A).

Taken together, these observations indicated that endogenous mammalian α-tubulin contains lysine methylation, as yet mediated by unknown enzyme(s). In addition, SET8 methyltransferase has the capacity to methylate α-tubulin, particularly at K311.

Transcription Factor LSF Associates with Both SET8 and Tubulin

Figures 3A, 3B, 3C:
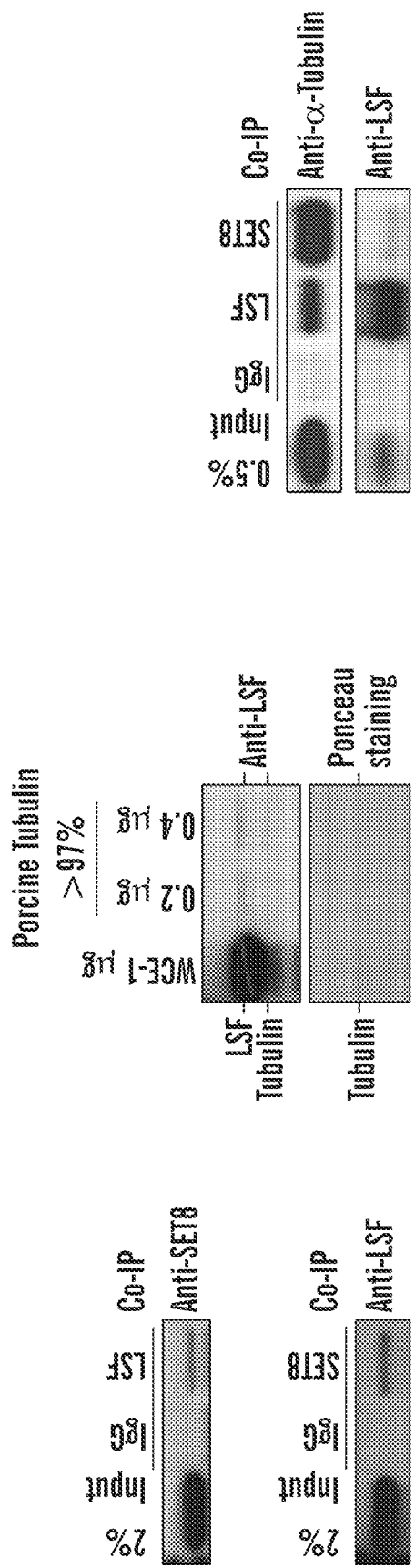

DNA-binding proteins recruit chromatin writers to modify histones [16], suggesting the possibility that other proteins might recruit SET8 to microtubules resulting in tubulin modification. Since less SET8 appeared to be bound to microtubules in prometaphase, and since treatment of cells with an LSF inhibitor resulted in a mitotic arrest at a similar point in mitosis [13], the inventors considered the transcription factor LSF to be a candidate for bringing SET8 to tubulin, perhaps to set up progression through prometaphase. In vitro, recombinant, purified LSF directly interacted with SET8, as shown in a GST pull-down assay (FIG. 6A). In addition, GFP-SET8 and 3×Flag-LSF significantly co-localized when both were expressed in cells (FIG. 6C). Finally, whether LSF, at endogenous levels, resides in the same complex as SET8 in cells was determined by co-immunoprecipitation experiments. Using either anti-LSF or anti-SET8 antibody to precipitate proteins from extracts, LSF and SET8 were indeed together in a complex (FIG. 3A).

To further test whether LSF might recruit SET8 to microtubules, it was investigated whether LSF-tubulin interactions occur in cells. Several types of experiments were performed. First, Biotin-tagged LSF was expressed in mammalian cells and proteomics analysis performed on protein complexes pulled down by streptavidin beads. As anticipated, several LSF binding partners, including paralogs LBP1A and LBP9, were prominently represented as peptides in the spectra but not in spectra from control streptavidin precipitates. Although unexpected for a transcription factor, tubulin peptides were also found by mass spectrometry, again highly represented but lacking in the control. Gene ontology analysis of the complete set of proteins specifically associated with LSF (~150) identified cell cycle: mitosis and cytoskeleton:microtubules as the most significantly overrepresented biological and component categories, respectively (Benjamini=1-2×10-3). Second, the possibility of relevant LSF-tubulin interactions was investigated by analyzing whether LSF was present in commercial, highly purified tubulin preparations from porcine brain. These preparations are well known to contain microtubule-associated proteins (MAPs). Strikingly, immunoblots using an LSF monoclonal antibody indeed detected a band comigrating with LSF (FIG. 3B). In fact, LSF was detected in this manner in all available commercially purified preparations of tubulin (between >99% and >97% pure tubulin). Finally, it was tested whether LSF interacted with tubulin in cellular extracts by co-immunoprecipitation. Cell extracts precipitated with anti-LSF antibody indicated robust co-precipitation of α-tubulin. As a positive control, based on the previous experiments, SET8 also robustly interacted with α-tubulin in the cell extract, and with LSF (FIG. 3C).

In order to determine whether the interaction between LSF and α-tubulin is direct and to map the regions on the proteins involved in their interactions, GST pull-down assays were performed. Various overlapping GST-fusion fragments of LSF and α-tubulin were incubated with purified porcine tubulin or recombinant purified His-LSF, respectively. The purified tubulin, consisting of α- and β-tubulin, directly interacted with LSF predominantly through its DNA binding domain (DBD) (FIG. 3D). Using a reciprocal approach, α-tubulin directly interacted with LSF through both N- and C-terminal fragments (FIG. 3E). Taken together, these results demonstrate that LSF interacts with α-tubulin directly, both in vivo and in vitro, and furthermore that LSF, although a transcription factor, appears to be a previously unidentified MAP.

LSF Facilitates Tubulin Polymerization In Vitro

Figure 4A:
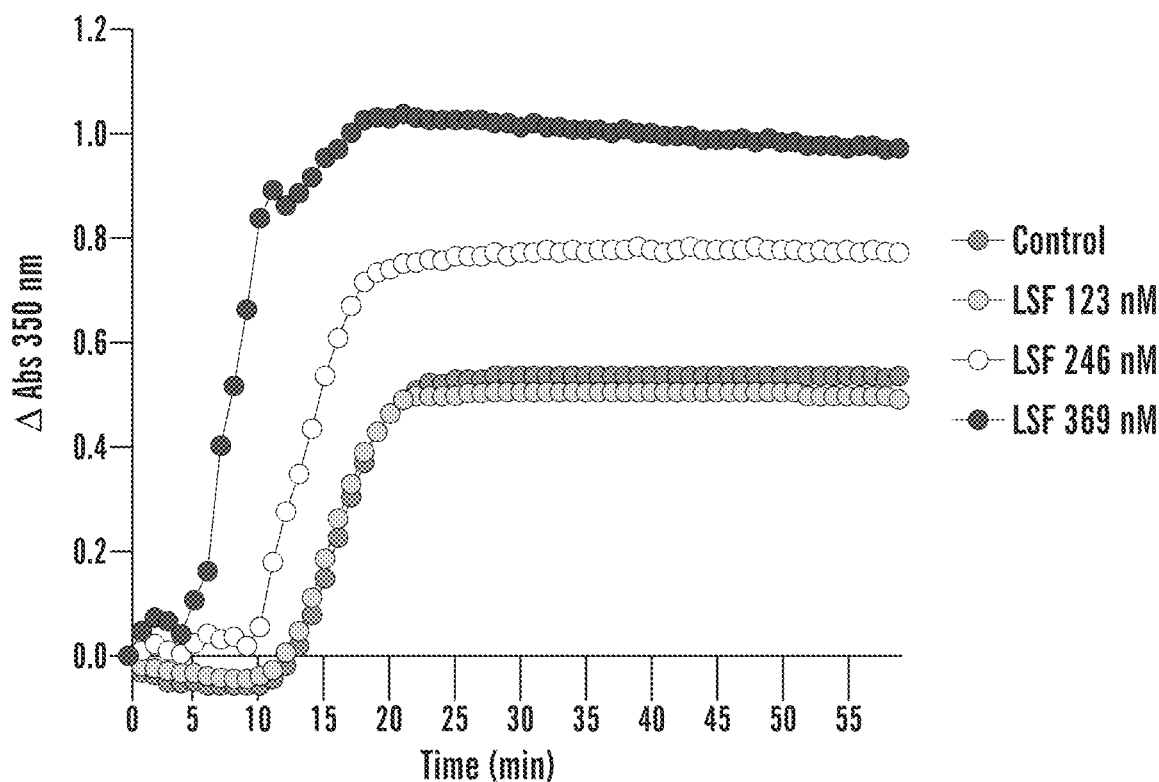
FIG. 4A-4D show that in vitro tubulin polymerization is enhanced by LSF, whereas LSF inhibition diminishes polymerization in vitro and causes spindle defects in cells.

Microtubule dynamics and function are modulated by its interactions with other proteins, including microtubule motor proteins and non-motor microtubule-associated proteins (MAPs) [17]. Whether LSF, like other MAPs, might be capable of modulating microtubule dynamics was tested using the standard in vitro tubulin polymerization assay in which the extent of polymerized microtubules is monitored by optical density over time. The commercially purified tubulin preparation was incubated with or without limiting amounts of LSF, at molar ratios ranging from 140-430:1 tubulin:LSF. Reproducibly, LSF significantly enhanced the initial rate of tubulin polymerization (FIG. 4A).

Figure 4B:
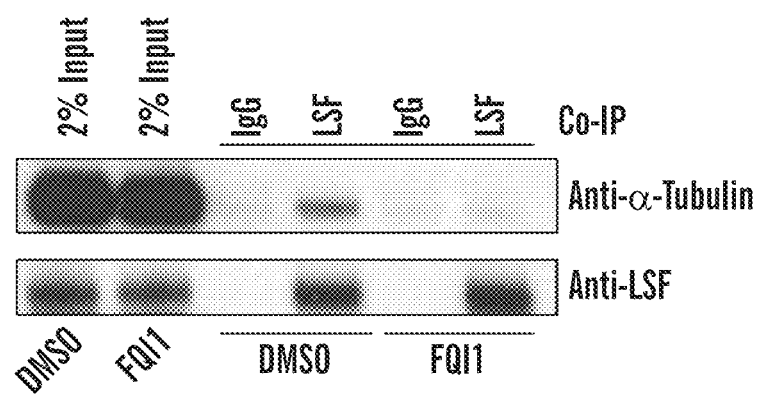
Figure 4C:
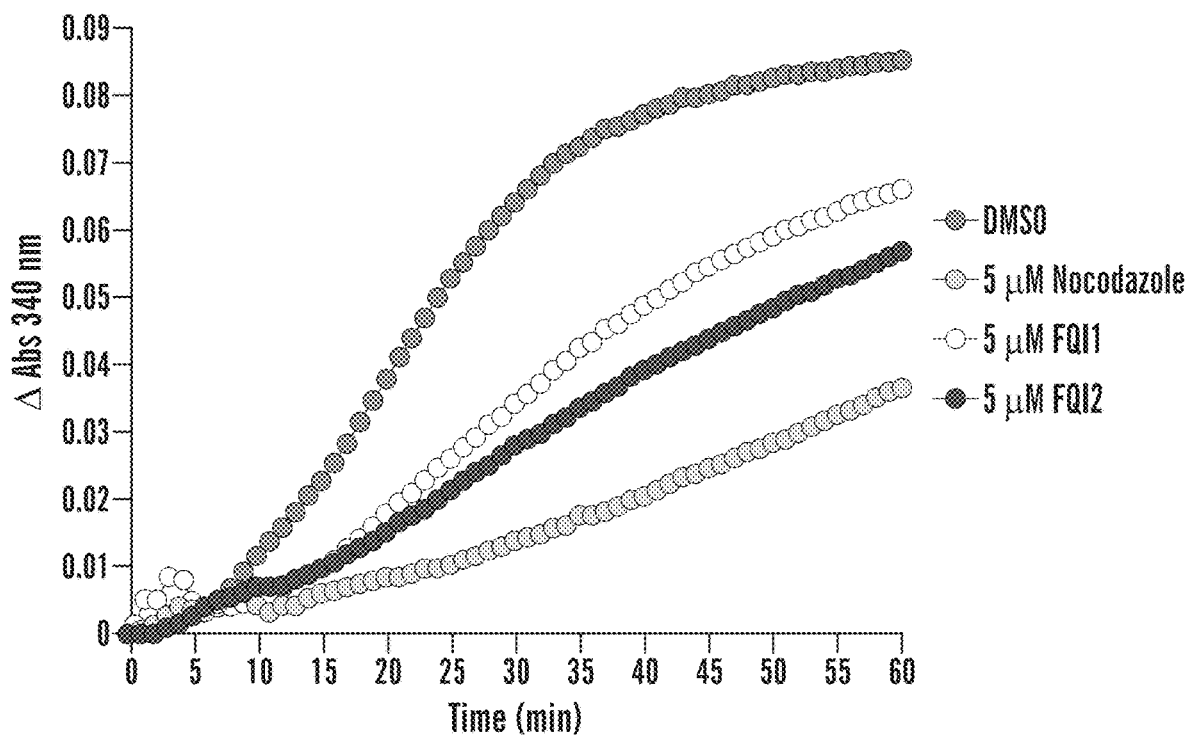

The LSF small molecule inhibitor, FQI1, inhibits LSF binding to DNA [18], as well as binding of LSF to certain protein partners [14]. Therefore, it was not unexpected that FQI1 also interrupted the LSF-tubulin interaction in vivo (FIG. 4B). Thus, FQI1 was used to interrogate the functionality of the LSF-tubulin interaction. Indeed, FQI1 inhibited tubulin polymerization in vitro (FIG. 4C), consistent with the presence of LSF in the purified tubulin preparation (FIG. 3B).

Figure 4D:
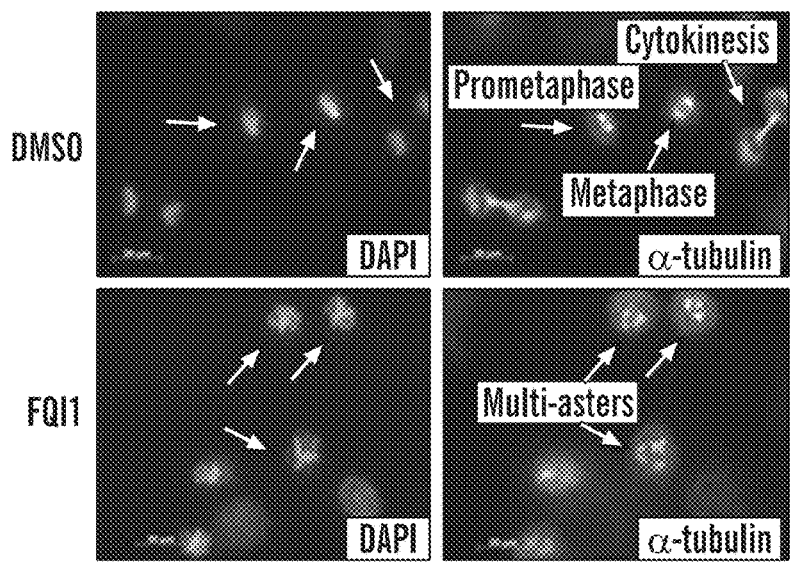

Since factors that enhance tubulin polymerization in vitro are not always biologically relevant, we tested whether FQI1 would perturb microtubules in cells. In order to limit the effect of FQI1 to inhibiting LSF protein-protein interactions, without affecting its transcriptional program, we synchronized cells in the cell cycle and then added FQI1 for a relatively short interval of time prior to entry into mitosis. Under these conditions, as the inventors previously reported [12], cells arrested in mitosis with condensed chromosomes (FIGS. 4D, 8A-8B). This was accompanied by a concentration-dependent increase in multi-aster formation in FQI1-treated cells, whereas no multi-asters were detectable in vehicle-treated cells (FIGS. 4D, 8C). In order to test whether these mitotic defects were indeed due to non-transcriptional consequences of FQI1, a washout experiment was performed in which FQI1 treated cells were arrested in mitosis, and then the compound removed. RNA polymerase II-dependent transcription of coding genes is largely inhibited during mitosis [19-21], although recent data indicate that limited transcription of genes critical for G1 phase remains [22]. If the mitotic arrest were due to dysregulation of LSF target genes critical for mitotic progression, transcription of those genes should not be able to reinitiate in mitosis and the defect would not be reversible. In contrast to this scenario, washout of compound from the FQI1-treated cells that were arrested in mitosis resulted in continued progression of the cells through mitosis and cell division (FIG. 8D). Thus, the FQI1-mediated mitotic defects, including spindle defects, appear to be due to a non-transcriptional mechanism. Given that FQI1 disrupts interactions between LSF and partner proteins, in particular with tubulin (FIG. 4B), these results are consistent with LSF-tubulin interactions facilitating microtubule dynamics critical for progression through mitosis.

LSF Promotes Tubulin Methylation by SET8

Figures 5A, 5B:
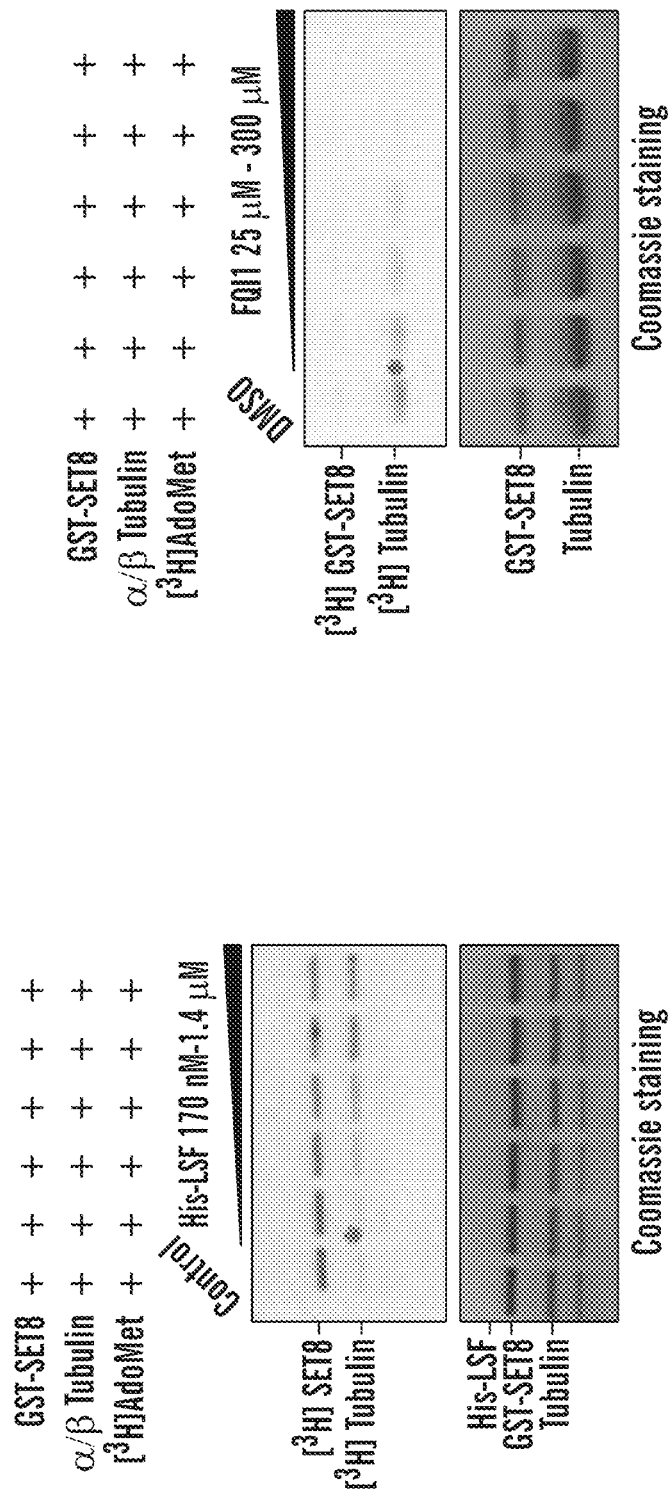
FIG. 5A-5E show that LSF and FQI1 oppositely affect tubulin methylation by SET8.
Figure 5D:
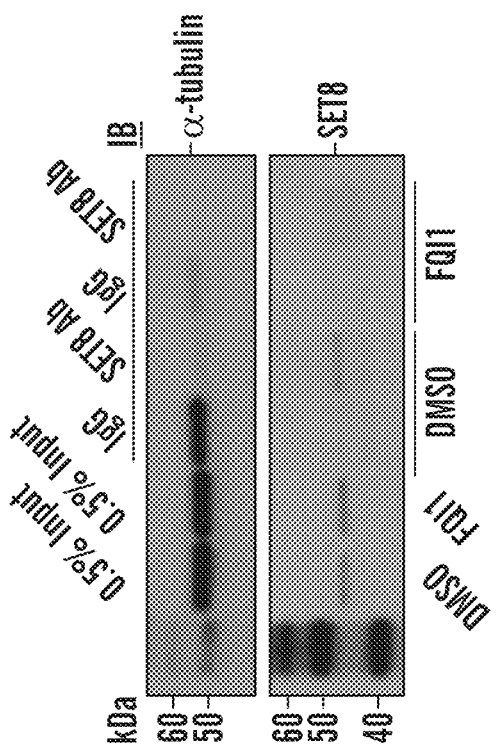
Figure 5C:
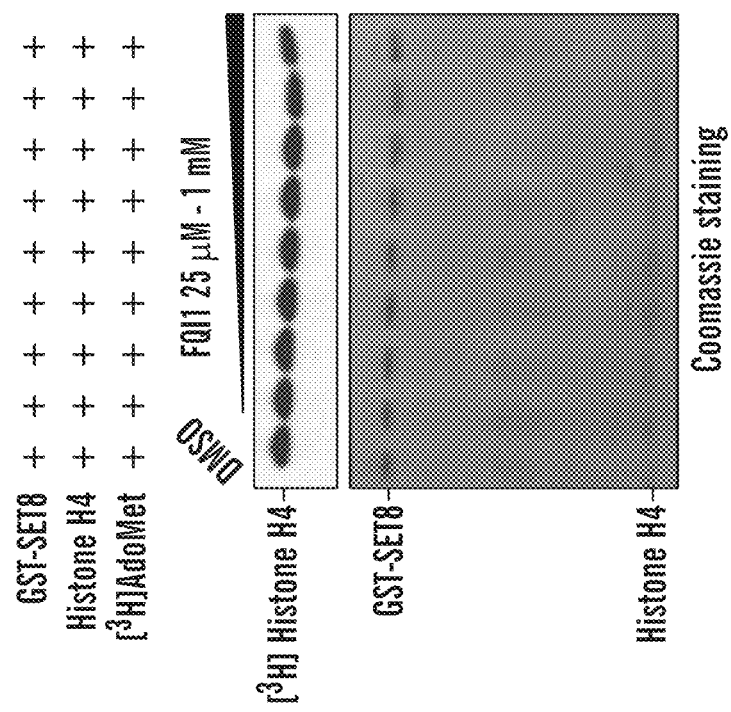
Figure 5E:
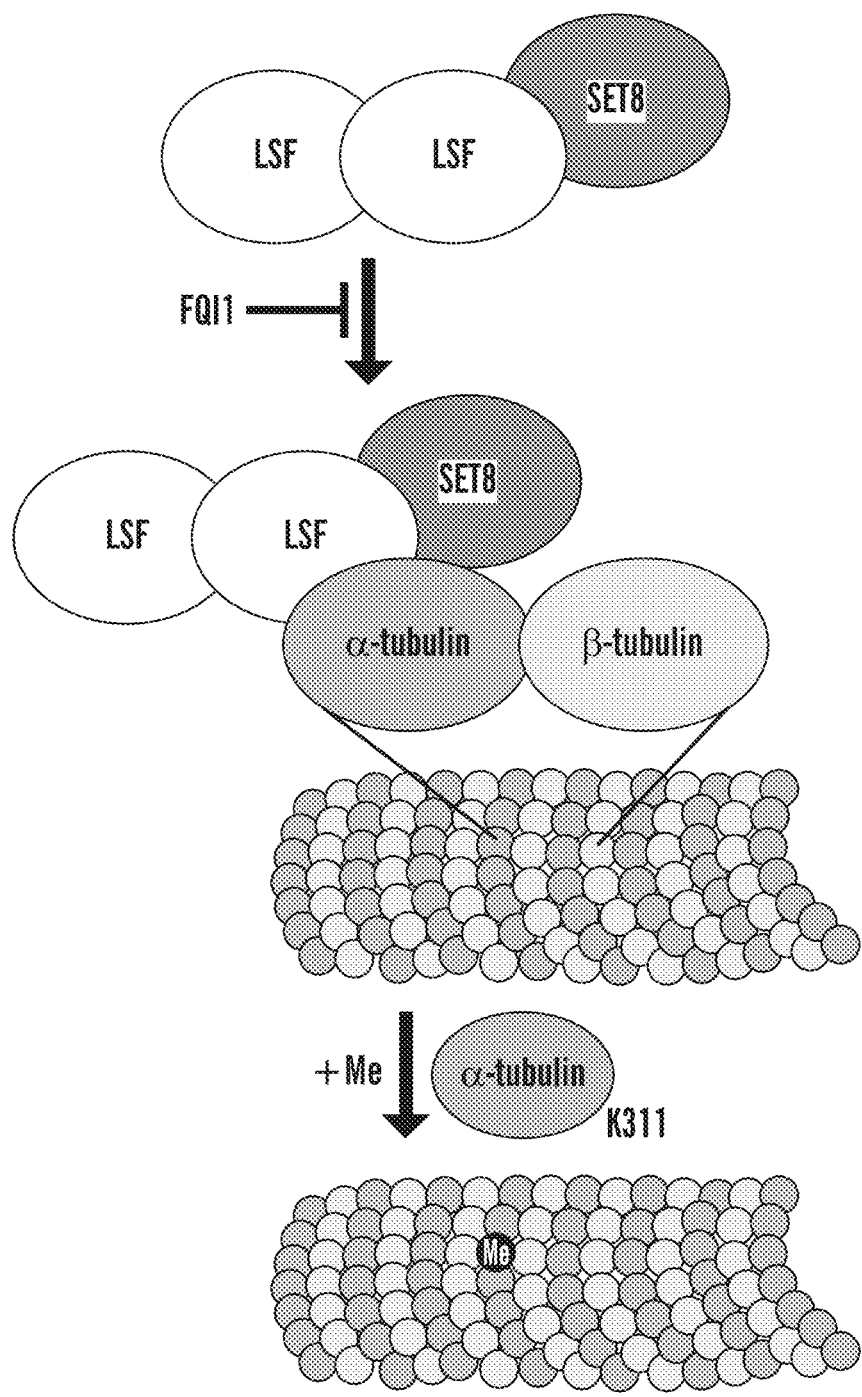

Physical interactions between tubulin, SET8 and LSF led the inventors to speculate that LSF may modulate the ability of SET8 to methylate tubulin. To test the hypothesis, recombinant SET8 and the methyl donor were incubated with tubulin in the presence of increasing concentrations of purified His-LSF (FIG. 5A). Indeed, tubulin methylation increased with increasing LSF from a 1:4 to 2:1 molar ratio of LSF:SET8, suggesting that LSF can mediate tubulin methylation by SET8. A similar experiment using recombinant MBP-α-tubulin as substrate provided the same result (FIG. 9A). Upon addition of FQI1 to reactions containing SET8, methyl donor, and tubulin, but not LSF, tubulin methylation decreased (FIG. 5B, compare lanes 1 and 2), consistent with the presence of LSF in the tubulin preparations and its ability to enhance SET8-dependent tubulin methylation. FQI1 also inhibited the ability of exogenously added LSF to enhance methylation of tubulin by SET8 (FIG. 9B, compare lanes 5,6 to lane 1). To exclude the possibility that SET8 catalytic activity is directly inhibited in the presence of FQI1, a parallel experiment was performed using histone H4 as substrate in the place of tubulin; in this case, FQI1 did not inhibit methylation of the substrate (FIG. 5C). Taken together, the data indicate that LSF is a positive modulator of tubulin methylation and FQI1, which abrogates the tubulin-LSF interaction (FIG. 4C), and blocks tubulin methylation by SET8. These data support the model that LSF recruits SET8 to tubulin (FIG. 5E).

DISCUSSION

A number of post-translational modifications of microtubules are well established, including the enzymes responsible for these modifications. However, thus far, only limited insights have been obtained regarding their biological roles, and tubulin PTMs have generally remained less amenable to straightforward in vitro functional studies. Moreover, only one study has identified lysine methylation of microtubules [15]. In that case, Walker's group reported that SETD2, known as a histone methyltransferase for a chromatin activation mark, H3K36me3, also methylates α-tubulin at K40. Furthermore, the loss of SETD2-mediated tubulin methylation resulted in mitotic microtubule defects and genomic instability. Here, the inventors describe distinct, novel lysine methylation of α-tubulin and identify the enzyme responsible for its modification as SET8. Importantly, they also demonstrate the surprising finding that a transcription factor, LSF, moonlights as a microtubule-associated protein, and that it can recruit SET8 to tubulin to facilitate its modification. This recruitment mechanism mirrors mechanisms of targeting of histone writers to chromatin, providing a further parallel between the generation of the histone and tubulin codes.

Tubulin PTMs are generally thought to regulate protein-protein interactions within the microtubule cytoskeleton, thereby regulating signaling events in the cell. To date, a large variety of microtubule associated proteins (MAPs) have been characterized, many of which stabilize and destabilize microtubules, are associated with the coupling of molecular motors and microtubules, and play critical roles in spindle formation [23]. Here, it is shown that LSF facilitates tubulin polymerization in vitro, and that LSF inhibition results in defective spindle formation in mitosis, with the implication that this is a consequence of the direct binding of LSF to tubulin. The data indicating that inhibition of LSF-tubulin interactions apparently affects spindle formation suggest that either LSF itself, or lysine methylation by SET8, modulate MT dynamics.

Precise modulation of SET8 levels is required for proper cell cycle progression, suggesting that SET8 and H4K20me1 may function as novel regulators of cell cycle progression, although the previous focus has been on regulation of S phase [24]. With the demonstration that SET8 can also methylate α-tubulin, the roles of non-histone substrates must be considered as causes for SET8-mediated regulation of the cell cycle, and in particular of mitosis when SET8 is most abundant.

Mitosis is a viewed as a vulnerable target for inhibition in cancer [25]. In that light, it is notable that LSF promotes oncogenesis in hepatocellular carcinoma (HCC), the sixth most common cancer worldwide and the second highest cause of cancer-related death globally [26]. LSF is overexpressed in human HCC cell lines, and over 90% of human HCC patient samples, showing significant correlation with stages and grades of the disease [10]. The initial lead LSF inhibitor, FQI1, induces apoptosis in an aggressive HCC cell line in vitro and significantly inhibits tumor growth in multiple mouse HCC models, with no observable toxicity to normal tissues [12,15]. These new findings that LSF interacts with tubulin and SET8, and that FQI1 disrupts the LSF-tubulin interaction, may be related to the impact of the LSF inhibitors in HCC cells and tumors. Expression both of particular tubulins (e.g. TUBA1B) and of SET8 are upregulated in HCC tumor samples, as compared to normal liver [27, 28]. Moreover, SET8 is required to maintain the malignant phenotype of various cancer types [29]. Given the current lack of effective treatments, further investigation into the relevance of the LSF-tubulin-SET8 pathway to HCC may aid in targeted and effective treatment.

Methods

Cell Culture, Immunoprecipitation, and Immunofluorescence

HEK293T, HeLa and COS7 cells were cultured in DMEM media supplemented with 10% FBS. FQI1 treatment of HEK293T cells was for 24 hours at 37° C. with 2.5 µM FQI1. Immunoprecipitation (IP) and immunofluorescence experiments were carried out as described previously [30, 31]. For the immunoprecipitation, 1 mg of total HEK293T cellular extract was incubated with 5 µg of either anti-SET8 antibody (Active Motif) or anti-LSF antibody (Millipore). The immunoprecipitates were blotted with anti-α tubulin, anti-β tubulin (Sigma T9026, T8328), anti-SET8 or anti-LSF (BD) antibodies as per the manufacturer's dilution recommendations. Cellular extracts were also immunoprecipitated with normal IgG (Cell Signaling Technology) as a negative control for all IP experiments.

For the detection of α-tubulin and SET8 co-localization, COS7 cells were grown on coverslips and transfected with a GFP-SET8 expression plasmid. After cells were fixed with paraformaldehyde, the cells were incubated with anti-α tubulin and visualized with an anti-mouse IgG coupled with Alexa Fluor 488 (Molecular Probes) and using a confocal microscope (Zeiss LSM510). For the detection of SET8 and LSF co-localization, COS7 cells were instead co-transfected with GFP-SET8 and 3×Flag-LSF expression plasmids; the epitope tagged LSF was detected by mouse anti-FLAG antibody (F3165, Sigma-Aldrich) and visualized with an anti-mouse IgG coupled with Alexa Fluor 488 (Molecular Probes). DAPI was used to stain nuclear DNA.

GST and MBP Pull Down Assays

LSF, SET8 and α-tubulin cDNAs were cloned into the pGEX-5X-1 vector (GE Healthcare) or pMalC4X (NEB) and GST-tagged proteins or MBP-tagged proteins were captured using Glutathione Sepharose beads (GE Healthcare) or amylose resin (NEB). Sepharose beads containing 10 µg of fusion protein were incubated with purified tubulin (MP-biomedical), and recombinant His-tagged LSF or SET8 purified from E. coli for 2 hours at 4° C. Protein bound to the beads was resolved by 10-20% SDS-PAGE. LSF, SET8 and tubulin were visualized by western blotting by using anti-LSF (BD), anti-SET8 (Active motif) and anti-α tubulin (Sigma), respectively.

Tubulin Polymerization Assay

Quantitative determination of tubulin polymerization in vitro was carried out using the in vitro polymerization assay kits from either Millipore (17-10194) or Cytoskeleton (FQI1 assay only) according to the manufacturer's conditions. For the Millipopre kit, thawed tubulin was mixed with purified His-LSF, His-SET8 proteins or FQI1 in 70 µL final volumes of 1×PB-GTP solutions, and the 96-well plate was transferred to the pre-warmed (37° C.) SpectraMax M5 Microplate Reader to read UV-Visible Absorbance. Tubulin polymerization was followed by measuring the turbidity variation (light scattering) every 1 min at 350 nm for 1 hr.

In Vitro Methylation Assays

One µg of recombinant GST-SET8 (in 50% glycerol) and 2 µg of the purified tubulin (MP-Bioscience) were incubated with radioactively labeled [3H] AdoMet at room temperature for overnight. As indicated, recombinant His-LSF protein or FQI1 inhibitor were added to the reaction. Samples were separated by electrophoresis through a 10% Tricine Gel (Invitrogen) and the gel was stained with Coomassie Brilliant Blue and incubated with EN3HANCE (PerkinElmer) solution. The gel was dried and exposed to autoradiography film for 1 week. For the peptide assays, the specific peptides of α-tubulin were synthesized from AnaSpec Inc. Sequences are listed in Table 3. Two sg of each peptide and 2 µg of purified SET8 or full-length SETD2 (Active Motif) were incubated with radioactively labeled [3H] AdoMet at room temperature overnight. Samples were spotted onto P81 filters (Whatman 3698325) and the filter were washed 3 times with 0.3 M ammonium bicarbonate. The ratio of incorporated [$^3$H]CH$_3$ was determined using liquid scintillation counting.

TABLE 3

List of α-tubulin peptides

| SEQ ID | Peptide ID | Sequence |
| --- | --- | --- |
| 1 | K40 | H-DGQMPSDKTIGGGDD-NH2 |
| 2 | K40-Ac | H-DGQMPSDK-AcTIGGGDD-NH2 |
| 3 | K304 | H-PANQMVKCDPRHG-NH2 |
| 4 | K311 | H-CDPRHGKYMACCL-NH2 |
| 5 | K311A | H-CDPRHGAYMACCL-NH2 |
| 6 | K311 S | H-CDPRHGSYMACCL-NH2 |

TABLE 3-continued

List of α-tubulin peptides

| SEQ ID | Peptide ID | Sequence |
|---|---|---|
| 7 | K311-Me | H-CDPRHGK-MeYMACCL-NH2 |
| 8 | K311-Ac | H-CDPRHGK-AcYMACCL-NH2 |

Mass-Spectrometric Analysis

Recombinant GST-SET8 and purified tubulin (MP-Bioscience) were incubated with nonradioactive AdoMet overnight at room temperature and the samples were separated by electrophoresis through a 10% Tricine Gel. Excised gel bands were digested with either subtilisin or trypsin. Individual digests were analyzed by nanoLC-MS (Easyn1000-Qexactive) and data analysis was performed using ProteomeDiscoverer2.0 with the SwissProt database June 2015.

REFERENCES

1. Janke, C., *The tubulin code: molecular components, readout mechanisms, and functions*. J Cell Biol, 2014. 206(4): p. 461-72.
2. Verhey, K. J. and J. Gaertig, *The tubulin code*. Cell Cycle, 2007. 6(17): p. 2152-60.
3. Song, Y. and S. T. Brady, *Post-translational modifications of tubulin: pathways to functional diversity of microtubules*. Trends Cell Biol, 2015. 25(3): p. 125-36.
4. Dillon, S. C., et al., *The SET-domain protein superfamily: protein lysine methyltransferases*. Genome Biol, 2005. 6(8): p. 227.
5. Fang, J., et al., *Purification and functional characterization of SET8, a nucleosomal histone H4-lysine 20-specific methyltransferase*. Curr Biol, 2002. 12(13): p. 1086-99.
6. Nishioka, K., et al., *PR-Set7 is a nucleosome-specific methyltransferase that modifies lysine 20 of histone H4 and is associated with silent chromatin*. Mol Cell, 2002. 9(6): p. 1201-13.
7. Rice, J. C., et al., *Mitotic-specific methylation of histone H4 Lys 20 follows increased PR-Set7 expression and its localization to mitotic chromosomes*. Genes Dev, 2002. 16(17): p. 2225-30.
8. Wu, S. and J. C. Rice, *A new regulator of the cell cycle: the PR-Set7 histone methyltransferase*. Cell Cycle, 2011. 10(1): p. 68-72.
9. Shi, X., et al., *Modulation of p53 function by SET8-mediated methylation at lysine 382*. Mol Cell, 2007. 27(4): p. 636-46.
10. Yoo, B. K., et al., *Transcription factor Late SV40 Factor (LSF) functions as an oncogene in hepatocellular carcinoma*. Proc Natl Acad Sci USA, 2010. 107(18): p. 8357-62.
11. Arand, J., et al., *In vivo control of CpG and non-CpG DNA methylation by DNA methyltransferases*. PLoS Genet, 2012. 8(6): p. e1002750.
12. Powell, C. M., et al., *Inhibition of the mammalian transcription factor LSF induces S-phase dependent apoptosis by downregulating thymidylate synthase expression*. EMBO J, 2000. 19(17): p. 4665-75.
13. Rajasekaran, D., et al., *Small molecule inhibitors of Late SV40 Factor (LSF) abrogate hepatocellular carcinoma (HCC): Evaluation using an endogenous HCC model*. Oncotarget, 2015. 6(28): p. 26266-77.
14. Chin, H. G., et al., *Transcription factor LSF-DNMT1 complex dissociation by FQI1 leads to aberrant DNA methylation and gene expression*. Oncotarget, 2016. 7(50): p. 83627-83640.
15. Park, I. Y., et al., *Dual Chromatin and Cytoskeletal Remodeling by SETD2*. Cell, 2016. 166(4): p. 950-962.
16. Zhang, T., S. Cooper, and N. Brockdorff, *The interplay of histone modifications—writers that read*. EMBO Rep, 2015. 16(11): p. 1467-81.
17. Janke, C. and J. C. Bulinski, *Post-translational regulation of the microtubule cytoskeleton: mechanisms and functions*. Nat Rev Mol Cell Biol, 2011. 12(12): p. 773-86.
18. Grant, T. J., et al., *Antiproliferative small-molecule inhibitors of transcription factor LSF reveal oncogene addiction to LSF in hepatocellular carcinoma*. Proc Natl Acad Sci USA, 2012. 109(12): p. 4503-8.
19. Delcuve, G. P., S. He, and J. R. Davie, *Mitotic partitioning of transcription factors*. J Cell Biochem, 2008. 105(1): p. 1-8.
20. Gottesfeld, J. M. and D. J. Forbes, *Mitotic repression of the transcriptional machinery*. Trends Biochem Sci, 1997. 22(6): p. 197-202.
21. Long, J. J., et al., *Repression of TFIIH transcriptional activity and TFIIH-associated cdk7 kinase activity at mitosis*. Mol Cell Biol, 1998. 18(3): p. 1467-76.
22. Palozola, K. C., et al., *Mitotic transcription and waves of gene reactivation during mitotic exit*. Science, 2017. 358(6359): p. 119-122.
23. Stanton, R. A., et al., *Drugs that target dynamic microtubules: a new molecular perspective*. Med Res Rev, 2011. 31(3):p. 443-81.
24. Milite, C., et al., *The emerging role of lysine methyltransferase SETD8 in human diseases*. Clin Epigenetics, 2016. 8: p. 102.
25. Komlodi-Pasztor, E., D. L. Sackett, and A. T. Fojo, *Inhibitors targeting mitosis: tales of how great drugs against a promising target were brought down by a flawed rationale*. Clin Cancer Res, 2012. 18(1): p. 51-63.
26. Laursen, L., *A preventable cancer*. Nature, 2014. 516(7529): p. S2-3.
27. Lu, C., et al., *Increased alpha-tubulin1b expression indicates poor prognosis and resistance to chemotherapy in hepatocellular carcinoma*. Dig Dis Sci, 2013. 58(9): p. 2713-20.
28. Guo, Z., et al., *A polymorphism at the miR-502 binding site in the 3'-untranslated region of the histone methyltransferase SET8 is associated with hepatocellular carcinoma outcome*. Int J Cancer, 2012. 131(6): p. 1318-22.
29. Hou, L., et al., *SET8 induces epithelialmesenchymal transition and enhances prostate cancer cell metastasis by cooperating with ZEB1*. Mol Med Rep, 2016. 13(2): p. 1681-8.
30. Andrews, N.C. and D. V. Faller, *A rapid micropreparation technique for extraction of DNA—binding proteins from limiting numbers of mammalian cells*. Nucleic Acids Res, 1991. 19(9): p. 2499.
31. Estève, P. O., et al., *Direct interaction between DNMT1 and G9a coordinates DNA and histone methylation during replication*. Genes Dev, 2006. 20(22): p. 3089-103.

Example 4: Lysine Methylation of α-Tubulin by Microtubule-Associated SET8 is Facilitated by LSF Microtubules (MTs) are major cytoskeletal components that play important roles in key cellular processes such as structural support, localization of organelles, and chromosome segregation [1,2]. A number of post-translational modifications (PTMs) of microtubules have been reported, which contribute to the functional diversity of microtubules and affect MT dynamics and organization [3]. This led to the hypothesis of a tubulin code, where tubulin modifications specify biological outcomes through changes in higher-order microtubule structure by recruiting and interacting with effector proteins. Notably, tubulin methylation has been less studied than other types of tubulin modification, such as detyrosination, glutamylation, glycylation, acetylation, and phosphorylation, although in the parallel histone code hypothesis, methylation is the most common and well-understood modification.

Example 5: Cell Growth Inhibition and Cellular Thermal Shift Assays for Exemplary Compounds FQI-34 and FQI-37

Cell lines and culture conditions: Human colon cancer cells Caco-2, HT29 and HCT15, human pancreatic cancer cells BxPC3, CFPAC-1, and CAPAN-2, liver cancer cells SNU423 and kidney cells HEK293, were obtained from American Type Culture Collection (Rockville, USA). HeLa, DLD1, U937, THP-1, and NIH3T3 cells were obtained from ATCC. Huh7 cells were obtained from (Japanese Cancer Resources Bank). HeLa cells, Huh7, DLD1 and NIH-3T3 cells were cultured in DMEM (Dulbecco's modification of Eagle's Medium; Corning) supplemented with 10% Fetal Bovine Serum (FBS; Invitrogen) and 10% Fetal Calf Serum (FCS; Atlanta Biologicals) respectively. U937, BxPC3, HCT15, SNU423 and THP-1 cells were grown in RPMI-1640 (Roswell Park Memorial Institute; Corning) supplemented with 10% Fetal Bovine Serum (FBS; Invitrogen). CFPAC-1 cells were cultured in Iscove's Modified Dulbecco's Medium (ATCC) supplemented with 10% FBS. CAPAN-2 and HT29 cells were cultured in McCoy's 5a medium supplemented with 10% FBS. Caco2 and HEK293 cells were grown in Eagle's Minimum Essential Medium (ATCC) with final 20% FBS concentration. All cells were maintained at 37° C. in 5% $CO_2$ at constant 70% humidity.

MTS cell proliferation assay: Cells were detached from the plates using trypsin (0.25% for 3 mins, ATCC) and counted using a hemocytometer and were plated at 3000-1500 cells per well, in a 96-well format. The cells were seeded in the inner wells of 96 well plates, and media was added to the outer wells (blank). For NIH-3T3, 1500 cells were seeded in the inner wells of 96-well plates, and after 20 hours cells were treated with compound or DMSO (vehicle control) at appropriate concentrations (DMSO at final concentration of 1%). For other adherent cells 3000 HeLa, BxPC3, CFPAC-1, CAPAN-2, HEK293, HCT15, HT29, CaCo2, DLD1, Huh7 or SNU423 cells were seeded in in each well approximately 20 hrs prior to the treatment. For U937 and THP-1 suspension cells, 2500 cells were added to the wells of a 96-well plate on the day of treatment. After a 72-hour (or 120 hrs for BxPC3, CAPAN-2, SNU423) incubation with compound or vehicle, cell growth was assessed via the Promega CellTiter 96® AQueous One Solution Cell Proliferation Assay, a colorimetric method to determine the number of viable cells. 20 μL of the CellTiter 96® AQueous One Solution Reagent was added directly into cultured wells and incubated for approximately one hour, after which the absorbance at 490 nm was read with a 96-well plate reader (Opys MR Microplate Reader). $GI_{50}$ values were determined from plots of the percentage of compound-treated cell growth to vehicle cell growth vs. compound concentration (GraphPad Prism; non-linear regression, log inhibitor verse normalized response with variable slope). Structures of the compounds are shown below and $GI_{50}$ values are summarized in Table 4.

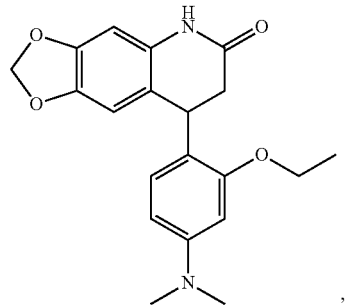
FQI-34

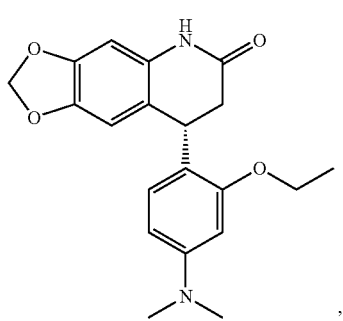
(S)-FQI-34

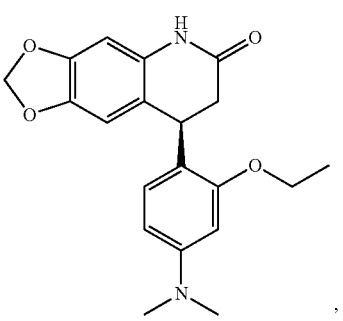
(R)-FQI-34)

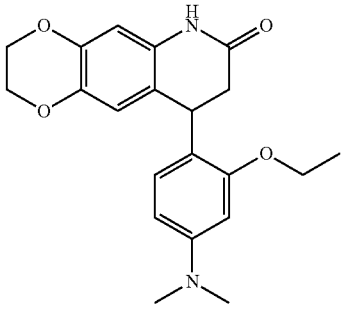
FQI-37

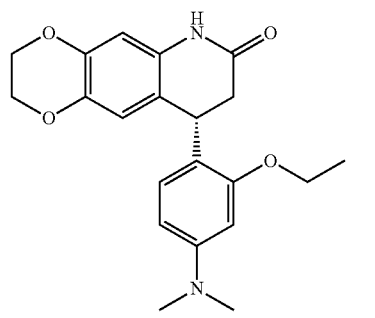
(S)-FQI-37 and

-continued

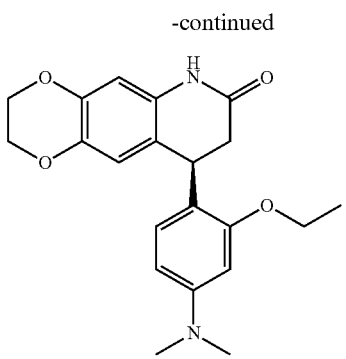

(R)-FQI-37

TABLE 4

| | GI$_{50}$ (µM) | | | | | | | | | | | | |
|---|---|---|---|---|---|---|---|---|---|---|---|---|---|
| | Cell line | | | | | | | | | | | | |
| Compound | SNU-423 | HEK-293 | NIH 3T3 | BxPC-3 | CAPAN-2 | CFPAC-1 | CaCo-2 | HCT-15 | HT-29 | U937 | THP-1 | HuH7 | HeLa |
| FQI-34 | 0.384 | 0.219 | 0.73 | 0.27 | 0.239 | 0.676 | 0.501 | 0.224 | 0.316 | 0.250 | 4.8 | 0.141 | 0.462 |
| (S)-FQI-34 | 0.05 | | 0.59 | | | | | | | | | 0.056 | 3.8 |
| (R)-FQI-34 | 0.251 | | 5.8 | | | | | | | | | 0.158 | 0.3 |
| FQI-37 | 0.141 | | | | | | 0.141 | 0.018 | 0.398 | | | 0.070 | |
| (S)-FQI-37 | 0.06 | | | | | | | | | | | 0.070 | |
| (R)-FQI-37 | 0.147 | | | | | | | | | | | 0.126 | |

As can be seen from the data summarized in Table 4, racemic FQI-37 is more effective (lower GI$_{50}$) relative to FQI-34 in all the cell lines except one, HT-29, in which both FQI-37 and FQI-34 were tested. In addition, S isomer of FQI-37 is relatively more effective than the R isomer of FQI-37. Also, the R isomer of FQI-37 is relatively more effective than the R isomer of FQI-35.

Cellular thermal shift assay[1,2]: Huh7 cells were cultured in DMEM media supplemented with 10% PBS. Cells were seeded into T75 flasks and allowed to reach 60-80% confluency. After trypsinization (0.25% Trypsin-EDTA, ATCC), the cell pellet was resuspended in media. Hematocytometer was used to count the cells and about 1 million cells were plated in two 10 cm plates (for convenience of cell detachment technique). Cells were left to adhere to the plate overnight. After 20 hours, old media was aspirated and replaced with new media supplemented with 50 uM drug or 0.1% final DMSO was added. Cells were treated three hours and media was aspirated and washed with PBS supplemented with 50 uM drug or 0.1% DMSO. The cells were detached using a cell scrapper by addition of 5 mL of freshly prepared PBS supplemented with 1 mM Pefabloc (Sigma-Aldrich) with either 50 uM FQI or 0.1% DMSO. Cells were pelleted at 1200 rpm and resuspended in 500 ul of PBS buffer with 1 mM Pefabloc with the drug or DMSO. Nine aliquots of 50 uL of cell suspension were prepared for each of the FQI treated and control cells. The samples were heat treated for 3 minutes (T100 Biorad thermal cycler), then cooled at the room temperature for 3 minutes. After this 3-min incubation, the samples were snap frozen in liquid nitrogen. The process is repeated three times by thawing the tubes in a heat block at 23 C, followed by a brief vortex at speed 4 for 8 seconds (VWR, mini vortex). After final freeze thaw lysate were centrifuged at 20,000×g for 10 minutes to separate soluble protein from aggregates. 45 µL of the supernatant containing the soluble protein was saved at −80° C. for immunoblot analysis. Equal amounts of supernatant (18 uL) were loaded onto a 10% polyacrylamide gel. Separated proteins were transferred onto polyvinylidene difluoride (PVDF) membranes. Membranes were blocked in 5% milk/TBST (50 mM Tris-Cl, pH 7.5, 150 mM NaCl, 0.1% Tween-20), and then probed overnight at 4° C. with primary antibody (anti-LSF (BD bioscience; 1:1000 dilution in 5% milk in TBST). Secondary goat anti-mouse HRP-IgG antibody (1:7000 in 5% milk) was incubated with membranes for 1 hour at room temperature. Protein bands were detected with Immobilon Western Chemiluminescent HRP-Substrate (Millipore) and developed on a Kodak RP X-OMAT Developer or Sapphire imager. Immunoblots were quantified using Image J and graphed using GraphPad PRISM. Area-under-curve (AUC) for the quantified Western blots were calculated with GraphPad PRISM. Non-parametric t-test was calculated to determine statistical significance between the curves. Tm$_{50}$ values were calculated using non-linear regression (inhibitor-vs-response, variable slope). Results are shown in FIGS. 31A-32B.

Example 6: FQI34/FQI1 Comparison

RPE-hTERT Flp-In cells were incubated in serum-free DMEM:F12 media for 24 hours to synchronize the cells in G0/G1. Cells were stimulated to reenter the cell cycle with DMEM:F12 media containing 10% Fetal Bovine Serum. After 24 hours, the cells were treated with DMSO (vehicle), FQI1 (2.5 µM or 5 µM), or FQI34 (250 nM or 500 nM) for one hour. The cells were washed twice with 1×Phosphate-buffered Saline and fixed with PHEM (3.7% formaldehyde in 100 mM PIPES at pH 6.8, 10 mM EGTA, 1 mM magnesium chloride, and 0.2% Triton X-100) for 10 minutes at room temperature. The fixed cells were stained for α-tubulin using a mouse anti-α-tubulin antibody (Fisher #62204). Secondary antibodies were: DMSO/FQI1 samples—goat anti-mouse IgG conjugated to Alexa 546 (Thermo Fisher #A11003); FQI34 samples—goat anti-mouse IgG conjugated to Texas Red (Fisher #T-862). DNA was stained with Hoechst 33342. Cells were imaged using a Nikon NiE using the 40× objective and images were captured using a DS-Qi1 Mc 12 bit camera. Scale bars and merged images were generated using Fiji software.

Immunofluorescent images of DNA and α-tubulin, as indicated, in RPE-hTERT Flp-In cells treated with DMSO (vehicle), compared to the indicated concentrations of FQI1 or FQI34 are shown in FIG. 33. As seen, FQI34 results in condensed, but nonaligned chromosomes and disrupted spindles, as does FQI1.

What is claimed is:

1. A compound having the structure:

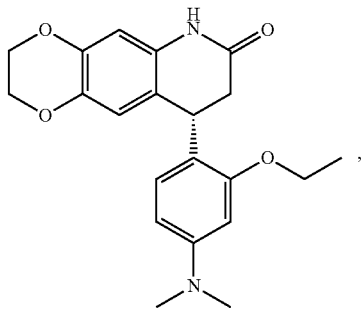

((S)-FQI-37)

and
wherein the compound inhibits Late Simian Virus 40 Factor (LSF).

2. A method for treating cancer in a subject, the method comprising administering an effective amount of a compound of claim 1 to a subject in need thereof.

3. The method of claim 2, wherein the cancer is selected from the group consisting of breast cancer, colon cancer, ovarian cancer, pancreatic cancer, lung cancer, kidney cancer, cancers of the hematopoietic system, cancers of the endometrium, cervical cancer, cancers of the upper digestive tract, stomach cancer, liver cancers and cancers of the small intestine.

4. The method of claim 3, wherein cancer is hepatocellular carcinoma (HCC), colon cancer, pancreatic cancer, hematopoietic cancer or cervical cancer.

5. A method of inhibiting tubulin methylation or modulating chromatin/cytoskeleton modification in a cell, the method comprising administering to the cell an effective amount of inhibitor of late SV40 factor, wherein the inhibitor of late SV40 factor is a compound of claim 1.

* * * * *